(12) United States Patent
Laurent et al.

(10) Patent No.: US 9,624,239 B2
(45) Date of Patent: Apr. 18, 2017

(54) PROTEIN KINASE INHIBITORS

(75) Inventors: Alain Laurent, Montreal (CA); Yannick Rose, Montreal (CA); Stephen Morris, Beaconsfield (CA); James Jaquith, Pincourt (CA)

(73) Assignee: Pharmascience Inc., Montreal, Quebec (CA)

( * ) Notice: Subject to any disclaimer, the term of this patent is extended or adjusted under 35 U.S.C. 154(b) by 404 days.

(21) Appl. No.: 14/009,635

(22) PCT Filed: Apr. 3, 2012

(86) PCT No.: PCT/CA2012/000333
§ 371 (c)(1),
(2), (4) Date: Oct. 28, 2013

(87) PCT Pub. No.: WO2012/135944
PCT Pub. Date: Oct. 11, 2012

(65) Prior Publication Data
US 2014/0045833 A1    Feb. 13, 2014

Related U.S. Application Data

(60) Provisional application No. 61/471,322, filed on Apr. 4, 2011.

(30) Foreign Application Priority Data

Dec. 1, 2011   (CA) .................................. 2760174

(51) Int. Cl.
| | | |
|---|---|---|
| *A61K 31/519* | (2006.01) | |
| *C07D 487/04* | (2006.01) | |
| *C07D 491/147* | (2006.01) | |
| *C07D 495/14* | (2006.01) | |
| *C12Q 1/48* | (2006.01) | |
| *C07D 487/14* | (2006.01) | |
| *C07K 14/47* | (2006.01) | |
| *C12N 9/12* | (2006.01) | |

(52) U.S. Cl.
CPC ......... *C07D 495/14* (2013.01); *C07D 487/04* (2013.01); *C07D 487/14* (2013.01); *C07D 491/147* (2013.01); *C07K 14/4703* (2013.01); *C12N 9/1205* (2013.01); *C12Q 1/485* (2013.01)

(58) Field of Classification Search
CPC .......................... C07D 487/04; C07D 491/147
See application file for complete search history.

(56) References Cited

FOREIGN PATENT DOCUMENTS

| CA | 2569016 A | 12/2005 |
|---|---|---|
| JP | 06247967 A | 9/1994 |

OTHER PUBLICATIONS

International Search Report dated Jul. 24, 2012 in International Application No. PCT/CA2012/000333.

*Primary Examiner* — Brian McDowell
(74) *Attorney, Agent, or Firm* — Leydig, Voit & Mayer, Ltd.

(57) ABSTRACT

The present invention relates to a novel family of inhibitors of protein kinases of Formula (1) wherein X is selected from $CH_2$, O, $S(0)n$, or $NR6$; and process for their production and pharmaceutical compositions thereof. In particular, the present invention relates to inhibitors of the members of the Tec, Src, Btk and Lck protein kinase families.

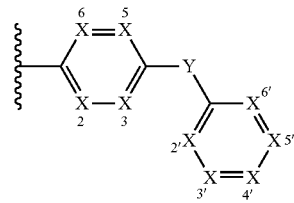

Formula 1

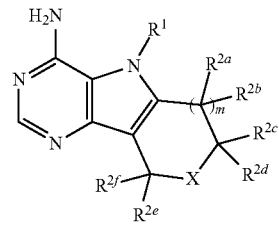

13 Claims, No Drawings

PROTEIN KINASE INHIBITORS

FIELD OF INVENTION

The present invention relates to a novel family of inhibitors of protein kinases. In particular, the present invention relates to inhibitors of the members of the Tec and Src protein kinase families, more particularly Btk and Lck.

BACKGROUND OF THE INVENTION

Protein kinases are a large group of intracellular and transmembrane signaling proteins in eukaryotic cells. These enzymes are responsible for transfer of the terminal (gamma) phosphate from ATP to specific amino acid residues of target proteins. Phosphorylation of specific tyrosine, serine or threonine amino-acid residues in target proteins can modulate their activity leading to profound changes in cellular signaling and metabolism. Protein kinases can be found in the cell membrane, cytosol and organelles such as the nucleus and are responsible for mediating multiple cellular functions including metabolism, cellular growth and division, cellular signaling, modulation of immune responses, and apoptosis. The receptor tyrosine kinases are a large family of cell surface receptors with protein tyrosine kinase activity that respond to extracellular cues and activate intracellular signaling cascades (Plowman et al. (1994) DN&P, 7(6):334-339).

Aberrant activation or excessive expression of various protein kinases are implicated in the mechanism of multiple diseases and disorders characterized by benign and malignant proliferation, excess angiogenesis, as well as diseases resulting from inappropriate activation of the immune system. Thus, inhibitors of select kinases or kinase families are expected to be useful in the treatment of cancer, autoimmune diseases, and inflammatory conditions including, but not limited to: solid tumors, hematological malignancies, arthritis, graft versus host disease, lupus erythematosus, psoriasis, colitis, illeitis, multiple sclerosis, uveitis, coronary artery vasculopathy, systemic sclerosis, atherosclerosis, asthma, transplant rejection, allergy, dermatomyositis, pemphigus and the like.

Examples of kinases that can be targeted to modulate disease include receptor tyrosine kinases such as members of the platelet-derived growth factor receptor (PDGFR), vascular endothelial growth factor receptor (VEGFR) families and intracellular proteins such as members of the Syk, SRC, and Tec families of kinases.

Tec kinases are non-receptor tyrosine kinases predominantly, but not exclusively, expressed in cells of hematopoietic origin (Bradshaw J M. Cell Signal. 2010, 22:1175-84). The Tec family includes Tec, Bruton's tyrosine kinase (Btk), inducible T-cell kinase (Itk), resting lymphocyte kinase (Rlk/Txk), and bone marrow-expressed kinase (Bmx/Etk). Btk is a Tec family kinase which is important in B-cell receptor signaling. Btk is activated by Src-family kinases and phosphorylates PLC gamma leading to effects on B-cell function and survival. Additionally, Btk is important in signal transduction in response to immune complex recognition by macrophage, mast cells and neutrophils. Btk inhibition is also important in survival of lymphoma cells (Herman, SEM. Blood 2011, 117:6287-6289) suggesting that inhibition of Btk may be useful in the treatment of lymphomas. As such, inhibitors of Btk and related kinases are of great interest as anti-inflammatory as well as anti-cancer agents.

cSRC is the prototypical member of the SRC family of tyrosine kinases which includes Lyn, Fyn, Lck, Hck, Fgr, Blk, Syk, Yrk, and Yes. cSRC is critically involved in signaling pathways involved in cancer and is often overexpressed in human malignancies (Kim L C, Song L, Haura E B. Nat Rev Clin Oncol. 2009 6(10):587-9). The role of cSRC in cell adhesion, migration and bone remodeling strongly implicate this kinase in the development and progression of bone metastases. cSRC is also involved in signaling downstream of growth factor receptor tyrosine kinases and regulates cell cycle progression suggesting that cSRC inhibition would impact cancer cell proliferation. Additionally, inhibition of SRC family members may be useful in treatments designed to modulate immune function. SRC family members, including Lck, regulate T-cell receptor signal transduction which leads to gene regulation events resulting in cytokine release, survival and proliferation. Thus, inhibitors of Lck have been keenly sought as immunosuppressive agents with potential application in graft rejection and T-cell mediated autoimmune disease (Martin et al. Expert Opin Ther Pat. 2010, 20:1573-93).

Inhibition of kinases using small molecule inhibitors has successfully led to several approved therapeutic agents used in the treatment of human conditions. Herein, we disclose a novel family of kinase inhibitors. Further, we demonstrate that modifications in compound substitution can influence kinase selectivity and therefore the biological function of that agent.

SUMMARY OF THE INVENTION

The present invention relates to a novel family of kinase inhibitors. Compounds of this class have been found to inhibit members of the Tec and Scr protein kinase families, more particularly including Btk and Lck.

Provided herein is a compound of Formula 1:

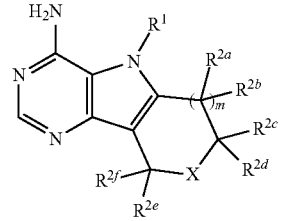

Formula 1 m is an integer from 0 to 1;
X is selected from $CH_2$, O, $S(O)_n$, $NR^6$;
n is an integer for 0 to 2;
$R^1$ is

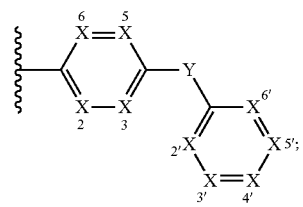

wherein Y is selected from O or $CH_2$;
wherein $X^2$, $X^3$, $X^5$, $X^6$, $X^{2'}$, $X^{3'}$, $X^{4'}$, $X^{5'}$, $X^{6'}$ are independently selected from CR and N;

each R is independently selected from hydrogen, halogen, —NO$_2$, —CN, alkyl, alkenyl, alkynyl, —OR$^3$, —OC(O)R$^3$, —OC(O)NR$^4$R$^5$, —NR$^4$R$^5$, —S(O)$_n$R$^3$, —C(O)R$^3$, —C(O)OR$^3$, —C(O)NR$^4$R$^5$, —S(O)$_2$NR$^4$R$^5$, —NR$^2$C(O)R$^3$, —NR$^2$S(O)$_n$R$^3$, —NR$^2$C(O)NR$^4$R$^5$, —NR$^2$S(O)$_2$NR$^4$R$^5$, aryl, heteroaryl, carbocyclyl, and heterocyclyl;

R$^2$ is selected from hydrogen, alkyl, alkenyl, alkynyl, heteroalkyl, carbocyclyl, heterocyclyl, aryl, heteroaryl.

R$^{2a}$, R$^{2b}$, R$^{2c}$, R$^{2d}$, R$^{2e}$, R$^{2f}$ are independently selected from hydrogen, alkyl, heteroalkyl, carbocyclyl, heterocyclyl, aryl, or heteroaryl. R$^{2a}$ and R$^{2b}$, R$^{2c}$ and R$^{2d}$ or R$^{2e}$ and R$^{2f}$ can be fused to form a 3 to 8 membered cycloalkyl or heterocyclyl ring system;

R$^3$ is selected from hydrogen, alkyl, alkenyl, alkynyl, heteroalkyl, carbocyclyl, heterocyclyl, aryl, heteroaryl;

R$^4$ and R$^5$ are independently selected from hydrogen, alkyl, heteroalkyl, carbocyclyl, heterocyclyl, aryl, heteroaryl or R$^4$ and R$^5$ can be fused to form a 3 to 8 membered heterocyclyl ring system;

R$^6$ is selected from hydrogen, alkyl, alkenyl, alkynyl, heteroalkyl, carbocyclyl, heterocyclyl, aryl, heteroaryl, —C(O)R$^4$, —C(O)OR$^4$, —S(O)$_2$R$^4$, —C(O)NR$^4$R$^5$, —S(O)$_2$NR$^4$R$^5$, —C(S)NR$^4$R$^5$;

The present invention encompasses all compounds described by Formula 1, including racemic mixtures, isomers, enantiomers, diastereoisomeric mixtures, tautomers, pharmaceutically acceptable salts, prodrugs and active metabolites thereof.

In certain embodiments, one or two occurrences of X are N.

In certain embodiments, each occurrence of X is independently CR.

In certain embodiments, compounds of Formula 1 may be further defined as:

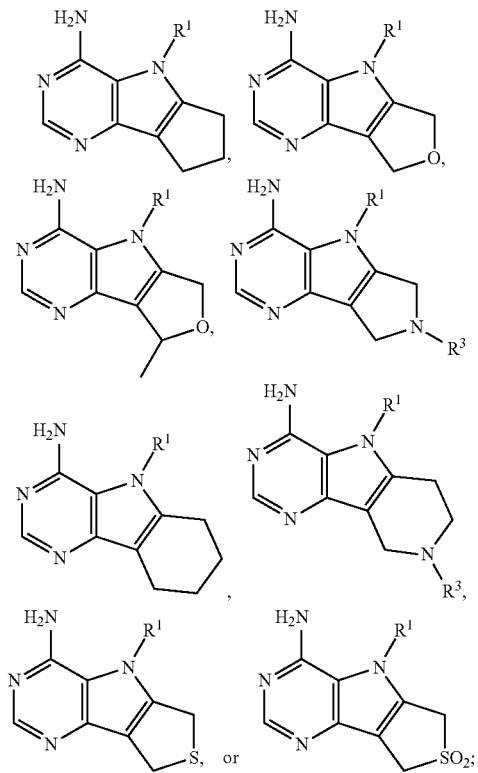

wherein R$^1$ may be defined as:

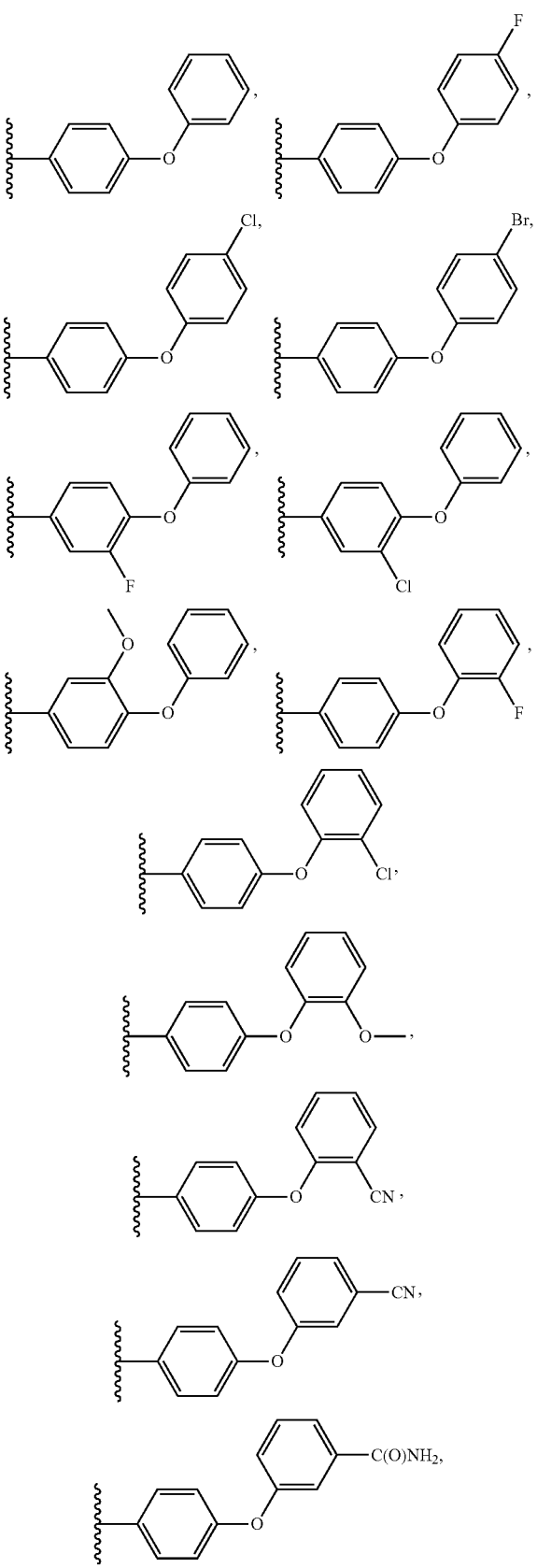

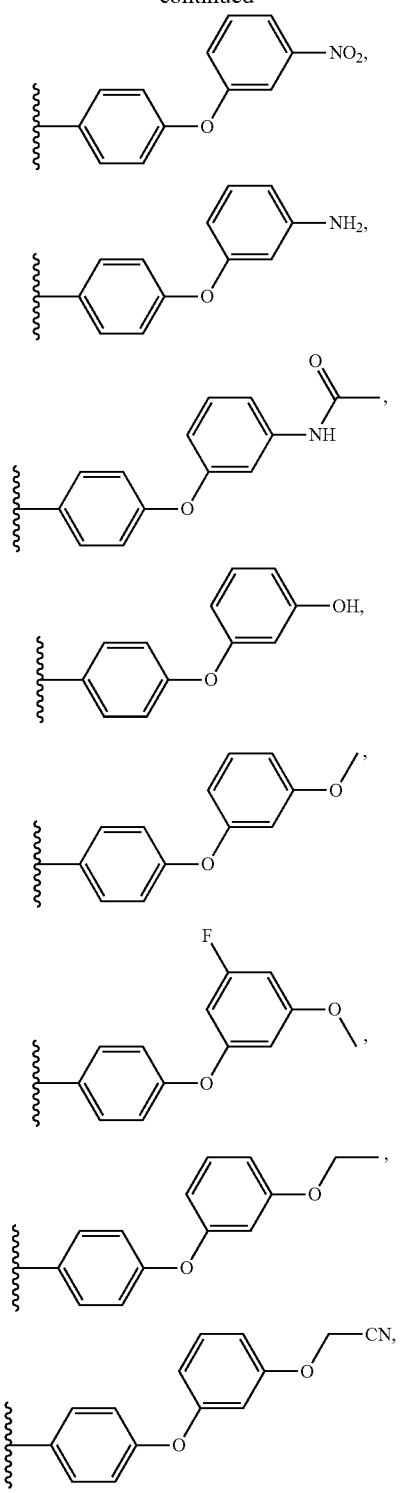
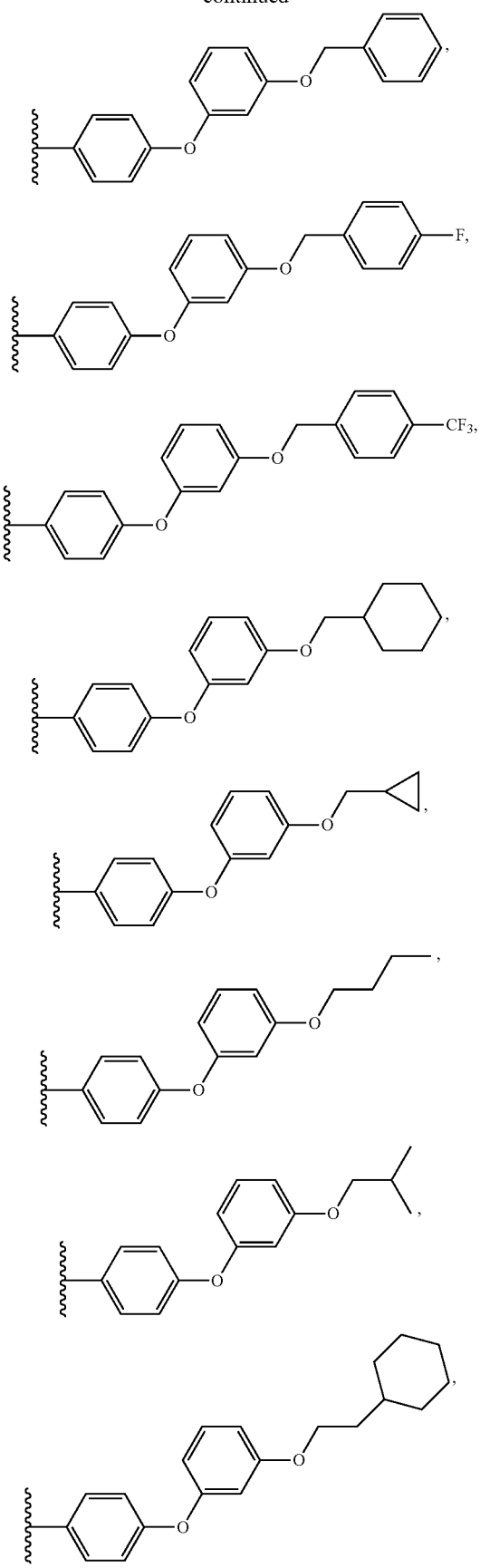

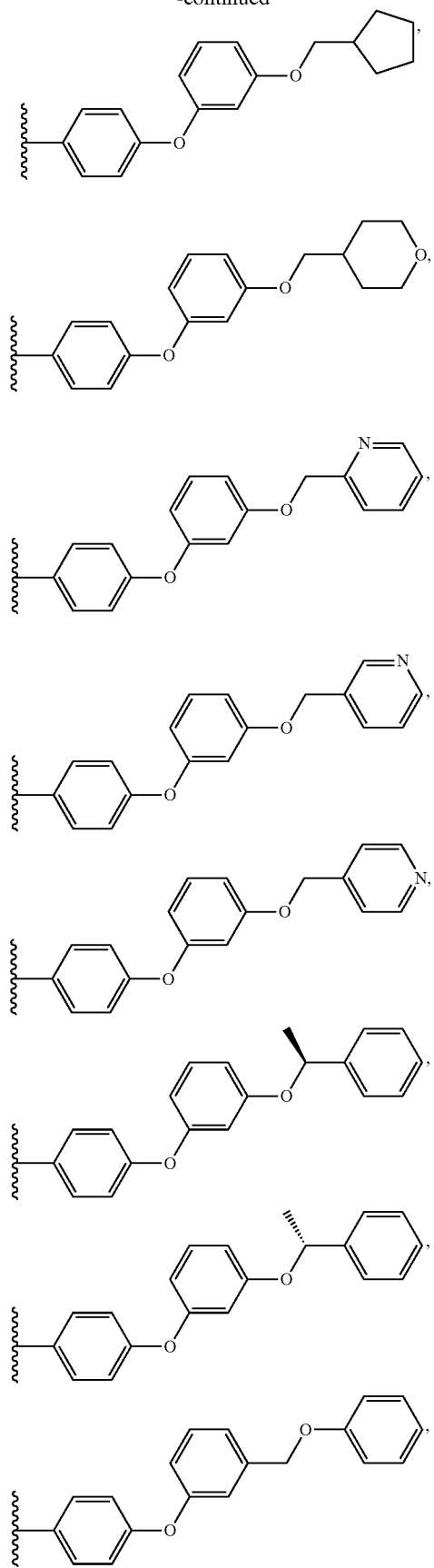
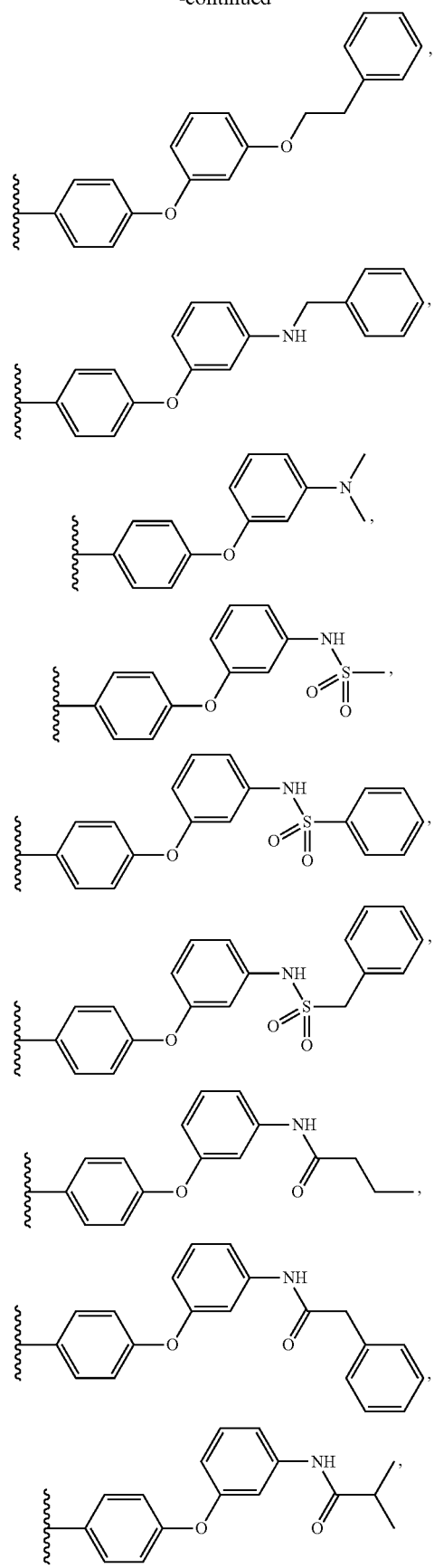

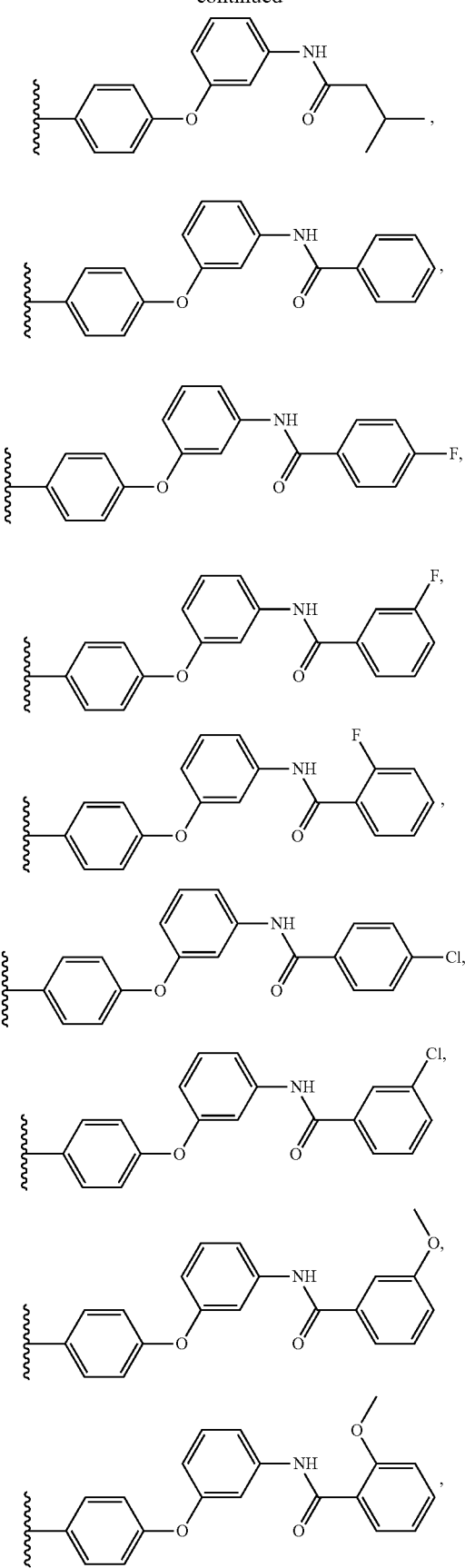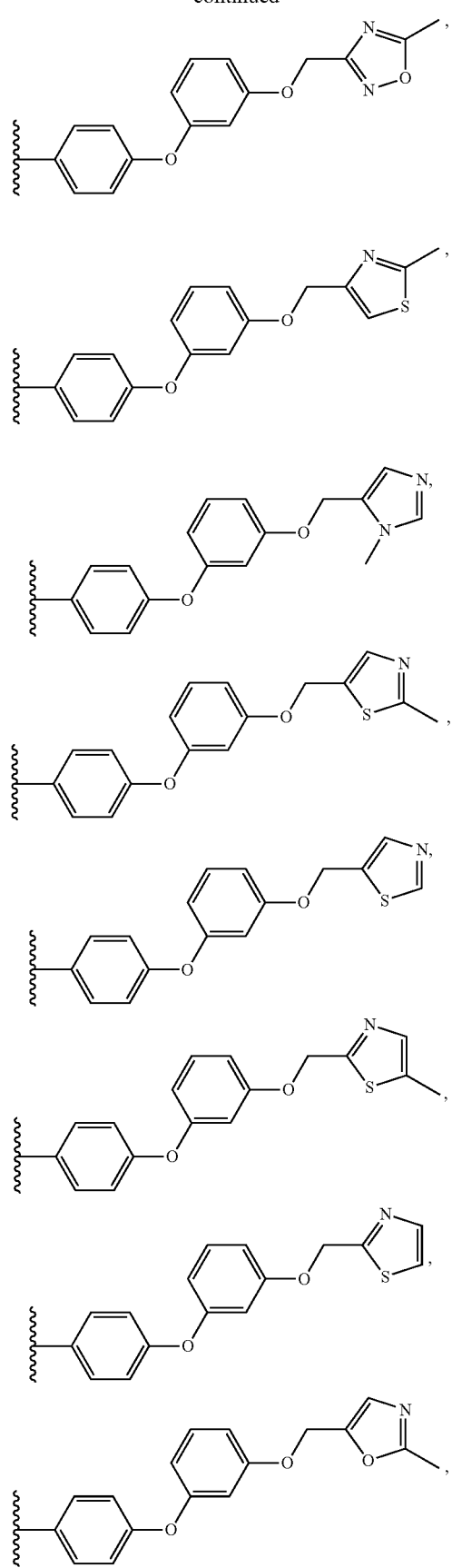

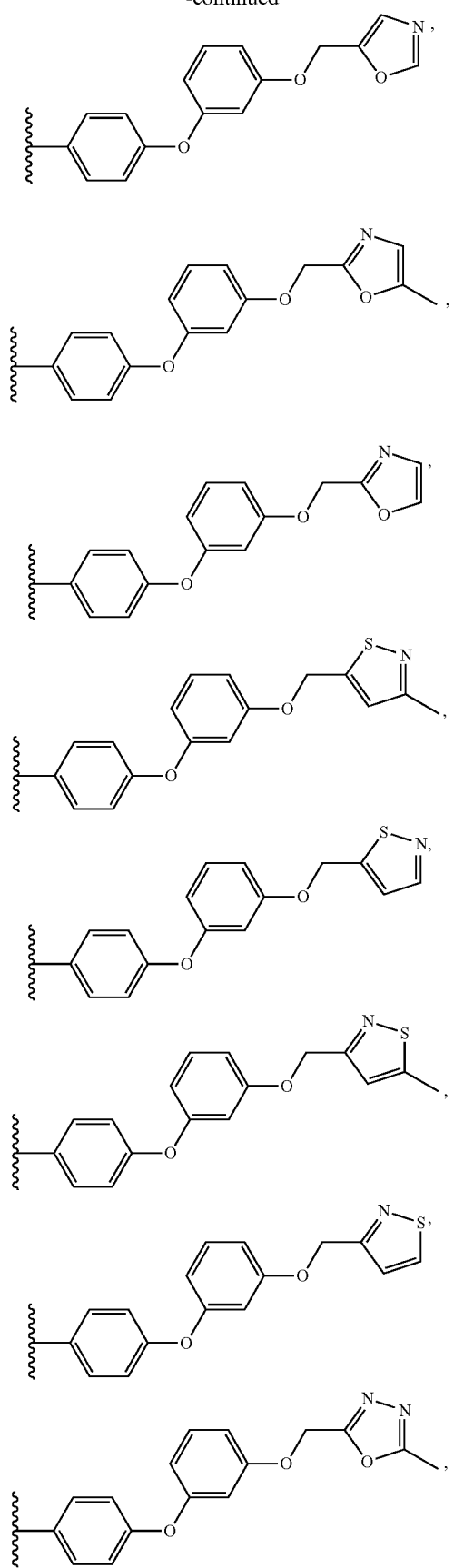
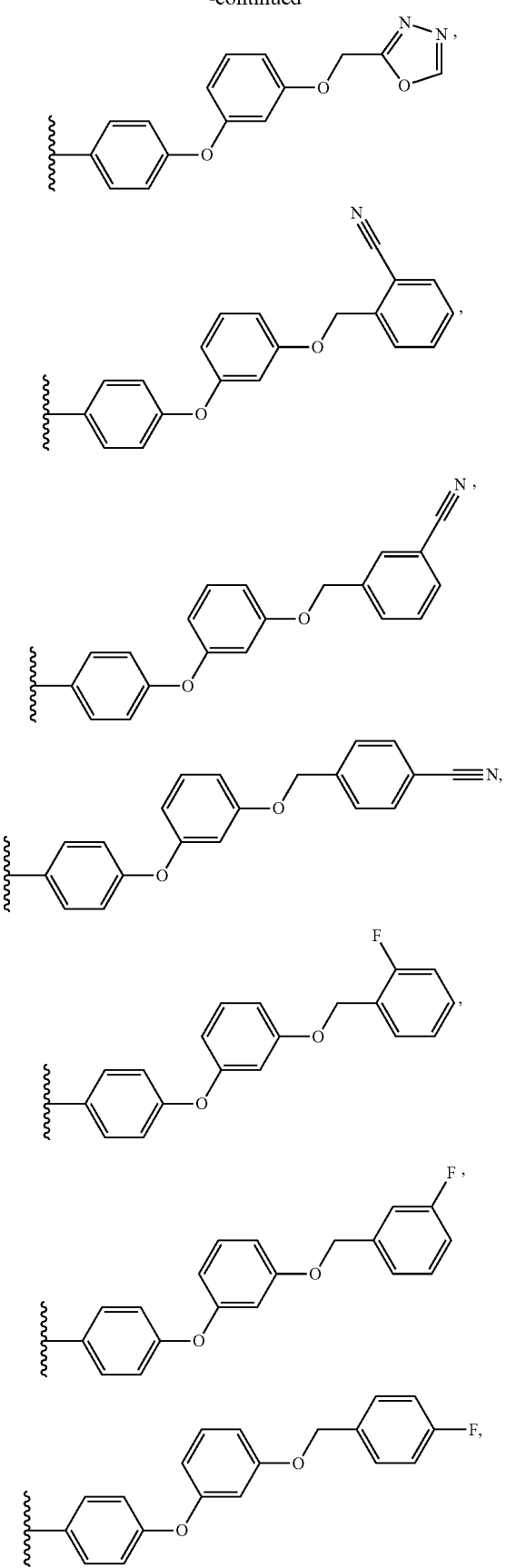

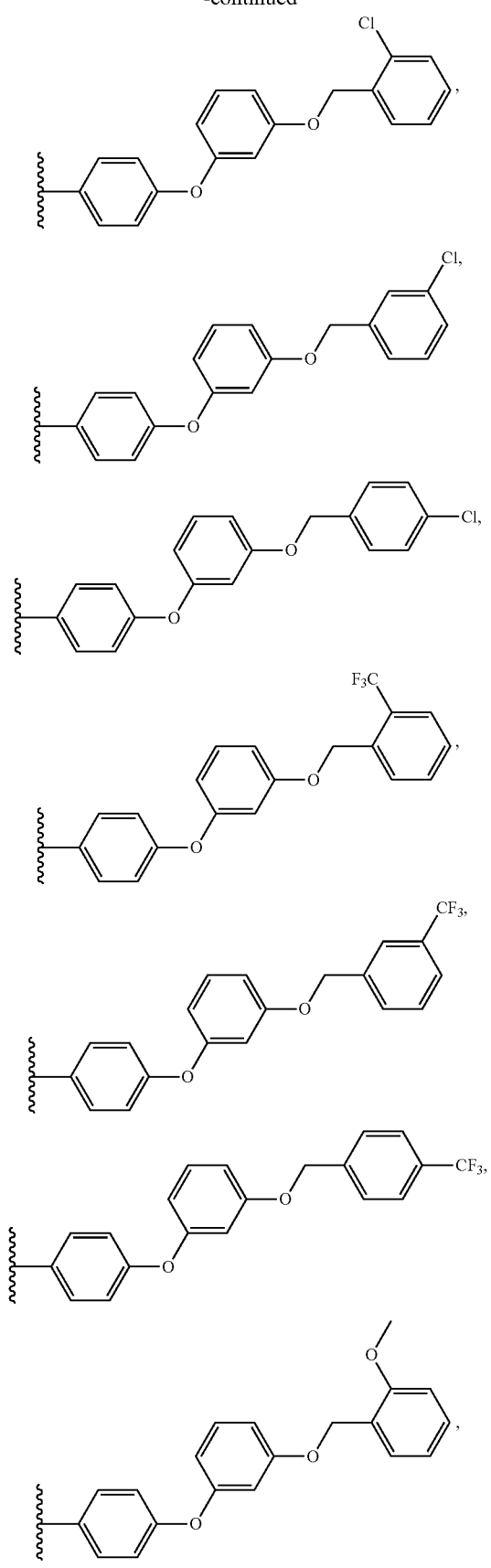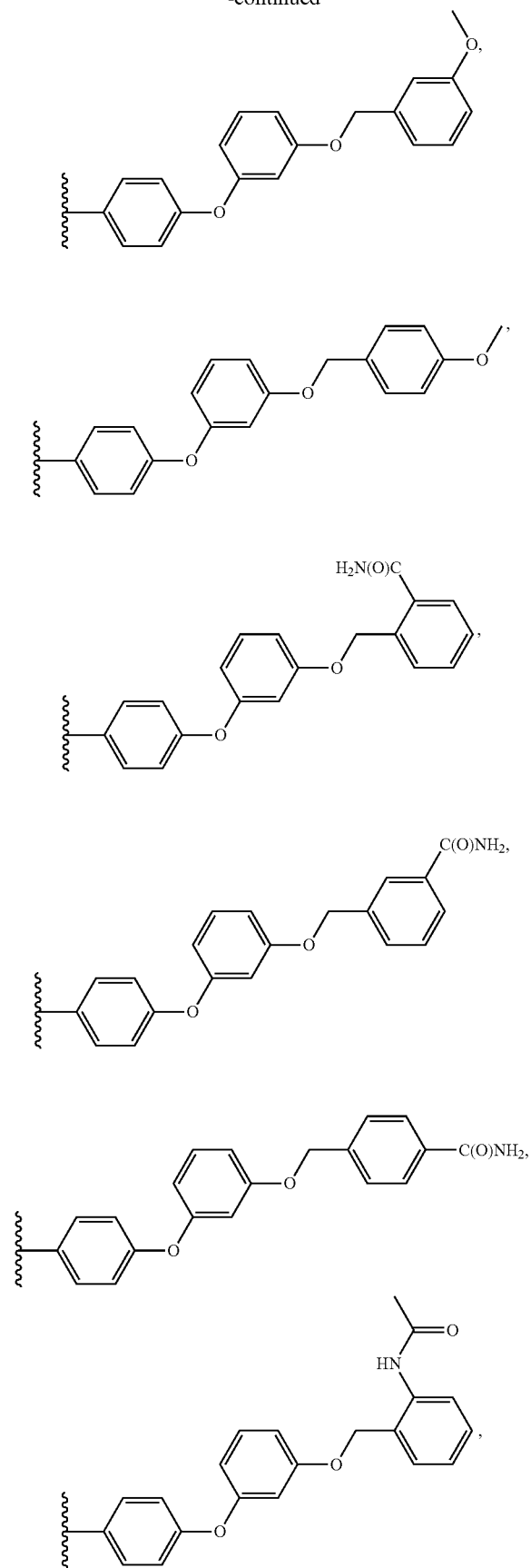

-continued
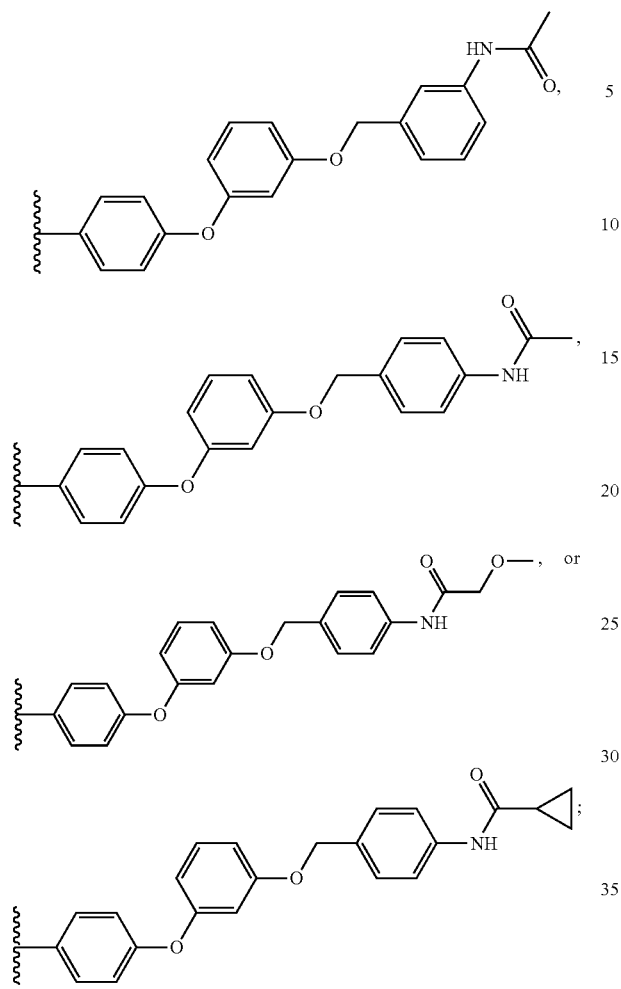
and wherein $R^{2e}$ may be defined as H, Me, Et, —CH$_2$CH$_2$CH$_2$OH, —CH$_2$CH$_2$CH$_2$OPh or —CH$_2$CH$_2$CH$_2$OCH$_2$Ph;
and wherein $R^3$ may be defined as H, Et,
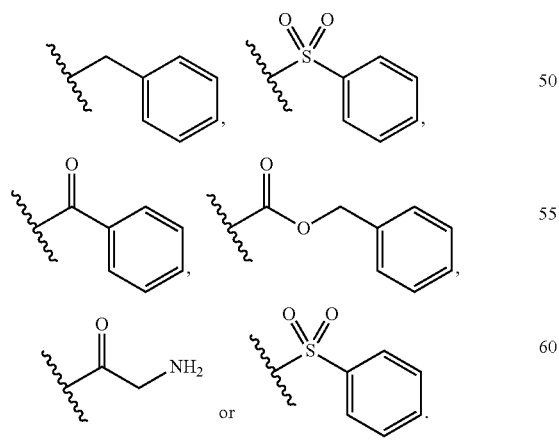
In certain embodiments $R^1$ is selected from the group consisting of:
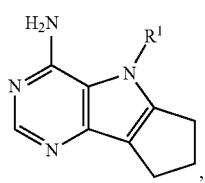
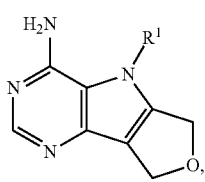
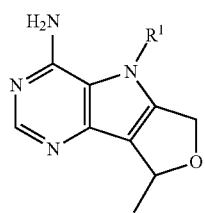
wherein $R^7$ is substituted or unsubstituted alkyl, aryl and heteroaryl.
Preferred embodiments include compounds of formula 1a, 1b and 1c:
1a
1b
1c wherein R¹ is selected from the groups consisting of:
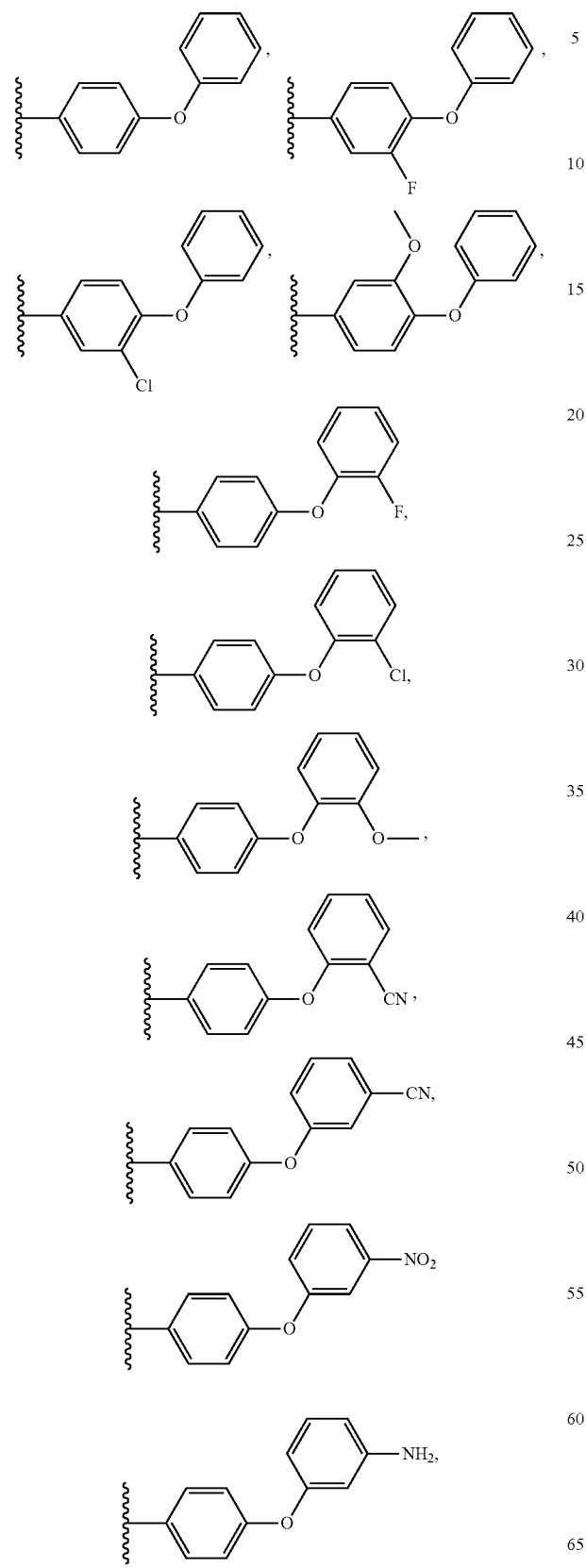
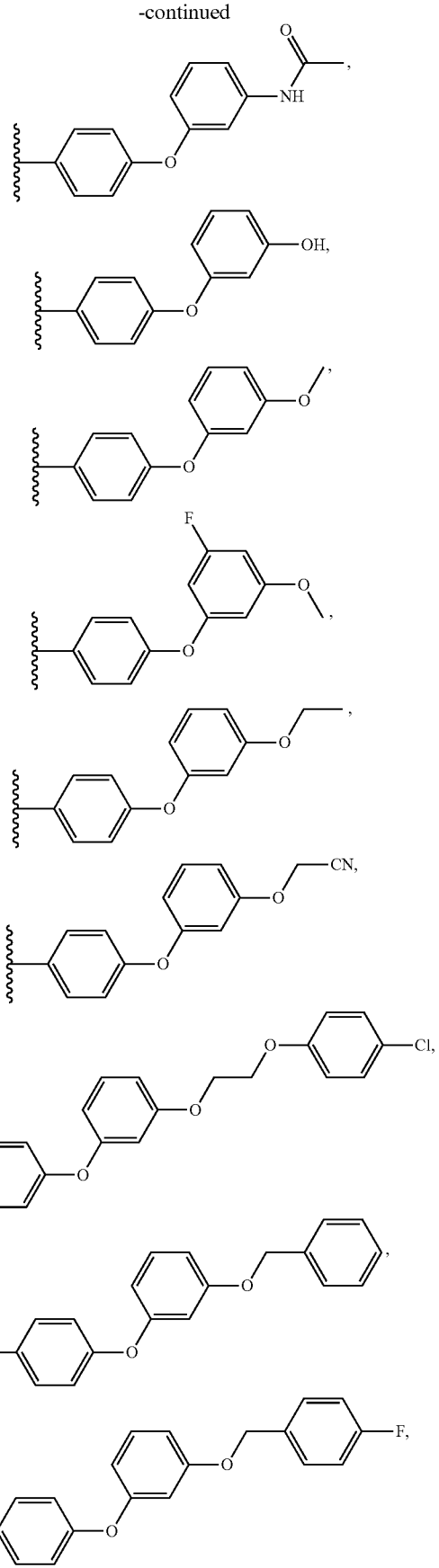

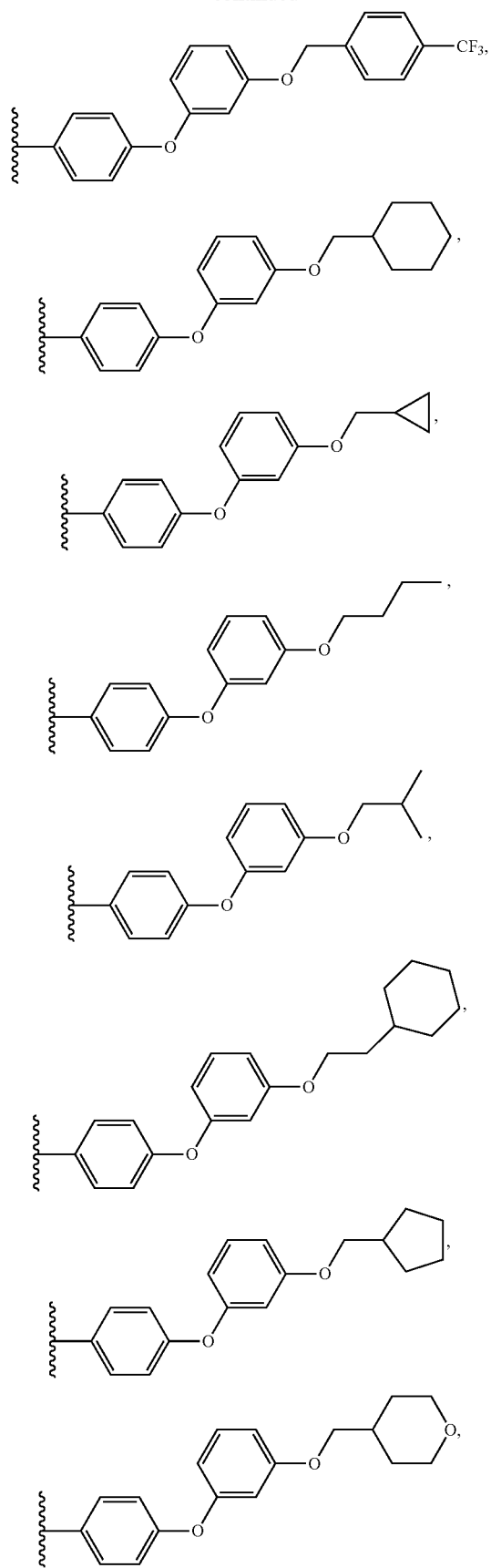
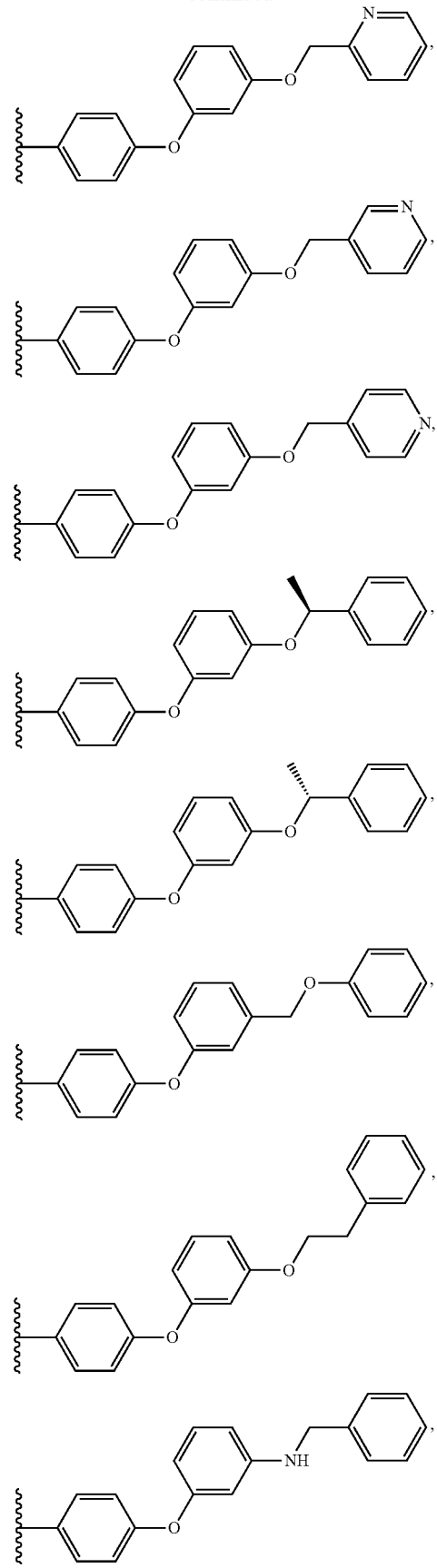

-continued
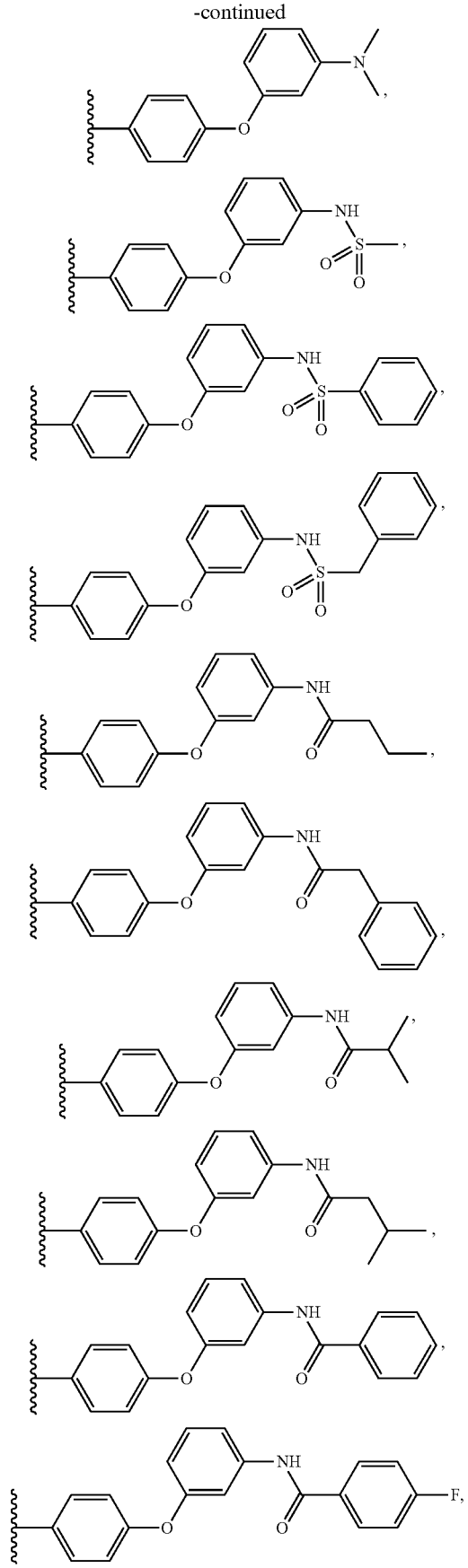
-continued
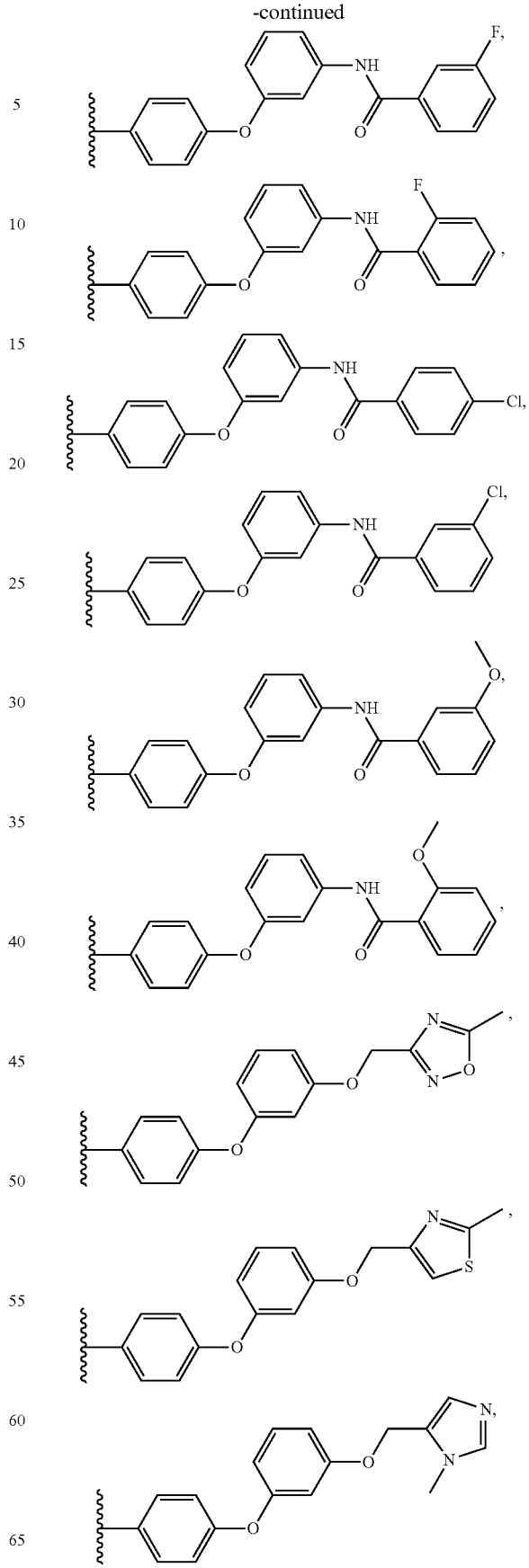

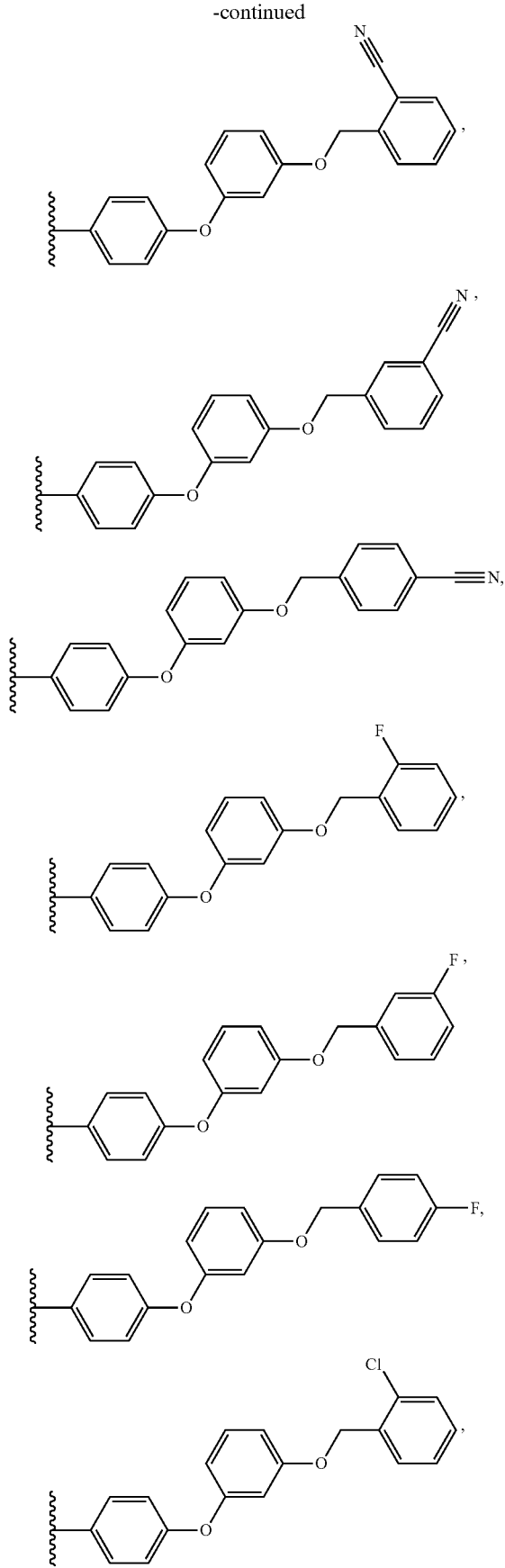
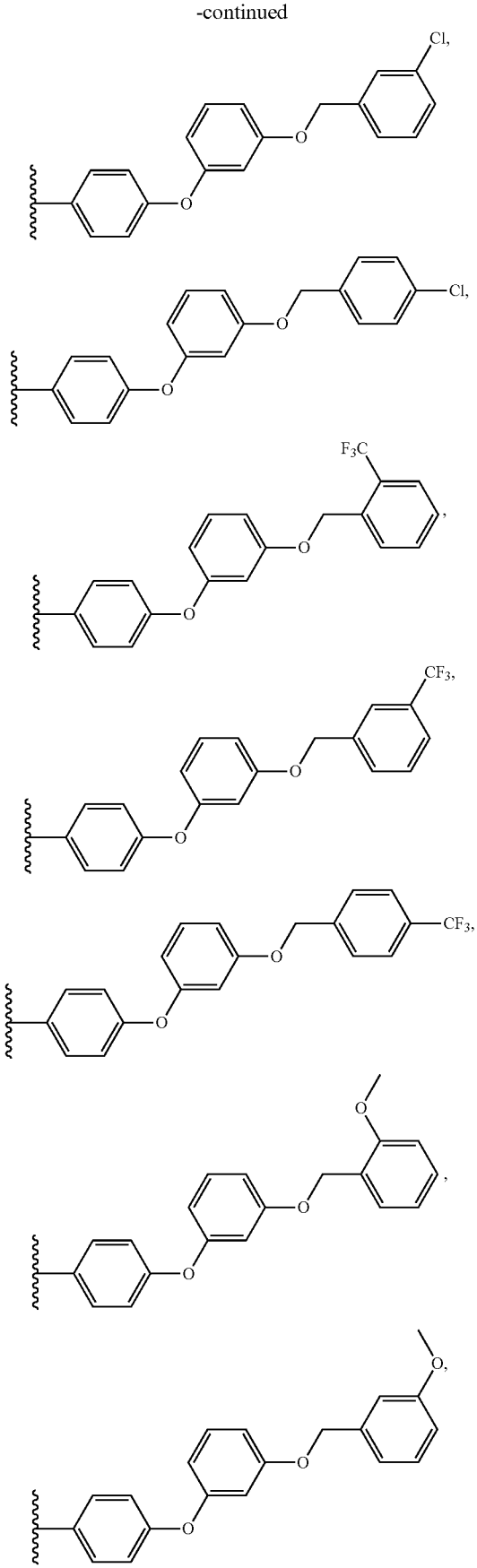

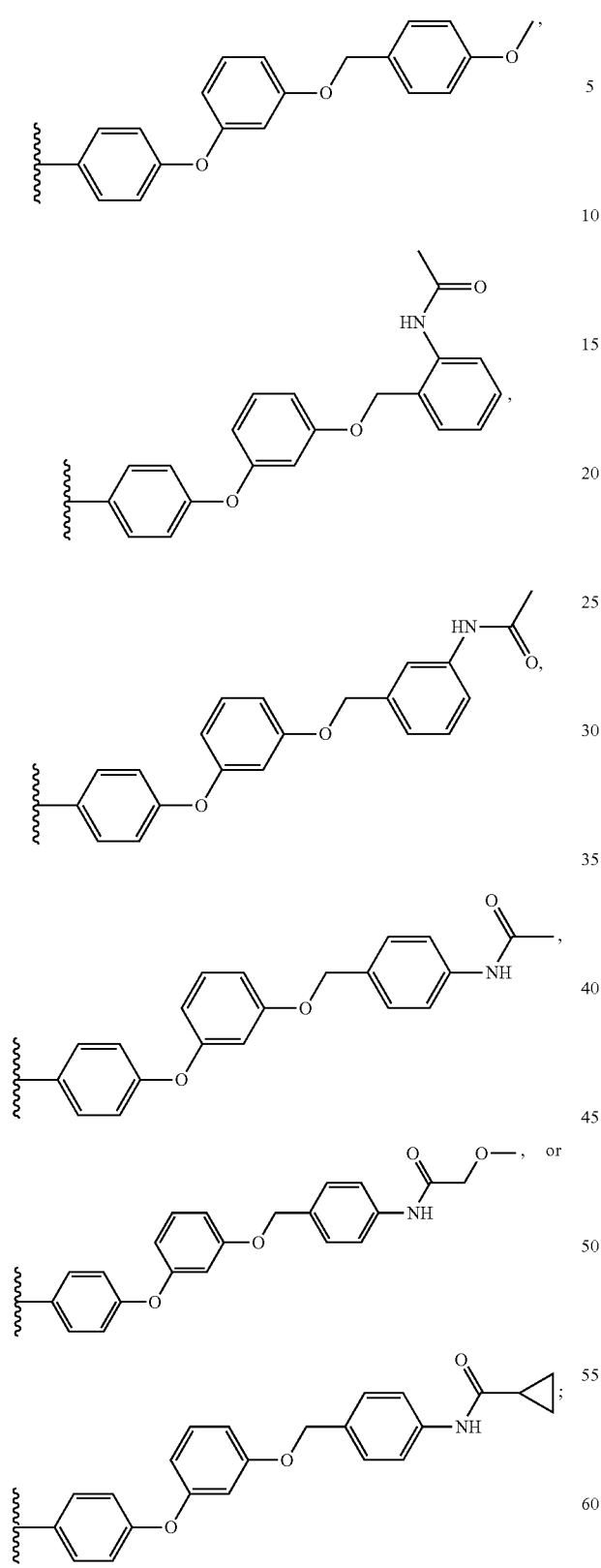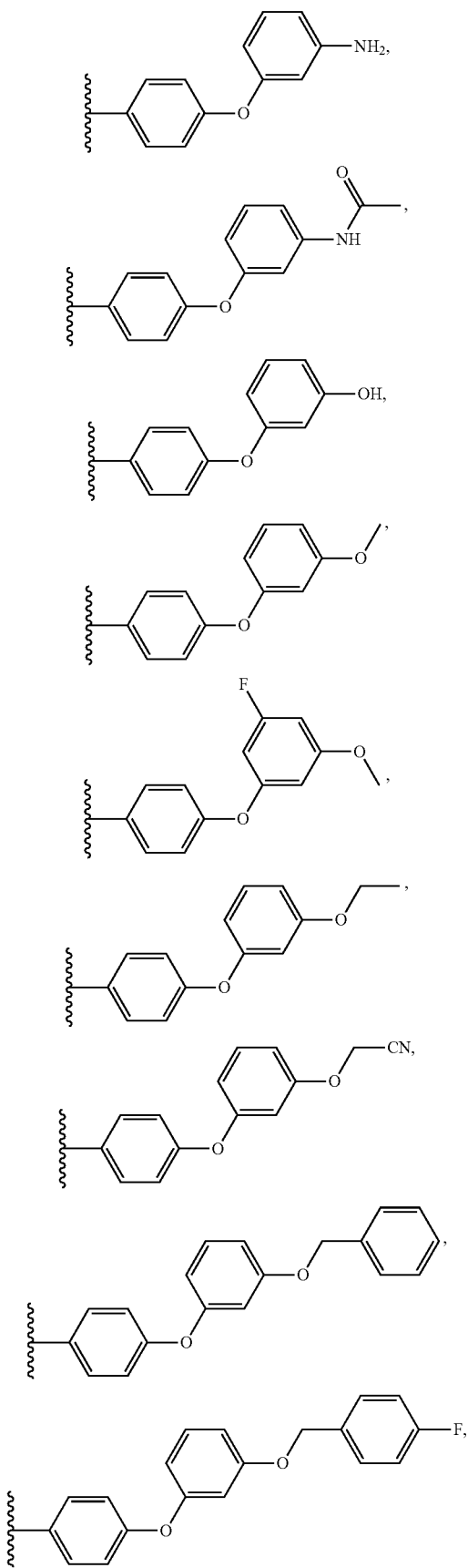
A more preferred embodiment includes compounds of Formula 1c where $R^1$ is selected from the group consisting of:

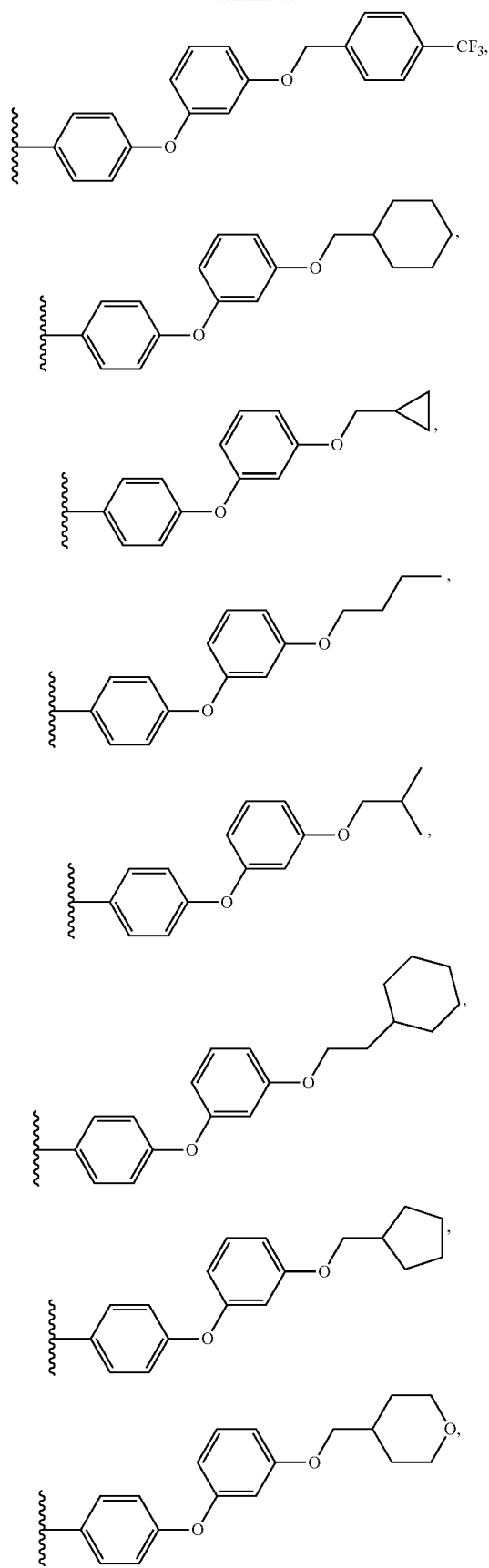
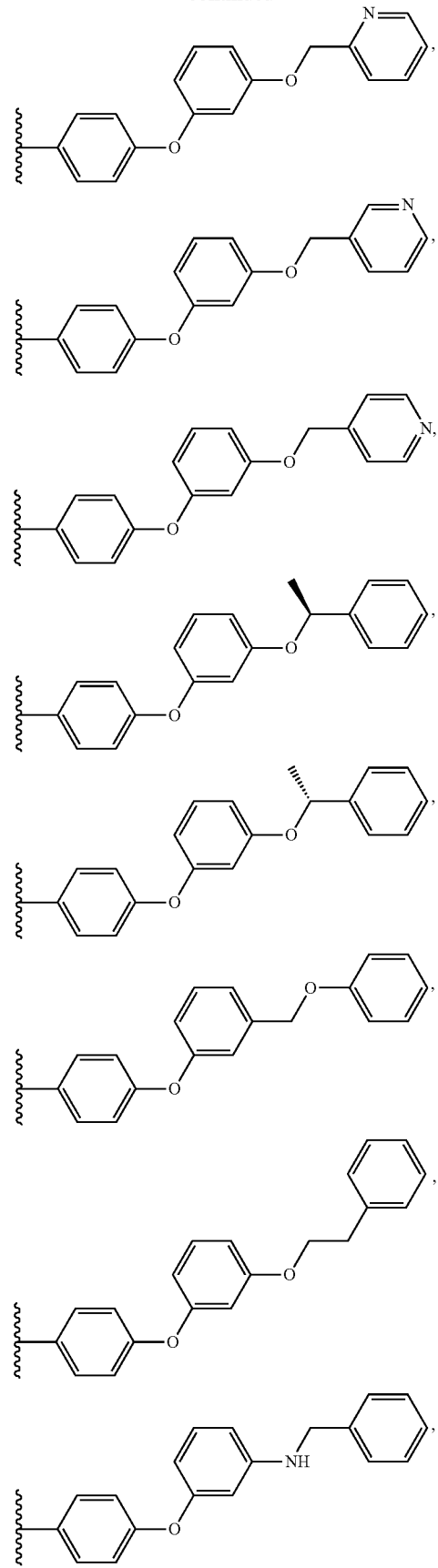

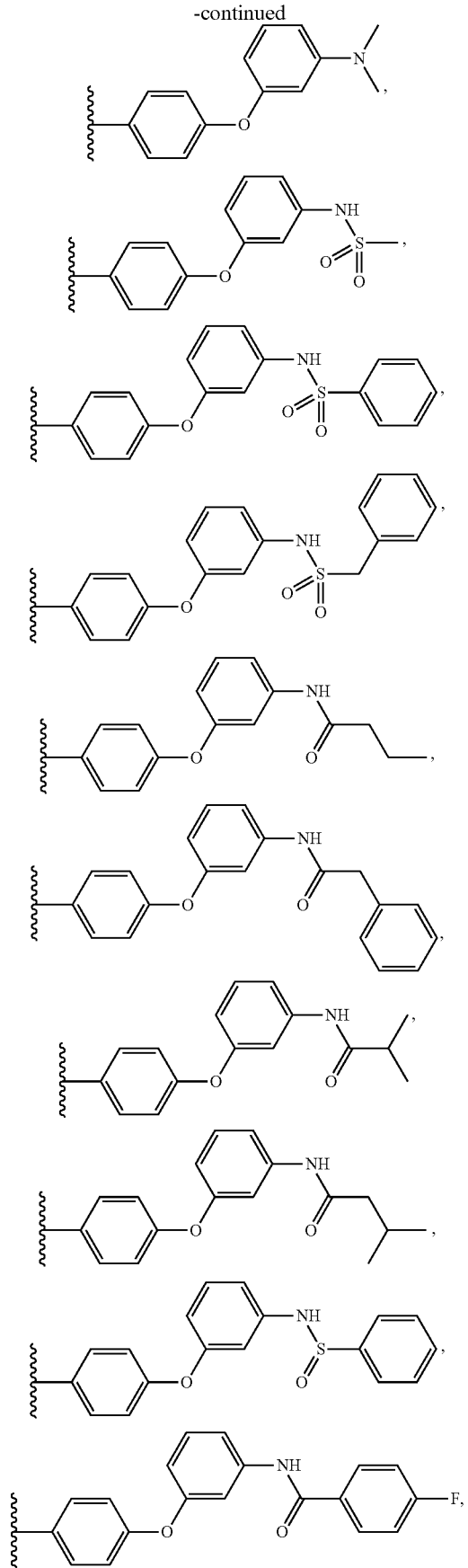
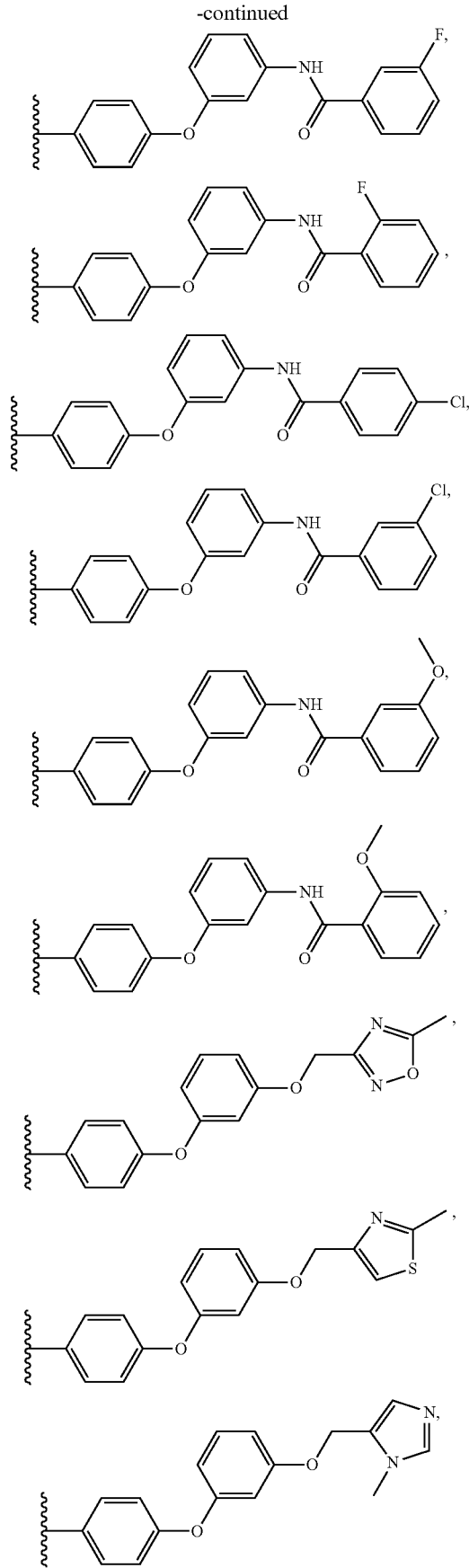

31
-continued
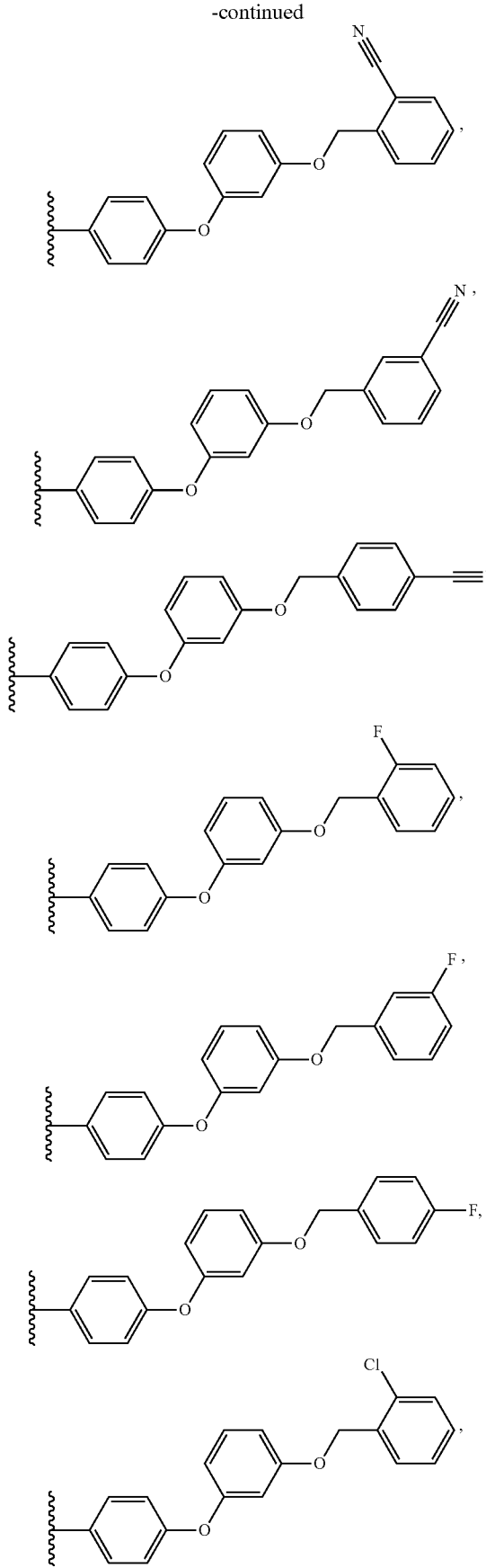
32
-continued
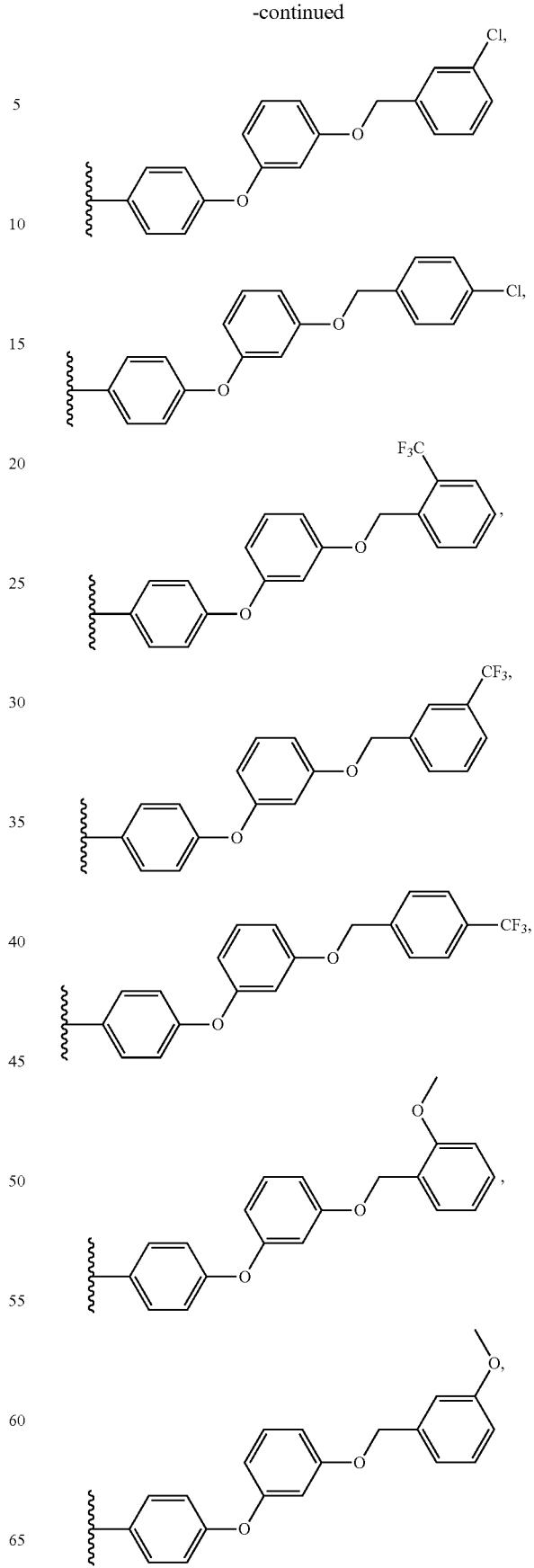

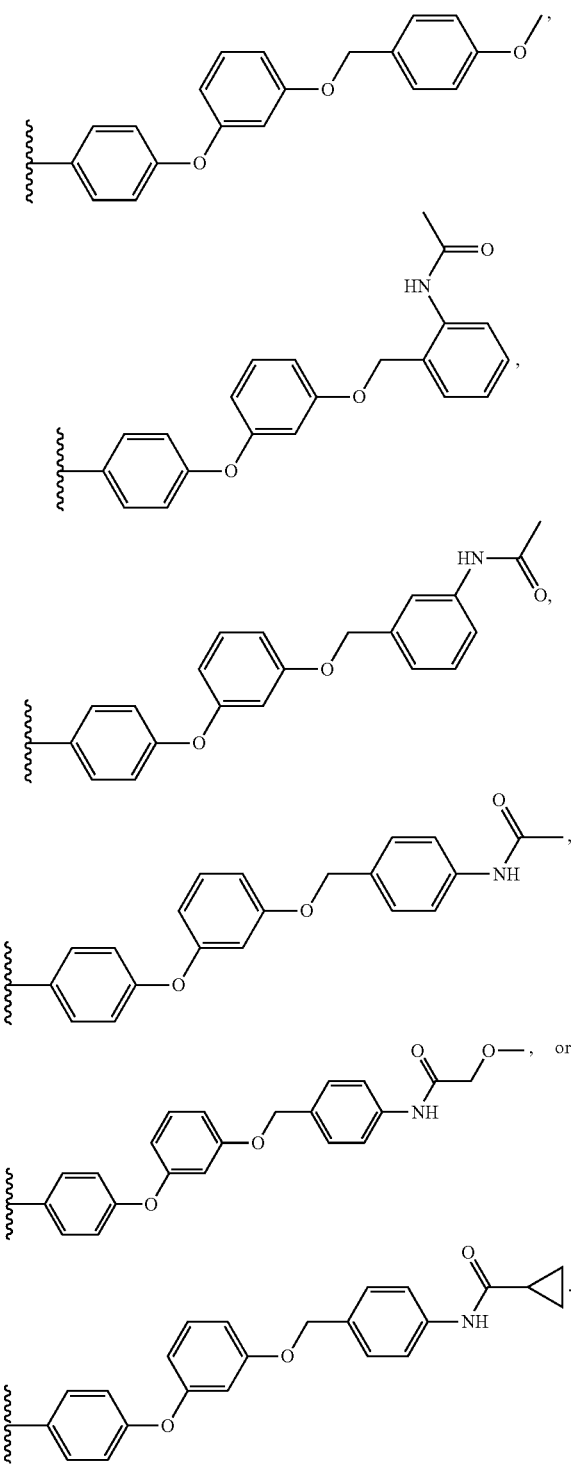

Another aspect of the present invention provides a pharmaceutical composition comprising an effective amount of a compound of Formula 1 and a pharmaceutically acceptable carrier, diluent or excipient.

In another aspect of the present invention, there is provided a use of the compound of Formula 1 as an inhibitor of protein kinase, more particularly, as an inhibitor of Btk, Lck, Blk or c-SRC kinases.

Another aspect of the present invention provides a method of modulating kinase function, the method comprising contacting a cell with a compound of the present invention in an amount sufficient to modulate the enzymatic activity of a given kinase or kinases, such as Btk, Lck, Blk or c-SRC, thereby modulating the kinase function.

Another aspect of the present invention provides a method of modulating the target kinase function, the method comprising a) contacting a cell with a compound of the present invention in an amount sufficient to modulate the target kinase function, thereby b) modulating the target kinase activity and signaling.

Another aspect of the present invention provides a probe, the probe comprising a compound of Formula 1 labeled with a detectable label or an affinity tag. In other words, the probe comprises a residue of a compound of Formula 1 covalently conjugated to a detectable label. Such detectable labels include, but are not limited to, a fluorescent moiety, a chemiluminescent moiety, a paramagnetic contrast agent, a metal chelate, a radioactive isotope-containing moiety, or biotin.

DETAILED DESCRIPTION OF PREFERRED EMBODIMENTS

The present invention relates to novel kinase inhibitors. The inventors have found these compounds to be effective inhibitors of protein kinases: including members of the tyrosine kinases Aurora, SRC (more specifically Lck) and Tec (more specifically Btk) kinase families.

Compounds of the present invention may be formulated into a pharmaceutical composition which comprises an effective amount of a compound of Formula 1 with a pharmaceutically acceptable diluent or carrier. For example, the pharmaceutical compositions may be in a conventional pharmaceutical form suitable for oral administration (e.g., tablets, capsules, granules, powders and syrups), parenteral administration (e.g., injections (intravenous, intramuscular, or subcutaneous)), drop infusion preparations, inhalation, eye lotion, topical administration (e.g., ointment), or suppositories. Regardless of the route of administration selected the compounds may be formulated into pharmaceutically acceptable dosage forms by conventional methods known to those skilled in the art.

The phrase "pharmaceutically acceptable" is employed herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition, or vehicle, such as a liquid or solid filler, diluent, excipient, solvent or encapsulating material. Each carrier must be acceptable in the sense of being compatible with the other ingredients of the formulation, including the active ingredient, and not injurious or harmful to the patient. Some examples of materials which can serve as pharmaceutically acceptable carriers include: (1) sugars, such as lactose, glucose, and sucrose; (2) starches, such as corn starch, potato starch, and substituted or unsubstituted β-cyclodextrin; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically acceptable salt" refers to the relatively non-toxic, inorganic and organic acid addition salts of the compound(s). These salts can be prepared in situ during the final isolation and purification of the compound(s), or by separately reacting a purified compound(s) in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like (See, for example, Berge et al. (1977) "Pharmaceutical Salts", J. Pharm. Sci. 66: 1-19).

In other cases, the compounds of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic inorganic and organic base addition salts of a compound(s). These salts can likewise be prepared in situ during the final isolation and purification of the compound(s), or by separately reacting the purified compound(s) in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

As used herein, the term "affinity tag" means a ligand or group, linked either to a compound of the present invention or to a protein kinase domain, that allows the conjugate to be extracted from a solution.

The term "alkyl" refers to substituted or unsubstituted saturated hydrocarbon groups, including straight-chain alkyl and branched-chain alkyl groups, including haloalkyl groups such as trifluoromethyl and 2,2,2-trifluoroethyl, etc. Representative alkyl groups include methyl, ethyl, n-propyl, isopropyl, n-butyl, t-butyl, isobutyl, sec-butyl, (cyclohexyl) methyl, cyclopropylmethyl, n-pentyl, n-hexyl, n-heptyl, n-octyl, and the like. The terms "alkenyl" and "alkynyl" refer to substituted or unsubstituted unsaturated aliphatic groups analogous in length and possible substitution to the alkyls described above, but that contain at least one double or triple bond respectively. Representative alkenyl groups include vinyl, propen-2-yl, crotyl, isopenten-2-yl, 1,3-butadien-2-yl), 2,4-pentadienyl, and 1,4-pentadien-3-yl. Representative alkynyl groups include ethynyl, 1- and 3-propynyl, and 3-butynyl. In certain preferred embodiments, alkyl substituents are lower alkyl groups, e.g., having from 1 to 6 carbon atoms. Similarly, alkenyl and alkynyl preferably refer to lower alkenyl and alkynyl groups, e.g., having from 2 to 6 carbon atoms. As used herein, "alkylene" refers to an alkyl group with two open valencies (rather than a single valency), such as $-(CH_2)_{1-10}-$ and substituted variants thereof.

The term "alkoxy" refers to an alkyl group having an oxygen attached thereto. Representative alkoxy groups include methoxy, ethoxy, propoxy, tert-butoxy and the like. An "ether" is two hydrocarbons covalently linked by an oxygen. Accordingly, the substituent of an alkyl that renders that alkyl an ether is or resembles an alkoxy.

The term "alkoxyalkyl" refers to an alkyl group substituted with an alkoxy group, thereby forming an ether.

The terms "amide" and "amido" are art-recognized as an amino-substituted carbonyl and includes a moiety that can be represented by the general formula:

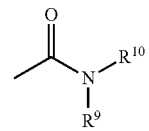

wherein $R^9$, $R^{10}$ are as defined above. Preferred embodiments of the amide will not include imides, which may be unstable.

The terms "amine" and "amino" are art-recognized and refer to both unsubstituted and substituted amines and salts thereof, e.g., a moiety that can be represented by the general formulae:

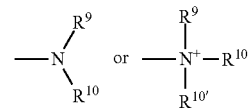

wherein $R^9$, $R^{10}$ and $R^{10'}$ each independently represent a hydrogen, an alkyl, an alkenyl, $-(CH_2)_m-R^8$, or $R^9$ and $R^{10}$ taken together with the N atom to which they are attached complete a heterocycle having from 4 to 8 atoms in the ring structure; $R^8$ represents an aryl, a cycloalkyl, a cycloalkenyl, a heterocyclyl or a polycyclyl; and m is zero or an integer from 1 to 8. In preferred embodiments, only one of $R^9$ or $R^{10}$ can be a carbonyl, e.g., $R^9$, $R^{10}$, and the nitrogen together do not form an imide. In even more preferred embodiments, $R^9$ and $R^{10}$ (and optionally $R^{10'}$) each independently represent a hydrogen, an alkyl, an alkenyl, or $-(CH_2)_m-R^8$. In certain embodiments, the amino group is basic, meaning the protonated form has a $pK_a \geq 7.00$.

The term "aralkyl", as used herein, refers to an alkyl group substituted with an aryl group.

The term "aryl" as used herein includes 5-, 6-, and 7-membered substituted or unsubstituted single-ring aromatic groups in which each atom of the ring is carbon. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, anthracene, and phenanthrene.

The terms "carbocycle" and "carbocyclyl", as used herein, refer to a non-aromatic substituted or unsubstituted ring in which each atom of the ring is carbon. The terms "carbocycle" and "carbocyclyl" also include polycyclic ring systems having two or more cyclic rings in which two or more carbons are common to two adjoining rings wherein at least one of the rings is carbocyclic, e.g., the other cyclic rings can be cycloalkyls, cycloalkenyls, cycloalkynyls, aryls, heteroaryls, and/or heterocyclyls. Representative carbocyclic groups include cyclopentyl, cyclohexyl, 1-cyclohexenyl, and 3-cyclohexen-1-yl, cycloheptyl.

The term "carbonyl" is art-recognized and includes such moieties as can be represented by the general formula:

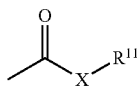

wherein X is a bond or represents an oxygen or a sulfur, and $R^{11}$ represents a hydrogen, an alkyl, an alkenyl, —$(CH_2)_m$—$R^8$ or a pharmaceutically acceptable salt. Where X is an oxygen and $R^{11}$ is not hydrogen, the formula represents an "ester". Where X is an oxygen, and $R^{11}$ is a hydrogen, the formula represents a "carboxylic acid".

The terms "heteroaryl" includes substituted or unsubstituted aromatic 5- to 7-membered ring structures, more preferably 5- to 6-membered rings, whose ring structures include one to four heteroatoms. The term "heteroaryl" also includes polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, isoxazole, oxazole, thiazole, triazole, pyrazole, pyridine, pyrazine, pyridazine and pyrimidine, and the like.

The term "heteroatom" as used herein means an atom of any element other than carbon or hydrogen. Preferred heteroatoms are nitrogen, oxygen, and sulfur.

The terms "heterocyclyl" or "heterocyclic group" refer to substituted or unsubstituted non-aromatic 3- to 10-membered ring structures, more preferably 3- to 7-membered rings, whose ring structures include one to four heteroatoms. The term terms "heterocyclyl" or "heterocyclic group" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, tetrahydrofuran, tetrahydropyran, piperidine, piperazine, pyrrolidine, morpholine, lactones, and lactams.

The term "hydrocarbon", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The terms "polycyclyl" or "polycyclic" refer to two or more rings (e.g., cycloalkyls, cycloalkenyls, cycloalkynyls, aryls, heteroaryls, and/or heterocyclyls) in which two or more carbons are common to two adjoining rings, e.g., the rings are "fused rings". Each of the rings of the polycycle can be substituted or unsubstituted.

As used herein, the term "probe" means a compound of the invention which is labeled with either a detectable label or an affinity tag, and which is capable of binding, either covalently or non-covalently, to a protein kinase domain. When, for example, the probe is non-covalently bound, it may be displaced by a test compound. When, for example, the probe is bound covalently, it may be used to form cross-linked adducts, which may be quantified and inhibited by a test compound.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

Compounds of the invention also include all isotopes of atoms present in the intermediates and/or final compounds. Isotopes include those atoms having the same atomic number but different mass numbers. For example, isotopes of hydrogen include deuterium and tritium.

General Synthetic Methods

General Synthetic Method A:

Compounds of general Formula 1-v were prepared in a four step process which is summarized in Scheme 1. Alkylation of $R^1NH_2$ with bromoacetonitrile provided intermediate 1-i. Condensation of 1-i with 1-ii in the presence of an acid such as p-toluenesulphonic acid, provided intermediate 1-iii. Treatment of intermediate 1-iii with a base such as tBuOK in t-BuOH provided intermediate 1-iv. Treatment of intermediate 1-iv with formamadine acetate in ethanol provided compounds of general formula 1-v.

Scheme 1

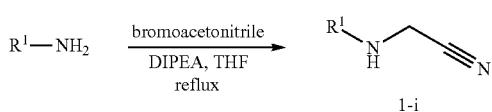

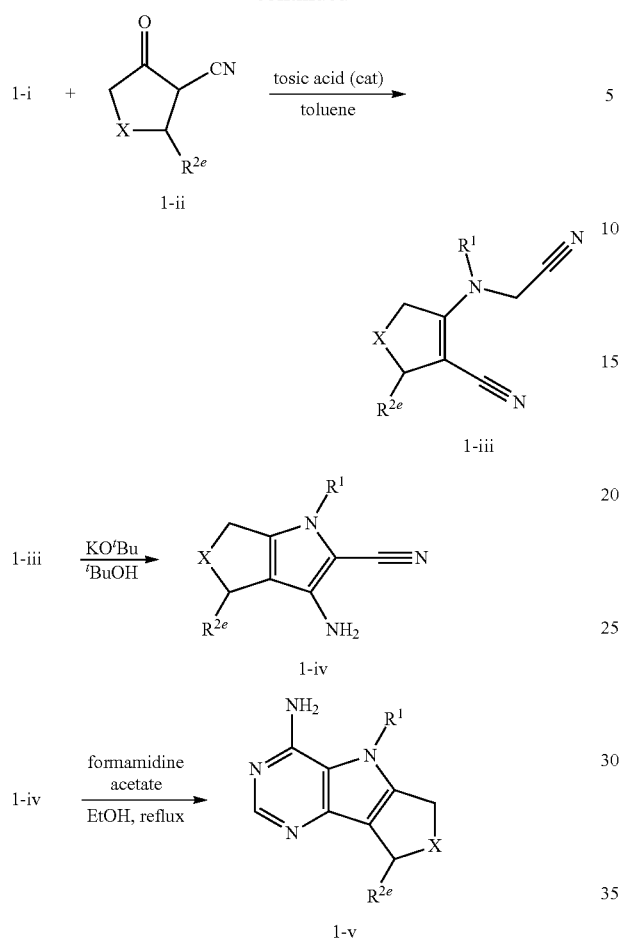

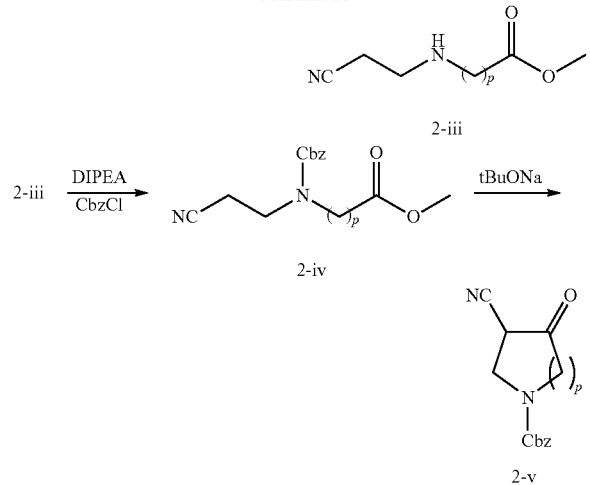

EXEMPLIFICATION

The following synthetic methods are intended to be representative of the chemistry used to prepare compounds of Formula 1 and are not intended to be limiting.

Synthesis of Compound 1:

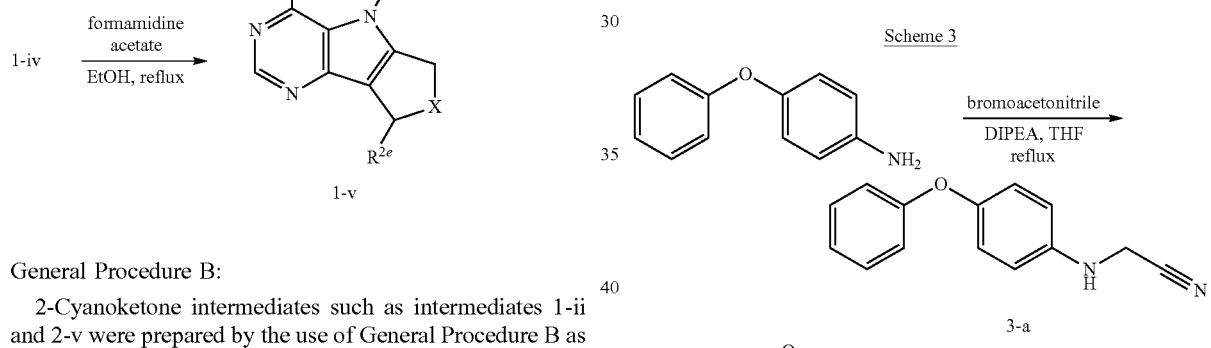

General Procedure B:

2-Cyanoketone intermediates such as intermediates 1-ii and 2-v were prepared by the use of General Procedure B as summarized in Scheme 2. For example, condensation of an amino acid derivative 2-i with acrylonitrile provided the N-alkyl amino acid 2-ii which was esterified in acidic methanol to provide amino ester 2-ii. Protection of the amino functionality using an appropriate protecting group such as Cbz provided intermediate such as 2-iv. Diekmann condensation of 2-iv in basic media provided intermediate 2-v.

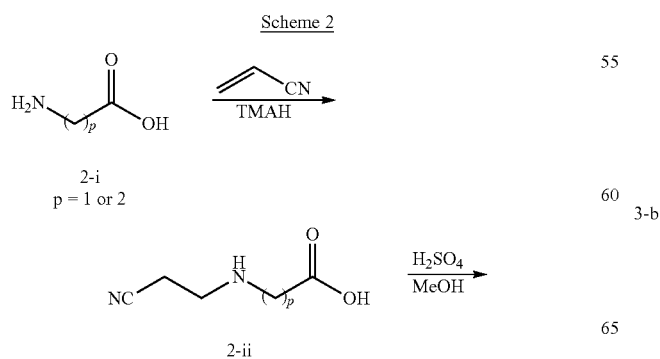

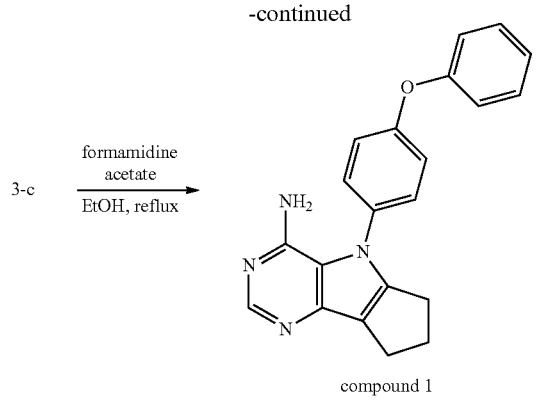

compound 1

Step 1: Intermediate 3-a

To a solution of 4-phenoxyaniline (12.5 g, 67.5 mmol) in THF (80 ml) were sequentially added bromoacetonitrile (8.90 g, 74.2 mmol) and DIPEA (14.14 ml, 81 mmol). The resulting solution was stirred at 80° C. overnight and then cooled to room temperature. Saturated aqueous ammonium chloride and ethyl acetate were added; the organic layer was separated, washed with saturated aqueous ammonium chloride and brine, dried over MgSO$_4$, filtered and concentrated under reduced pressure. Hexane was added to the residue, a precipitate formed, intermediate 3-a was collected by filtration as a beige solid.

Step 2: Intermediate 3-b

To a solution of intermediate 3-a (6.0 g, 26.8 mmol) in toluene (100 mL) were added 2-oxocyclopentanecarbonitrile (2.92 g, 26.8 mmol) and 4-methylbenzenesulfonic acid hydrate (509 mg, 2.68 mmol). The reaction was refluxed for 5 hours using a Dean-Stark and then cooled to room temperature. Saturated aqueous NaHCO$_3$ and ethyl acetate were added, the organic layer was separated, washed with brine, dried over MgSO$_4$, filtered and concentrated under reduced pressure. Diethyl ether was added to the residue, a precipitate formed, intermediate 3-b was collected by filtration as a beige solid.

Step 3: Intermediate 3-c

To a solution of intermediate 3-b (2.80 g, 8.88 mmol) in tert-butanol (20 mL) was added sodium tert-butoxide (939 mg, 9.77 mmol). The resulting suspension was stirred at 80° C. for 2 hours and then cooled to room temperature. Saturated aqueous ammonium chloride and ethyl acetate were added, the organic layer was separated, the aqueous phase was extracted with ethyl acetate, the combined organic extracts were washed with brine, dried over MgSO$_4$, filtered and concentrated under reduced pressure to provide intermediate 3-c as a beige solid.

Step 4: Compound 1

To a solution of intermediate 3-c (300 mg, 0.95 mmol) in EtOH was added formamidine acetate (792 mg, 7.61 mmol), the reaction was stirred at reflux for 1 hour and then cooled to room temperature. The reaction was concentrated in vacuo to half volume. A precipitate formed and was collected by filtration, washed with methanol and diethyl ether to provide compound 1 as white solid. MS (m/z) M+H=343.2

Compound 1 Mono-methanesulfonic Acid Salt

Various medicinally acceptable addition salts of the compounds represented by Formula 1 may be prepared by the treatment of compounds of Formula 1 with an appropriate quantity of a medicinally acceptable acid. For example, as depicted in Scheme 3, the mono-methanesulfonic acid salt of compound 1 may be prepared by the treatment of compound 1 with 1 to 2 equivalence of methanesulfonic acid in an appropriate solvent to provide the mono-methanesulfonic acid salt of compound 1.

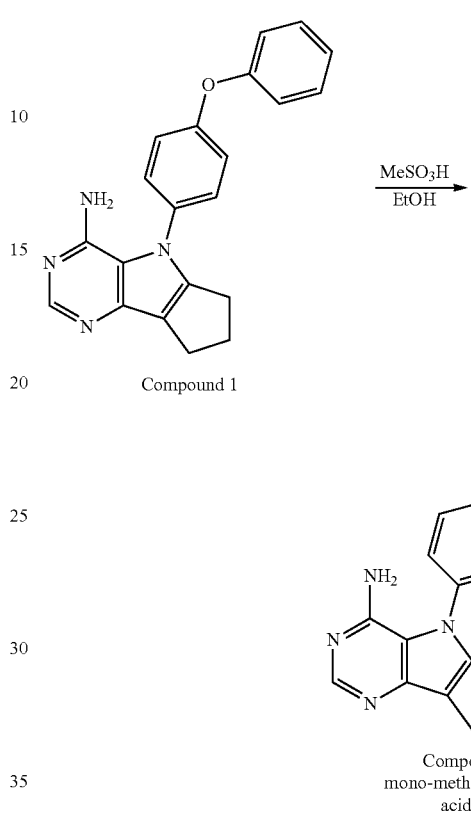

Compound 1 (2.25 g, 6.57 mmol) was suspended in ethanol (250 ml) and treated with methanesulfonic acid (0.448 ml, 6.90 mmol). The suspension was stirred for 1 hour. Solvent was concentrated to approximately 50 mL and diethyl ether (200 mL) was added. The resulting white solid was filtered, washed with diethyl ether (2×20 mL) and dried in vacuo to provide Compound 1 mono-methanesulfonic acid salt. MS (m/z) M+H=343.2

Synthesis of Compound 13:

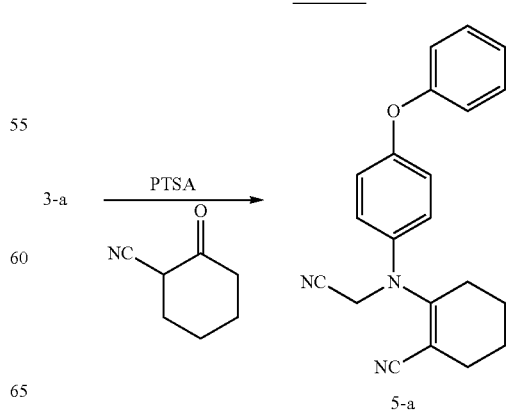

Synthesis of Intermediate 6-d

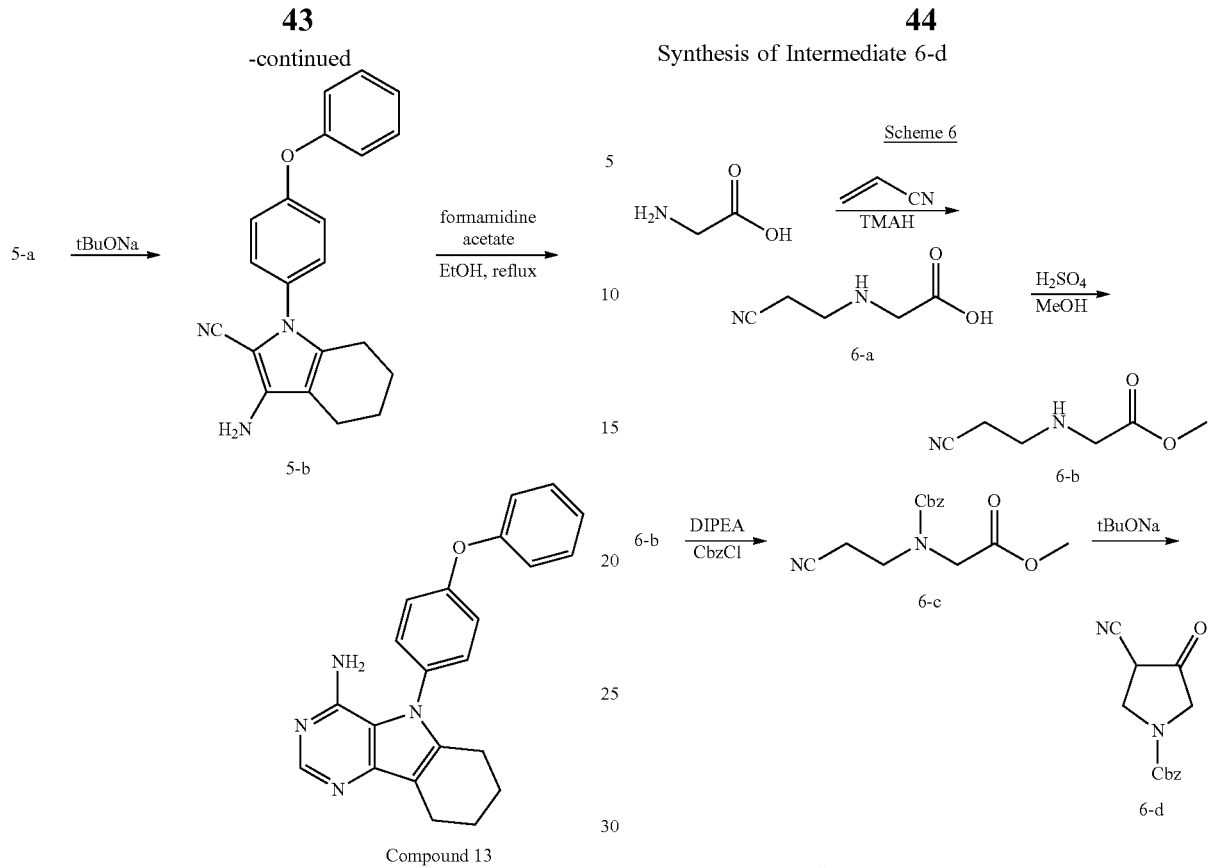

Step 1 Intermediate 5-a

To a solution of intermediate 3-a (1.82 g, 8.12 mmol) in toluene (32 mL) were added 2-oxocyclohexanecarbonitrile (1.0 g, 8.12 mmol) and 4-methylbenzenesulfonic acid hydrate (154 mg, 0.81 mmol). The reaction was refluxed overnight using a Dean-Stark and then cooled to room temperature. Saturated aqueous NaHCO$_3$ and ethyl acetate were added, the organic layer was separated, washed with brine, dried over MgSO$_4$, filtered and concentrated under reduced pressure. Purification by silica gel chromatography provided intermediate 5-a as a yellow oil.

Step 2: Intermediate 5-b

To a solution of intermediate 5-a (600 mg, 1.82 mmol) in tert-butanol (20 mL) was added sodium tert-butoxide (193 mg, 2.0 mmol), the reaction was stirred at 100° C. for 1 hour and then cooled to room temperature. Saturated aqueous ammonium chloride and ethyl acetate were added, the organic layer was separated, the aqueous phase was extracted with ethyl acetate, the combined organic extracts were washed with brine, dried over MgSO$_4$, filtered and concentrated under reduced pressure to provide intermediate 5-b as beige solid.

Step 3: Compound 13

To a solution of intermediate 5-b (600 mg, 1.82 mmol) in EtOH was added formamidine acetate (1.52 g, 14.57 mmol), the reaction was stirred at reflux for 3 hours and then cooled to room temperature. The reaction was concentrated in vacuo to half volume; a precipitate formed and was collected by filtration, washed with methanol and diethyl ether to provide compound 13 as white solid. MS (m/z) M+H=357.2

Step 1: Intermediate 6-a

Glycine (15.0 g, 200 mmol) was suspended in water (30 mL) and TMAH 1.0 M in water (200 mL, 200 mmol) was added. The mixture was cooled to 10° C., acrylonitrile (11.67 g, 220 mmol) was added and the reaction was stirred overnight and allowed to warm to room temperature slowly. The mixture was neutralized with concentrated HCl (15 mL) then concentrated to 50 mL and diluted with ethanol (100 mL). A precipitate formed and was collected by filtration, washed with ethanol to provide intermediate 6-a as a white solid.

Step 2: Intermediate 6-b

Sulfuric acid (10.2 mL) was added to a suspension of intermediate 6-a (16.2 g, 126 mmol) in MeOH (150 mL) and the reaction mixture was stirred at reflux overnight and then cooled to room temperature. The solvent was evaporated and the residue was diluted with 20% sodium hydroxide until a pH of 8 was obtained. The aqueous layer was extracted three times with dichloromethane; the combined organic extracts were dried over MgSO$_4$, filtered and concentrated in vacuo to provide intermediate 6-b as colorless oil.

Step 3: Intermediate 6-c

To a solution of intermediate 6-b (12.7 g, 89 mmol) in dichloromethane (100 ml) cooled to 0° C., were added benzyl chloroformate (13.97 ml, 98 mmol) and DIPEA (17.16 ml, 98.0 mmol) and the reaction was stirred at room temperature for 18 hrs. The reaction mixture was concentrated to half volume. Water and ethyl acetate were added; the organic layer was separated, washed with 10% citric acid, saturated aqueous NaHCO$_3$, and brine, dried over anhydrous MgSO$_4$, filtered and concentrated in vacuo to provide intermediate 6-c as yellow oil.

Step 4: Intermediate 6-d

Sodium tert-butoxide (2.56 g, 26.7 mmol) was added to a solution of intermediate 7-c (6.7 g, 24.25 mmol) in toluene (80 mL), the reaction was stirred overnight at 80° C. and then cooled to room temperature. 1N HCl and ethyl acetate were added, the reaction was stirred for 15 minutes, the organic layer was separated, washed with brine, dried over MgSO$_4$, filtered and concentrated in vacuo. Purification by silica gel chromatography provided intermediate 6-d as a yellow oil.

Synthesis of Intermediate 7-d

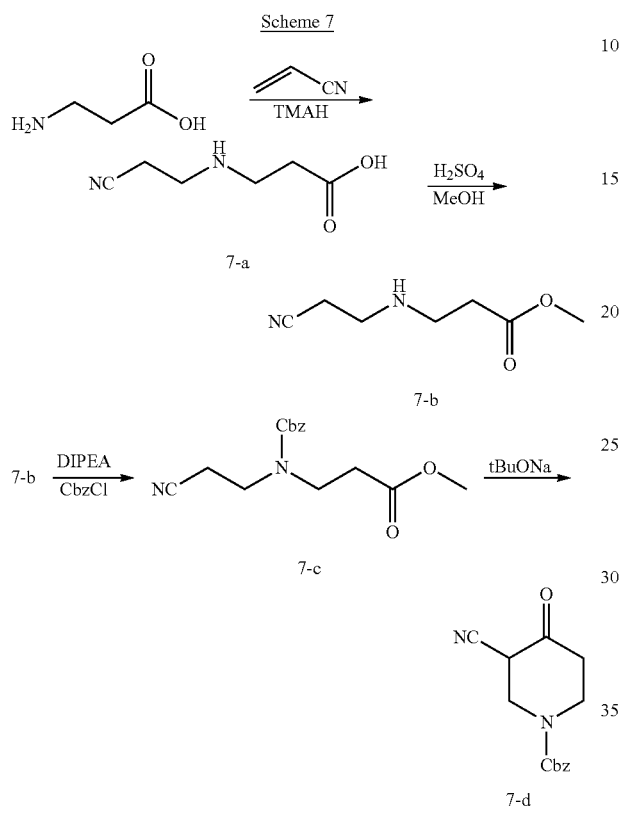

Step 1: Intermediate 7-a

β-Alanine (17.82 g, 200 mmol) was suspended in water (30 mL) and TMAH 1.0 M in water (200 mL, 200 mmol) was added. The mixture was cooled to 10° C., acrylonitrile (11.67 g, 220 mmol) was added and the reaction was stirred overnight and allowed to warm to room temperature slowly. The mixture was neutralized with concentrated HCl (15 mL) then concentrated to 50 mL and diluted with ethanol (100 mL). A precipitate formed and was collected by filtration, washed with ethanol to provide intermediate 7-a as a white solid.

Step 2: Intermediate 7-b

Sulfuric acid (6.07 ml, 114 mmol) was added to a suspension of intermediate 7-a (16.2 g, 114 mmol) in MeOH (150 ml) and the reaction was stirred at reflux overnight and then cooled to room temperature. The solvent was evaporated and the residue was diluted with 20% sodium hydroxide until pH=8. The aqueous layer was extracted 3 times with dichloromethane; the combined organic extracts were dried over MgSO$_4$, filtered and concentrated in vacuo to provide intermediate 7-b as a colorless oil.

Step 3: Intermediate 7-c

To a solution of intermediate 7-b (3.4 g, 21.77 mmol) in dichloromethane, cooled to 0° C., were added benzyl chloroformate (3.40 ml, 23.95 mmol) and DIPEA (4.18 ml, 23.95 mmol) and the reaction was stirred at room temperature for 18 hours. The reaction was concentrated in vacuo to half volume. Water and ethyl acetate were added, the organic layer was separated, washed with 10% aqueous citric acid, saturated aqueous NaHCO$_3$ and brine, dried over anhydrous MgSO$_4$, filtered and concentrated in vacuo. Purification by silica gel chromatography provided intermediate 7-c as a yellow oil.

Step 4: Intermediate 7-d

To a solution of intermediate 7-c (5.2 g, 17.91 mmol) in toluene (50 ml) was added sodium tert-butoxide (1.89 g, 19.70 mmol) and the reaction was stirred at 80° C. for 18 hours and then cooled to room temperature. 1N HCl and ethyl acetate were added, the reaction was stirred for 15 minutes, the organic layer was separated, washed with brine, dried over MgSO$_4$, filtered and concentrated in vacuo. Purification by silica gel chromatography provided intermediate 7-d as a yellow oil.

Synthesis of Compound 5

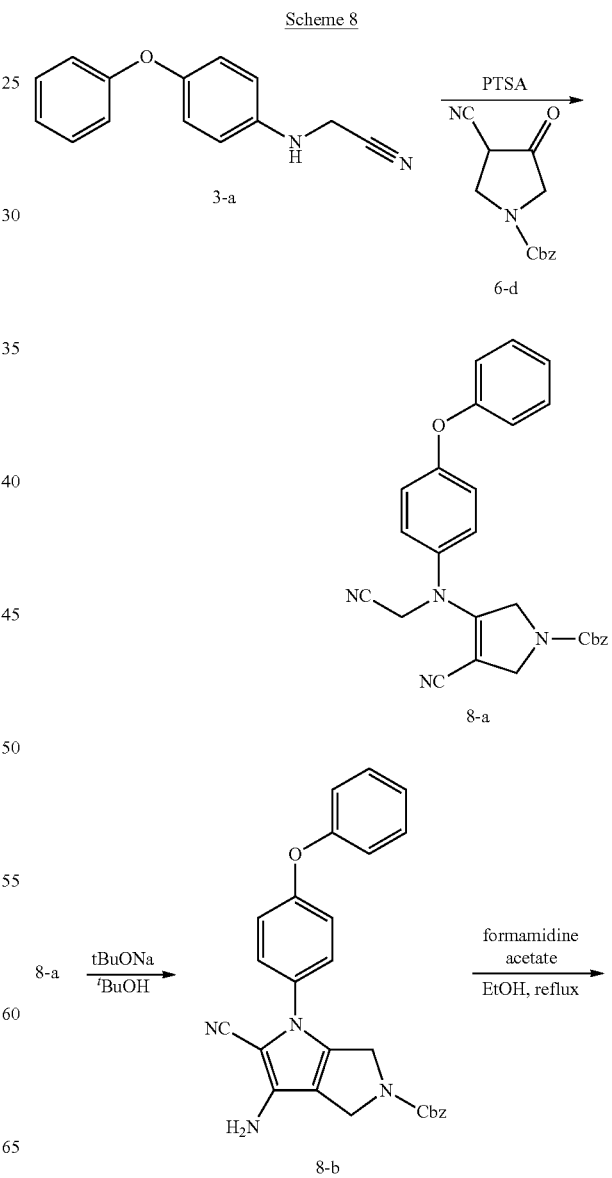

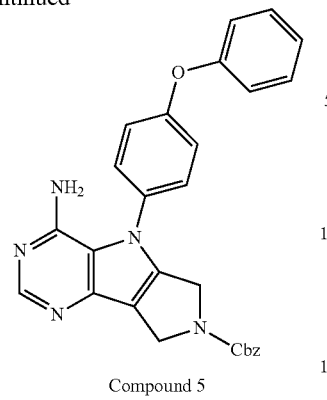

Compound 5

Step 1: Intermediate 8-a

To a solution of intermediate 3-a (2.45 g, 10.92 mmol), in toluene (50 mL), were added intermediate 6-d (3.2 g, 13.10 mmol) and 4-methylbenzenesulfonic acid hydrate (208 mg, 1.09 mmol), the reaction was refluxed for 5 hours using a Dean-Stark and then cooled to room temperature. Saturated aqueous NaHCO$_3$ and ethyl acetate were added, the organic layer was separated, washed with brine, dried over MgSO$_4$, filtered and concentrated under reduced pressure. Methanol was added to the residue, a precipitate formed, intermediate 8-a was collected by filtration as an off-white solid.

Step 2: Intermediate 8-b

To a solution of intermediate 8-a (3.0 g, 6.66 mmol) in tert-butanol (20 mL) was added sodium tert-butoxide (704 mg, 7.33 mmol), the reaction was stirred at 100° C. for 1 hour and then cooled to room temperature. Water was added and pH was adjusted to 7 with 1N HCl. Ethyl acetate was then added, the organic layer was separated, washed with brine, dried over MgSO$_4$, filtered and concentrated in vacuo to provide intermediate 8-b as beige solid.

Step 3: Compound 5

To a solution of intermediate 8-b (2.60 g, 5.77 mmol) in ethanol was added formamidine acetate (4.81 g, 46.5 mmol) and the reaction was stirred at reflux for 3 hours. The reaction was concentrated to half volume; water was added, a precipitate formed and was collected by filtration. Purification by silica gel chromatography provided compound 5 as an off-white solid. MS (m/z) M+H=478.1

Synthesis of Compound 6

Scheme 9

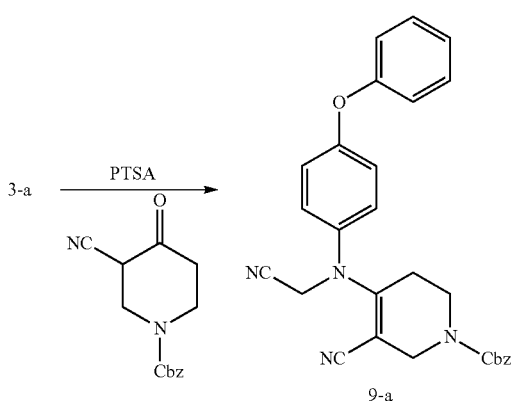

9-a

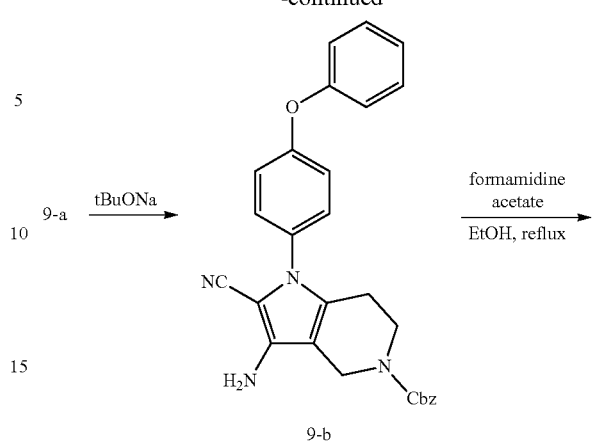

9-b

Compound 6

Step 1: Intermediate 9-a

To a solution of intermediate 3-a (7.24 g, 32.3 mmol) in toluene (160 mL) were added intermediate 6-d (10.0 g, 38.7 mmol) and 4-methylbenzenesulfonic acid hydrate (614 mg, 3.23 mmol), the reaction was refluxed for 3 hours using a Dean-Stark and then cooled to room temperature. Saturated aqueous NaHCO$_3$ and ethyl acetate were added, the organic layer was separated, washed with brine, dried over MgSO$_4$, filtered and concentrated under reduced pressure. Purification by silica gel chromatography provided intermediate 9-a as a beige foam.

Step 2: Intermediate 9-b

To a solution of intermediate 9-a (4.2 g, 9.04 mmol) in tert-butanol (50 mL) was added sodium tert-butoxide (956 mg, 9.95 mmol), the reaction was stirred at 100° C. for 1 hour and then cooled to room temperature. Water was added and the pH was adjusted to 7 with 1N HCl. A precipitate formed, intermediate 9-b was collected by filtration as beige solid.

Step 3: Compound 6

To a solution of intermediate 9-b (4.25 g, 9.15 mmol) in ethanol was added formamidine acetate (7.62 g, 73.2 mmol), the reaction was stirred at reflux for 3 hours and then cooled to room temperature. The reaction was concentrated in vacuo to half volume; water was added, a precipitate formed and was collected by filtration, washed with ethyl acetate to provide compound 6 as beige solid. MS (m/z) M+H=492.2

Synthesis of Compound 7

Scheme 10

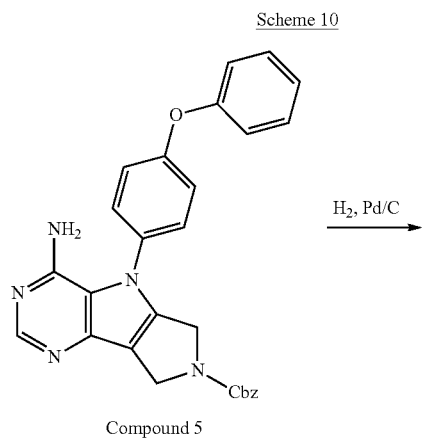

Compound 5

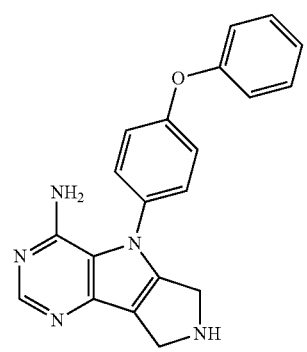

Compound 7

To a solution of compound 5 (1.5 g, 3.14 mmol) in methanol and stirred under nitrogen was added 10% Pd/C (669 mg, 3.14 mmol) and formic acid (1.0 ml, 26.1 mmol). The reaction mixture was purged with $H_2$ and stirred for 24 hours. The reaction was then filtered through celite and the filtrate was concentrated in vacuo. 1N HCl in diethyl ether was added to the residue and compound 7.2HCl was collected by filtration as an off-white solid. MS (m/z) M+H=344.2

Synthesis of Compound 10

Scheme 11

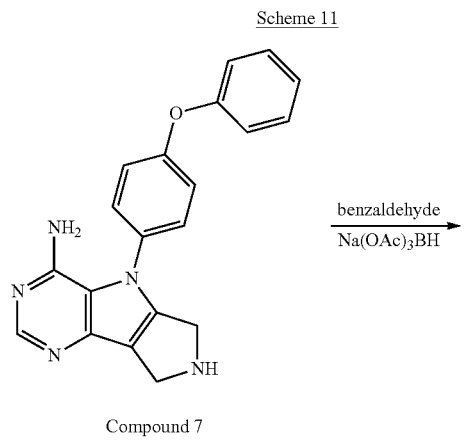

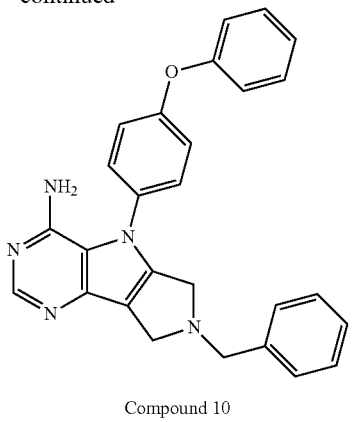

Compound 10

To a solution of compound 7 (200 mg, 0.58 mmol) in THF (10 ml) were sequentially added benzaldehyde (59 μl, 0.582 mmol), acetic acid (3.3 μl, 0.058 mmol) and sodium triacetoxyborohydride (370 mg, 1.747 mmol) and the suspension was stirred at room temperature overnight. Saturated aqueous $NaHCO_3$ and ethyl acetate were added, the organic layer was separated, washed with brine, dried over $MgSO_4$, filtered and concentrated in vacuo. Purification by silica gel chromatography provided compound 10 as a white solid. MS (m/z) M+H=434.2

Synthesis of Compound 18

Scheme 12

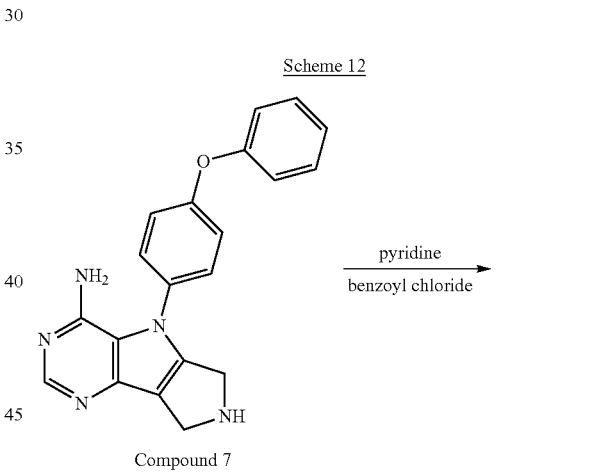

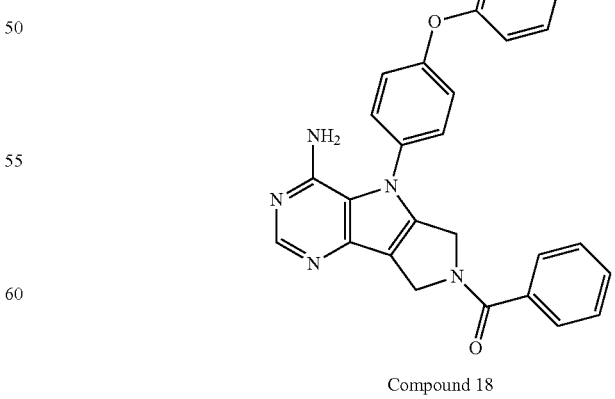

Compound 18

To a solution of compound 7 (300 mg, 0.58 mmol) in THF (5 mL) and pyridine (5 mL) were sequentially added benzoyl chloride (152 µL, 1.31 mmol) and DMAP (21 mg, 0.17 mmol). The reaction was stirred at 80° C. overnight and then cooled to room temperature. A solution of saturated aqueous ammonium chloride and ethyl acetate were added, the organic layer was separated, washed with brine, dried over MgSO$_4$, filtered and concentrated in vacuo. Purification by silica gel chromatography provided compound 18 as white solid. MS (m/z) M+H=448.3

Synthesis of Compound 9

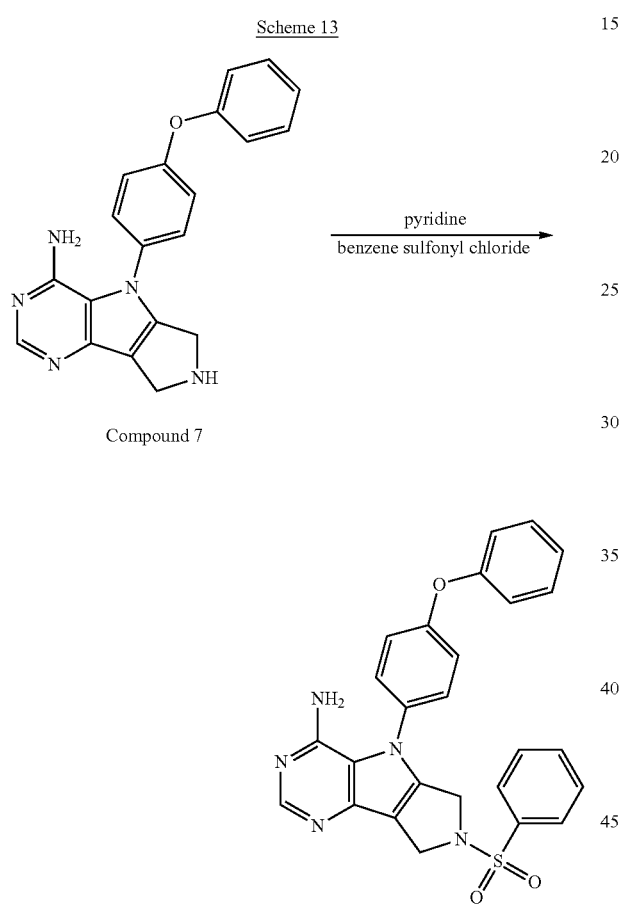

Scheme 13

Compound 7

Compound 9

To a solution of compound 7 (200 mg, 0.58 mmol) in THF (5 mL) and pyridine (5 mL) were sequentially added benzenesulfonyl chloride (350 mg, 1.97 mmol) and DMAP (71 mg, 0.58 mmol). The reaction was stirred at 80° C. for 3 days and then cooled to room temperature. A saturated aqueous solution of ammonium chloride and ethyl acetate were added, the organic layer was separated, washed with brine, dried over MgSO$_4$, filtered and concentrated in vacuo. Purification by silica gel chromatography provided compound 9 as a yellow solid. MS (m/z) M+H=484.1

Synthesis of Compound 19

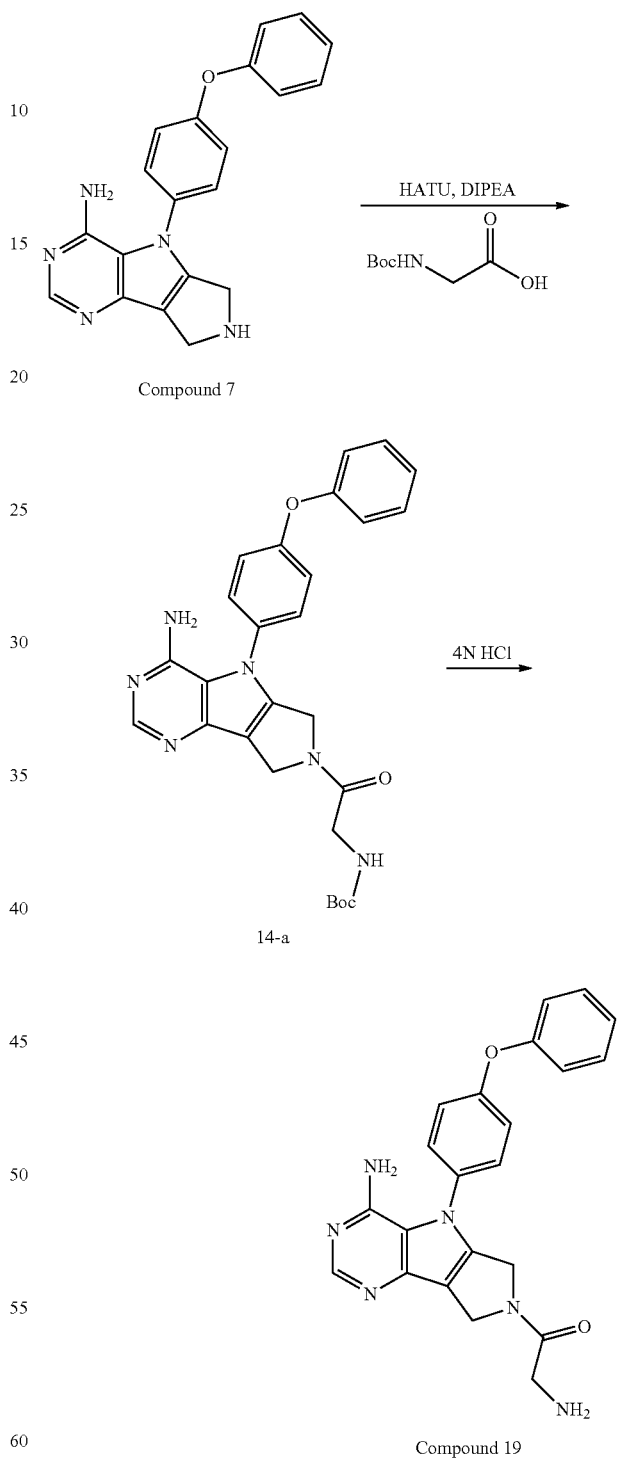

Scheme 14

Compound 7

14-a

Compound 19

Step 1: Intermediate 14-a

To a solution of compound 7 (300 mg, 0.87 mmol) and Boc-Gly-OH (168 mg, 0.96 mmol) in DMF were added HATU (332 mg, 0.87 mmol) and DIPEA (304 µL, 1.74 mmol) and the reaction was then stirred at room temperature for 1 hour. Water was added; a precipitate formed and was collected by filtration to provide intermediate 14-a as a beige solid.

Step 2: Compound 19

4N HCl in 1,4-dioxane (5.0 ml, 20.0 mmol) was added to intermediate 14-a (400 mg, 0.79 mmol) in methanol (5 ml) and the suspension was stirred at room temperature for 1 hour. Volatiles were removed under reduced pressure, ethyl acetate was added to the residue, a precipitate formed and was collected by filtration to provide compound 19.2HCl as a white solid. MS (m/z) M+H=401.2

Synthesis of Compound 8

Scheme 15

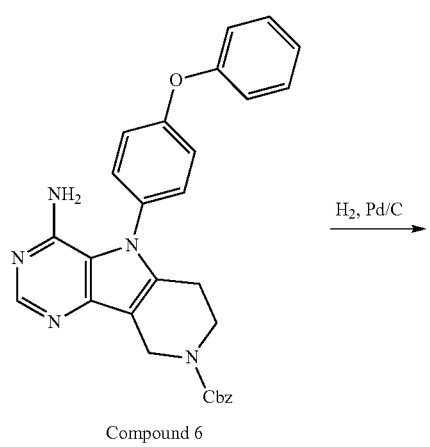

Compound 6

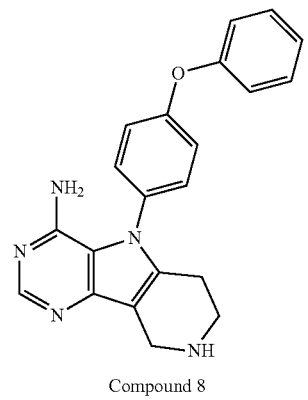

Compound 8

To a solution of compound 6 (1.20 g, 2.44 mmol) in methanol and stirred under nitrogen was added 10% Pd/C (52 mg, 0.24 mmol). The reaction mixture was purged with $H_2$ and stirred at room temperature for 24 hours. The reaction was then filtered through celite and the filtrate was concentrated in vacuo. 1N HCl in diethyl ether was added to the residue and compound 8.2HCl was collected by filtration as an off-white solid. MS (m/z) M+H=358.2

Synthesis of Compound 11

Scheme 16

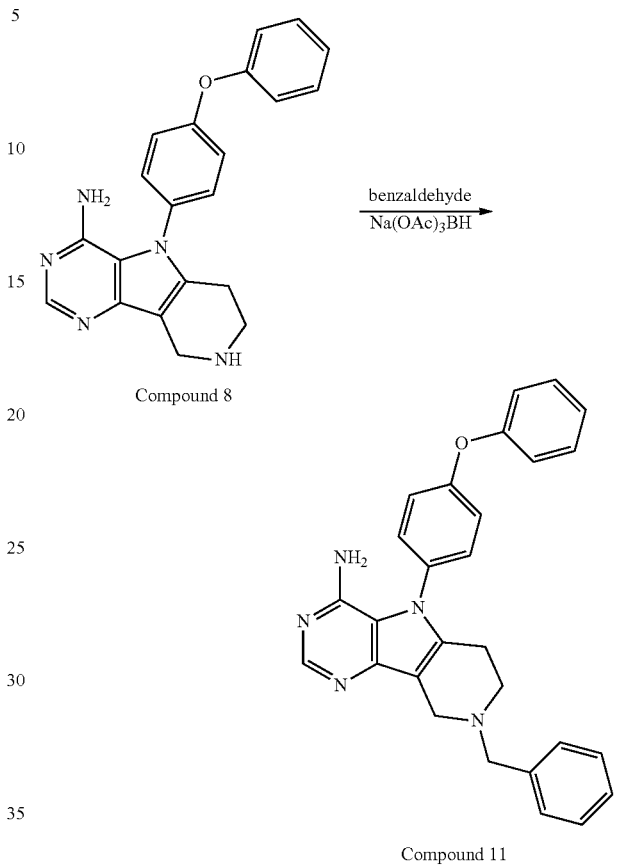

Compound 8

Compound 11

To a solution of compound 8 (200 mg, 0.58 mmol) in THF (10 ml) were sequentially added benzaldehyde (57 μl, 0.56 mmol) and sodium triacetoxyborohydride (356 mg, 1.68 mmol) and the suspension was stirred at room temperature overnight. Saturated aqueous $NaHCO_3$ and ethyl acetate were added, the organic layer was separated, washed with brine, dried over $MgSO_4$, filtered and concentrated in vacuo. Purification by silica gel chromatography provided compound 11 as a yellow solid. MS (m/z) M+H=448.2

Synthesis of Compound 16

Scheme 17

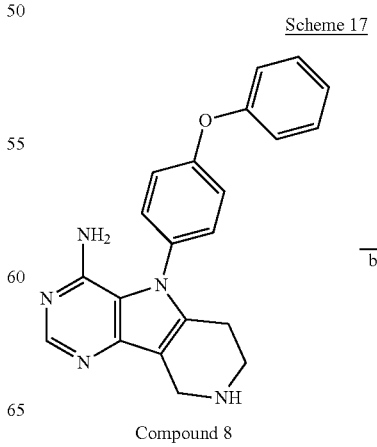

Compound 8

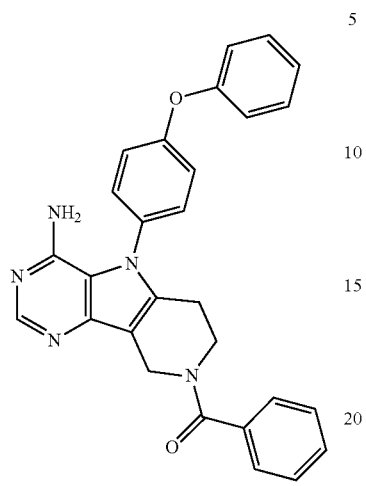

Compound 16

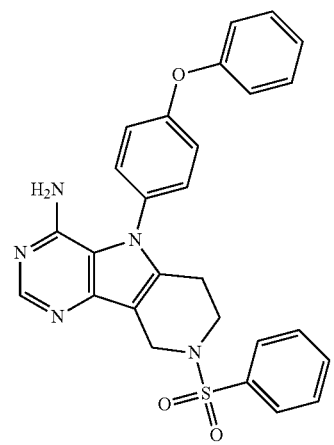

Compound 12

To a solution of compound 8 (300 mg, 0.84 mmol) in THF (5 mL) and pyridine (5 mL) were sequentially added benzoyl chloride (146 μL, 1.25 mmol) and DMAP (21 mg, 0.17 mmol). The reaction was stirred at 80° C. overnight and then cooled to room temperature. A solution of saturated aqueous ammonium chloride and ethyl acetate were added, the organic layer was separated, washed with brine, dried over MgSO$_4$, filtered and concentrated in vacuo. Purification by silica gel chromatography provided compound 16 as a white solid. MS (m/z) M+H=462.1

Synthesis of Compound 12

To a solution of compound 8 (200 mg, 0.56 mmol) in THF (5 mL) and pyridine (5 mL) were sequentially added benzenesulfonyl chloride (260 mg, 1.47 mmol) and DMAP (14 mg, 0.11 mmol). The reaction was stirred at 80° C. overnight and then cooled to room temperature. A solution of saturated aqueous ammonium chloride and ethyl acetate were added, the organic layer was separated, washed with brine, dried over MgSO$_4$, filtered and concentrated in vacuo. Purification by silica gel chromatography provided compound 12 as a yellow solid. MS (m/z) M+H=498.1

Synthesis of Compound 17

Scheme 18

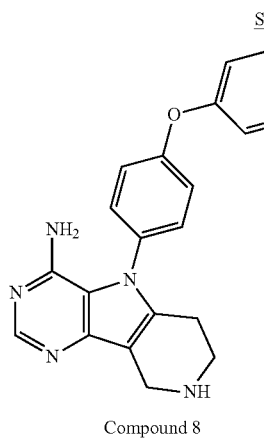

Compound 8

Scheme 19

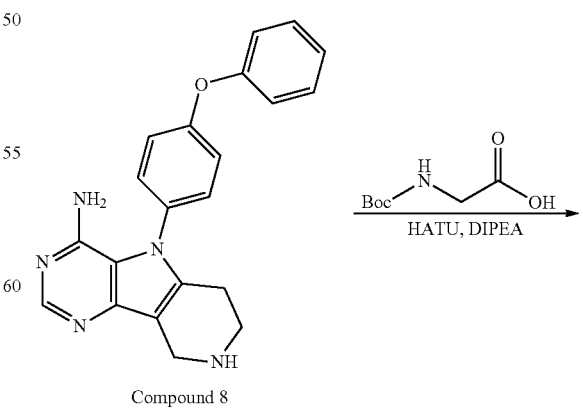

Compound 8

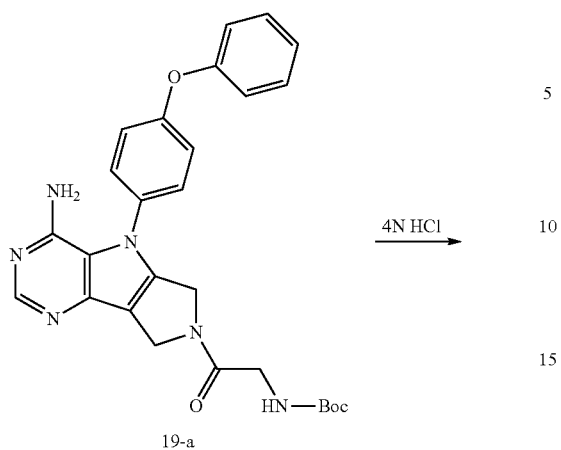

19-a

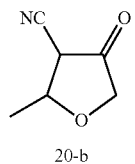

20-b

A solution of butyl 2-hydroxyacetate 20-a (47.2 g, 357 mmol) in THF (50 mL) was added dropwise to a suspension of sodium hydride (14.28 g, 357 mmol) in THF (250 mL). The mixture is treated at reflux with a solution of crotonitrile (23.96 g, 357 mmol) in THF (50 mL) and the mixture is held at reflux for 2 hours then cooled to room temperature. The solvent was evaporated; 2N NaOH (200 mL) and diethyl ether (200 mL) were added to the residue. The organic layer was separated; the aqueous phase was extracted twice with diethyl ether and then acidified to pH 1 with concentrated HCl (75 mL). The aqueous phase was then extracted with 3 times with dichloromethane; the combined organic extracts were dried over MgSO4, filtered and concentrated under vacuum to provide intermediate 20-b as beige oil.

Synthesis of Compound 20

Compound 17

Step 1: Intermediate 19-a

To a solution of compound 8 (300 mg, 0.83 mmol) and Boc-Gly-OH (162 mg, 0.92 mmol) in DMF were added HATU (319 mg, 0.83 mmol) and DIPEA (292 µL, 1.67 mmol) and the reaction was then stirred at room temperature for 1 hour. Water was added; a precipitate formed and was collected by filtration to provide intermediate 19-a as a beige solid.

Step 2: Compound 24

4N HCl (5 ml, 20.00 mmol) in 1,4-dioxane was added to intermediate 19-a (130 mg, 0.253 mmol) in MeOH (5 ml) and the suspension was stirred at room temperature for 1 hour. Volatiles were removed under reduced pressure, ethyl acetate was added to the residue, a precipitate formed and was collected by filtration to provide compound 17.2HCl as a white solid. MS (m/z) M+H=415.1

Synthesis of Intermediate 20-b

Scheme 20

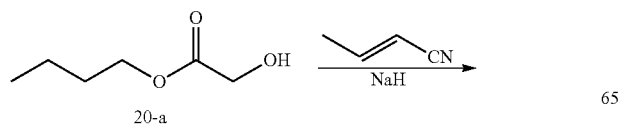

20-a

Scheme 21

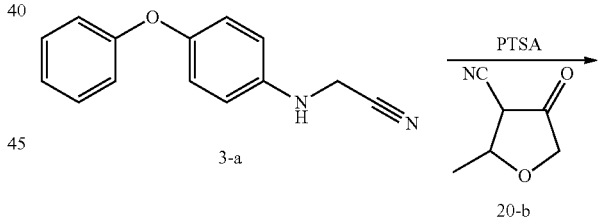

3-a

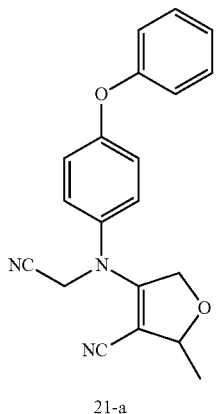

21-a

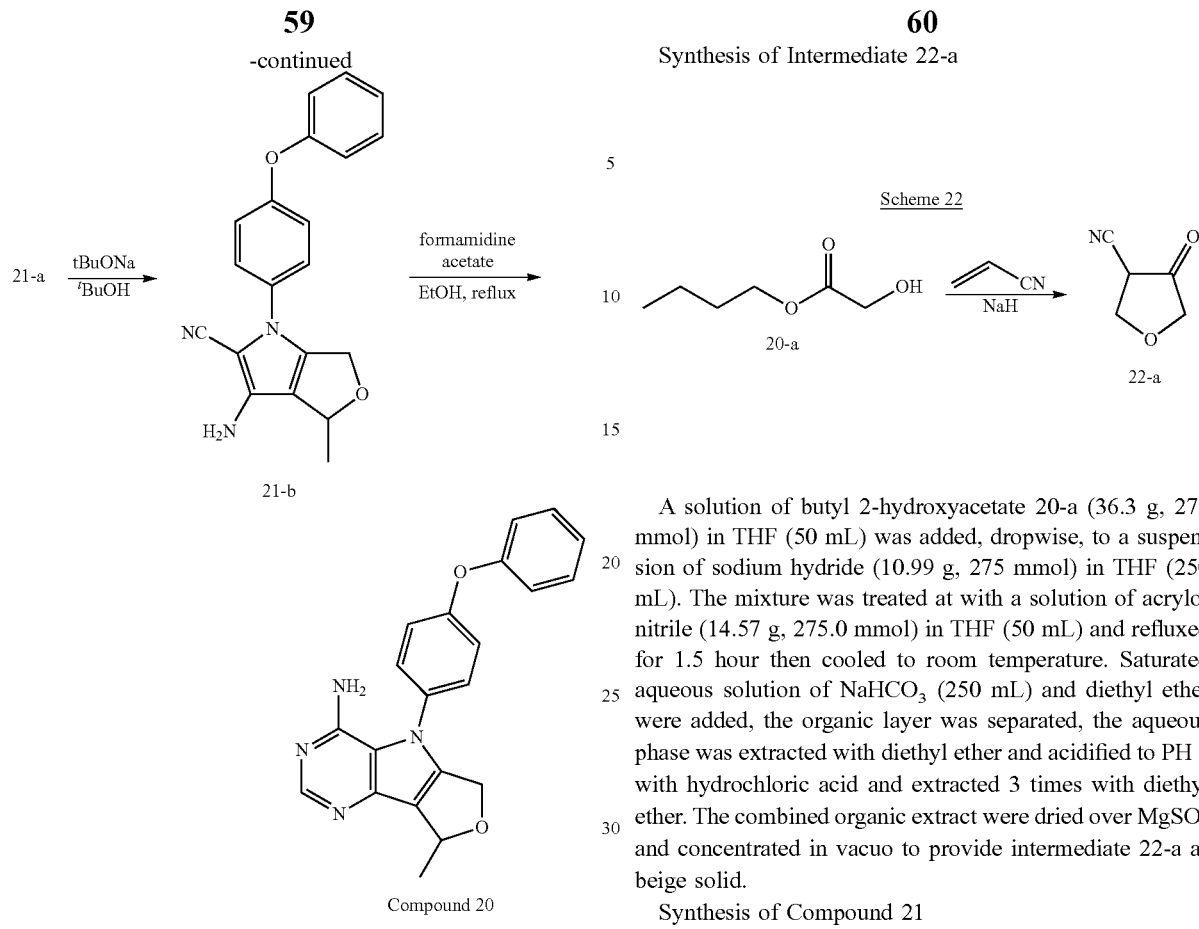

Step 1: Intermediate 21-a

To a solution of intermediate, 3-a (14.34 g, 63.9 mmol), in toluene (250 mL), was added intermediate 20-b (10.0 g, 80.0 mmol) and 4-methylbenzenesulfonic acid hydrate (1.21 g, 6.39 mmol). The reaction was refluxed for 3 hours using a Dean-Stark and then cooled to room temperature. Saturated aqueous NaHCO₃ and ethyl acetate were added, the organic layer was separated, washed with brine, dried over MgSO₄, filtered and concentrated under reduced pressure to provide intermediate 21-a as a beige solid.

Step 2: Intermediate 21-b

To a solution of intermediate 21-a (22.0 g, 66.4 mmol) in tert-butanol (330 mL) was added sodium tert-butoxide (7.02 g, 73.0 mmol), the reaction was stirred at 80° C. for 15 minutes and then cooled to room temperature. 1 N HCl and ethyl acetate were added, the organic layer was separated, washed with brine, dried over MgSO₄, filtered and concentrated in vacuo. Diethyl ether was added to the residue; a precipitate formed and was collected by filtration to provide intermediate 21-b as beige solid.

Step 3: Compound 20

To a solution of intermediate 21-b (22.0 g, 66.4 mmol) in ethanol was added formamidine acetate (27.6 g, 266.0 mmol), the reaction was stirred at reflux for 1.5 hour and then cooled to room temperature. The reaction was concentrated in vacuo to half volume; water was added, a precipitate formed and was collected by filtration. Purification by reverse phase chromatography eluting with a 10% methanol in 0.1% HCl to 40% methanol in 0.1% HCl gradient provided compound 20.HCl as a white solid. MS (m/z) M+H=359.2

Synthesis of Intermediate 22-a

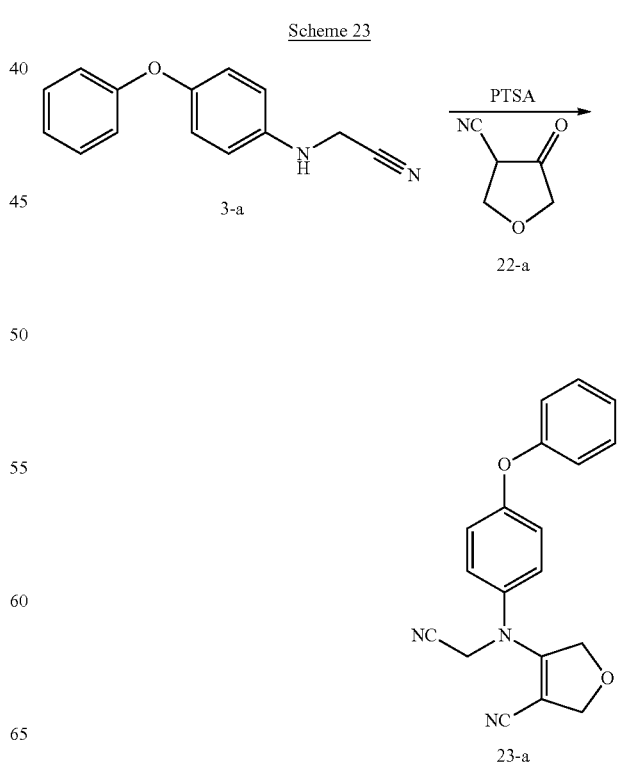

A solution of butyl 2-hydroxyacetate 20-a (36.3 g, 275 mmol) in THF (50 mL) was added, dropwise, to a suspension of sodium hydride (10.99 g, 275 mmol) in THF (250 mL). The mixture was treated at with a solution of acrylonitrile (14.57 g, 275.0 mmol) in THF (50 mL) and refluxed for 1.5 hour then cooled to room temperature. Saturated aqueous solution of NaHCO₃ (250 mL) and diethyl ether were added, the organic layer was separated, the aqueous phase was extracted with diethyl ether and acidified to PH 1 with hydrochloric acid and extracted 3 times with diethyl ether. The combined organic extract were dried over MgSO₄ and concentrated in vacuo to provide intermediate 22-a as beige solid.

Synthesis of Compound 21

Synthesis of Intermediate 24-e

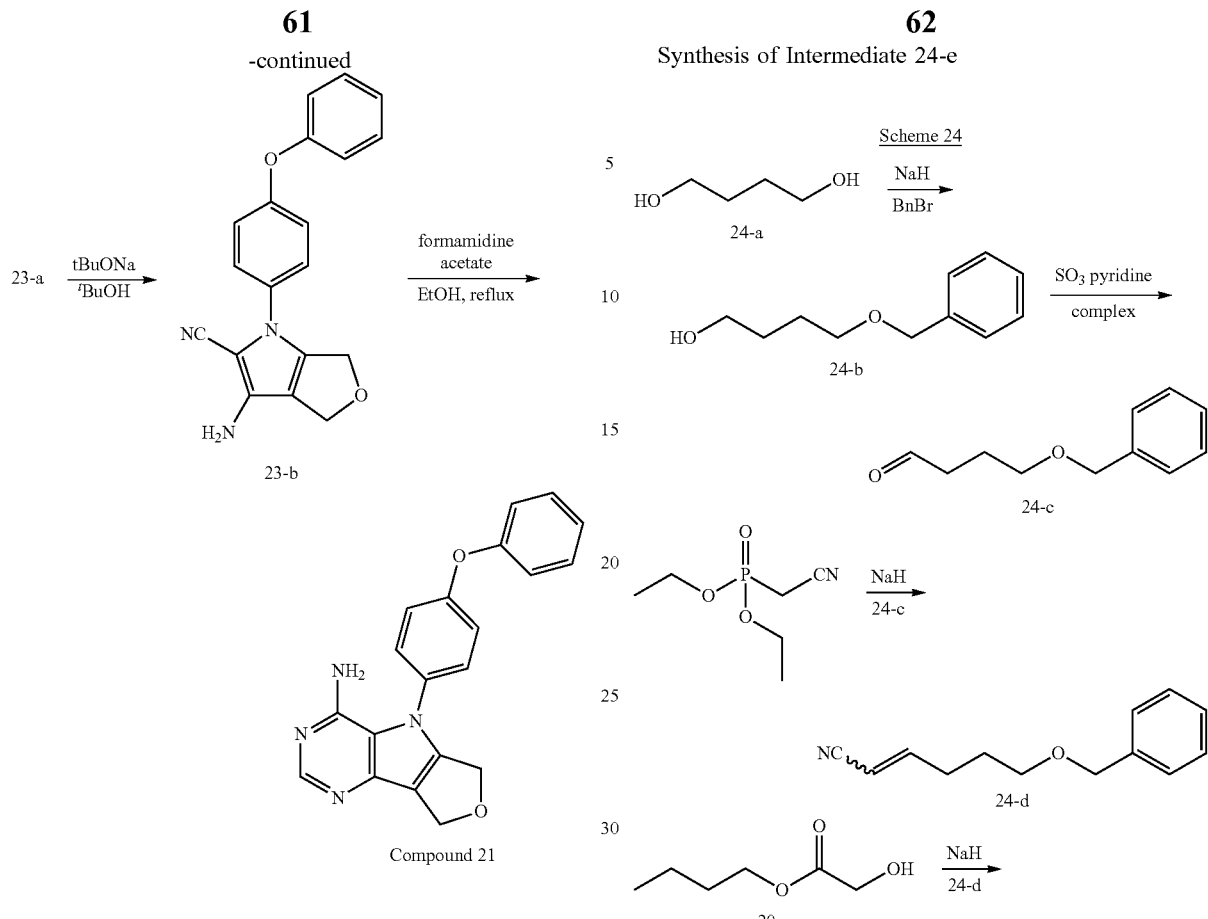

Step 1: Intermediate 23-a

To a solution of intermediate 3-a (2.5 g, 11.1 mmol) in toluene (55 mL) was added intermediate 22-a (1.85 g, 16.7 mmol) and 4-methylbenzenesulfonic acid hydrate (212 mg, 1.11 mmol). The reaction was refluxed for 3 hours using a Dean-Stark and then cooled to room temperature. Saturated aqueous NaHCO$_3$ and ethyl acetate were added, the organic layer was separated, washed with brine, dried over MgSO$_4$, filtered and concentrated under reduced pressure. Purification by silica gel chromatography provided intermediate 23-a as a beige solid.

Step 2: Intermediate 23-b

To a solution of intermediate 23-a (3.0 g, 9.45 mmol) in tert-butanol (80 mL) was added sodium tert-butoxide (909 mg, 9.45 mmol), the reaction was stirred at 100° C. for 1 hour and then cooled to room temperature. 1N HCl and ethyl acetate were added, the organic layer was separated, washed with brine, dried over MgSO$_4$, filtered and concentrated in vacuo to provide intermediate 23-b as beige solid. MS (m/z) M+H=318.3

Step 3: Compound 21

To a solution of intermediate 23-b (2.8 g, 8.82 mmol) in ethanol was added formamidine acetate (4.59 g, 44.1 mmol), the reaction was stirred at reflux for 3 hours and then cooled to room temperature. The reaction was concentrated to half volume; water was added, a precipitate formed and was collected by filtration. Purification by reverse phase chromatography eluting with a 0.1% HCl/methanol gradient, provided compound 21.HCl as a white solid. MS (m/z) M+H=345.2

Step 1: Intermediate 24-b

To a suspension of sodium hydride (8.86 g, 222 mmol) in THF (500 ml), cooled to 0° C., were added butane-1,4-diol, 24-a (19.63 ml, 222 mmol), dropwise, over a period of 15 minutes. The reaction was stirred at 0° C. for 30 minutes. (Bromomethyl)benzene (23.71 ml, 199 mmol) was added dropwise over a period of 15 minutes followed by tetrabutylammonium bromide (7.14 g, 22.15 mmol). The reaction was allowed to warm to room temperature and stirred overnight. The reaction mixture was then added to 5% HCl at 0° C. with vigorous stirring, diethyl ether was added. The organic layer was separated, the aqueous phase was extracted twice with diethyl ether, and the combined organic extracts were dried over anhydrous MgSO$_4$, filtered and concentrated in vacuo to provide intermediate 24-b as yellow oil.

Step 2: Intermediate 24-c

To a solution of intermediate 24-b (10.0 g, 55.5 mmol) in dichloromethane (200 mL), cooled to 0° C., was added DMSO (15.76 ml, 222 mmol) and DIPEA (33.8 ml, 194 mmol). SO$_3$ pyridine complex (17.66 g, 111 mmol) in DMSO (15 mL) was then added and the mixture was stirred for 2 hours at 0° C. Water and ethyl acetate were added; the organic layer was separated, washed with water, saturated aqueous NaHCO$_3$ and brine, dried over MgSO$_4$, filtered and concentrated under reduced pressure to provide intermediate 24-c as yellow oil.

Step 3: Intermediate 24-d

To a suspension of sodium hydride (2.22 g, 55.5 mmol) in THF (50 ml) cooled to 0° C., was added dropwise a solution of diethyl cyanomethylphosphonate (9.84 g, 55.5 mmol) in THF (50 mL), after stirring for 15 minutes a solution of intermediate 24-c (9.9 g, 55.5 mmol) in THF (50 mL) was then added dropwise. The reaction mixture was allowed to warm to room temperature and stirred overnight. Water and diethyl ether were added, the organic layer was separated, the aqueous phase was extracted with diethyl ether, and the combined organic extracts were washed with brine, dried over MgSO$_4$, filtered and concentrated under reduced pressure. Purification by silica gel chromatography provided intermediate 24-d as yellow oil.

Step 3: Intermediate 24-e

A solution of butyl 2-hydroxyacetate 20-a (5.12 g, 38.8 mmol) in THF (25 mL) was added dropwise to a suspension of sodium hydride (1.55 g, 38.8 mmol) in THF (50 mL). The mixture was treated with intermediate 24-d (7.8 g, 38.8 mmol) in THF (25 mL) and the mixture is held at reflux for 3 hours, then cooled to room temperature. The solvent was evaporated; 2N NaOH (100 mL) and diethyl ether (100 mL) were added to the residue. The organic layer was separated, the aqueous phase was extracted twice with diethyl ether and then acidified to pH 1 with concentrated HCl. The aqueous layer was then extracted with 3 times with dichloromethane; the combined organic extracts were dried over MgSO$_4$, filtered and concentrated under reduced pressure to provide intermediate 24-e as beige oil.

Synthesis of Compound 26

Scheme 25

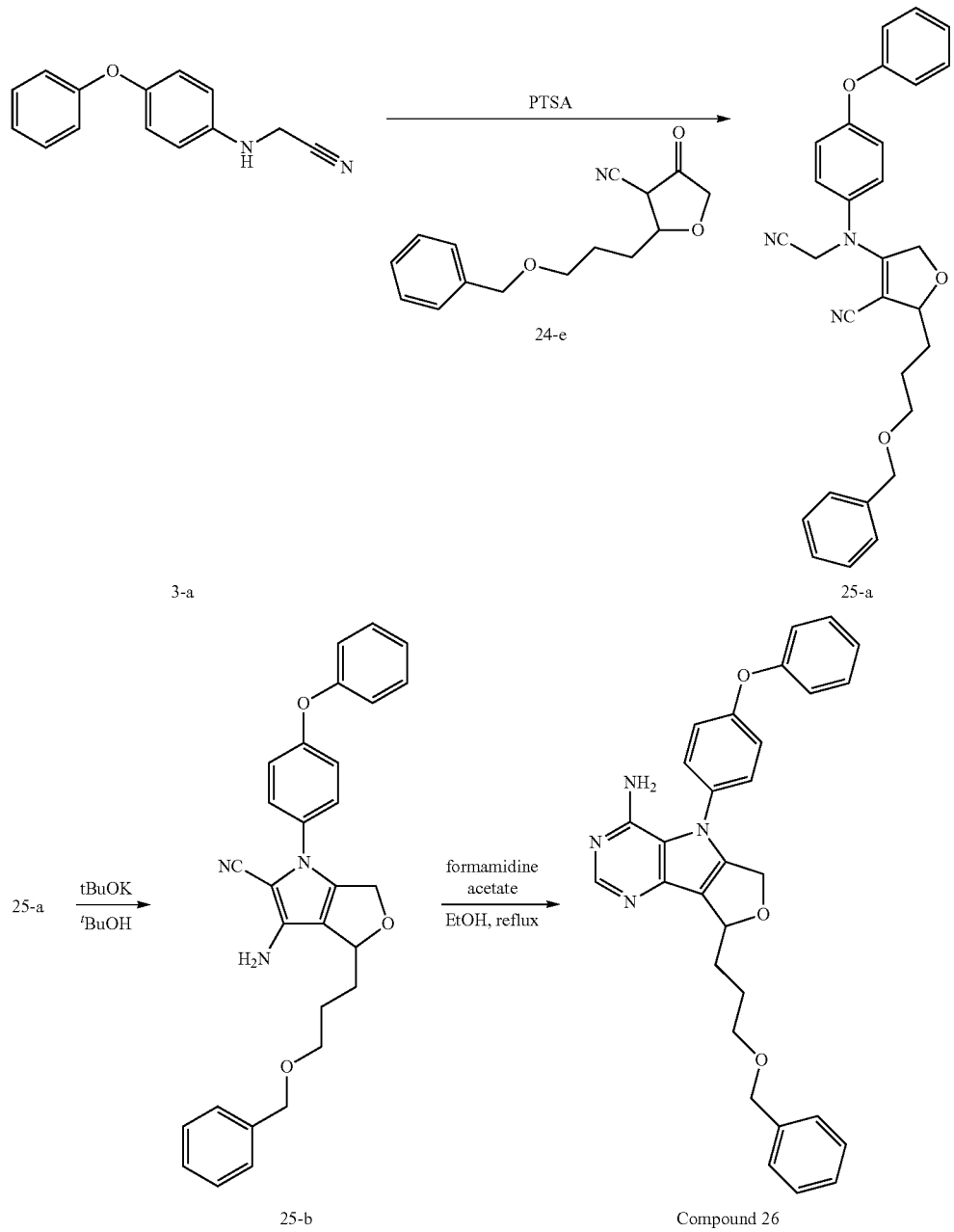

Step 1: Intermediate 25-a

To a solution of intermediate 3-a (692 mg, 3.10 mmol) in toluene (20 mL) were added intermediate 24-e (1.20 g, 4.63 mmol) and 4-methylbenzenesulfonic acid hydrate (59 mg, 0.30 mmol). The reaction was refluxed overnight using a Dean-Stark trap and then cooled to room temperature. Saturated aqueous NaHCO₃ and ethyl acetate were added, the organic layer was separated, washed with brine, dried over MgSO₄, filtered and concentrated under reduced pressure to provide intermediate 25-a as brown oil.

Step 2: Intermediate 25-b

To a solution of intermediate 25-a (1.5 g, 3.22 mmol) in tert-butanol (16 mL) was added a 1.0 M solution of potassium tert-butoxide in THF (3.54 mL, 3.54 mmol). The reaction was stirred at 80° C. for 30 minutes and then cooled to room temperature. 1N HCl and ethyl acetate were added, the organic layer was separated, washed with brine, dried over MgSO₄, filtered and concentrated in vacuo to provide intermediate 25-b as beige solid.

Step 3: Compound 26

To a solution of intermediate 25-b (1.5 g, 3.22 mmol) in ethanol was added formamidine acetate (2.68 g, 25.8 mmol). The reaction was stirred at reflux for 3 hours and then cooled to room temperature. The reaction was concentrated in vacuo to half volume; water and ethyl acetate were added, the organic layer was separated, washed with brine, dried over MgSO₄, filtered and concentrated under reduced pressure. Purification by reverse phase chromatography eluting with a 0.1% HCl/methanol gradient, provided compound 26.HCl as a white solid. MS (m/z) M+H=493.3

Synthesis of Intermediate 26-b

Scheme 26

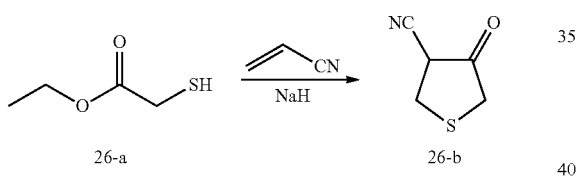

To a 25% solution of sodium methoxide in methanol (37.7 ml, 165 mmol), cooled to 0° C., was sequentially added dropwise ethyl 2-mercaptoacetate (13 ml, 118 mmol) and acrylonitrile (7.76 ml, 118 mmol) and the reaction was stirred at reflux for 1 hour. The solvent was evaporated; water and diethyl ether were added to the residue. The organic layer was separated; the aqueous phase was acidified to pH=1 with concentrated HCl. The aqueous phase was then extracted 3 times with diethyl ether. The combined organic extracts were washed with brine, dried over anhydrous MgSO₄, filtered and concentrated under reduced pressure to provide intermediate 26-b as beige oil.

Synthesis of Compound 63

Scheme 27

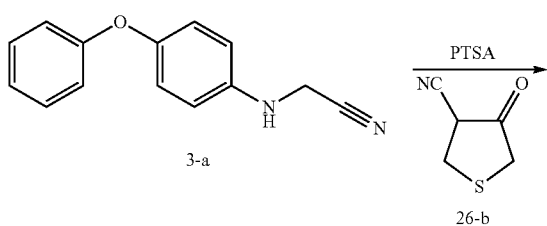

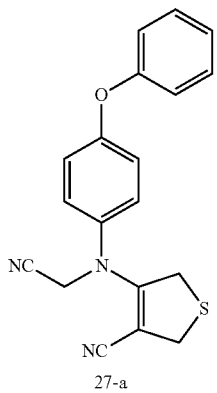

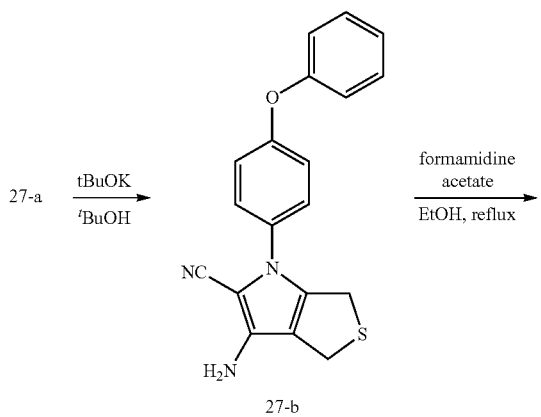

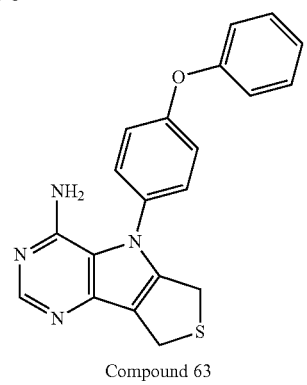

Compound 63

Step 1: Intermediate 27-a

To a solution of intermediate 3-a (5.29 g, 23.59 mmol) in toluene (100 mL) were added intermediate 26-b (3.0 g, 23.59 mmol) and 4-methylbenzenesulfonic acid hydrate (449 mg, 2.35 mmol). The reaction was refluxed for 4 hours using a Dean-Stark trap and then cooled to room temperature. Saturated aqueous NaHCO₃ and ethyl acetate were added, the organic layer was separated, washed with brine, dried over MgSO₄, filtered and concentrated under reduced pressure. Purification by silica gel chromatography provided intermediate 27-a as beige solid.

Step 2: Intermediate 27-b

To a solution of intermediate 27-a (8.0 g, 24.0 mmol) in tert-butanol (100 mL) was added a 1.0 M solution of potassium tert-butoxide in THF (23.99 mL, 23.99 mmol), and the reaction was stirred at 90° C. for 2 hours and then cooled to room temperature. Water and ethyl acetate were added, the organic layer was separated, washed with brine, dried over MgSO₄, filtered and concentrated in vacuo to provide intermediate 27-b as beige solid.

Step 3: Compound 63

To a solution of intermediate 27-b (8.0 g, 23.99 mmol) in ethanol was added formamidine acetate (19.98 g, 192 mmol), the reaction was stirred at reflux overnight and then cooled to room temperature. The reaction was concentrated in vacuo to half volume; water and ethyl acetate were added, the organic layer was separated, washed with saturated aqueous $NaHCO_3$ and brine, dried over anhydrous $MgSO_4$, filtered and concentrated under reduced pressure. Purification by silica gel chromatography provided compound 63 as beige solid. MS (m/z) M+H=361.2

Synthesis of Compound 65

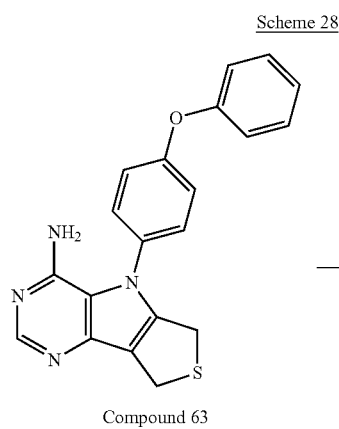

Scheme 28

Compound 63

→

Compound 65

To a solution of compound 63 (1 g, 2.77 mmol) in a 1:1:1 mixture of tetrahydrofuran/methanol/water was added oxone (1.70 g, 2.77 mmol) and the solution was stirred at room temperature for 1 hour. Water and ethyl acetate were added, the organic layer was separated, washed with brine, dried over $MgSO_4$, filtered and concentrated under reduced pressure. Purification by silica gel chromatography provided compound 65 as white solid. MS (m/z) M+H=393.2

Synthesis of Compound 43

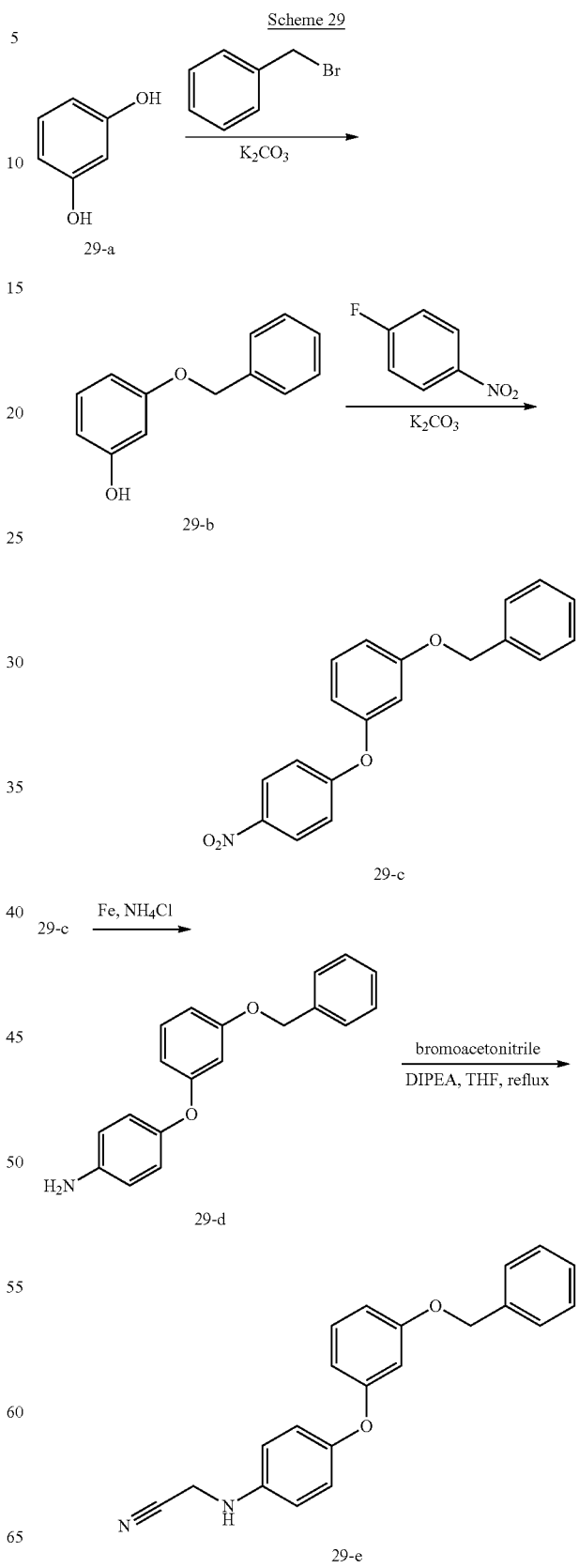

Scheme 29

-continued

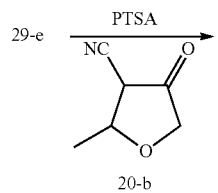

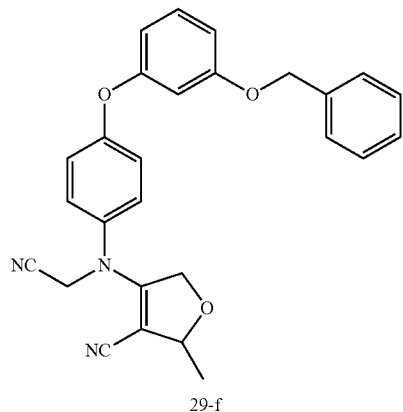

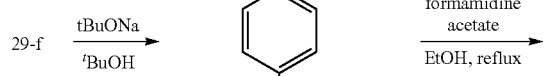

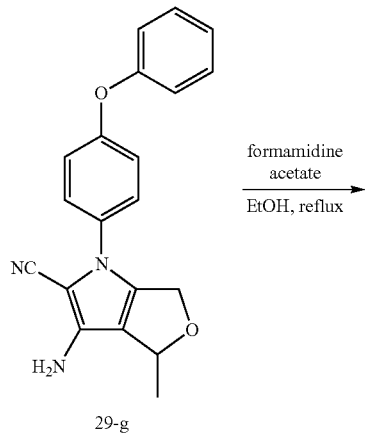

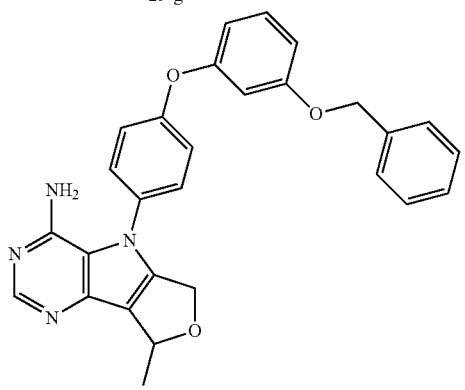

Compound 43

Step 1: Intermediate 29-b

Benzyl bromide (27.0 ml, 227 mmol) was added, dropwise, to a stirred suspension of resorcinol (25 g, 227 mmol) and potassium carbonate (31.4 g, 227 mmol) in acetone (150 ml) and the reaction was heated under reflux overnight. Volatiles were removed under reduced pressure. Water and ethyl acetate were added, the organic layer was separated, washed with brine dried over MgSO$_4$, filtered and concentrated under reduced pressure. Purification by silica gel chromatography provided intermediate 29-b as beige oil.

Step 2: Intermediate 29-c

To a solution of 1-fluoro-4-nitrobenzene (12.17 g, 86.0 mmol) in DMSO (150 ml) were added intermediate 29-b (19.0 g, 95 mmol), K$_2$CO$_3$ (13.11 g, 95 mmol) and the reaction was stirred at 150° C. for 18 hours. A saturated aqueous solution of ammonium chloride and diethyl ether were added, the organic layer was separated, the aqueous layer was extracted with diethyl ether, the combined organic extracts were washed with brine, dried over MgSO$_4$, filtered and concentrated under reduced pressure to provide intermediate 29-c as brown solid.

Step 3: Intermediate 29-d

To a solution of intermediate 29-c (14.1 g, 43.9 mmol) in ethanol (150 ml) and water (50 ml) were sequentially added ammonium chloride (11.74 g, 219 mmol), iron (9.80 g, 176 mmol) and the reaction mixture was stirred at reflux overnight and then cooled to room temperature. Volatiles were removed in vacuo. Water and ethyl acetate were added; the organic layer was separated, washed with saturated aqueous NaHCO$_3$ and brine, dried over MgSO$_4$, filtered and concentrated under reduced pressure to provide intermediate 29-d as beige solid.

Step 4: Intermediate 29-e

To a solution of intermediate 29-d (10.8 g, 37.1 mmol) and 2-bromoacetonitrile (5.34 g, 44.5 mmol) in THF (100 mL) was added DIPEA (7.77 ml, 44.5 mmol) and the reaction was stirred at 80° C. overnight. A solution of saturated aqueous ammonium chloride and ethyl acetate were added, the organic layer was separated, washed with Saturated aqueous ammonium chloride and brine, dried over MgSO$_4$, filtered and concentrated under reduced pressure to provide intermediate 29-e as brown oil.

Step 5: Intermediate 29-f

To a solution of intermediate 29-e (12.5 g, 37.8 mmol) in toluene (50 ml) were added intermediate 20-b (7.10 g, 56.8 mmol) and 4-methylbenzenesulfonic acid hydrate (720 mg, 3.78 mmol). The reaction was refluxed for 6 hours using a dean-stark and then cooled to room temperature. A solution of saturated aqueous NaHCO$_3$ and ethyl acetate were added, the organic layer was separated, washed with brine, dried over MgSO$_4$, filtered and concentrated under reduced pressure. Purification by silica gel chromatography provided intermediate 29-f as a beige foam.

Step 6: Intermediate 29-g

To a solution of intermediate 29-f (8.2 g, 18.74 mmol) in tert-butanol (50.0 ml) was added potassium tert-butoxide (2.31 g, 20.62 mmol) and the reaction was stirred at 80° C. for 1 hour and then cooled to room temperature. A solution of saturated aqueous ammonium chloride and ethyl acetate were added, the organic layer was separated, the aqueous phase was extracted with ethyl acetate, the combined organic extracts were washed with brine, dried over MgSO$_4$, filtered and concentrated under reduced pressure to provide intermediate 29-g as beige solid.

Step 8: Compound 43

To a solution of intermediate 29-g (8.20 g, 18.74 mmol) in ethanol (75 ml) was added formamidine acetate (15.61 g, 150.0 mmol) and the reaction was stirred at 80° C. for 3 hours and then cooled to room temperature. Volatiles were removed in vacuo. A solution of saturated aqueous NaHCO$_3$ and ethyl acetate were added to the residue, the organic layer was separated, washed with brine, dried over MgSO$_4$, filtered and concentrated under reduced pressure. Purification by reverse phase chromatography eluting with a 0.1% HCl/methanol gradient provided compound 43.HCl as a white solid. MS (m/z) M+H=465.2

Synthesis of Compound 44

Scheme 30

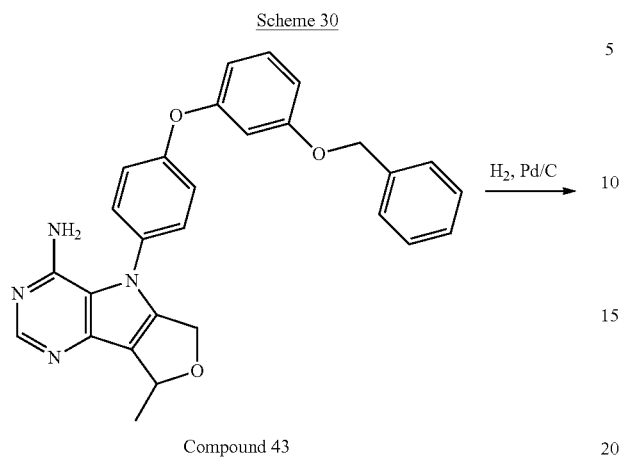

Compound 43

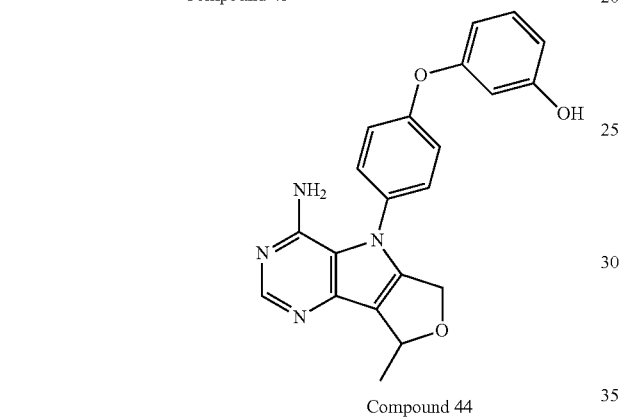

Compound 44

To a solution of compound 43 (3.85 g, 8.29 mmol) in methanol and stirred under nitrogen was added 10% Pd/C (882 mg, 8.29 mmol). The reaction mixture was purged with $H_2$ and stirred at room temperature for 3 hours. The reaction was then filtered through celite and the filtrate was concentrated in vacuo. Ethyl acetate was added to the residue; a precipitate formed and was collected by filtration to provide compound 44 as a white solid. MS (m/z) M+H=375.2

Synthesis of Compound 46

Scheme 31

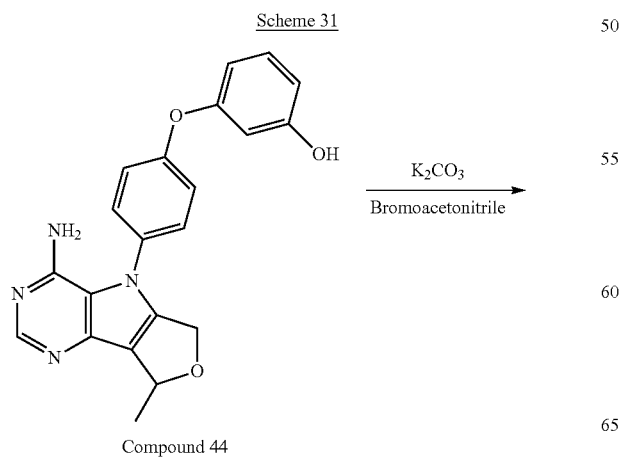

Compound 44

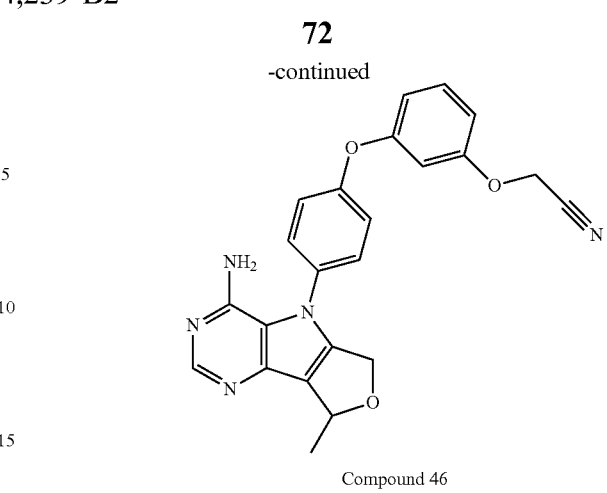

Compound 46

To a solution of compound 44 (129 mg, 0.345 mmol) in DMF (3 ml) were sequentially added potassium carbonate (99 mg, 0.718 mmol), bromoacetonitrile (30 μl, 0.43 mmol) and the solution was stirred at 90° C. overnight. Water and ethyl acetate were added, the organic layer was separated, washed with brine, dried over $MgSO_4$, filtered and concentrated under reduced pressure. Purification by reverse phase chromatography eluting with a 0.1% aqueous HCl/methanol gradient provided compound 46.HCl as a white solid. MS (m/z) M+H=414.2

Synthesis of Compound 48

Scheme 32

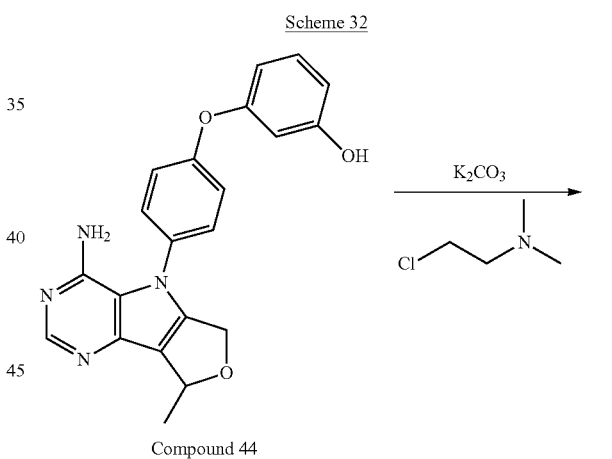

Compound 44

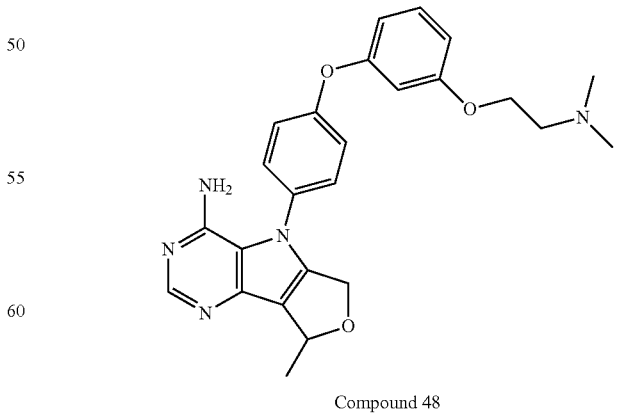

Compound 48

To a solution of compound 44 (200 mg, 0.53 mmol) in DMF (3 ml) were sequentially added potassium carbonate (221 mg, 1.60 mmol), tetrabutylammonium bromide (9.87 mg, 0.027 mmol) and 2-chloro-N,N-dimethylethanamine hydrochloride salt (85 mg, 0.588 mmol) and the solution was stirred was stirred at room temperature for 3 hours. Water and ethyl acetate were added, the organic layer was separated, washed with brine, dried over MgSO$_4$, filtered and concentrated under reduced pressure. Purification by reverse phase chromatography eluting with a 0.1% aqueous HCl/methanol gradient provided compound 48.2HCl as a white solid. MS (m/z) M+H=446.4

Synthesis of Compound 49

Scheme 33

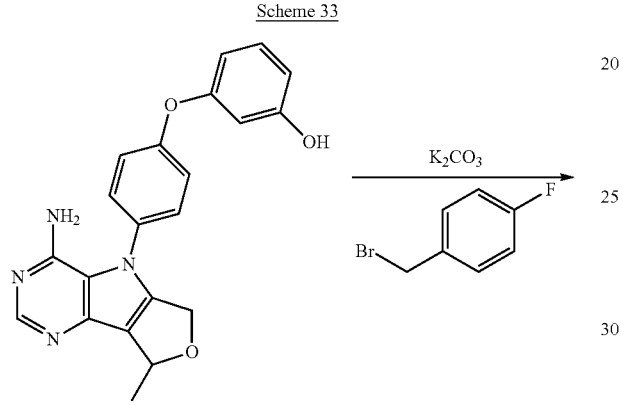

Compound 49

To a solution of compound 44 (200 mg, 0.53 mmol) in DMF (3 ml) were sequentially added potassium carbonate (200 mg, 1.44 mmol), 4-fluorobenzyl bromide (111 mg, 0.58 mmol) and the reaction was stirred for 4 hours at room temperature. Water and ethyl acetate were added, the organic layer was separated, washed with brine, dried over MgSO$_4$, filtered and concentrated under reduced pressure. Purification by silica gel chromatography provided compound 49 as a white solid. MS (m/z) M+H=483.2

Synthesis of Compound 54

Scheme 34

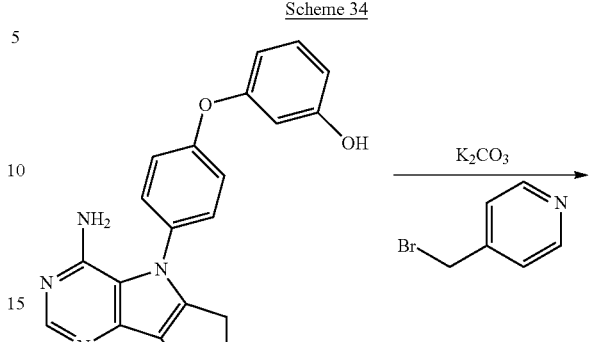

Compound 44

Compound 54

To a solution of compound 44 (200 mg, 0.53 mmol) in DMF (3 ml) were sequentially added potassium carbonate (200 mg, 1.447 mmol), 4-(bromomethyl)pyridine HBr salt (149 mg, 0.58 mmol) and the reaction was stirred at room temperature for 4 hours. Water and ethyl acetate were added, the organic layer was separated, washed with brine, dried over MgSO$_4$, filtered and concentrated under reduced pressure. Purification by reverse phase chromatography eluting with a 0.1% aqueous HCl/methanol gradient provided compound 54.2HCl as a white solid. MS (m/z) M+H=466.2

Synthesis of Compound 56

Scheme 35

Compound 44

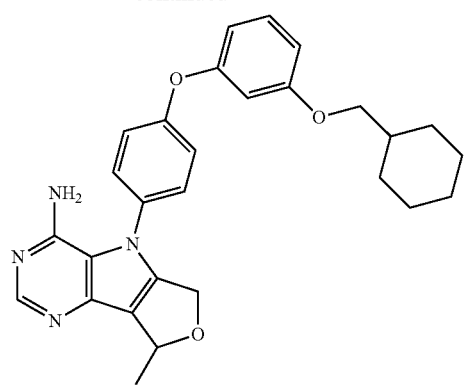

Compound 56

To a solution of compound 44 (200 mg, 0.53 mmol) in DMF (3 mL) were sequentially added potassium carbonate (148 mg, 1.068 mmol), (bromomethyl)cyclohexane (104 mg, 0.588 mmol) and the solution was stirred at 90° C. for 18 hours. Water and ethyl acetate were added, the organic layer was separated, washed with brine, dried over MgSO$_4$, filtered and concentrated under reduced pressure. Purification by reverse phase chromatography eluting with a 0.1% aqueous HCl/methanol gradient provided compound 56.HCl as a white solid. MS (m/z) M+H=471.3.

Synthesis of Compound 45

Scheme 36

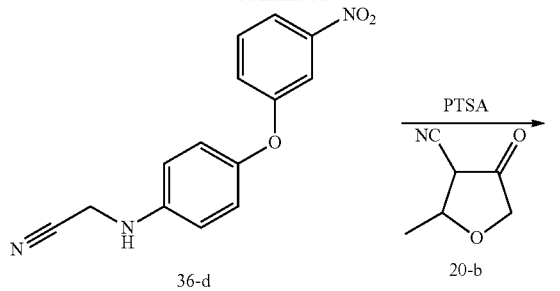

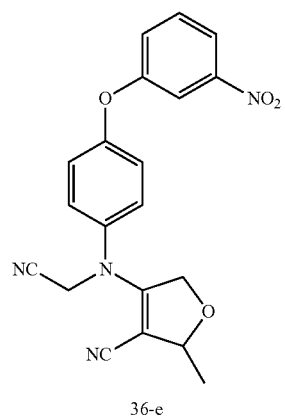

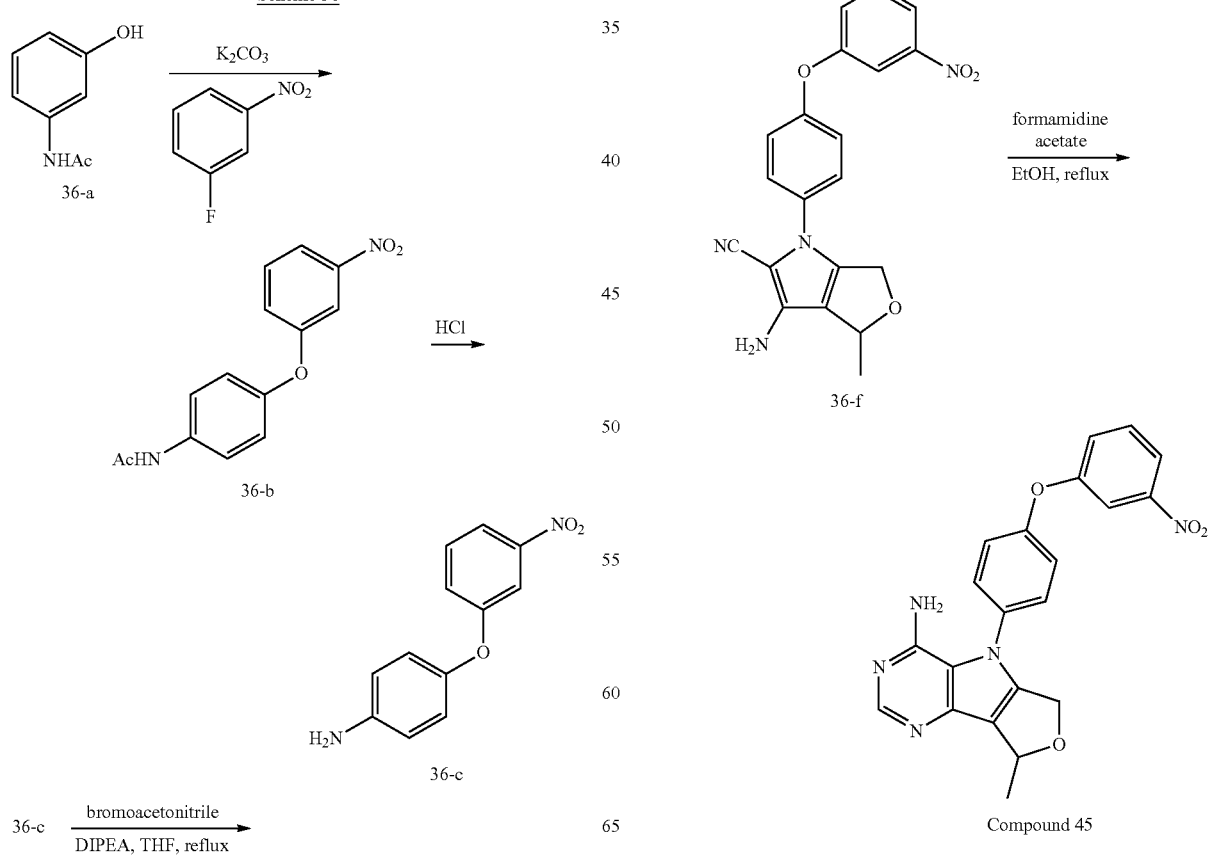

Step 1: Intermediate 36-b

To a solution of N-(4-hydroxyphenyl)acetamide 36-a (10 g, 66.2 mmol) and 1-fluoro-3-nitrobenzene (8.49 g, 60.1 mmol) in DMF (100 ml) was added potassium carbonate (9.14 g, 66.2 mmol) and the reaction was heated at 150° C. overnight and then cooled to room temperature. The reaction was poured into one liter of ice-cold water and stirred for 30 minutes. A precipitate formed and was collected by filtration, washed with water and dried under vacuo to provide intermediate 36-b as a yellow solid.

Step 2: Intermediate 36-c

Intermediate 36-b (11.9 g, 43.7 mmol) was heated to 95° C. in 12N HCl (70 mL) for 48 hours. After cooling to room temperature, a precipitate formed and was collected by filtration, washed with diethyl ether to provide intermediate 36-c as beige solid.

Step 3: Intermediate 36-d

To a solution of intermediate 36-c (7.20 g, 27.0 mmol) and 2-bromoacetonitrile (4.21 g, 35.1 mmol) in THF (50 mL) was added DIPEA (14.15 ml, 81.0 mmol) at room temperature and the reaction was stirred at 80° C. overnight. A solution of saturated aqueous ammonium chloride and ethyl acetate were added, the organic layer was separated, washed with a saturated aqueous solution of ammonium chloride and brine, dried over MgSO$_4$, filtered and concentrated under reduced pressure to provide intermediate 36-d as beige solid.

Step 4: Intermediate 36-e

To a solution of intermediate 36-d (3.0 g, 11.14 mmol) in toluene (50 ml) were added intermediate 20-b (2.79 g, 22.28 mmol) and 4-methylbenzenesulfonic acid hydrate (212 mg, 1.11 mmol). The reaction was refluxed for 3 hours using a Dean-Stark trap and then cooled to room temperature. A solution of saturated aqueous NaHCO$_3$ and ethyl acetate were added, the organic layer was separated, washed with brine, dried over MgSO$_4$, filtered and concentrated under reduced pressure. Purification by silica gel chromatography provided intermediate 36-e as a yellow oil.

Step 5: Intermediate 36-f

To a solution of intermediate 36-e (1.0 g, 2.66 mmol) in tert-butanol (13 mL) was added a 1.0 M solution of potassium tert-butoxide in THF (2.92 mL, 2.92 mmol), the reaction was stirred at 50° C. for 30 minutes and then cooled to room temperature. A solution of saturated aqueous ammonium chloride and ethyl acetate were added, the organic layer was separated, washed with brine, dried over MgSO$_4$, filtered and concentrated under reduced pressure to provide intermediate 36-f as beige solid.

Step 8: Compound 45

To a solution of intermediate 36-f (1.0 g, 2.66 mmol) in ethanol (33 ml) was added formamidine acetate (2.21 g, 21.26 mmol) and the reaction was stirred at 80° C. for 2 hours and then cooled to room temperature. Volatiles were removed in vacuo. A solution of saturated aqueous ammonium chloride and ethyl acetate were added to the residue, the organic layer was separated, washed with brine, dried over MgSO$_4$, filtered and concentrated under reduced pressure. Purification by reverse phase chromatography eluting with 0.1% aqueous HCl/methanol gradient provided compound 45.HCl as a white solid. MS (m/z) M+H=404.2

Synthesis of Compound 47

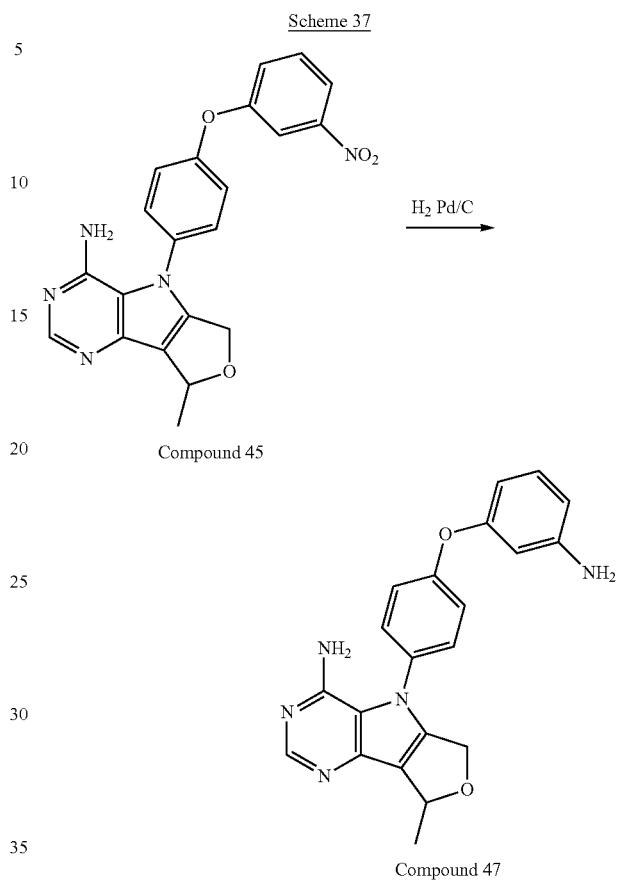

Scheme 37

Compound 45

Compound 47

To a solution of compound 45 (55 mg, 0.14 mmol) in methanol was added 10% Pd/C (51 mg, 0.05 mmol). The reaction mixture was purged with H$_2$ and stirred at room temperature overnight. The reaction was then filtered through celite and the filtrate was concentrated in vacuo. Purification by reverse phase chromatography eluting with a 0.1% aqueous HCl/methanol gradient provided compound 47.2HCl as yellow solid. MS (m/z) M+H=374.2

Synthesis of Intermediate 38-b

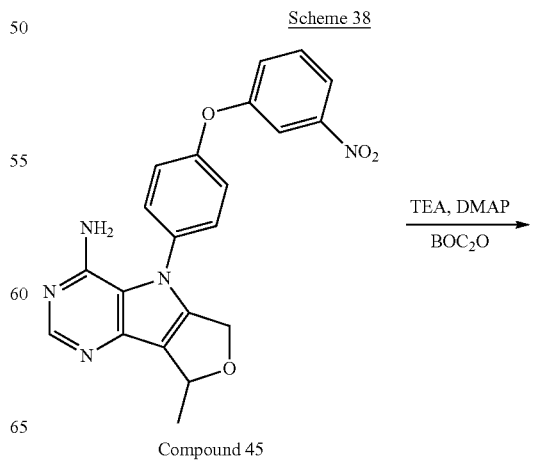

Scheme 38

Compound 45

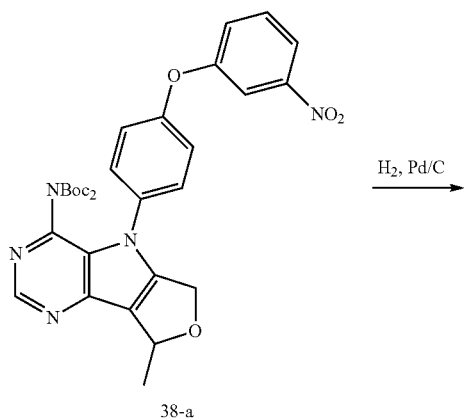

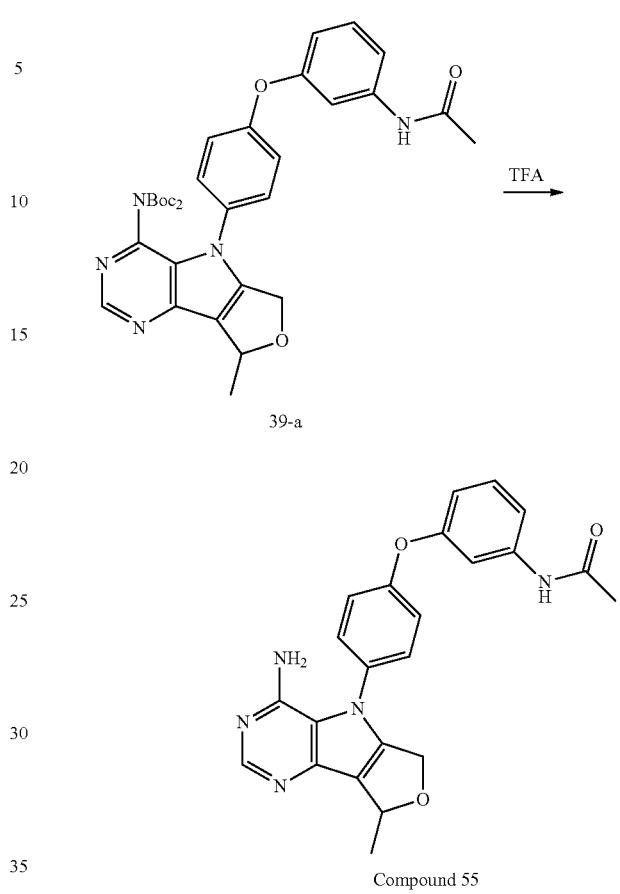

Step 1: Intermediate 38-a

To a solution of compound 45 (570 mg, 1.413 mmol) in THF (14.0 ml) were sequentially added BOC₂O (1.96 ml, 8.48 mmol), DMAP (3.5 mg, 0.283 mmol) and DIPEA (740 μl, 4.24 mmol) and the reaction was stirred for 5 days at room temperature. A saturated aqueous solution of ammonium chloride and ethyl acetate were added, the organic layer was separated, washed with brine, dried over MgSO₄, filtered and concentrated under reduced pressure. Purification by silica gel chromatography provided intermediate 38-a as a brown solid.

Step 2: Intermediate 38-b

To a solution of intermediate 38-a (190 mg, 0.31 mmol) in ethyl acetate and stirred under nitrogen was added 10% Pd/C (117 mg, 0.11 mmol). The reaction mixture was purged with H₂ and stirred at room temperature overnight. The reaction was then filtered through celite and the filtrate was concentrated in vacuo. Purification by reverse phase chromatography provided intermediate 38-b as brown solid.

Synthesis of Compound 55

Step 1: Intermediate 39-a

To a solution of intermediate 38-b (105 mg, 0.183 mmol) in THF (3.05 ml) were sequentially added DIPEA (64 μl, 0.36 mmol), acetyl chloride (14 μl, 0.201 mmol) and the reaction was stirred at room temperature for 2 hours. A solution saturated aqueous of ammonium chloride and ethyl acetate were added, the organic layer was separated, washed with brine, dried over MgSO₄, filtered and concentrated under reduced pressure. Purification by silica gel chromatography provided intermediate 39-a as a yellow solid.

Step 2: Compound 55

To a solution of intermediate 39-a (57 mg, 0.09 mmol) in dichloromethane (1.0 ml) cooled to 0° C. was added TFA (1.07 ml, 13.89 mmol) and the reaction was then stirred at room temperature for 1 hour. Volatiles were removed in vacuo. Purification by reverse phase chromatography eluting with a 0.1% aqueous HCl/methanol gradient provided compound 55.HCl as white solid. MS (m/z) M+H=416.3

Synthesis of Compound 66

Scheme 39

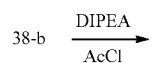

Scheme 40

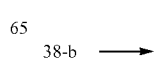

-continued

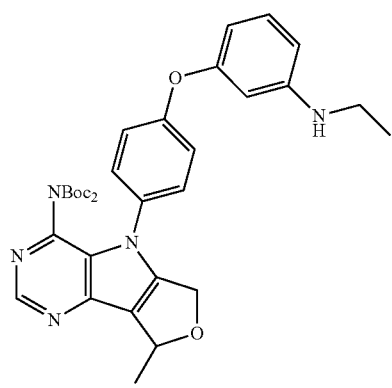

40-a

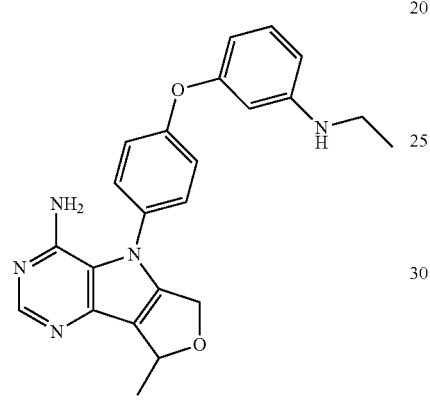

Compound 66

Step 1: Intermediate 40-a

To a solution of intermediate 38-b (80 mg, 0.13 mmol) and acetaldehyde (94 µl, 0.14 mmol) in methanol (0.5 ml) was added sodium cyanoborohydride (53 mg, 0.84 mmol) and the reaction was stirred at room temperature for 24 hours. A solution of saturated aqueous NaNCO₃ and ethyl acetate were added, the organic layer was separated, washed with brine, dried over MgSO₄, filtered and concentrated under reduced pressure. Purification by silica gel chromatography provided intermediate 40-a as a yellow foam.

Step 2: Compound 66

To a solution of intermediate 40-a (60 mg, 0.10 mmol) in dichloromethane (0.5 ml) cooled to 0° C. was added TFA (499 µl, 6.48 mmol) and the reaction was then stirred at room temperature for 1 hour. Volatiles were removed in vacuo. Purification by reverse phase chromatography eluting with a 10% methanol in 0.1% aqueous HCl/methanol gradient provided compound 66.2HCl as yellow solid. MS (m/z) M+H=402.2

Synthesis of Compound 69

Scheme 41

38-b ⟶

-continued

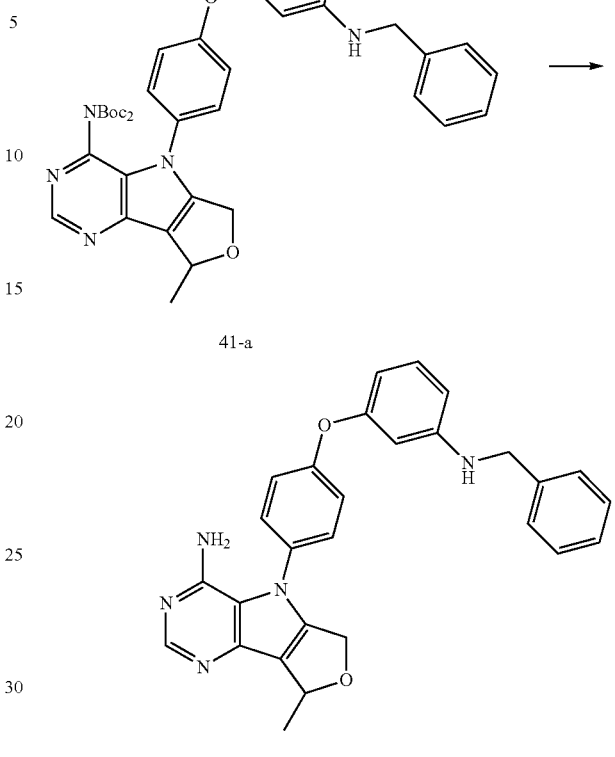

41-a

Compound 69

Step 1: Intermediate 41-a

To a solution of intermediate 38-b (110 mg, 0.192 mmol) and benzaldehyde (41 mg, 0.38 mmol) in methanol (2.0 ml) was added sodium cyanoborohydride (24 mg, 0.38 mmol) and the reaction was stirred at room temperature for 24 hours. A solution of saturated aqueous NaHCO₃ and ethyl acetate were added, the organic layer was separated, washed with brine, dried over MgSO₄, filtered and concentrated under reduced pressure. Purification by silica gel chromatography provided intermediate 41-a as a yellow oil.

Step 2: Compound 69

To a solution of intermediate 41-a (110 mg, 0.16 mmol) in dichloromethane (0.5 ml) cooled to 0° C. was added TFA (830 µl, 10.8 mmol) and the reaction was then stirred at room temperature for 1 hour. Volatiles were removed in vacuo. Purification by reverse phase chromatography eluting with a 0.1% aqueous HCl/methanol gradient provided compound 69.2HCl as yellow solid. MS (m/z) M+H=464.2

Synthesis of Compound 37

Scheme 42

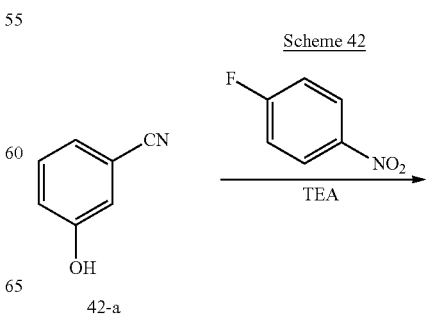

42-a

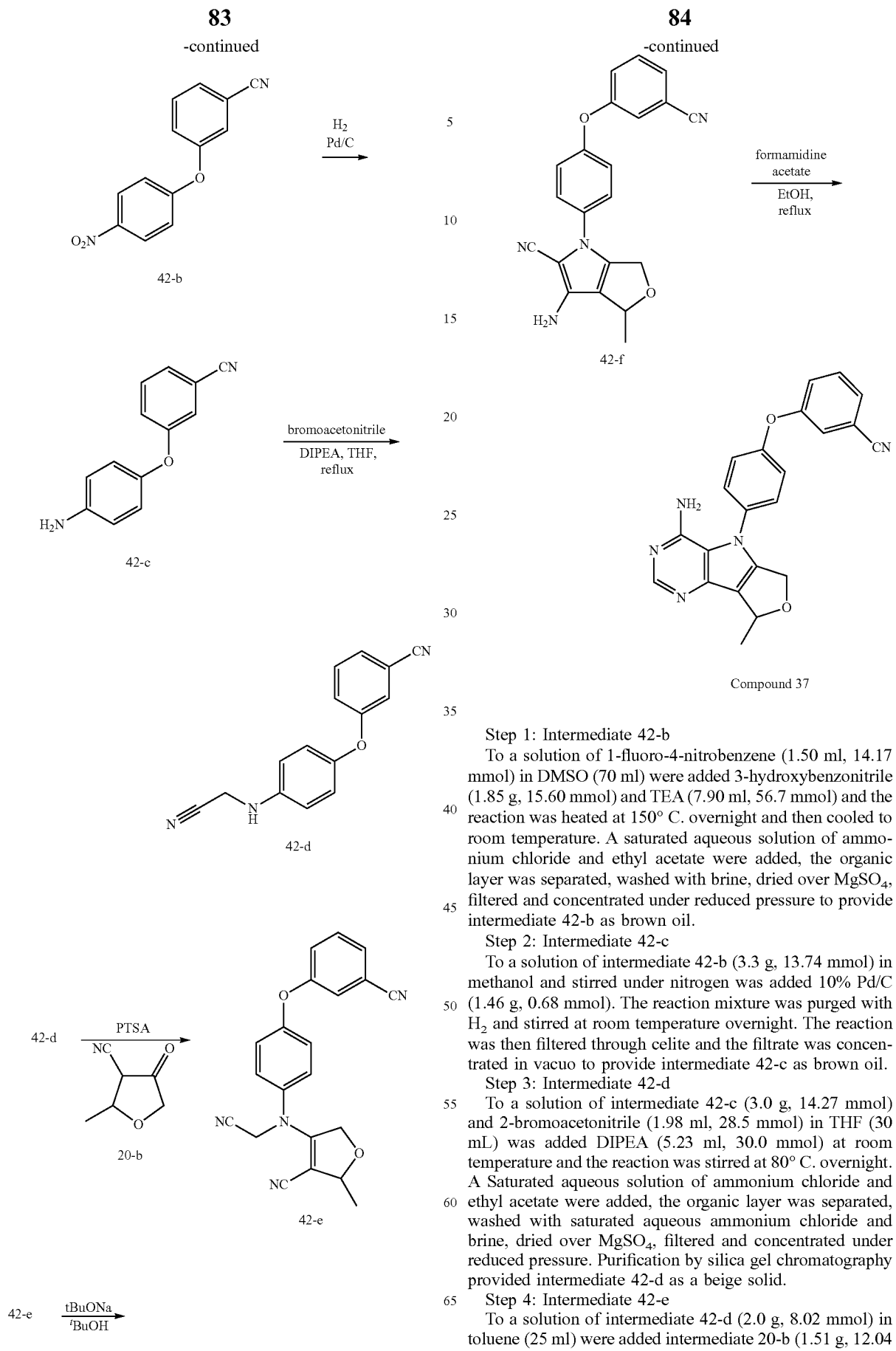

Step 1: Intermediate 42-b

To a solution of 1-fluoro-4-nitrobenzene (1.50 ml, 14.17 mmol) in DMSO (70 ml) were added 3-hydroxybenzonitrile (1.85 g, 15.60 mmol) and TEA (7.90 ml, 56.7 mmol) and the reaction was heated at 150° C. overnight and then cooled to room temperature. A saturated aqueous solution of ammonium chloride and ethyl acetate were added, the organic layer was separated, washed with brine, dried over $MgSO_4$, filtered and concentrated under reduced pressure to provide intermediate 42-b as brown oil.

Step 2: Intermediate 42-c

To a solution of intermediate 42-b (3.3 g, 13.74 mmol) in methanol and stirred under nitrogen was added 10% Pd/C (1.46 g, 0.68 mmol). The reaction mixture was purged with $H_2$ and stirred at room temperature overnight. The reaction was then filtered through celite and the filtrate was concentrated in vacuo to provide intermediate 42-c as brown oil.

Step 3: Intermediate 42-d

To a solution of intermediate 42-c (3.0 g, 14.27 mmol) and 2-bromoacetonitrile (1.98 ml, 28.5 mmol) in THF (30 mL) was added DIPEA (5.23 ml, 30.0 mmol) at room temperature and the reaction was stirred at 80° C. overnight. A Saturated aqueous solution of ammonium chloride and ethyl acetate were added, the organic layer was separated, washed with saturated aqueous ammonium chloride and brine, dried over $MgSO_4$, filtered and concentrated under reduced pressure. Purification by silica gel chromatography provided intermediate 42-d as a beige solid.

Step 4: Intermediate 42-e

To a solution of intermediate 42-d (2.0 g, 8.02 mmol) in toluene (25 ml) were added intermediate 20-b (1.51 g, 12.04 mmol) and 4-methylbenzenesulfonic acid hydrate (153 mg, 0.80 mmol). The reaction was refluxed for 3 hours using a dean-stark and then cooled to room temperature. Saturated aqueous NaHCO$_3$ and ethyl acetate were added, the organic layer was separated, washed with brine, dried over MgSO$_4$, filtered and concentrated under reduced pressure to provide intermediate 42-e as brown solid.

Step 5: Intermediate 42-f

To a solution of intermediate 42-e (2.9 g, 8.14 mmol) in tert-butanol (40 mL) was added a 1.0 M solution of potassium tert-butoxide in THF (8.95 mL, 8.95 mmol), the reaction was stirred at 80° C. for 30 minutes and then cooled to room temperature. A saturated aqueous solution of ammonium chloride and ethyl acetate were added, the organic layer was separated, washed with brine, dried over MgSO$_4$, filtered and concentrated under reduced pressure to provide intermediate 42-f as brown solid.

Step 6: Compound 37

To a solution of intermediate 42-f (600 mg, 1.68 mmol) in ethanol (7.0 ml) was added formamidine acetate (1.20 g, 11.53 mmol) and the reaction was stirred at 80° C. for 2 hours and then cooled to room temperature. Volatiles were removed in vacuo. Saturated aqueous ammonium chloride and ethyl acetate were added to the residue, the organic layer was separated, washed with brine, dried over MgSO$_4$, filtered and concentrated under reduced pressure. Purification by reverse phase chromatography eluting with a 10% methanol in 0.1% HCl to 40% methanol in 0.1% HCl gradient provided compound 37.HCl as a beige solid. MS (m/z) M+H=384.3

Synthesis of Compound 38

To a solution of compound 37 (250 mg, 0.65 mmol) in DMSO (13.0 ml) were sequentially added 1N sodium hydroxide (652 µl, 0.65 mmol), H$_2$O$_2$ (100 µl, 0.97 mmol) and the mixture was stirred at room temperature for 15 minutes.

Water was added; a precipitate formed and was collected by filtration, washed with diethyl ether to provide compound 38 as white solid. MS (m/z) M+H=402.2

Synthesis of Compound 39

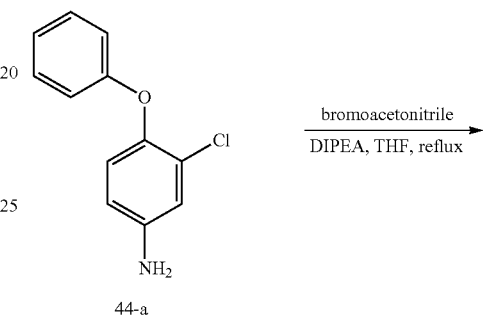

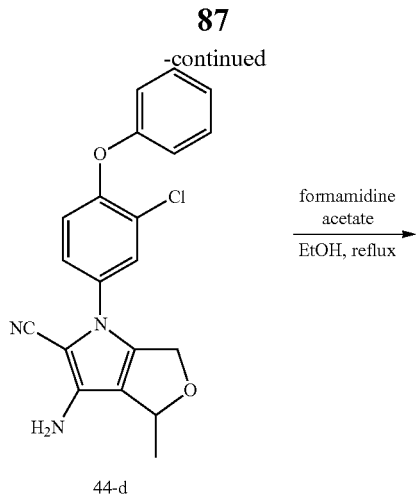

44-d

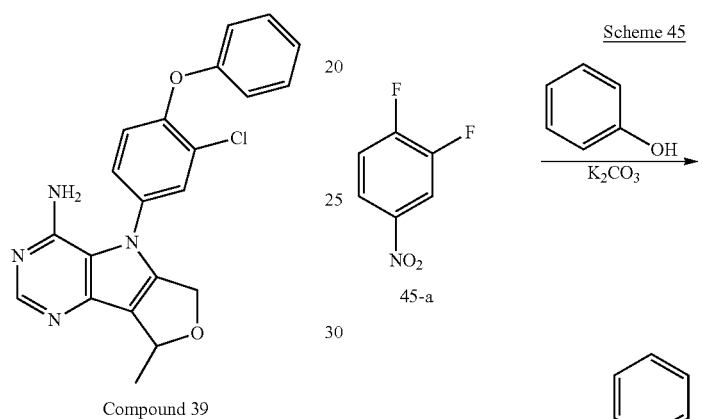

Compound 39

Step 1: Intermediate 44-b

To a solution of intermediate 44-a (3.0 g, 11.71 mmol) and 2-bromoacetonitrile (2.44 ml, 35.1 mmol) in THF (110 mL) was added DIPEA (8.77 ml, 50.4 mmol) at room temperature and the reaction was stirred at 80° C. overnight. Saturated aqueous ammonium chloride and ethyl acetate were added, the organic layer was separated, washed with a saturated aqueous solution of ammonium chloride and brine, dried over MgSO$_4$, filtered and concentrated under reduced pressure to provide intermediate 44-b as brown oil.

Step 2: Intermediate 44-c

To a solution of intermediate 44-b (3.02 g, 11.67 mmol) in toluene (110 ml) were added intermediate 20-b (1.75 g, 14.01 mmol) and 4-methylbenzenesulfonic acid hydrate (222 mg, 1.16 mmol). The reaction was refluxed for 18 hours using a dean-stark and then cooled to room temperature. Saturated aqueous NaHCO$_3$ and ethyl acetate were added, the organic layer was separated, washed with brine, dried over MgSO$_4$, filtered and concentrated under reduced pressure. Purification by silica gel chromatography provided intermediate 44-c as a yellow oil.

Step 3: Intermediate 44-d

To a solution of intermediate 44-c (3.04 g, 8.31 mmol) in tert-butanol (80 mL) was added a 1.0 M solution of potassium tert-butoxide in THF (9.14 mL, 9.14 mmol), the reaction was stirred at 80° C. for 18 hours and then cooled to room temperature. 10% Aqueous HCl and ethyl acetate were added, the organic layer was separated, washed with brine, dried over MgSO$_4$, filtered and concentrated under reduced pressure to provide intermediate 44-d as brown solid. MS (m/z) M+H=366.3

Step 4: Compound 39

To a solution of intermediate 44-d (3.03 g, 8.28 mmol) in ethanol (83.0 ml) was added formamidine acetate (6.90 g, 66.30 mmol) and the reaction was stirred at 80° C. for 18 hours and then cooled to room temperature. Volatiles were removed in vacuo. A saturated aqueous solution of ammonium chloride and ethyl acetate were added to the residue, the organic layer was separated, washed with brine, dried over MgSO$_4$, filtered and concentrated under reduced pressure. Purification by reverse phase chromatography eluting with a 0.1% aqueous HCl/methanol gradient provided compound 39.HCl as a pale yellow solid. MS (m/z) M+H=393.6

Synthesis of Compound 40

Scheme 45

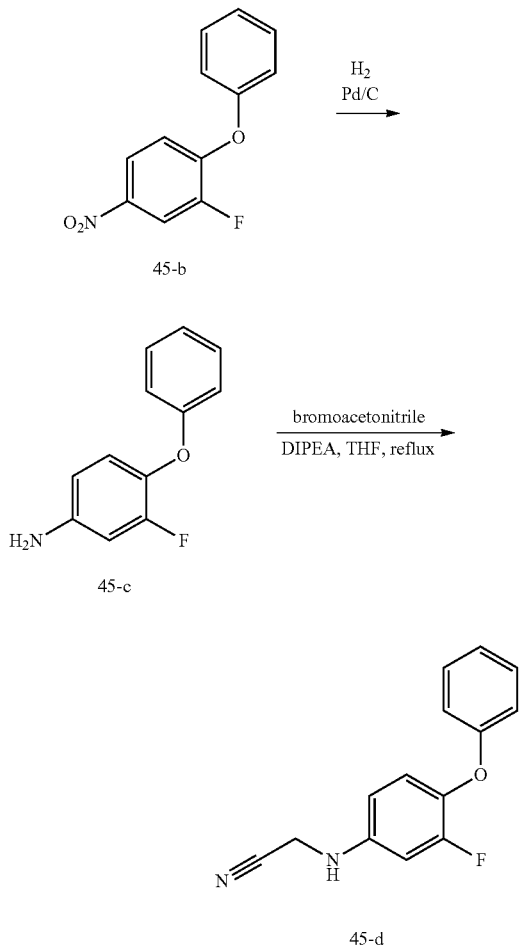

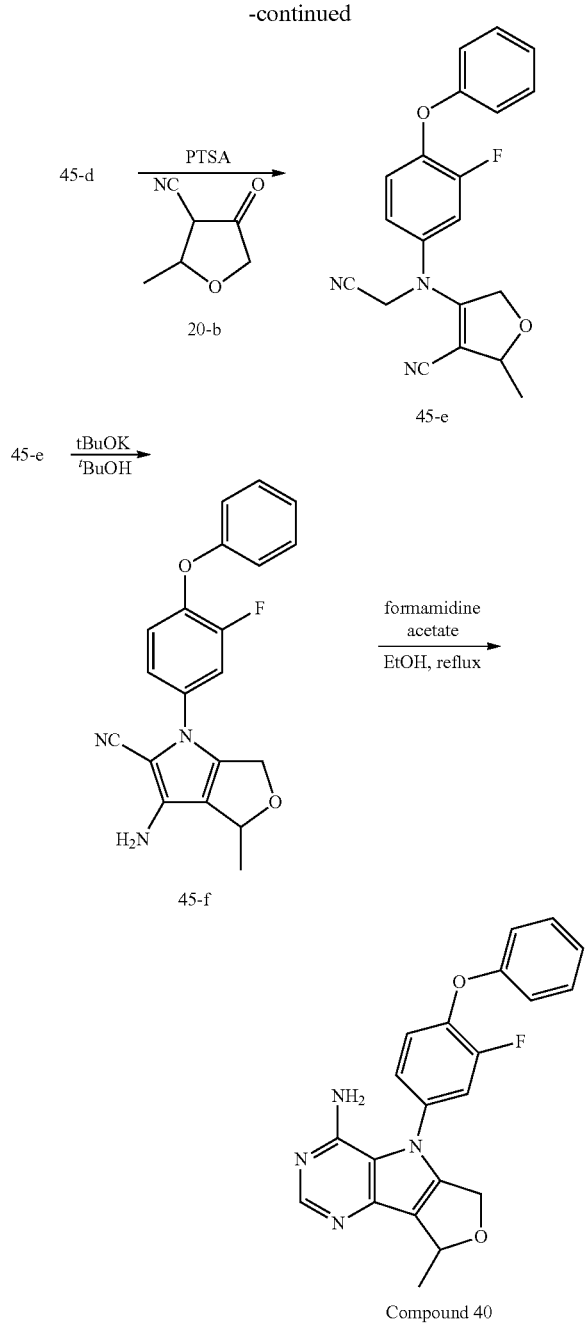

Step 1: Intermediate 45-b

To a solution of intermediate 1,2-difluoro-4-nitrobenzene 45-a (2.08 ml, 18.86 mmol) in DMF (37 ml) were sequentially added phenol (1.95 g, 20.74 mmol), potassium carbonate (2.87 g, 20.74 mmol) and the reaction was stirred at 150° C. overnight and then cooled to room temperature. Volatiles were removed in vacuo.

Water and ethyl acetate were added, the organic layer was separated, washed with brine, dried over MgSO$_4$, filtered and concentrated under reduced pressure to provide intermediate 45-b as brown oil.

Step 2: Intermediate 45-c

To a solution of intermediate 45-b (4.4 g, 18.87 mmol) in methanol (90 ml) and stirred under nitrogen was added 10% Pd/C (1.00 g, 94.3 mmol). The reaction mixture was purged with H$_2$ and stirred at room temperature overnight. The reaction was then filtered through celite and the filtrate was concentrated in vacuo to provide intermediate 45-c as brown oil. MS (m/z) M+H=204.1

Step 3: Intermediate 45-d

To a solution of intermediate 45-c (3.83 g, 18.85 mmol) and 2-bromoacetonitrile (3.94 ml, 56.5 mmol) in THF (95 mL) was added DIPEA (10.83 ml, 62.2 mmol) at room temperature and the reaction was stirred at 80° C. overnight. Saturated aqueous ammonium chloride and ethyl acetate were added, the organic layer was separated, washed with a saturated aqueous solution of ammonium chloride and brine, dried over MgSO$_4$, filtered and concentrated under reduced pressure. Purification by silica gel chromatography provided intermediate 45-d as a brown oil.

Step 4: Intermediate 45-e

To a solution of intermediate 45-d (4.50 g, 18.58 mmol) in toluene (190 ml) were added intermediate 20-b (3.25 g, 26.0 mmol) and 4-methylbenzenesulfonic acid hydrate (707 mg, 3.72 mmol). The reaction was refluxed for 18 hours using a Dean-Stark apparatus and then cooled to room temperature. A saturated aqueous solution of NaHCO$_3$ and ethyl acetate were added, the organic layer was separated, washed with brine, dried over MgSO$_4$, filtered and concentrated under reduced pressure. Purification by silica gel chromatography provided intermediate 45-e as a yellow oil.

Step 5: Intermediate 45-f

To a solution of intermediate 45-e (3.31 g, 9.47 mmol) in tert-butanol (95 mL) was added a 1.0 M solution of potassium tert-butoxide in THF (10.42 mL, 10.42 mmol), the reaction was stirred at 80° C. for 18 hours and then cooled to room temperature. 10% Aqueous HCl and ethyl acetate were added, the organic layer was separated, washed with brine, dried over MgSO$_4$, filtered and concentrated under reduced pressure to provide intermediate 45-f as brown solid. MS (m/z) M+H=350.4

Step 6: Compound 40

To a solution of intermediate 45-f (3.30 g, 9.45 mmol) in ethanol (95.0 ml) was added formamidine acetate (7.87 g, 76.0 mmol) and the reaction was stirred at 80° C. for 18 hours and then cooled to room temperature. Volatiles were removed in vacuo. Saturated aqueous ammonium chloride and ethyl acetate were added to the residue, the organic layer was separated, washed with brine, dried over MgSO$_4$, filtered and concentrated under reduced pressure. Purification by reverse phase chromatography eluting with a 0.1% aqueous HCl/methanol gradient provided compound 40.HCl as a white solid. MS (m/z) M+H=377.2

Synthesis of Compound 80

Scheme 46

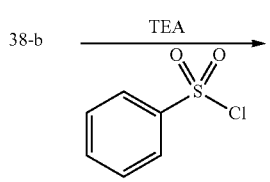

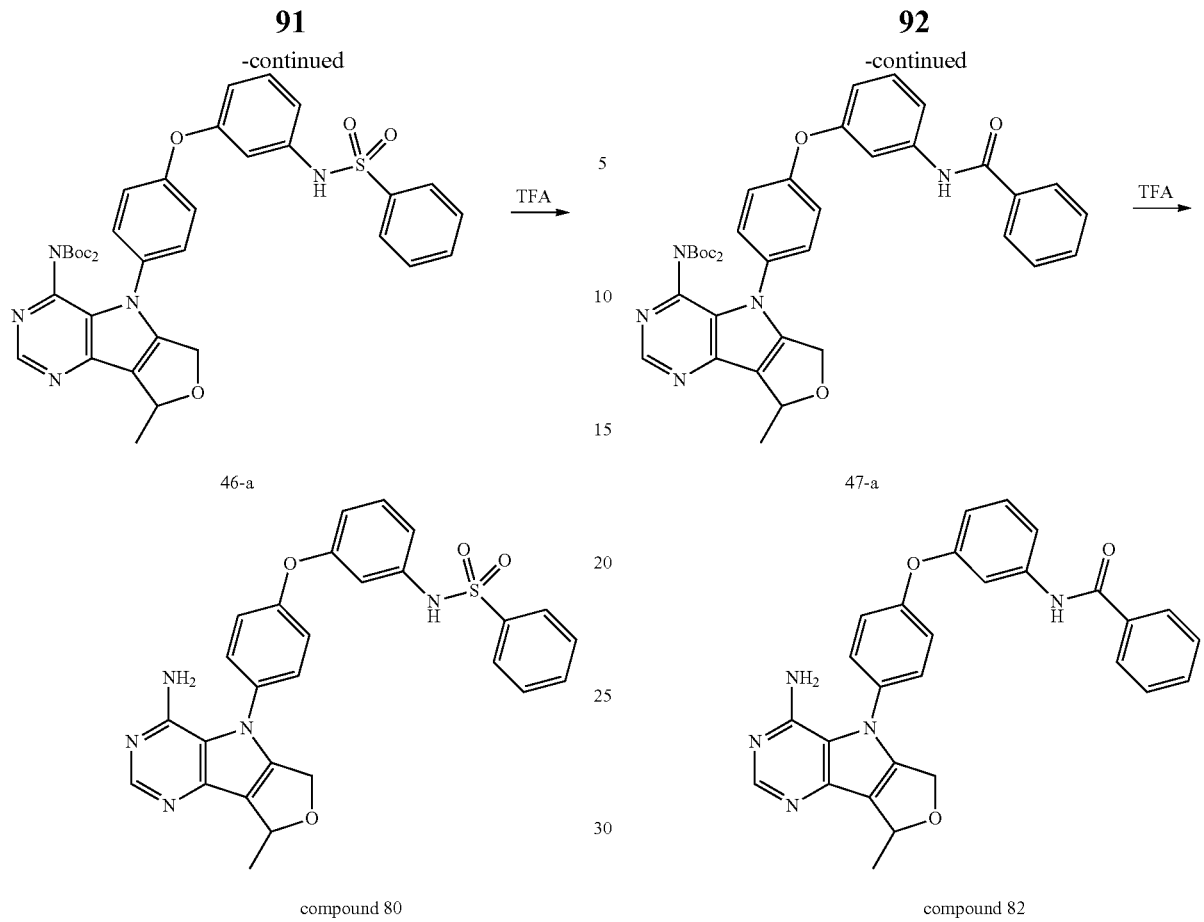

46-a compound 80

47-a compound 82

Step 1: Intermediate 46-a

To a solution of intermediate 38-b (100 mg, 0.17 mmol) in THF (2.90 ml) were sequentially added TEA (27 µl, 0.19 mmol), benzenesulfonyl chloride (33 µl, 0.26 mmol) and the reaction was stirred at room temperature for 2 days. Saturated aqueous ammonium chloride and ethyl acetate were added, the organic layer was separated, washed with brine, dried over MgSO$_4$, filtered and concentrated under reduced pressure. Purification by silica gel chromatography provided intermediate 46-a as a yellow solid.

Step 2: Compound 80

To a solution of intermediate 46-a (100 mg, 0.14 mmol) in dichloromethane (1.0 ml) cooled to 0° C. was added TFA (97 µl, 12.61 mmol) and the reaction was then stirred at room temperature for 1 hour. Volatiles were removed under reduced pressure. Purification by reverse phase chromatography eluting with a 0.1% HCl/methanol gradient provided compound 80.HCl as white solid. MS (m/z) M+H=514.1

Synthesis of Compound 82

Step 1: Intermediate 47-a

To a solution of intermediate 38-b (100 mg, 0.17 mmol) in THF (2.90 ml) were sequentially added DIPEA (61 µl, 0.35 mmol), benzoyl chloride (27 mg, 0.19 mmol) and the reaction was stirred at room temperature for 2 hours. Saturated aqueous ammonium chloride and ethyl acetate were added, the organic layer was separated, washed with brine, dried over MgSO$_4$, filtered and concentrated under reduced pressure. Purification by silica gel chromatography provided intermediate 47-a as a yellow solid.

Step 2: Compound 82

To a solution of intermediate 47-a (118 mg, 0.17 mmol) in dichloromethane (1.0 ml) cooled to 0° C. was added TFA (1.07 ml, 13.93 mmol) and the reaction was then stirred at room temperature for 1 hour. Volatiles were removed under reduced pressure. Purification by reverse phase chromatography eluting with a 0.1% aqueous HCl/methanol gradient provided compound 82.HCl as white solid. MS (m/z) M+H=478.2

Synthesis of Intermediate 48-e

Scheme 47

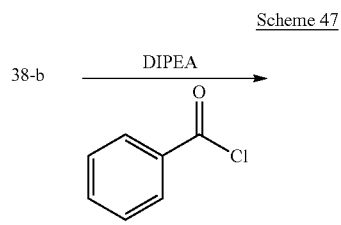

Scheme 48

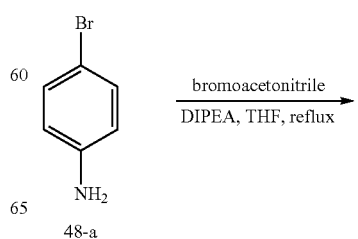

48-a

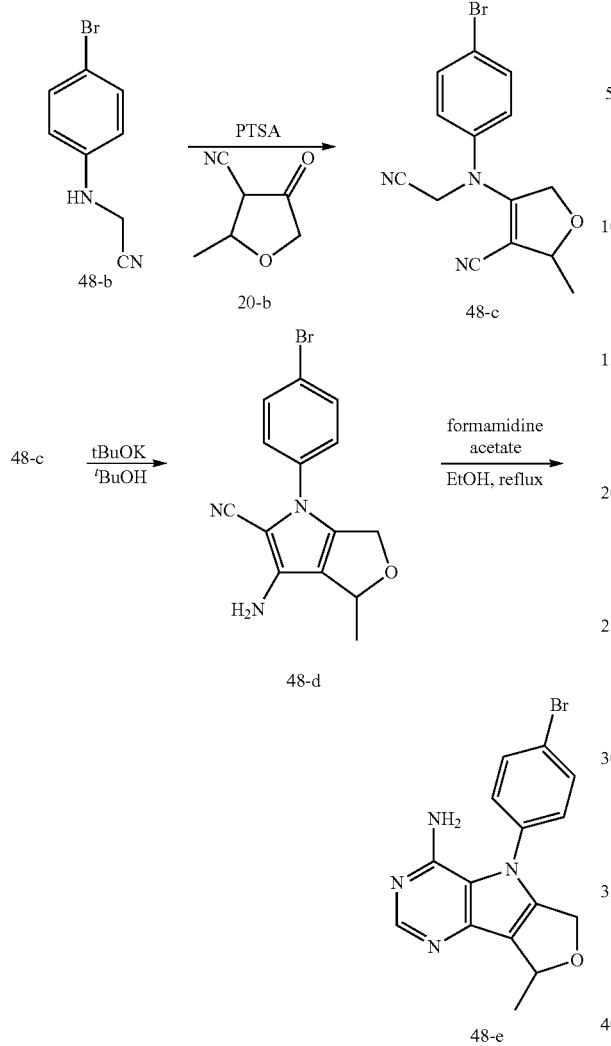

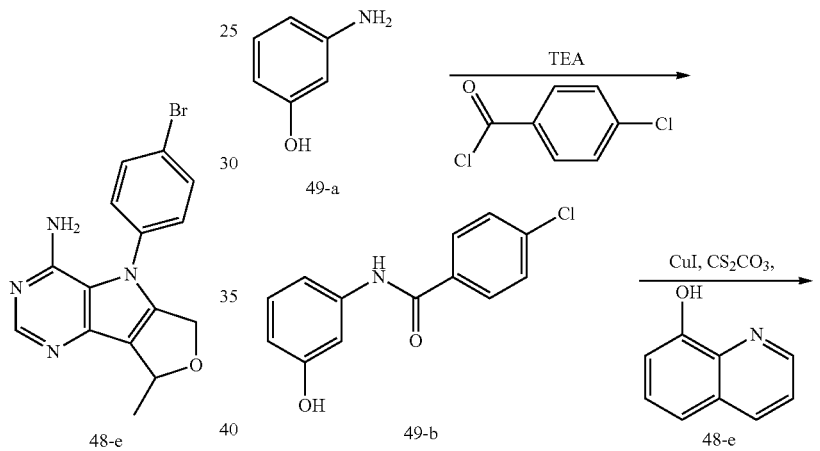

Step 1: Intermediate 48-b

To a solution of 4-bromoaniline, 48-a (36.0 g, 209 mmol), and 2-bromoacetonitrile (30.1 g, 251 mmol) in THF (200 ml) was added DIPEA (54.8 ml, 314 mmol) and the reaction was stirred at 80° C. overnight then cooled to room temperature. Saturated aqueous ammonium chloride and ethyl acetate were added, the organic layer was separated, washed with a saturated aqueous solution of ammonium chloride and brine, dried over MgSO$_4$, filtered and concentrated under reduced pressure. Hexane was added to the residue; a precipitate formed and was collected by filtration to provide intermediate 48-b as beige solid.

Step 2: Intermediate 48-c

To a solution of intermediate 20-b (10.1 g, 81.0 mmol) in toluene (50 ml) were added intermediate 48-a (9.46 g, 44.8 mmol) and 4-methylbenzenesulfonic acid hydrate (853 mg, 4.48 mmol). The reaction was refluxed for 3 hours using a Dean-Stark apparatus and then cooled to room temperature. A saturated aqueous solution of NaHCO$_3$ and ethyl acetate were added, the organic layer was separated, washed with brine, dried over MgSO$_4$, filtered and concentrated under reduced pressure to provide intermediate 48-c as brown oil.

Step 3: Intermediate 48-d

To a solution of intermediate 48-c (14.25 g, 44.8 mmol) in tBuOH (50.0 ml) was added a 1.0 M THF solution of potassium tert-butoxide (44.8 ml, 44.8 mmol), the reaction was stirred at 80° C. for 1 hour and then cooled to room temperature. A saturated aqueous solution of ammonium chloride and ethyl acetate were added, the organic layer was separated, the aqueous phase was extracted with ethyl acetate, the combined organic extracts were washed with brine, dried over MgSO$_4$, filtered and concentrated under reduced pressure to provide intermediate 48-d as a brown solid.

Step 4: Intermediate 48-e

To a solution of intermediate 48-d (14.25 g, 44.8 mmol) in ethanol (100 ml) was added formamidine acetate (37.3 g, 358.0 mmol), the reaction was stirred at 80° C. overnight and then cooled to room temperature. Volatiles were removed in vacuo. Saturated aqueous ammonium chloride and ethyl acetate were added to the residue, the organic layer was separated, washed with brine, dried over MgSO$_4$, filtered and concentrated under reduced pressure. Purification by silica gel chromatography provided intermediate 48-e as beige solid.

Synthesis of Compound 120

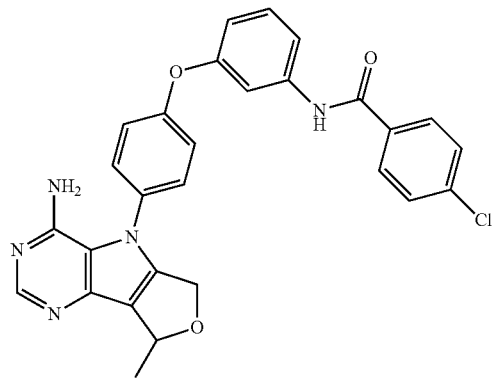

Compound 120

Step 1: Intermediate 49-b

To a stirred solution of 3-aminophenol, 49-a (3.0 g, 27.5 mmol), in ethyl acetate (50 ml), were sequentially added TEA (3.81 ml, 27.5 mmol) and 4-chlorobenzoyl chloride (4.81 g, 27.5 mmol) at 0° C. and the reaction mixture was stirred at 0° C. for 2 hours. 10% Aqueous citric acid was added; a precipitate formed and was collected by filtration, washed with diethyl ether to provide intermediate 49-b as white solid.

Step 2: Compound 120

A solution of intermediate 48-e (200 mg, 0.58 mmol), intermediate 49-b (359 mg, 1.44 mmol), quinolin-8-ol (17 mg, 0.11 mmol), copper (I) iodide (110 mg, 0.58 mmol) and cesium carbonate (378 mg, 1.15 mmol) in dimethylacetamide (2.90 ml) was degassed with argon for 10 minutes, heated in a sealed tube at 120° C. for 3 hours and then cooled to room temperature. Water and ethyl acetate were added, the organic layer was separated, the aqueous layer was extracted twice with ethyl acetate, the combined organic extracts were washed with brine, dried over MgSO$_4$, filtered and concentrated under reduced pressure. Purification by reverse phase chromatography eluting with a 0.1% aqueous HCl/methanol gradient provided compound 120.HCl as beige solid. MS (m/z) M+H=512.3

Synthesis of Compound 126

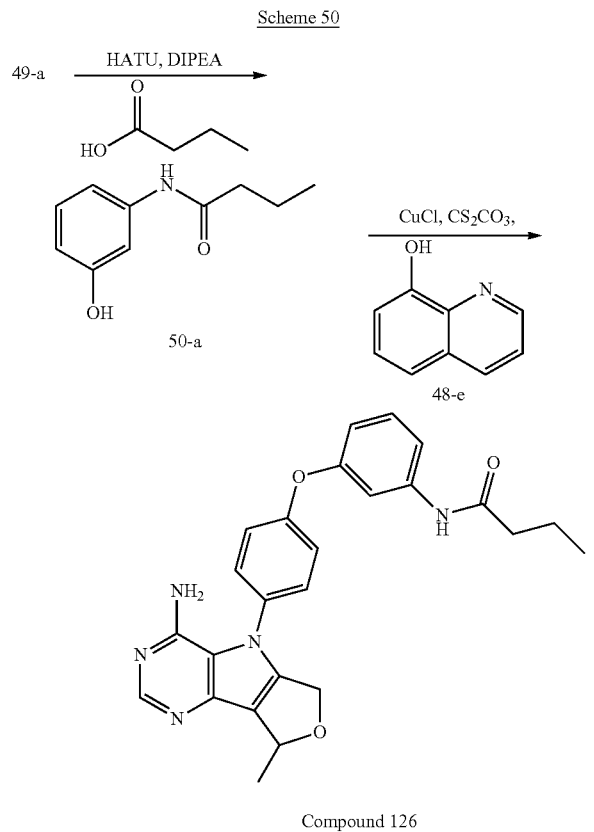

Compound 126

Step 1: Intermediate 50-a

To a solution of butyric acid (4.04 g, 45.8 mmol) in DMF (100 ml) cooled to 0° C. were sequentially added, 3-aminophenol 49-a (5.0 g, 45.8 mmol), HATU (19.16 g, 50.4 mmol) and DIPEA (9.60 ml, 55.0 mmol). The reaction mixture was stirred overnight at room temperature. A saturated aqueous solution of ammonium chloride and ethyl acetate were added, the organic layer was separated, washed with 1N HCl, a saturated aqueous solution of NaHCO$_3$ and brine, dried over MgSO$_4$, filtered and concentrated under reduced pressure. Purification by silica gel chromatography provided intermediate 50-a as white solid.

Step 2: Compound 126

A solution of intermediate 48-e (200 mg, 0.58 mmol), intermediate 50-a (104 mg, 0.57 mmol), quinolin-8-ol (17 mg, 0.11 mmol), copper (I) chloride (11.4 mg, 0.11 mmol) and cesium carbonate (566 mg, 1.74 mmol) in dimethylacetamide (5.7 ml) was degassed with argon for 10 minutes, heated in a sealed tube at 140° C. for 3 hours and then cooled to room temperature. Water and ethyl acetate were added, the organic layer was separated, the aqueous layer was extracted twice with ethyl acetate, the combined organic extracts were washed with brine, dried over MgSO$_4$, filtered and concentrated under reduced pressure. Purification by reverse phase chromatography eluting with 10-70% methanol in 0.1% HCl gradient provided compound 126.HCl as beige solid. MS (m/z) M+H=444.2

Synthesis of Compound 89

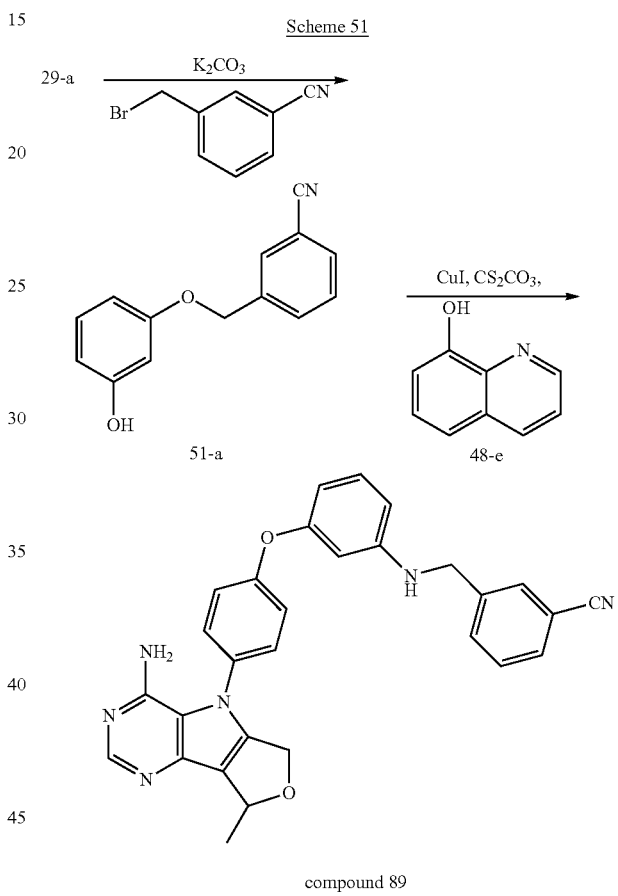

compound 89

Step 1: Intermediate 51-a

To a solution of 2-(bromomethyl)benzonitrile (1 g, 5.10 mmol) and resorcinol, 29-a (2.81 g, 25.5 mmol), in acetone (50 ml) was added cesium carbonate (3.32 g, 10.20 mmol) and the reaction was refluxed for 2 hours. Volatiles were removed in vacuo. Saturated aqueous ammonium chloride and ethyl acetate were added, the organic layer was separated, washed with brine, dried over MgSO$_4$, filtered and concentrated under reduced pressure. Purification by silica gel chromatography provided intermediate 51-a as white solid.

Step 2: Compound 89

A solution of intermediate 48-e (406 mg, 1.17 mmol), intermediate 51-a (530 mg, 2.35 mmol), quinolin-8-ol (34 mg, 0.23 mmol), copper (I) iodide (45 mg, 0.23 mmol) and cesium carbonate (767 mg, 2.35 mmol) in dimethylacetamide (11.8 ml) was degassed with argon for 10 minutes, heated in a sealed tube at 170° C. for 2 hours and then cooled to room temperature. Water and ethyl acetate were added, the organic layer was separated, the aqueous layer was extracted twice with ethyl acetate, the combined organic extracts were washed with brine, dried over MgSO₄, filtered and concentrated under reduced pressure. Purification by reverse phase chromatography eluting with 10-70% methanol in 0.1% HCl gradient provided compound 89.HCl as white solid. MS (m/z) M+H=490.1

Synthesis of Compound 92

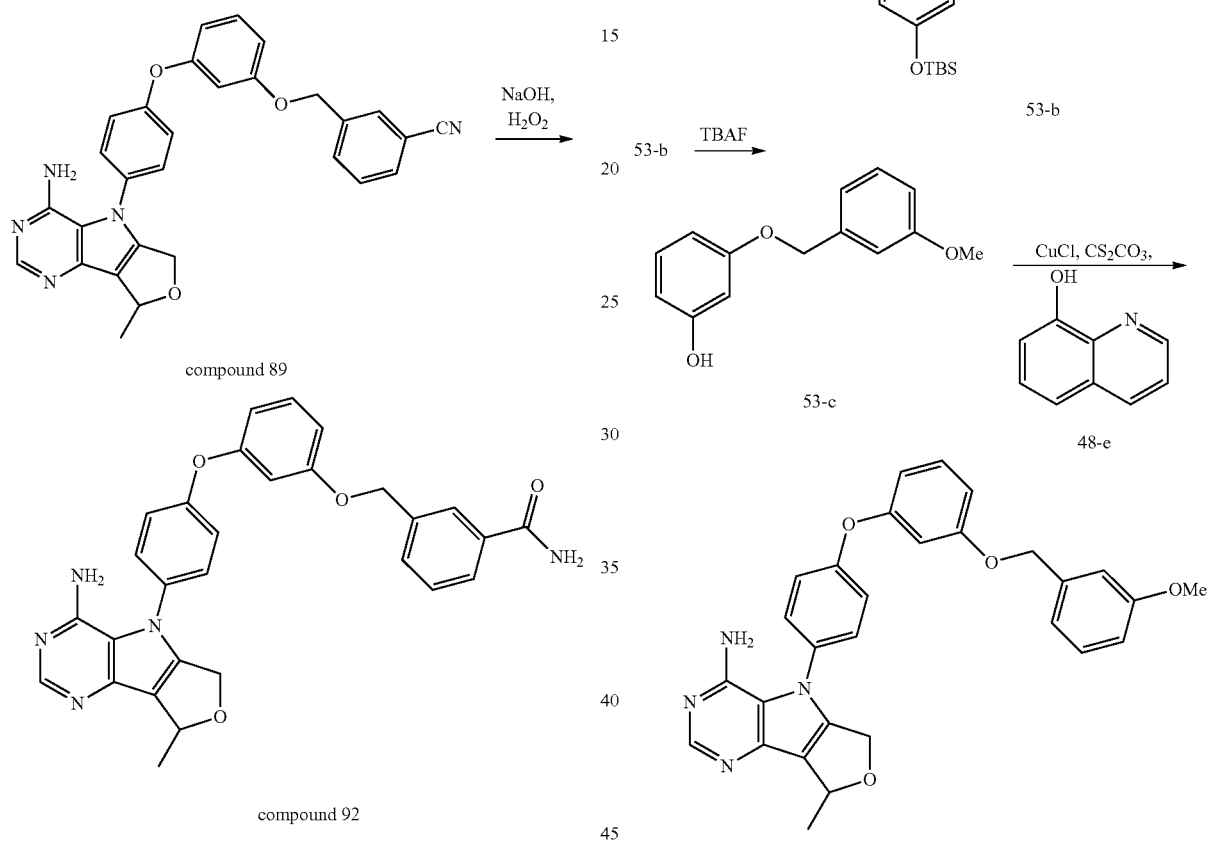

To a solution of compound 89 (70 mg, 0.14 mmol) in methanol (1.4 ml) and DMSO (1.4 ml) were sequentially added 1N sodium hydroxide (107 μl, 0.21 mmol), H₂O₂ (4.3 μl, 0.0.14 mmol) and the mixture was stirred at room temperature for 2 hours. Water and ethyl acetate were added, the organic layer was separated, the aqueous layer was extracted twice with ethyl acetate, the combined organic extracts were washed with brine, dried over MgSO₄, filtered and concentrated under reduced pressure. Purification by reverse phase chromatography eluting with 10-70% methanol in 0.1% HCl gradient provided compound 92.HCl as white solid. MS (m/z) M+H=508.1

Synthesis of Compound 103

Step 1: Intermediate 53-a

To a solution of resorcinol, 29-a (15.0 g, 136 mmol), in DMF (100 ml) cooled to 0° C. were sequentially added imidazole (19.48 g, 286 mmol) and tert-butylchlorodimethylsilane (21.56 g, 143 mmol). The mixture was stirred at room temperature overnight. Saturated aqueous ammonium chloride and ethyl acetate were added, the organic layer was separated, washed 3 times with a saturated aqueous solution of ammonium chloride and brine, dried over MgSO₄, filtered and concentrated under reduced pressure. Purification by silica gel chromatography provided intermediate 53-a as colorless oil.

Step 2: Intermediate 53-b

To a solution of (3-methoxyphenyl)methanol (1.38 g, 10.0 mmol) in THF (20 mL) were sequentially added intermediate 53-a (2.69 g, 12.0 mmol), triphenylphosphine (3.15 g, 12.0 mmol) and DIAD (2.36 ml, 12.0 mmol) and the reaction was then stirred for 1 hour at room temperature. Saturated aqueous ammonium chloride and ethyl acetate were added, the organic layer was separated, washed with brine, dried over MgSO$_4$, filtered and concentrated under reduced pressure. Purification by silica gel chromatography provided intermediate 53-b as colorless oil.

Step 3: Intermediate 53-c

Tetrabutylammonium fluoride trihydrate (2.88 g, 9.14 mmol) was added to a solution of intermediate 53-b (2.10 g, 6.10 mmol) in THF (10 mL) and the reaction was stirred at room temperature overnight. Saturated aqueous ammonium chloride and ethyl acetate were added, the organic layer was separated, washed with brine, dried over MgSO$_4$, filtered and concentrated under reduced pressure. Purification by silica gel chromatography provided intermediate 53-c as colorless oil.

Step 3: Compound 103

A solution of intermediate 48-e (200 mg, 0.57 mmol), intermediate 53-c (233 mg, 1.0 mmol), quinolin-8-ol (16.8 mg, 0.11 mmol), copper (I) chloride (11.5 mg, 0.11 mmol) and cesium carbonate (566 mg, 1.74 mmol) in dimethylacetamide (5.7 ml) was degassed with argon for 10 minutes, heated in a sealed tube at 140° C. for 3 hours and then cooled to room temperature. Water and ethyl acetate were added, the organic layer was separated, the aqueous layer was extracted twice with ethyl acetate, the combined organic extracts were washed with brine, dried over MgSO$_4$, filtered and concentrated under reduced pressure. Purification by reverse phase chromatography eluting with 10-70% methanol in 0.1% HCl gradient provided compound 103.HCl as white solid. MS (m/z) M+H=495.1

Synthesis of Compound 105

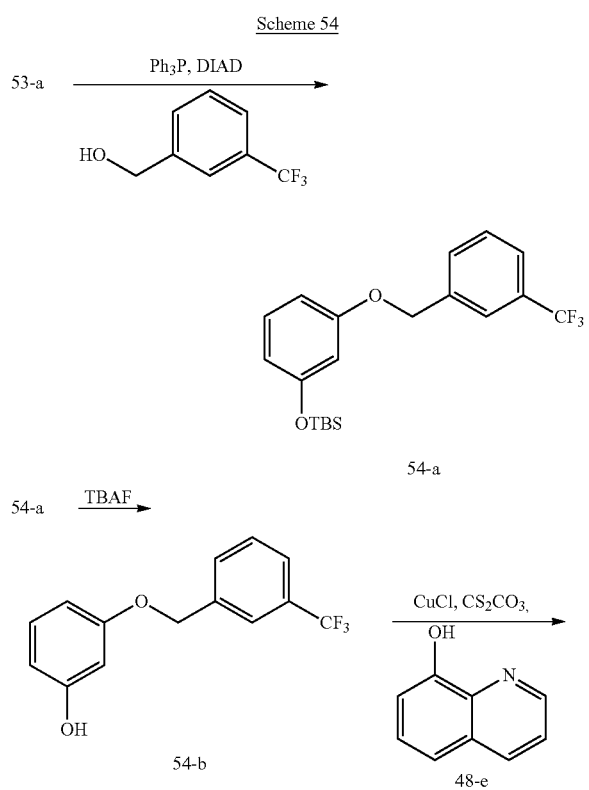

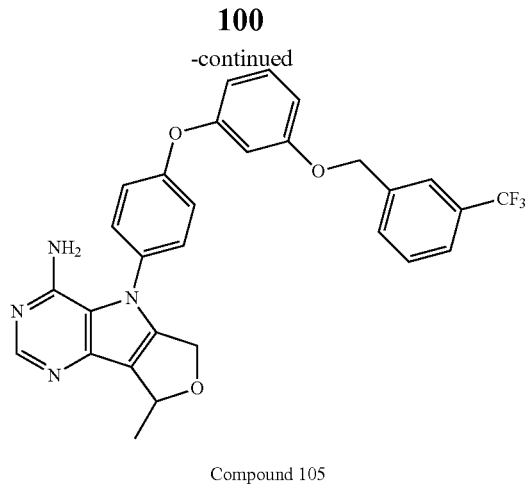

Compound 105

Step 1: Intermediate 54-a

To a solution of (3-(trifluoromethyl)phenyl) methanol (1.41 g, 8.0 mmol) in THF (20 mL) were sequentially added intermediate 53-a (2.15 g, 9.6 mmol), triphenylphosphine (2.52 g, 9.6 mmol) and DIAD (1.89 ml, 9.6 mmol) drop wise at room temperature. The reaction was then stirred for 1 hour. Saturated aqueous ammonium chloride and ethyl acetate were added, the organic layer was separated, washed with brine, dried over MgSO$_4$, filtered and concentrated under reduced pressure. Purification by silica gel chromatography provided intermediate 54-a as a colorless oil.

Step 2: Intermediate 54-b

Tetrabutylammonium fluoride trihydrate (2.72 g, 8.63 mmol) was added to a solution of intermediate 54-a (2.20 g, 5.75 mmol) in THF (10 mL) and stirred at room temperature overnight. Saturated aqueous ammonium chloride and ethyl acetate were added, the organic layer was separated, washed with brine, dried over MgSO$_4$, filtered and concentrated under reduced pressure. Purification by silica gel chromatography provided intermediate 54-b as colorless oil.

Step 3: Compound 105

A solution of intermediate 48-e (200 mg, 0.57 mmol), intermediate 54-b (272 mg, 1.01 mmol), quinolin-8-ol (16.8 mg, 0.11 mmol), copper (I) chloride (11.5 mg, 0.11 mmol) and cesium carbonate (566 mg, 1.74 mmol) in dimethylacetamide (5.7 ml) was degassed with argon for 10 minutes, heated in a sealed tube at 140° C. for 3 hours and then cooled to room temperature. Water and ethyl acetate were added, the organic layer was separated, the aqueous layer was extracted twice with ethyl acetate, the combined organic extracts were washed with brine, dried over MgSO$_4$, filtered and concentrated under reduced pressure. Purification by reverse phase chromatography eluting with 10-70% methanol in 0.1% HCl gradient provided compound 105.HCl as white solid. MS (m/z) M+H=533.0

Synthesis of Compound 106

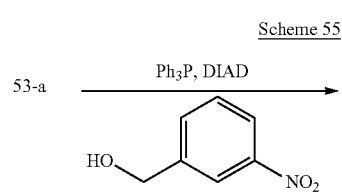

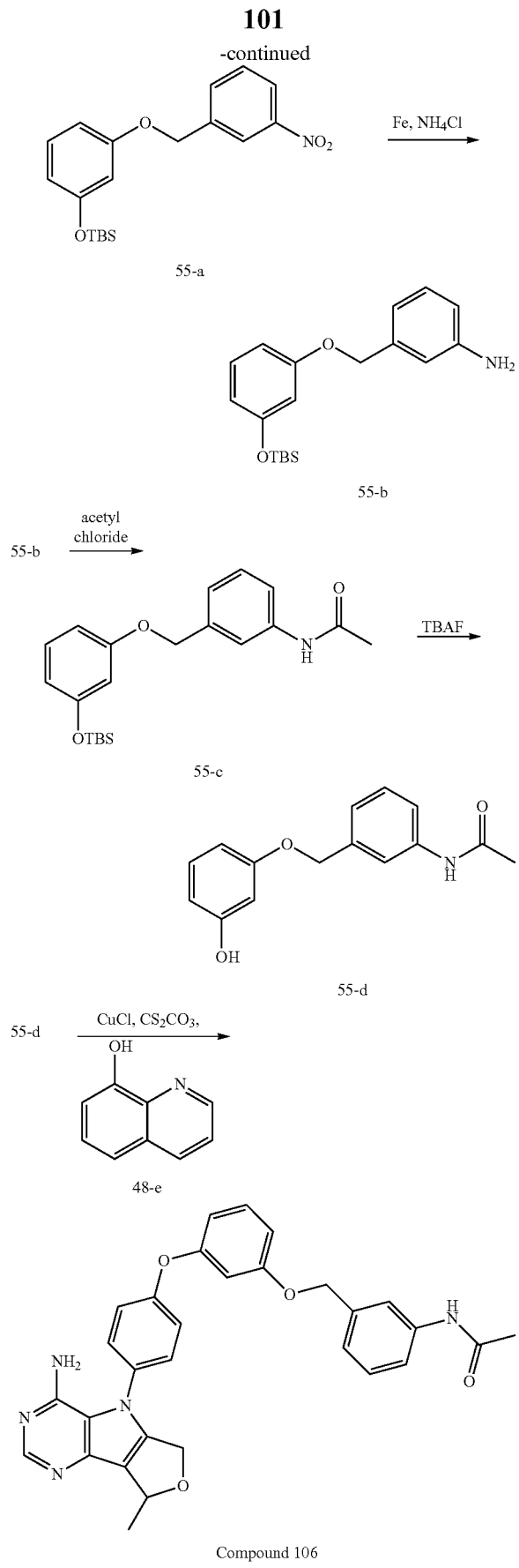

Step 2: Intermediate 55-a

To a solution of (3-nitrophenyl)methanol in THF (816 mL) were sequentially added intermediate 53-a (21.98 g, 98.0 mmol), triphenylphosphine (25.7 g, 98.0 mmol) and DIAD (19.29 ml, 98.0 mmol), drop wise at room temperature and then stirred for 1 hour. Saturated aqueous ammonium chloride and ethyl acetate were added, the organic layer was separated, washed with brine, dried over $MgSO_4$, filtered and concentrated under reduced pressure. Purification by silica gel chromatography provided intermediate 55-a as a yellow oil.

Step 2: Intermediate 55-b

To a solution of intermediate 55-a (1.89 g, 5.26 mmol) in ethanol (26 ml) and water (26 ml) were sequentially added ammonium chloride (1.4 g, 26.3 mmol), iron (4.17 g, 74.7 mmol) and the reaction mixture was stirred at reflux overnight and then cooled to room temperature. The reaction mixture was filtered over celite and volatiles were removed in vacuo. Water and ethyl acetate were added; the organic layer was separated, washed with saturated aqueous $NaHCO_3$ and brine, dried over $MgSO_4$, filtered and concentrated under reduced pressure to provide intermediate 55-b as beige oil.

Step 3: Intermediate 55-c

To a solution of intermediate 55-b (359 mg, 1.0 mmol) in dichloromethane (10.0 ml), cooled to 0° C., was added acetyl chloride (85 μl, 1.20 mmol) and the reaction was stirred at room temperature overnight. Volatiles were removed under reduced pressure. Purification by silica gel chromatography provided intermediate 55-c as orange oil.

Step 4: Intermediate 55-d

To a solution of intermediate 55-c (404 mg, 1.08 mmol) in THF (10.0 ml) was added a 1.0M solution of tetrabutylammonium fluoride in THF (1.30 ml, 1.30 mmol) and the reaction was stirred at room temperature for 30 minutes. Saturated aqueous ammonium chloride and ethyl acetate were added, the organic layer was separated, washed with brine, dried over $MgSO_4$, filtered and concentrated under reduced pressure. Purification by silica gel chromatography provided intermediate 55-d as yellow solid.

Step 4: Compound 106

A solution of intermediate 48-e (111 mg, 0.32 mmol), intermediate 55-d (124 mg, 0.48 mmol), quinolin-8-ol (9.3 mg, 0.06 mmol), copper (I) chloride (6.36 mg, 0.06 mmol) and cesium carbonate (314 mg, 0.96 mmol) in dimethylacetamide (3.2 ml) was degassed with argon for 10 minutes, heated in a sealed tube at 140° C. for 1 hour and then cooled to room temperature. Water and ethyl acetate were added, the organic layer was separated, the aqueous layer was extracted twice with ethyl acetate, the combined organic extracts were washed with brine, dried over $MgSO_4$, filtered and concentrated under reduced pressure. Purification by reverse phase chromatography eluting with 10-70% methanol in 0.1% HCl gradient provided compound 106.HCl as yellow solid. MS (m/z) M+H=522.1

Synthesis of Compound 113

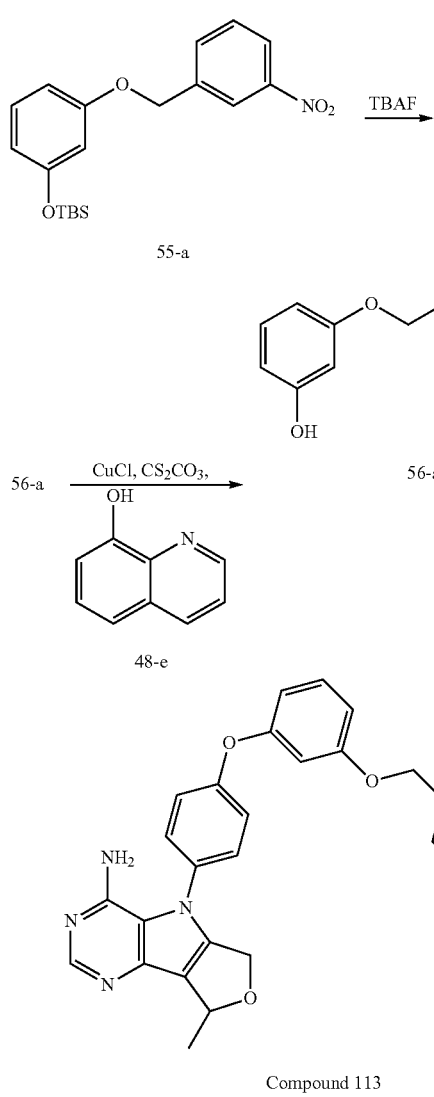

Compound 113

Step 1: Intermediate 59-a

To a solution of intermediate 55-a (399 mg, 1.11 mmol) in THF (10.0 ml) was added a 1.0M solution of tetrabutylammonium fluoride in THF (1.33 ml, 1.33 mmol) and the reaction was stirred at room temperature for 30 minutes. Saturated aqueous ammonium chloride and ethyl acetate were added, the organic layer was separated, washed with brine, dried over MgSO$_4$, filtered and concentrated under reduced pressure. Purification by silica gel chromatography provided intermediate 56-a as a white solid.

Step 2: Compound 113

A solution of intermediate 48-e (236 mg, 0.68 mmol), intermediate 56-a (112 mg, 0.45 mmol), quinolin-8-ol (13 mg, 0.09 mmol), copper (I) chloride (9.0 mg, 0.09 mmol) and cesium carbonate (446 mg, 1.37 mmol) in dimethylacetamide (3.2 ml) was degassed with argon for 10 minutes, heated in a sealed tube at 120° C. for 3 hours and then cooled to room temperature. Water and ethyl acetate were added, the organic layer was separated, the aqueous layer was extracted twice with ethyl acetate, the combined organic extracts were washed with brine, dried over MgSO$_4$, filtered and concentrated under reduced pressure. Purification by reverse phase chromatography eluting with 10-70% methanol in 0.1% HCl gradient provided compound 113.HCl as yellow solid. MS (m/z) M+H=510.1

Synthesis of Compound 116

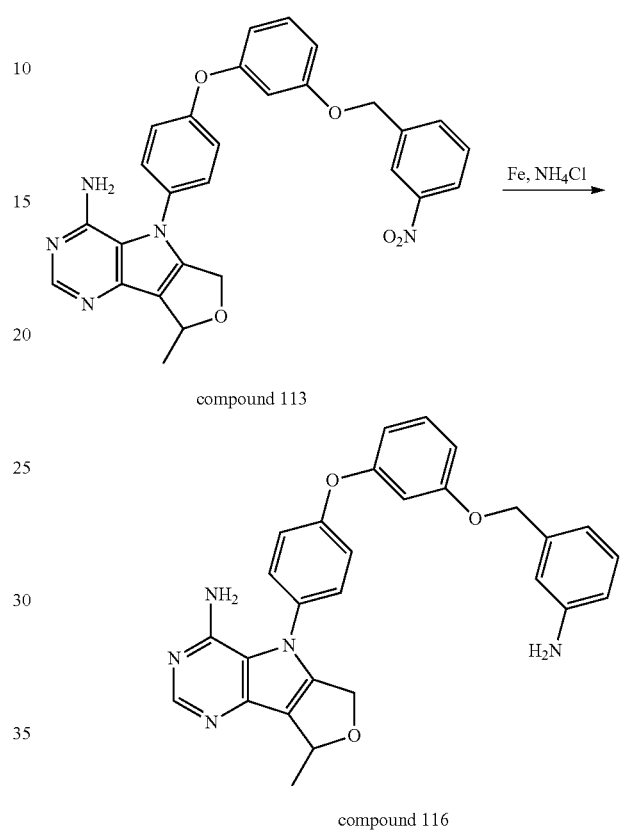

compound 116

To a solution of compound 113 (47 mg, 0.09 mmol) in ethanol (0.5 ml) and water (0.5 ml) were sequentially added ammonium chloride (25 mg, 0.46 mmol), iron (21 mg, 0.37 mmol) and the reaction mixture was stirred at reflux overnight and then cooled to room temperature. The reaction mixture was filtered over celite and volatiles were removed in vacuo. Water and ethyl acetate were added to the residue; the organic layer was separated, washed with saturated aqueous NaHCO$_3$ and brine, dried over MgSO$_4$, filtered and concentrated under reduced pressure. Purification by reverse phase chromatography eluting with 10-70% methanol in 0.1% HCl gradient provided compound 116.2HCl as yellow solid. MS (m/z) M+H=480.3

Synthesis of Compound 132

Scheme 58

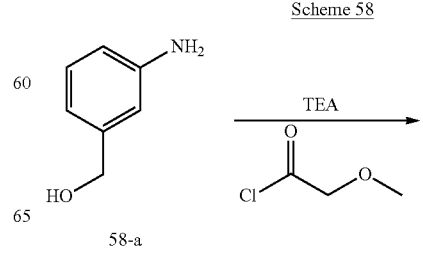

58-a

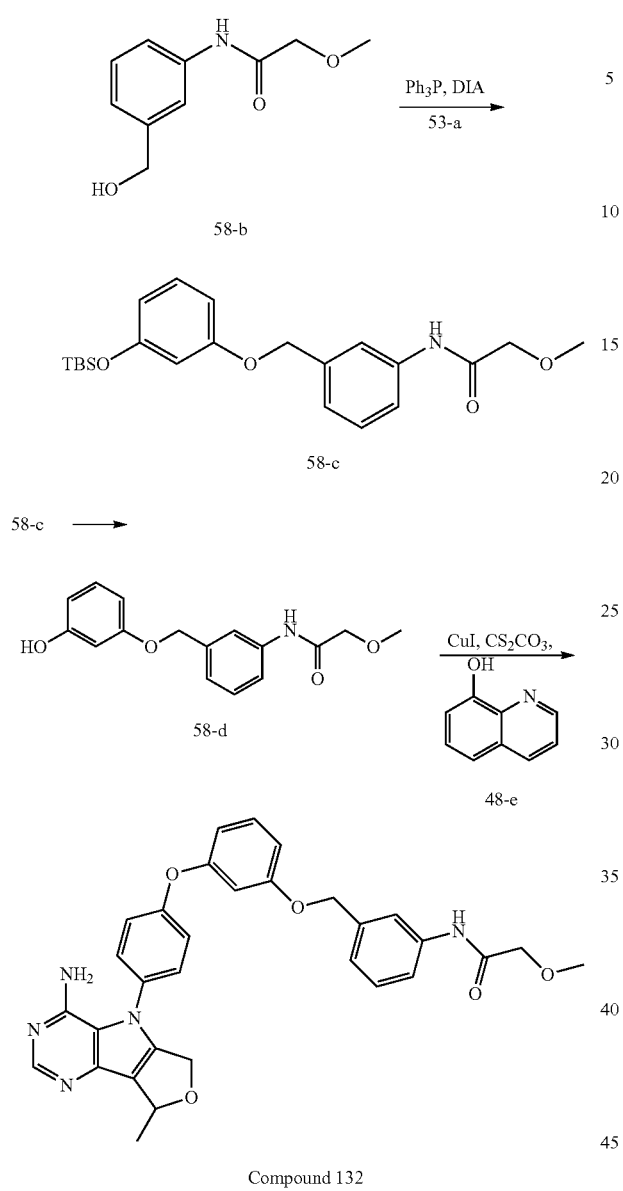

Compound 132

Step 1: Intermediate 58-b

To a solution of intermediate 58-a (1.0 g, 8.12 mmol) in THF (10.0 ml) cooled to 0° C. was added 2-methoxyacetyl chloride (881 mg, 8.12 mmol) and the reaction was stirred at room temperature overnight. Volatiles were removed under reduced pressure. Purification by silica gel chromatography provided intermediate 58-b as orange oil.

Step 1: Intermediate 58-c

To a solution of intermediate 58-b (725 mg, 4.46 mmol) in THF (20 mL) were sequentially added intermediate 53-a (1.0 g, 4.46 mmol), triphenylphosphine (1.17 g, 4.46 mmol) and DIAD (878 µl, 4.46 mmol) drop wise at room temperature and the reaction was then stirred for 1 hour. Saturated aqueous ammonium chloride and ethyl acetate were added, the organic layer was separated, washed with brine, dried over MgSO₄, filtered and concentrated under reduced pressure. Purification by silica gel chromatography provided intermediate 58-c as yellow solid.

Step 1: Intermediate 58-d

To a solution of intermediate 58-c (600 mg, 0.58 mmol) in THF (10.0 ml) was added a 1.0M solution of tetrabutylammonium fluoride in THF (1.64 ml, 1.64 mmol) and the reaction was stirred at room temperature for 30 minutes. Saturated aqueous ammonium chloride and ethyl acetate were added, the organic layer was separated, washed with brine, dried over MgSO₄, filtered and concentrated under reduced pressure. Purification by silica gel chromatography provided intermediate 58-d as white solid.

Step 1: Compound 132

A solution of intermediate 48-e (200 mg, 0.58 mmol), intermediate 58-d (200 mg, 0.69 mmol), quinolin-8-ol (17 mg, 0.11 mmol), copper (I) iodide (132 mg, 0.69 mmol) and cesium carbonate (378 mg, 1.15 mmol) in dimethylacetamide (2.9 ml) was degassed with argon for 10 minutes, heated in a sealed tube at 140° C. for 2 hours and then cooled to room temperature. Water and ethyl acetate were added, the organic layer was separated, the aqueous layer was extracted twice with ethyl acetate, the combined organic extracts were washed with brine, dried over MgSO₄, filtered and concentrated under reduced pressure. Purification by reverse phase chromatography eluting with 10-70% methanol in 0.1% HCl gradient provided compound 132.HCl as yellow solid. MS (m/z) M+H=552.1

Synthesis of Compound 102

Scheme 59

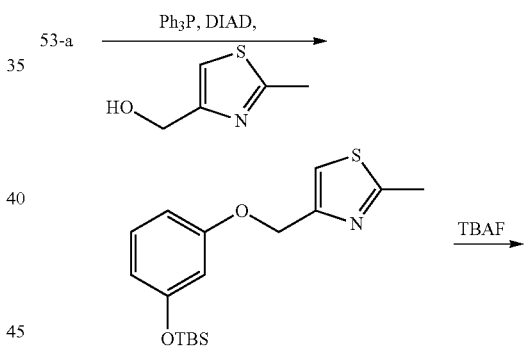

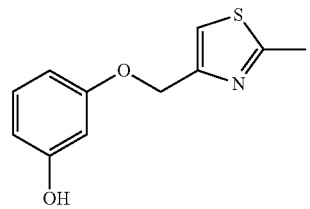

-continued

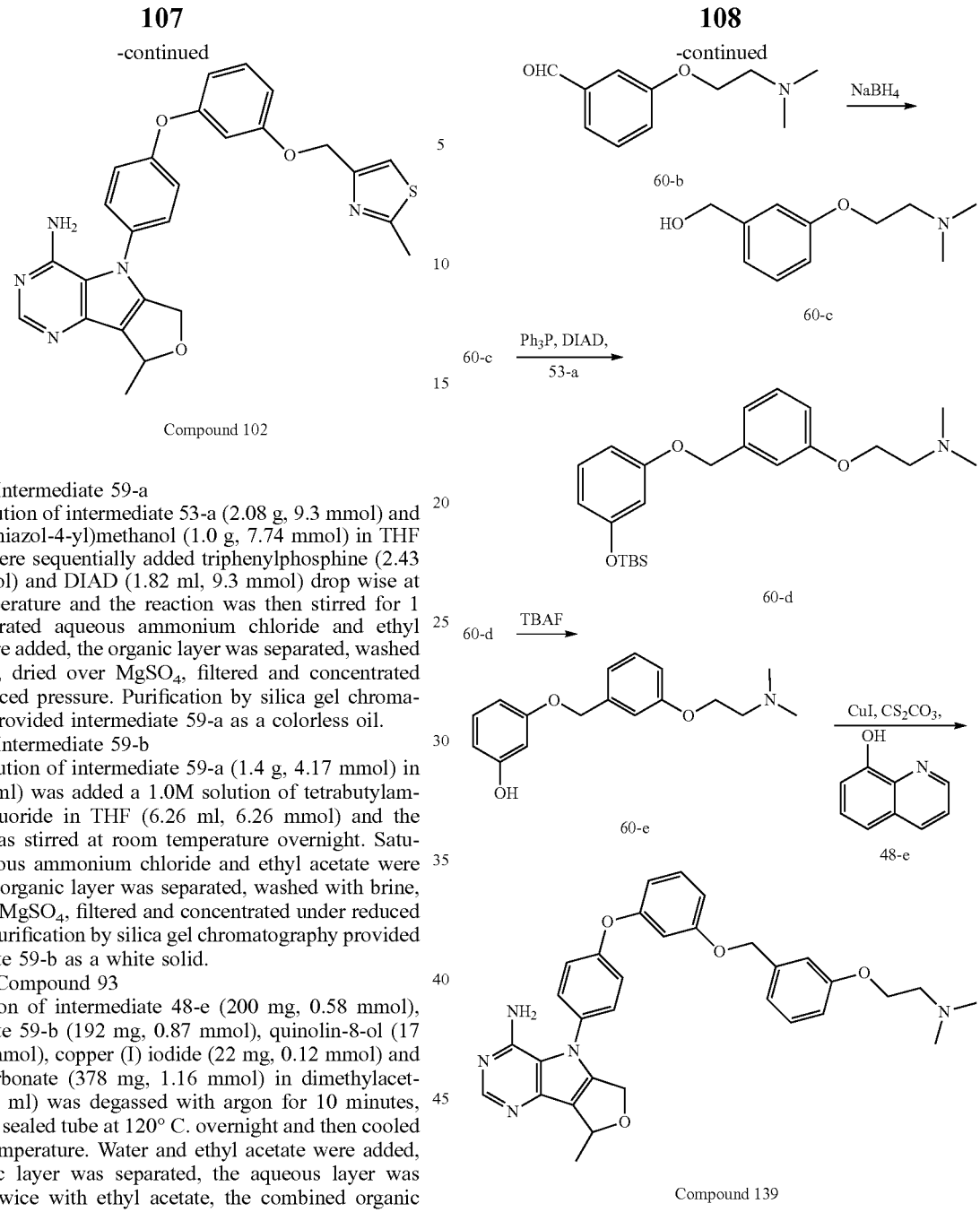

Compound 102

Step 1: Intermediate 59-a

To a solution of intermediate 53-a (2.08 g, 9.3 mmol) and (2-methylthiazol-4-yl)methanol (1.0 g, 7.74 mmol) in THF (20 mL) were sequentially added triphenylphosphine (2.43 g, 9.3 mmol) and DIAD (1.82 ml, 9.3 mmol) drop wise at room temperature and the reaction was then stirred for 1 hour. Saturated aqueous ammonium chloride and ethyl acetate were added, the organic layer was separated, washed with brine, dried over MgSO$_4$, filtered and concentrated under reduced pressure. Purification by silica gel chromatography provided intermediate 59-a as a colorless oil.

Step 3: Intermediate 59-b

To a solution of intermediate 59-a (1.4 g, 4.17 mmol) in THF (5.0 ml) was added a 1.0M solution of tetrabutylammonium fluoride in THF (6.26 ml, 6.26 mmol) and the reaction was stirred at room temperature overnight. Saturated aqueous ammonium chloride and ethyl acetate were added, the organic layer was separated, washed with brine, dried over MgSO$_4$, filtered and concentrated under reduced pressure. Purification by silica gel chromatography provided intermediate 59-b as a white solid.

Step 1: Compound 93

A solution of intermediate 48-e (200 mg, 0.58 mmol), intermediate 59-b (192 mg, 0.87 mmol), quinolin-8-ol (17 mg, 0.12 mmol), copper (I) iodide (22 mg, 0.12 mmol) and cesium carbonate (378 mg, 1.16 mmol) in dimethylacetamide (2.9 ml) was degassed with argon for 10 minutes, heated in a sealed tube at 120° C. overnight and then cooled to room temperature. Water and ethyl acetate were added, the organic layer was separated, the aqueous layer was extracted twice with ethyl acetate, the combined organic extracts were washed with brine, dried over MgSO$_4$, filtered and concentrated under reduced pressure. Purification by reverse phase chromatography eluting with 10-70% methanol in 0.1% HCl gradient provided compound 102.HCl as yellow solid. MS (m/z) M+H=486.2

Synthesis of Compound 139

Scheme 60

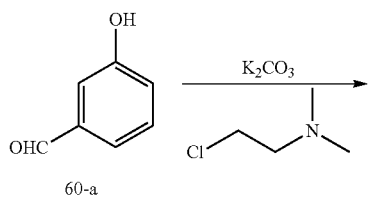

Step 1: Intermediate 60-b

A suspension of 3-hydroxybenzaldehyde 60-a (16.97 g, 139 mmol) and potassium carbonate (28.8 g, 208 mmol) in DMF was stirred at 80° C. for 30 minutes. 2-Chloro-N,N-dimethylethanamine HCl salt (10.01 g, 69.5 mmol) was added and the reaction was stirred at 80° C. for 5 hours, then cooled to room temperature. Water and ethyl acetate were added, the organic layer was separated, washed 3 times with brine, dried over MgSO$_4$, filtered and concentrated under reduced pressure. Purification by silica gel chromatography provided intermediate 60-b as a beige oil.

Step 2: Intermediate 60-c

To a solution of intermediate 60-b (6.5 g, 33.6 mmol) in methanol (100 ml) was added sodium borohydride (636 mg, 16.82 mmol), in several portions, and the reaction was then stirred at room temperature for 2 hours. Volatiles were removed under reduced pressure. Water and ethyl acetate were added to the residue, the organic layer was separated, washed with brine, dried over MgSO₄, filtered and concentrated under reduced pressure to provide intermediate 60-c as a beige oil.

Step 3: Intermediate 60-d

To a solution of intermediate 53-a (1.80 g, 8.02 mmol) in THF (20 mL) were sequentially added intermediate 60-c (1.4 g, 7.291), triphenylphosphine (2.29 g, 8.75 mmol) and DIAD (1.70 ml, 8.75 mmol), drop wise, at room temperature. The reaction was stirred for 18 hours. Volatiles were removed under reduced pressure. Purification by silica gel chromatography provided intermediate 60-d as white solid.

Step 4: Intermediate 60-e

To a solution of intermediate 60-d (2.73 g, 7.30 mmol) in THF (36.0 ml) was added a 1.0M solution of tetrabutylammonium fluoride in THF (7.30 ml, 7.30 mmol) and the reaction was stirred at room temperature for 30 minutes. Saturated aqueous ammonium chloride and ethyl acetate were added, the organic layer was separated, washed with brine, dried over MgSO₄, filtered and concentrated under reduced pressure. Purification by silica gel chromatography provided intermediate 60-e as white solid.

Step 5: Compound 139

A solution of intermediate 48-e (200 mg, 0.58 mmol), intermediate 60-e (275 mg, 0.95 mmol), quinolin-8-ol (17 mg, 0.11 mmol), copper (I) iodide (22 mg, 0.11 mmol) and cesium carbonate (378 mg, 1.15 mmol) in dimethylacetamide (2.9 ml) was degassed with argon for 10 minutes, heated in a sealed tube at 140° C. for 2 hours and then cooled to room temperature. Water and ethyl acetate were added, the organic layer was separated, the aqueous layer was extracted twice with ethyl acetate, the combined organic extracts were washed with brine, dried over MgSO₄, filtered and concentrated under reduced pressure. Purification by reverse phase chromatography eluting with 10-70% methanol in 0.1% HCl gradient provided compound 139.2HCl as beige solid. MS (m/z) M+H=552.1

Synthesis of Compound 85

Scheme 61

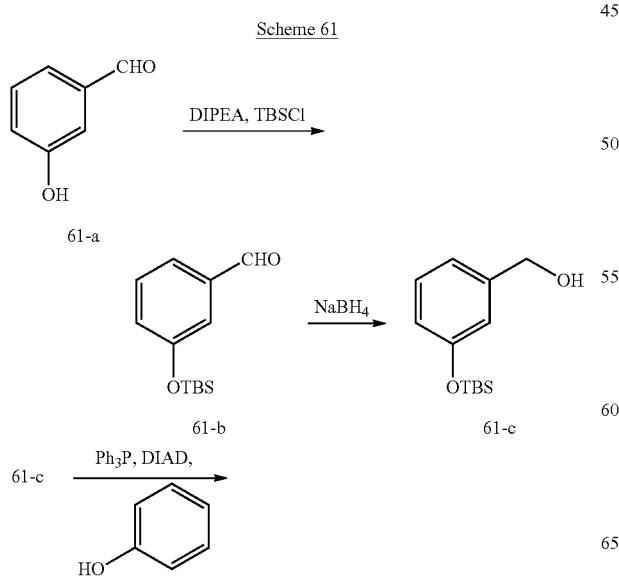

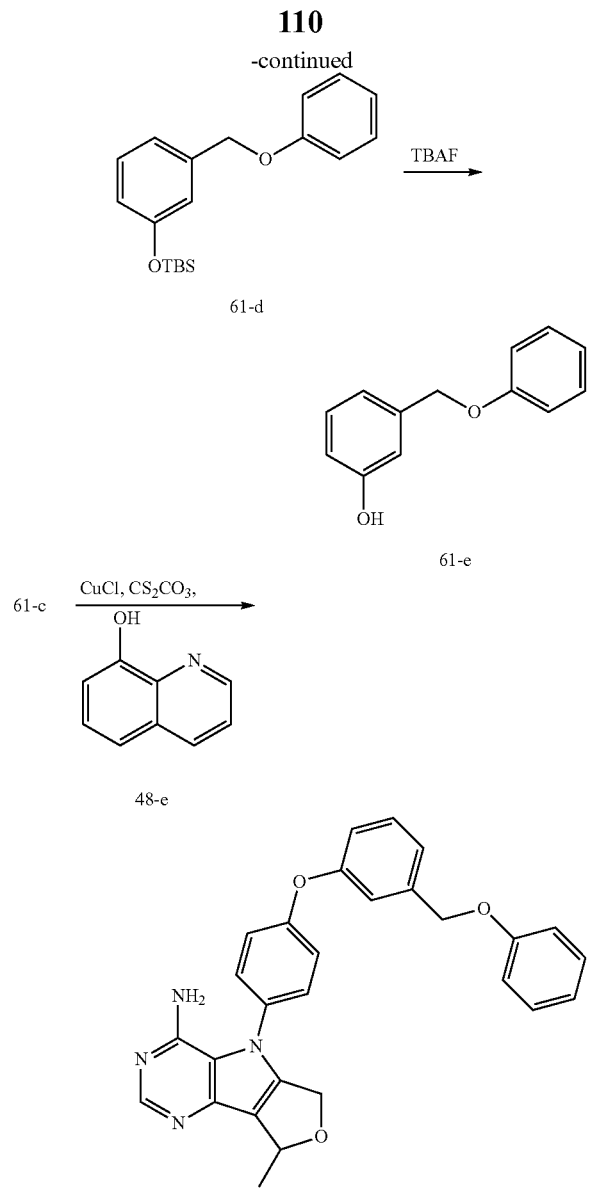

Step 1: Intermediate 61-b

To a solution of 3-hydroxybenzaldehyde, 61-a (14.73 g, 121 mmol), in dichloromethane (100 mL) were sequentially added triethylamine (25.08 ml, 181 mmol), tert-butylchlorodimethylsilane (20.0 g, 133 mmol) portion wise and the reaction was stirred at room temperature overnight. 10% Citric acid was added, the organic layer was separated, washed with brine, dried over MgSO₄, filtered and concentrated under reduced pressure. Purification by silica gel chromatography provided intermediate 61-b as yellow oil.

Step 2: Intermediate 61-c

To a solution of intermediate 61-b (16.0 g, 67.7 mmol) in methanol (100 ml) cooled to 0° C. was added portion wise sodium borohydride (1.28 g, 33.8 mmol). After the addition was completed the reaction was stirred at room temperature for 2 hours. Volatiles were removed under reduced pressure. Water and ethyl acetate were added to the residue, the organic layer was separated, washed with brine, dried over MgSO₄, filtered and concentrated under reduced pressure to provide intermediate 61-c as yellow oil.

Step 3: Intermediate 61-d

To a solution of intermediate 61-d (1.0 g, 4.19 mmol) in THF (42 mL) were sequentially added phenol (474 mg, 5.03 mmol), triphenylphosphine (1.32 g, 5.03 mmol) and DIAD (991 µl, 5.03 mmol) drop wise at room temperature and the reaction was then stirred for 1 hour. Saturated aqueous ammonium chloride and ethyl acetate were added, the organic layer was separated, washed with brine, dried over $MgSO_4$, filtered and concentrated under reduced pressure. Purification by silica gel chromatography provided intermediate 61-d as yellow oil.

Step 4: Intermediate 61-e

To a solution of intermediate 61-d (763 mg, 2.42 mmol) in THF (25.0 ml) was added a 1.0M solution of tetrabutylammonium fluoride in THF (2.91 ml, 2.91 mmol) and the reaction was stirred at room temperature for 30 minutes. A saturated aqueous solution of ammonium chloride and ethyl acetate were added, the organic layer was separated, washed with brine, dried over $MgSO_4$, filtered and concentrated under reduced pressure. Purification by silica gel chromatography provided intermediate 61-e as colorless oil.

Step 5: Compound 85

A solution of intermediate 48-e (284 mg, 0.82 mmol), intermediate 61-e (329 mg, 1.64 mmol), quinolin-8-ol (23.8 mg, 0.16 mmol), copper (I) chloride (16.3 mg, 0.16 mmol) and cesium carbonate (803 mg, 2.46 mmol) in dimethylacetamide (8.2 ml) was degassed with nitrogen for 10 minutes, heated in a sealed tube at 170° C. for 2 hours and then cooled to room temperature. Water and ethyl acetate were added, the organic layer was separated, the aqueous layer was extracted twice with ethyl acetate, the combined organic extracts were washed with brine, dried over $MgSO_4$, filtered and concentrated under reduced pressure. Purification by reverse phase chromatography eluting with 10-70% methanol in 0.1% HCl gradient provided compound 85.HCl as white solid. MS (m/z) M+H=465.2

Synthesis of Compound 137

Scheme 62

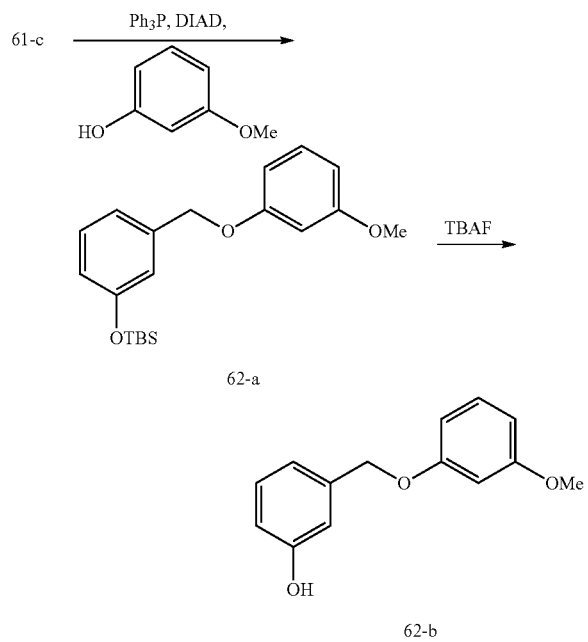

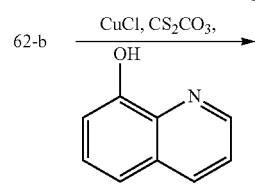

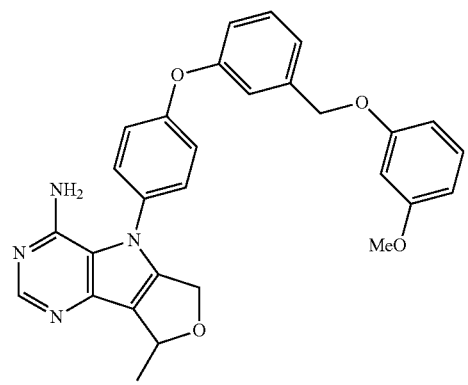

Compound 137

Step 1: Intermediate 62-a

To a solution of intermediate 61-c (1.0 g, 4.19 mmol) in THF (42 mL) were sequentially added 3-methoxyphenol (552 µl, 5.03 mmol), triphenylphosphine (1.32 g, 5.03 mmol) and DIAD (991 µl, 5.03 mmol) drop wise at room temperature and the reaction was then stirred for 1 hour. Saturated aqueous ammonium chloride and ethyl acetate were added, the organic layer was separated, washed with brine, dried over $MgSO_4$, filtered and concentrated under reduced pressure. Purification by silica gel chromatography provided intermediate 62-a as a colorless oil.

Step 2: Intermediate 62-b

To a solution of intermediate 62-a (677 mg, 1.96 mmol) in THF (20.0 ml) was added tetrabutylammonium fluoride (514 mg, 1.96 mmol) and the reaction was stirred at room temperature for 1 hour. Saturated aqueous ammonium chloride and ethyl acetate were added, the organic layer was separated, washed with brine, dried over $MgSO_4$, filtered and concentrated under reduced pressure. Purification by silica gel chromatography provided intermediate 62-b as white solid.

Step 3: Compound 137

A solution of intermediate 48-e (180 mg, 0.52 mmol), intermediate 62-b (100 mg, 0.43 mmol), quinolin-8-ol (13.0 mg, 0.08 mmol), copper (I) chloride (8.6 mg, 0.08 mmol) and cesium carbonate (425 mg, 1.30 mmol) in dimethylacetamide (4.3 ml) was degassed with argon for 10 minutes, heated in a sealed tube at 120° C. for 3 hours and then cooled to room temperature. Water and ethyl acetate were added, the organic layer was separated, the aqueous layer was extracted twice with ethyl acetate, the combined organic extracts were washed with brine, dried over $MgSO_4$, filtered and concentrated under reduced pressure. Purification by reverse phase chromatography eluting with 10-70% methanol in 0.1% HCl gradient provided compound 137.HCl as white solid. MS (m/z) M+H=495.1

Synthesis of Compound 141

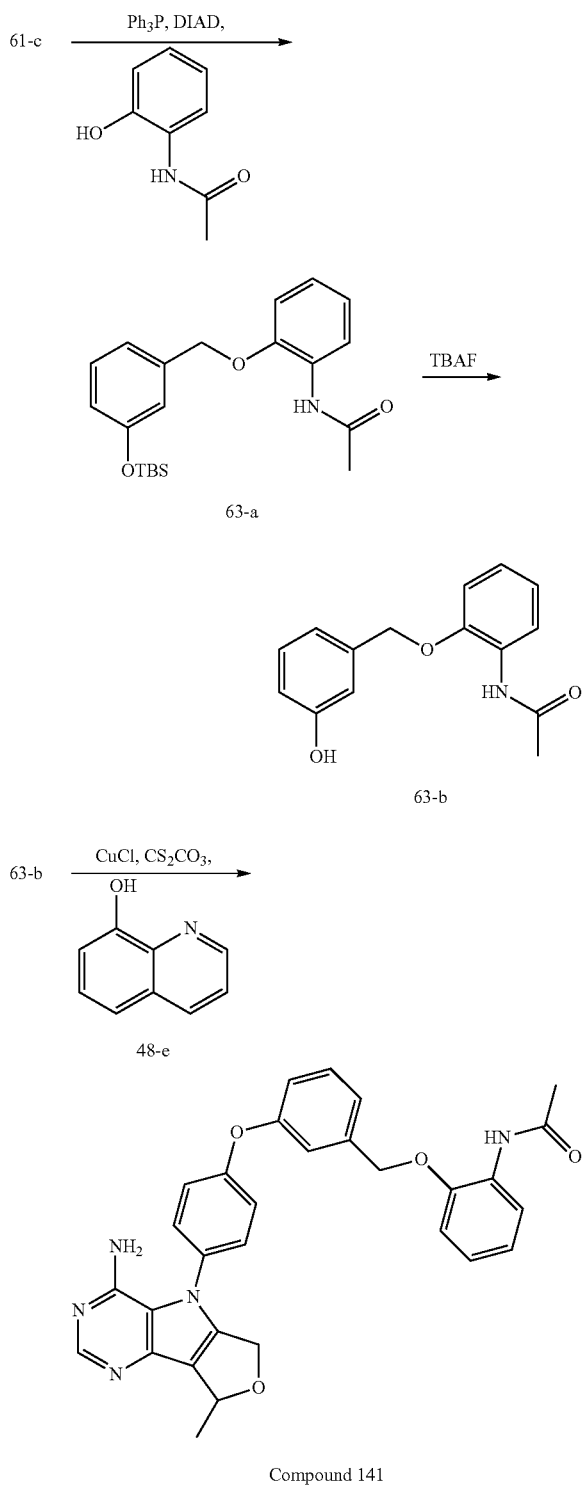

Step 1: Intermediate 63-a

To a solution of intermediate 61-c (500 mg, 2.09 mmol) in THF (42 mL) were sequentially added 2-acetamidophenol (380 mg, 2.52 mmol), triphenylphosphine (660 mg, 2.52 mmol) and DIAD (496 μl, 2.52 mmol), drop wise, at room temperature; the reaction was then stirred at reflux for 2 hours then cooled to room temperature. A saturated aqueous solution of ammonium chloride and ethyl acetate were added, the organic layer was separated, washed with brine, dried over $MgSO_4$, filtered and concentrated under reduced pressure. Purification by silica gel chromatography provided intermediate 63-a as a colorless oil.

Step 2: Intermediate 63-b

To a solution of intermediate 63-a (243 mg, 0.65 mmol) in THF (6.0 ml) was added a 1.0M solution of tetrabutylammonium fluoride in THF (654 μl, 654 mmol) and the reaction was stirred at room temperature for 2 hours. Saturated aqueous ammonium chloride and ethyl acetate were added, the organic layer was separated, washed with brine, dried over $MgSO_4$, filtered and concentrated under reduced pressure. Purification by silica gel chromatography provided intermediate 63-b as a yellow solid.

Step 3: Compound 141

A solution of intermediate 48-e (161 mg, 0.47 mmol), intermediate 63-b (100 mg, 0.39 mmol), quinolin-8-ol (11 mg, 0.08 mmol), copper (I) chloride (7.7 mg, 0.08 mmol) and cesium carbonate (380 mg, 1.16 mmol) in dimethylacetamide (4 ml) was degassed with argon for 10 minutes, heated in a sealed tube at 120° C. for 3 hours and then cooled to room temperature. Water and ethyl acetate were added, the organic layer was separated, the aqueous layer was extracted twice with ethyl acetate, the combined organic extracts were washed with brine, dried over $MgSO_4$, filtered and concentrated under reduced pressure. Purification by reverse phase chromatography eluting with 10-70% methanol in 0.1% HCl gradient provided compound 141.HCl as yellow solid. MS (m/z) M+H=522.1

Synthesis of Intermediate 64

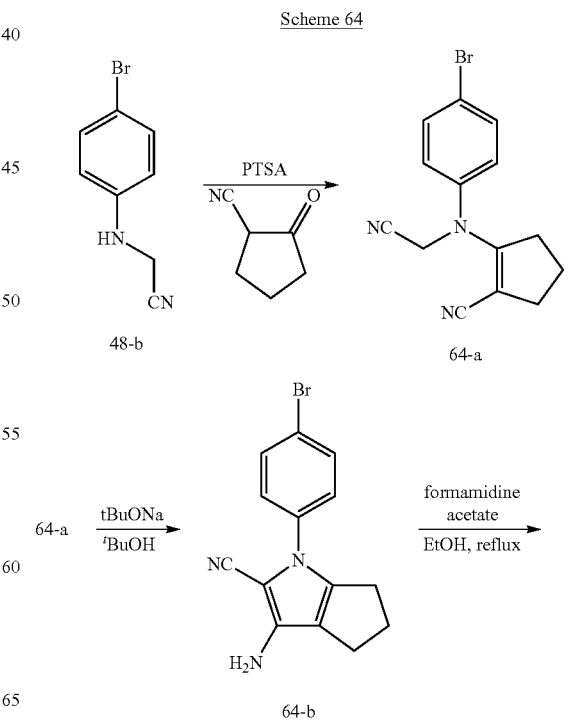

-continued

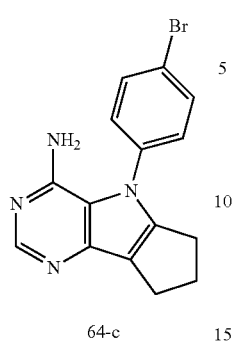

64-c

Step 1: Intermediate 64-a

To a solution of intermediate 48-b (10.0 g, 92.0 mmol) in toluene (50 ml) were added 2-oxocyclopentanecarbonitrile (8.0 g, 73.3 mmol) and 4-methylbenzenesulfonic acid hydrate (930 mg, 4.89 mmol). The reaction was refluxed for 3 hours using a dean-stark and then cooled to room temperature. Saturated aqueous NaHCO$_3$ and ethyl acetate were added, the organic layer was separated, washed with brine, dried over MgSO$_4$, filtered and concentrated under reduced pressure. Purification by silica gel chromatography provided intermediate 64-a as a brown solid.

Step 2: Intermediate 64-b

To a solution of intermediate 64-a (4.70 g, 15.55 mmol) in THF (10 mL) and tBuOH (20.0 ml) was added sodium tert-butoxide (1.92 g, 17.11 mmol) and the reaction was stirred at 80° C. for 1 hour and then cooled to room temperature. Saturated aqueous ammonium chloride and ethyl acetate were added, the organic layer was separated, the aqueous phase was extracted with ethyl acetate, the combined organic extracts were washed with brine, dried over MgSO$_4$, filtered and concentrated under reduced pressure to provide intermediate 64-b as a brown solid.

Step 3: Intermediate 64-c

To a solution of intermediate 64-b (5.2 g, 17.21 mmol) in ethanol (50 ml) was added formamidine acetate (17.92 g, 172.0 mmol) and the reaction was stirred at 80° C. overnight and then cooled to room temperature. Volatiles were removed in vacuo. Saturated aqueous ammonium chloride and ethyl acetate were added to the residue, the organic layer was separated, washed with brine, dried over MgSO$_4$, filtered and concentrated under reduced pressure. Purification by silica gel chromatography provided intermediate 64-c as beige solid.

Synthesis of Compound 129

Scheme 65

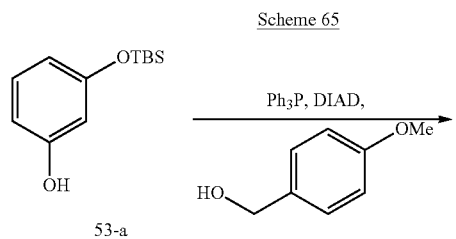

53-a

-continued

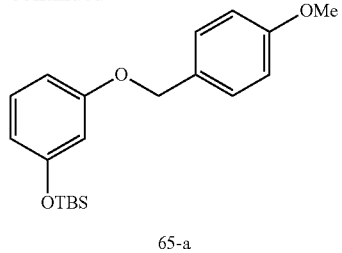

65-a

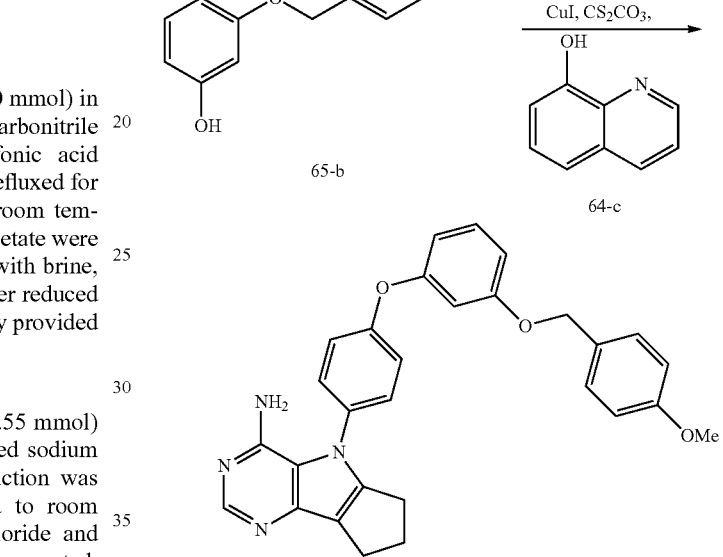

Compound 129

Step 1: Intermediate 65-a

To a solution of intermediate 53-a (2.69 g, 12.0 mmol) in THF (20 mL) were sequentially added (4-methoxyphenyl)methanol (1.38 g, 10.0 mmol triphenylphosphine (3.15 g, 12.0 mmol) and DIAD (2.36 ml, 12.0 mmol) drop wise at room temperature and the reaction was then stirred for 1 hour. Saturated aqueous ammonium chloride and ethyl acetate were added, the organic layer was separated, washed with brine, dried over MgSO$_4$, filtered and concentrated under reduced pressure. Purification by silica gel chromatography provided intermediate 65-a as a colorless oil.

Step 2: Intermediate 65-b

To a solution of intermediate 65-a (2.19 g, 6.97 mmol) in THF (10.0 ml) was added tetrabutylammonium fluoride trihydrate (2.19 g, 6.97 mmol) and the reaction was stirred at room temperature overnight. Saturated aqueous ammonium chloride and ethyl acetate were added, the organic layer was separated, washed with brine, dried over MgSO$_4$, filtered and concentrated under reduced pressure. Purification by silica gel chromatography provided intermediate 65-b as a white solid.

Step 2: Compound 129

A solution of intermediate 64-c (200 mg, 0.61 mmol), intermediate 65-b (280 mg, 1.21 mmol), quinolin-8-ol (18.0 mg, 0.12 mmol), copper (I) iodide (23 mg, 0.12 mmol) and cesium carbonate (396 mg, 1.21 mmol) in DMA (6.1 ml) was degassed with nitrogen for 10 minutes, heated in a sealed tube at 120° C. for 18 hours and then cooled to room temperature. Water and ethyl acetate were added, the organic layer was separated, the aqueous layer was extracted twice with ethyl acetate, the combined organic extracts were washed with brine, dried over MgSO$_4$, filtered and concentrated under reduced pressure. Purification by reverse phase chromatography eluting with 10-70% methanol in 0.1% HCl gradient provided compound 129.HCl as a beige solid. MS (m/z) M+H=479.1

Synthesis of Compound 117

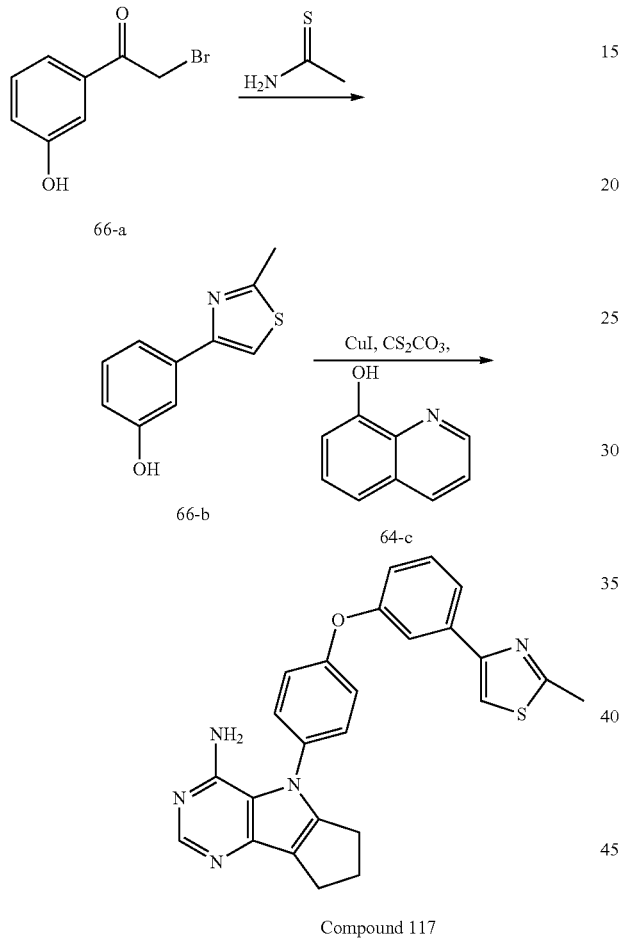

Compound 117

Step 1: Intermediate 66-b

To a solution of 2-bromo-1-(3-hydroxyphenyl)ethanone 66-a (3.0 g, 13.95 mmol) in EtOH (30 ml) was added thioacetamide (1.25 g, 16.74 mmol) and the reaction was stirred at 80° C. for 3 hours and then cooled to room temperature. A precipitate formed and was collected by filtration to provide intermediate 66-b as beige solid.

Step 2: Compound 117

A solution of intermediate 64-c (200 mg, 0.61 mmol), intermediate 66-b (232 mg, 1.21 mmol), quinolin-8-ol (18.0 mg, 0.12 mmol), copper (I) iodide (23 mg, 0.12 mmol) and cesium carbonate (396 mg, 1.21 mmol) in DMA (6.1 ml) was degassed with argon for 10 minutes, heated in a sealed tube at 130° C. overnight and then cooled to room temperature. Water and ethyl acetate were added, the organic layer was separated, the aqueous layer was extracted twice with ethyl acetate, the combined organic extracts were washed with brine, dried over MgSO$_4$, filtered and concentrated under reduced pressure. Purification by reverse phase chromatography eluting with 10-70% methanol in 0.1% HCl gradient provided compound 117.HCl as white solid. MS (m/z) M+H=440.1

Synthesis of Intermediate 67-c

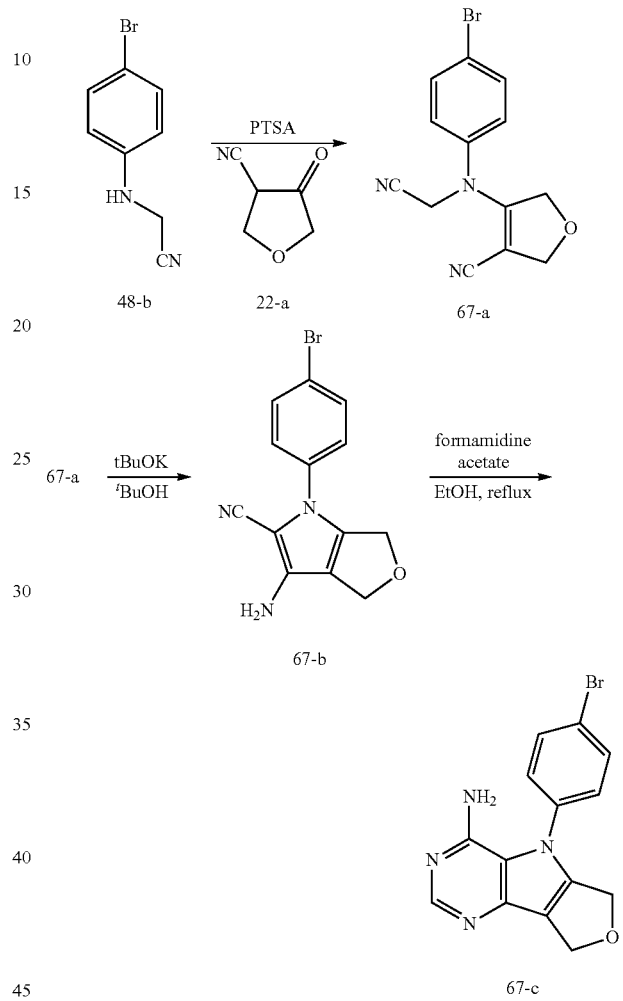

Step 1: Intermediate 67-a

To a solution of intermediate 48-b (15.3 g, 72.5 mmol) in toluene (50 ml) were added 4-oxotetrahydrofuran-3-carbonitrile 22-a (14.5 g, 131.0 mmol) and 4-methylbenzenesulfonic acid hydrate (1.37 g, 7.25 mmol). The reaction was refluxed for 3 hours using a Dean-Stark apparatus and then cooled to room temperature. Saturated aqueous NaHCO$_3$ and ethyl acetate were added, the organic layer was separated, washed with brine, dried over MgSO$_4$, filtered and concentrated under reduced pressure. Purification by silica gel chromatography provided intermediate 67-a as a brown solid.

Step 2: Intermediate 67-b

To a solution of intermediate 67-a (18.6 g, 61.2 mmol) in tBuOH (400 ml) was added a 1.0M solution potassium tert-butoxide in THF (61.2 ml, 61.2 mmol) and the reaction was stirred at 80° C. for 1 hour and then cooled to room temperature. Saturated aqueous ammonium chloride and ethyl acetate were added, the organic layer was separated, the aqueous phase was extracted with ethyl acetate, the combined organic extracts were washed with brine, dried over MgSO₄, filtered and concentrated under reduced pressure to provide intermediate 67-b as a brown solid.

Step 3: Intermediate 67-c

To a solution of intermediate 67-b (18.6 g, 61.2 mmol) in ethanol (200 ml) was added formamidine acetate (31.8 g, 306.0 mmol) and the reaction was stirred at 80° C. overnight and then cooled to room temperature. Volatiles were removed in vacuo. Saturated aqueous ammonium chloride and ethyl acetate were added to the residue, the organic layer was separated, washed with brine, dried over MgSO₄, filtered and concentrated under reduced pressure. Purification by silica gel chromatography provided intermediate 67-c as beige solid.

Synthesis of Compound 142

Step 1: Intermediate 68-a

To a solution of intermediate 61-c (1.0 g, 2.09 mmol) in THF (42 mL) were sequentially added 2-hydroxybenzonitrile (600 mg, 5.03 mmol), triphenylphosphine (1.32 g, 5.03 mmol) and DIAD (991 μl, 5.03 mmol), drop wise, at room temperature. The reaction was then stirred at reflux for 2 hours then cooled to room temperature. Saturated aqueous ammonium chloride and ethyl acetate were added, the organic layer was separated, washed with brine, dried over MgSO₄, filtered and concentrated under reduced pressure. Purification by silica gel chromatography provided intermediate 68-a as a colorless oil.

Step 2: Intermediate 68-b

To a solution of intermediate 68-a (1.22 g, 3.62 mmol) in THF (36.0 ml) was added tetrabutylammonium fluoride (946 mg, 3.62 mmol) and the reaction was stirred at room temperature for 1 hour. A saturated aqueous ammonium chloride and ethyl acetate were added, the organic layer was separated, washed with brine, dried over MgSO₄, filtered and concentrated under reduced pressure. Purification by silica gel chromatography provided intermediate 68-b as white solid.

Step 2: Compound 142

A solution of intermediate 67-c (100 mg, 0.30 mmol), intermediate 68-b (68.0 mg, 0.30 mmol), quinolin-8-ol (8.8 mg, 0.06 mmol), copper (I) chloride (6.0 mg, 0.06 mmol) and cesium carbonate (295 mg, 0.90 mmol) in dimethylacetamide (3.0 ml) was degassed with argon for 10 minutes, heated in a sealed tube at 140° C. for 3 hours and then cooled to room temperature. Water and ethyl acetate were added, the organic layer was separated, the aqueous layer was extracted twice with ethyl acetate, the combined organic extracts were washed with brine, dried over MgSO₄, filtered and concentrated under reduced pressure. Purification by silica gel chromatography provided compound 142 as a tan solid. MS (m/z) M+H=476.1

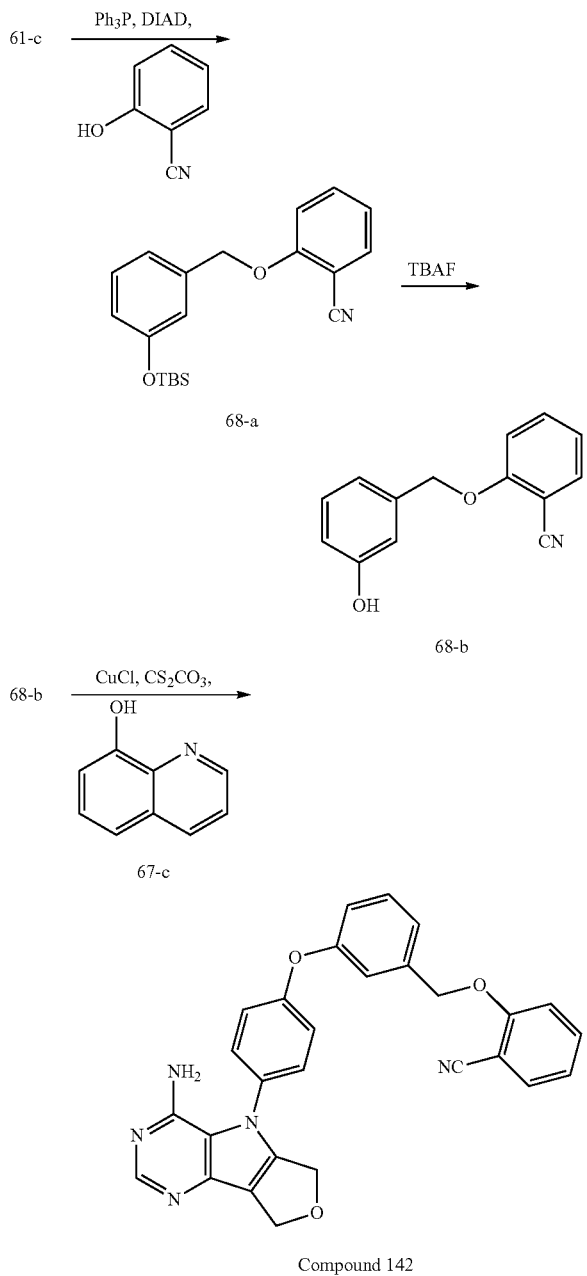

Scheme 68 / Compound 142

Compounds 2, 3, 4, 22, 23 and 68 can be prepared according to a similar method to compound 1.

Compound 18 can be prepared according to a similar method to compound 16.

Compounds 14 and 15 can be prepared according to a similar method to compounds 10 and 11.

Compounds 28, 29, 31, 32, 33, 34, 35, 41, 42, 58, 59, 60, 72, 74, 79, 88 can be prepared according to a similar method to compound 20.

Compounds 53 and 75 can be prepared according to a similar method to compound 54.

Compounds 51, 52 and 73 can be prepared according to a similar method to compound 48.

Compounds 50, 57, 64, 67 can be prepared according to a similar method to compound 49.

Compound 70 can be prepared according to a similar method to compound 69.

Compounds 76 and 81 can be prepared according to a similar method to compound 80.

Compounds 84 can be prepared according to a similar method to compound 82.

Compounds 77, 78, 86, 87, 93, 94, 95, 96, 97, 98, 99, 100, 101, 104, 107, 108, 109, 124, 135, 136, 138 and 140 can be prepared according to a similar method to compounds 89, 92, 102, 105, 106, 113, 116 and 132.

Compounds 131 and 134 can be prepared according to a similar method to compounds 85, 137 and 141.

Compounds 110, 111, 112, 114, 118, 119, 121, 125 and 127 can be prepared according to a similar method to compounds 120 and 126.

Table 1 summarizes some illustrative embodiments of the compounds of Formula 1.

TABLE 1

| Example Compounds of Formula 1 | | |
|---|---|---|
| Compound | Structure | MS (m/z) |
| 1 | | $[M + H]^+ = 343.2$ |
| 2 | | $[M + H]^+ = 361.2$ |
| 3 | | $[M + H]^+ = 421.6$ |
| 4 | | $[M + H]^+ = 377.2$ |

TABLE 1-continued
Example Compounds of Formula 1
| Compound | Structure | MS (m/z) |
|---|---|---|
| 5 | 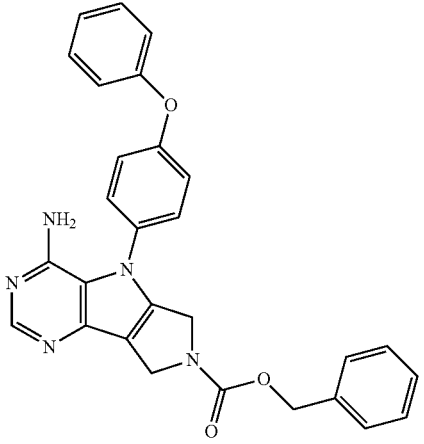 [SMILES: Nc1ncnc2c3c(n(-c4ccc(Oc5ccccc5)cc4)c12)CN(C(=O)OCc1ccccc1)C3] | [M + H]⁺ = 478.1 |
| 6 | 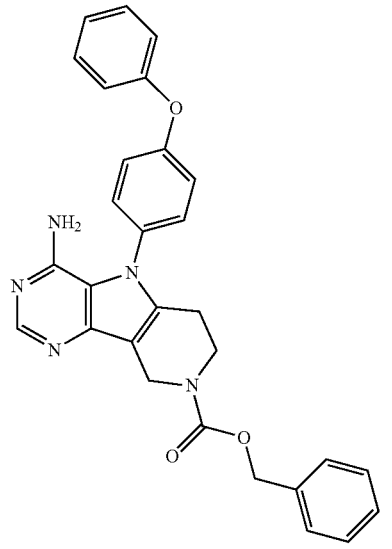 [SMILES: Nc1ncnc2c3c(n(-c4ccc(Oc5ccccc5)cc4)c12)CCN(C(=O)OCc1ccccc1)C3] | [M + H]⁺ = 492.1 |
| 7 | 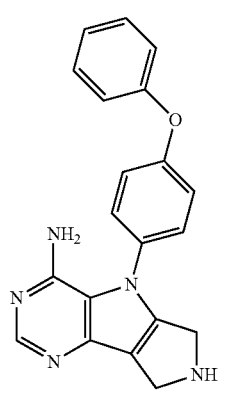 [SMILES: Nc1ncnc2c3c(n(-c4ccc(Oc5ccccc5)cc4)c12)CNC3] | [M + H]⁺ = 344.2 |

TABLE 1-continued
Example Compounds of Formula 1
| Compound | Structure | MS (m/z) |
|---|---|---|
| 8 | 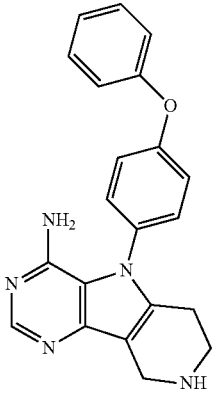 [SMILES: Nc1ncnc2c3c(n(-c4ccc(Oc5ccccc5)cc4)c12)CCNC3] | [M + H]⁺ = 358.2 |
| 9 | 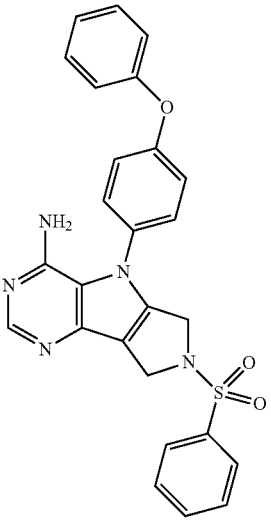 [SMILES: Nc1ncnc2c3c(n(-c4ccc(Oc5ccccc5)cc4)c12)CN(S(=O)(=O)c1ccccc1)C3] | [M + H]⁺ = 484.1 |
| 10 | 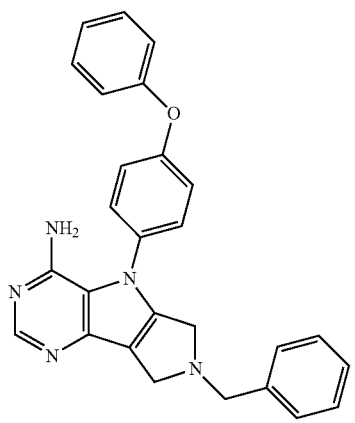 [SMILES: Nc1ncnc2c3c(n(-c4ccc(Oc5ccccc5)cc4)c12)CN(Cc1ccccc1)C3] | [M + H]⁺ = 434.2 |

TABLE 1-continued

Example Compounds of Formula 1

| Compound | Structure | MS (m/z) |
|---|---|---|
| 11 | 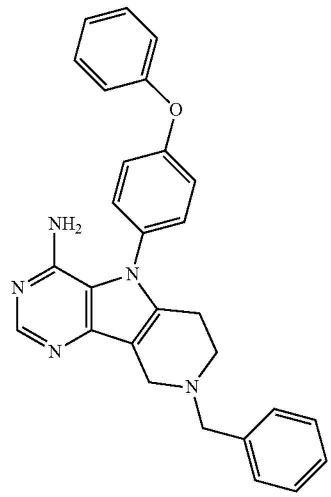 [SMILES: Nc1ncnc2c3c(n(-c4ccc(Oc5ccccc5)cc4)c12)CCN(Cc1ccccc1)C3] | $[M + H]^+ = 448.2$ |
| 12 | 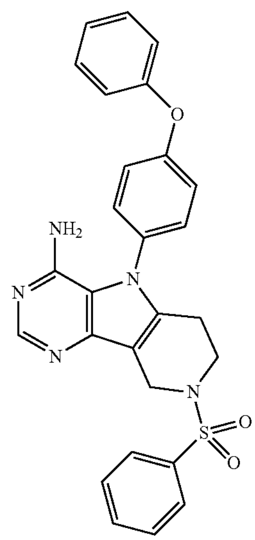 [SMILES: Nc1ncnc2c3c(n(-c4ccc(Oc5ccccc5)cc4)c12)CCN(S(=O)(=O)c1ccccc1)C3] | $[M + H]^+ = 498.1$ |
| 13 | 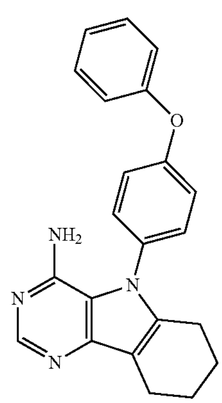 [SMILES: Nc1ncnc2c3c(n(-c4ccc(Oc5ccccc5)cc4)c12)CCCC3] | $[M + H]^+ = 357.2$ |

TABLE 1-continued
Example Compounds of Formula 1
| Compound | Structure | MS (m/z) |
|---|---|---|
| 14 | 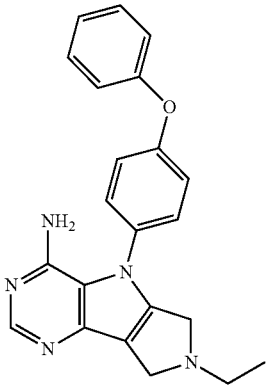 [SMILES: CCN1Cc2c(n(-c3ccc(Oc4ccccc4)cc3)c3c(N)ncnc23)C1] | [M + H]⁺ = 372.2 |
| 15 | 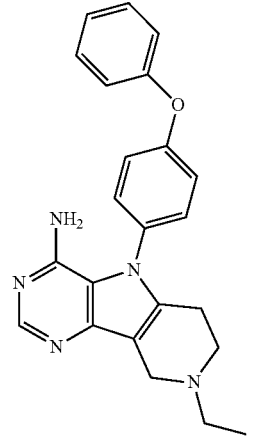 [SMILES: CCN1CCc2c(c3ncnc(N)c3n2-c2ccc(Oc3ccccc3)cc2)C1] | [M + H]⁺ = 386.3 |
| 16 | 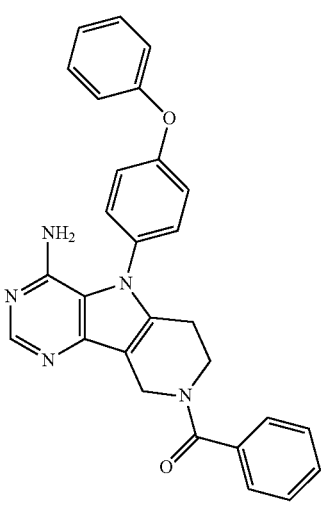 [SMILES: Nc1ncnc2c3c(n(-c4ccc(Oc5ccccc5)cc4)c12)CCN(C(=O)c1ccccc1)C3] | [M + H]⁺ = 462.1 |

TABLE 1-continued
Example Compounds of Formula 1
| Compound | Structure | MS (m/z) |
|---|---|---|
| 17 | 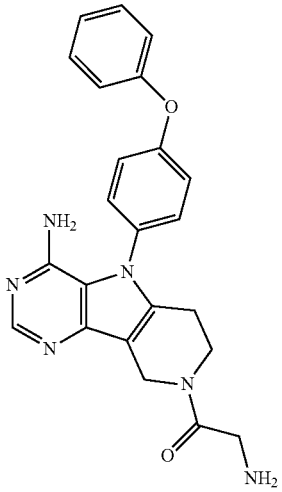 [SMILES: NCC(=O)N1CCc2c(c3ncnc(N)c3n2-c2ccc(Oc3ccccc3)cc2)C1] | [M + H]+ = 415.1 |
| 18 | 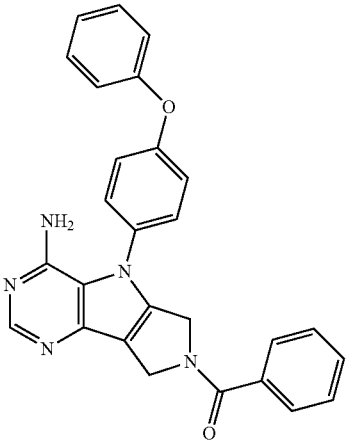 [SMILES: Nc1ncnc2c3c(n(-c4ccc(Oc5ccccc5)cc4)c12)CN(C(=O)c1ccccc1)C3] | [M + H]+ = 448.3 |
| 19 | 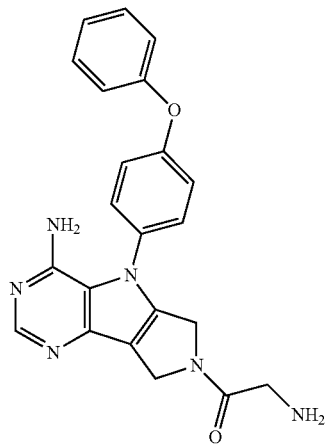 [SMILES: NCC(=O)N1Cc2c(n(-c3ccc(Oc4ccccc4)cc3)c3c(N)ncnc23)C1] | [M + H]+ = 401.2 |

TABLE 1-continued

Example Compounds of Formula 1

| Compound | Structure | MS (m/z) |
|---|---|---|
| 20 | 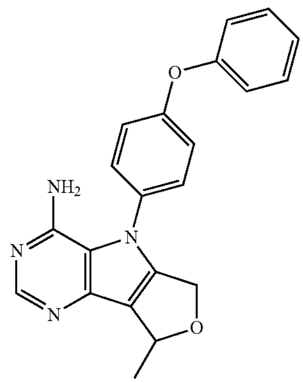 | [M + H]⁺ = 359.2 |
| 21 | 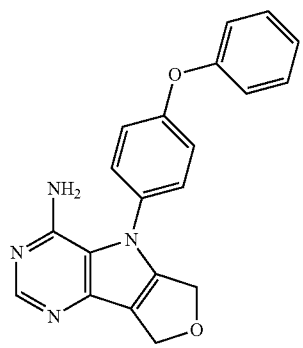 [SMILES: Nc1ncnc2c3c(n(-c4ccc(Oc5ccccc5)cc4)c12)COC3] | [M + H]⁺ = 345.2 |
| 22 | 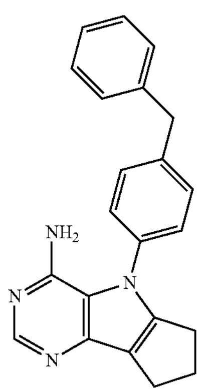 [SMILES: Nc1ncnc2c3c(n(-c4ccc(Cc5ccccc5)cc4)c12)CCC3] | [M + H]⁺ = 341.3 |
| 23 | 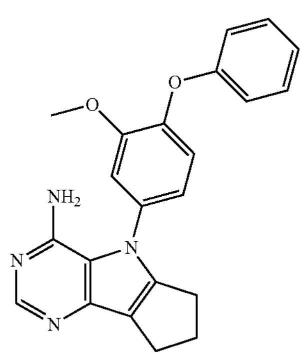 [SMILES: COc1cc(-n2c3c(c4ncnc(N)c42)CCC3)ccc1Oc1ccccc1] | [M + H]⁺ = 373.2 |

TABLE 1-continued

Example Compounds of Formula 1

| Compound | Structure | MS (m/z) |
|---|---|---|
| 24 | 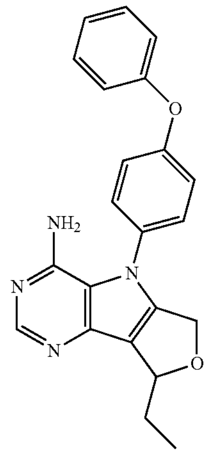 [SMILES: CCC1OCc2c1c1ncnc(N)c1n2-c1ccc(Oc2ccccc2)cc1] | $[M + H]^+ = 373.3$ |
| 25 | 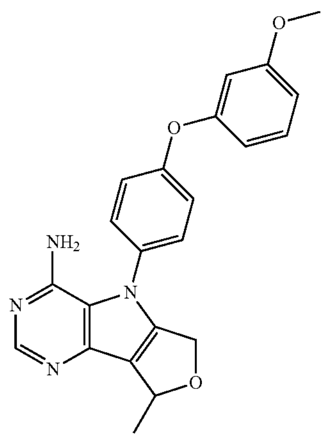 [SMILES: COc1cccc(Oc2ccc(-n3c4c(c5ncnc(N)c53)C(C)OC4)cc2)c1] | $[M + H]^+ = 389.2$ |
| 26 | 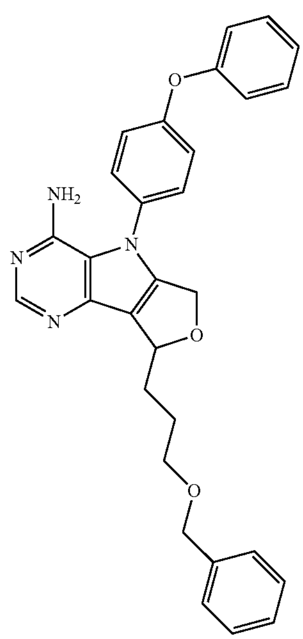 [SMILES: Nc1ncnc2c3c(n(-c4ccc(Oc5ccccc5)cc4)c12)COC3CCCOCc1ccccc1] | $[M + H]^+ = 493.3$ |

TABLE 1-continued

Example Compounds of Formula 1

| Compound | Structure | MS (m/z) |
|---|---|---|
| 27 | 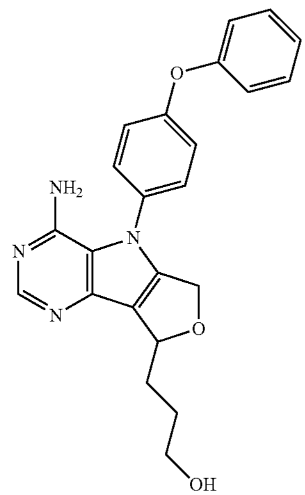 [SMILES: Nc1ncnc2c3c(n(-c4ccc(Oc5ccccc5)cc4)c12)COC3CCCO] | [M + H]⁺ = 403.3 |
| 28 | 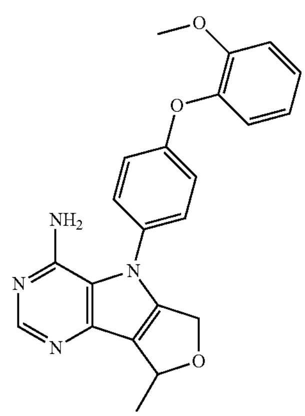 [SMILES: COc1ccccc1Oc1ccc(-n2c3c(c4ncnc(N)c42)C(C)OC3)cc1] | [M + H]⁺ = 389.3 |
| 29 | 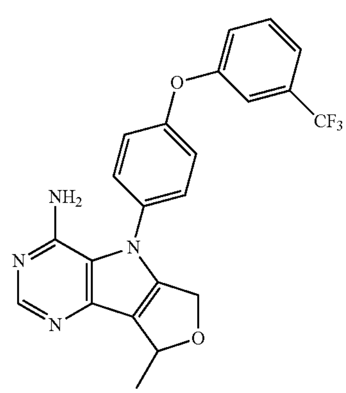 | [M + H]⁺ = 427.2 |

TABLE 1-continued

Example Compounds of Formula 1

| Compound | Structure | MS (m/z) |
|---|---|---|
| 30 | 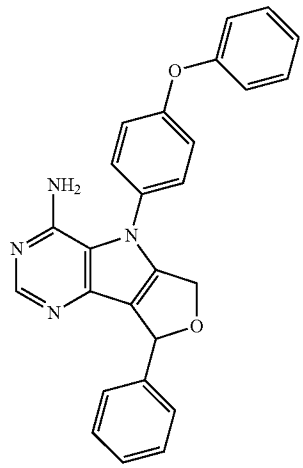 [SMILES: Nc1ncnc2c3c(n(-c4ccc(Oc5ccccc5)cc4)c12)COC3c1ccccc1] | [M + H]⁺ = 421.2 |
| 31 | 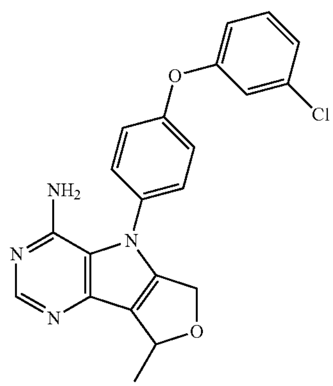 [SMILES: CC1OCc2c1c1ncnc(N)c1n2-c1ccc(Oc2cccc(Cl)c2)cc1] | [M + H]⁺ = 393.4 |
| 32 | 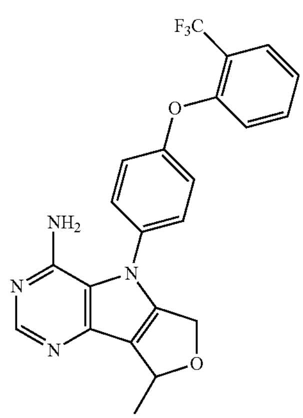 | [M + H]⁺ = 427.2 |

TABLE 1-continued

Example Compounds of Formula 1

| Compound | Structure | MS (m/z) |
|---|---|---|
| 33 | 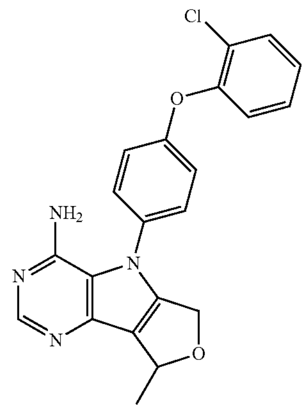 [SMILES: CC1OCc2c1c1ncnc(N)c1n2-c1ccc(Oc2ccccc2Cl)cc1] | [M + H]⁺ = 393.4 |
| 34 | 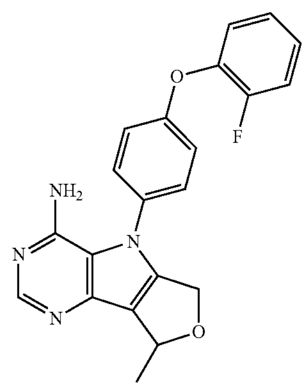 [SMILES: CC1OCc2c1c1ncnc(N)c1n2-c1ccc(Oc2ccccc2F)cc1] | [M + H]⁺ = 377.2 |
| 35 | 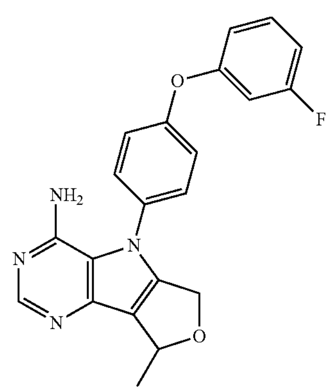 [SMILES: CC1OCc2c1c1ncnc(N)c1n2-c1ccc(Oc2cccc(F)c2)cc1] | [M + H]⁺ = 377.4 |

TABLE 1-continued

Example Compounds of Formula 1

| Compound | Structure | MS (m/z) |
|---|---|---|
| 36 | 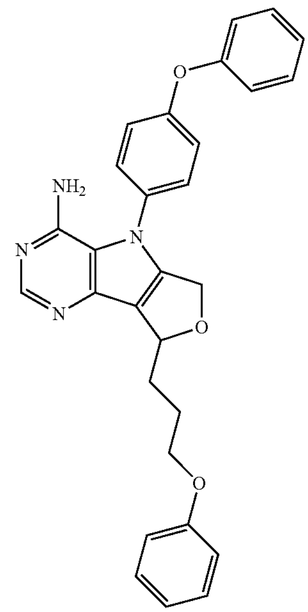 [SMILES: Nc1ncnc2c3c(n(-c4ccc(Oc5ccccc5)cc4)c12)COC3CCCOc1ccccc1] | [M + H]⁺ = 479.3 |
| 37 | 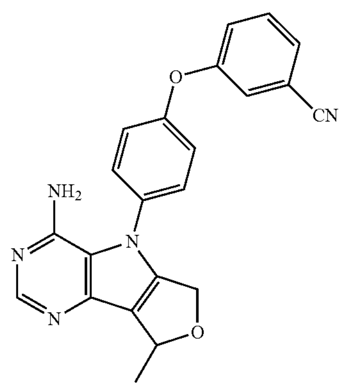 [SMILES: CC1OCc2c1c1ncnc(N)c1n2-c1ccc(Oc2cccc(C#N)c2)cc1] | [M + H]⁺ = 384.3 |
| 38 | 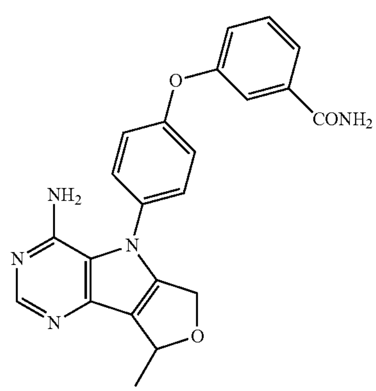 [SMILES: CC1OCc2c1c1ncnc(N)c1n2-c1ccc(Oc2cccc(C(N)=O)c2)cc1] | [M + H]⁺ = 402.2 |

TABLE 1-continued

Example Compounds of Formula 1

| Compound | Structure | MS (m/z) |
|---|---|---|
| 39 | 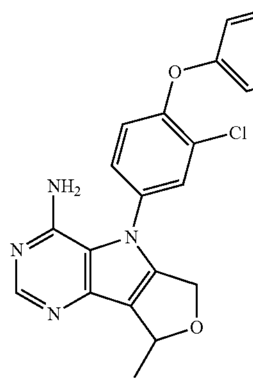 | [M + H]+ = 393.6 |
| 40 | 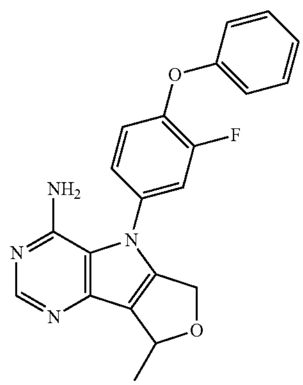 | [M + H]+ = 377.2 |
| 41 | 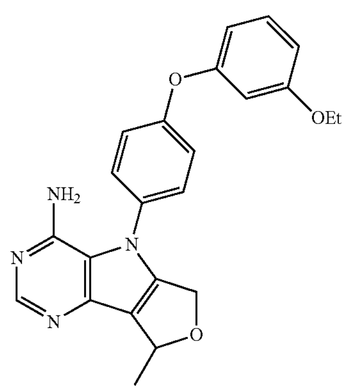 [SMILES: CCOc1cccc(Oc2ccc(-n3c4c(c5ncnc(N)c53)C(C)OC4)cc2)c1] | [M + H]+ = 403.3 |
| 42 | 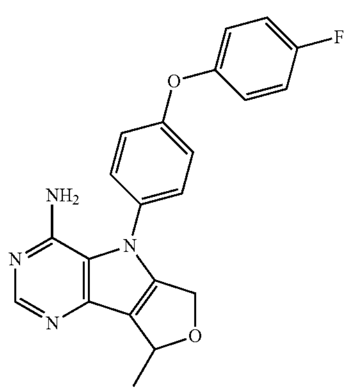 [SMILES: CC1OCc2c1c1ncnc(N)c1n2-c1ccc(Oc2ccc(F)cc2)cc1] | [M + H]+ = 377.2 |

TABLE 1-continued

Example Compounds of Formula 1

| Compound | Structure | MS (m/z) |
|---|---|---|
| 43 | 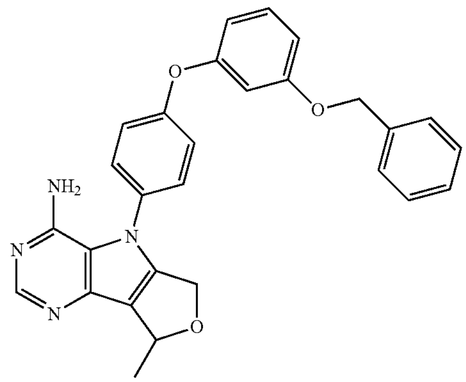 [SMILES: CC1OCc2c1c1ncnc(N)c1n2-c1ccc(Oc2cccc(OCc3ccccc3)c2)cc1] | [M + H]⁺ = 465.2 |
| 44 | 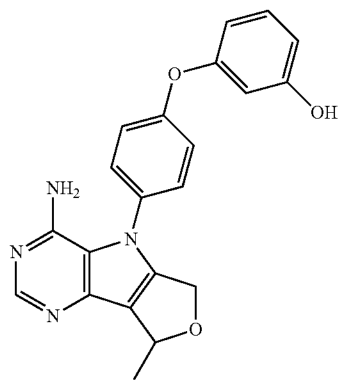 [SMILES: CC1OCc2c1c1ncnc(N)c1n2-c1ccc(Oc2cccc(O)c2)cc1] | [M + H]⁺ = 375.2 |
| 45 | 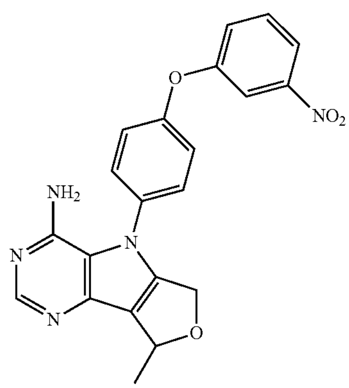 | [M + H]⁺ = 404.2 |
| 46 | 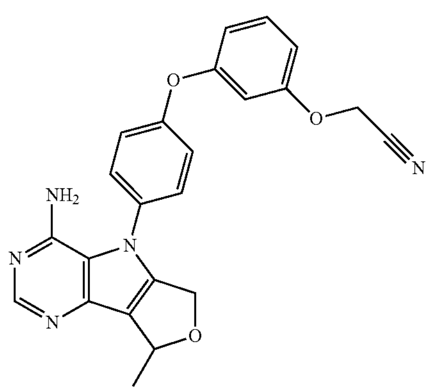 [SMILES: CC1OCc2c1c1ncnc(N)c1n2-c1ccc(Oc2cccc(OCC#N)c2)cc1] | [M + H]⁺ = 414.2 |

TABLE 1-continued

Example Compounds of Formula 1

| Compound | Structure | MS (m/z) |
|---|---|---|
| 47 | 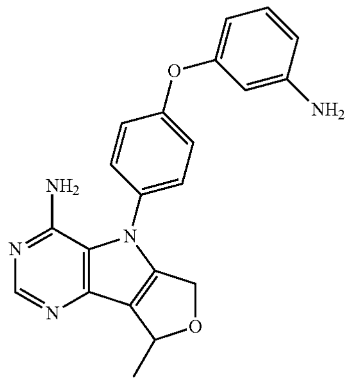 | [M + H]⁺ = 374.2 |
| 48 | 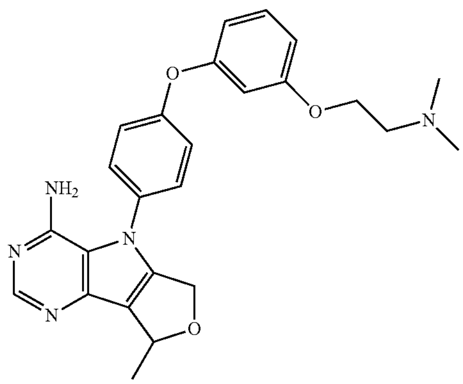 [SMILES: CC1OCc2c1c1ncnc(N)c1n2-c1ccc(Oc2cccc(OCCN(C)C)c2)cc1] | [M + H]⁺ = 446.4 |
| 49 | 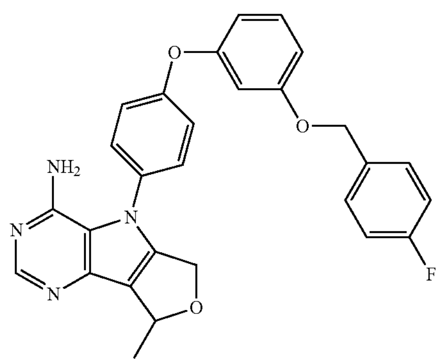 [SMILES: CC1OCc2c1c1ncnc(N)c1n2-c1ccc(Oc2cccc(OCc3ccc(F)cc3)c2)cc1] | [M + H]⁺ = 483.2 |
| 50 | 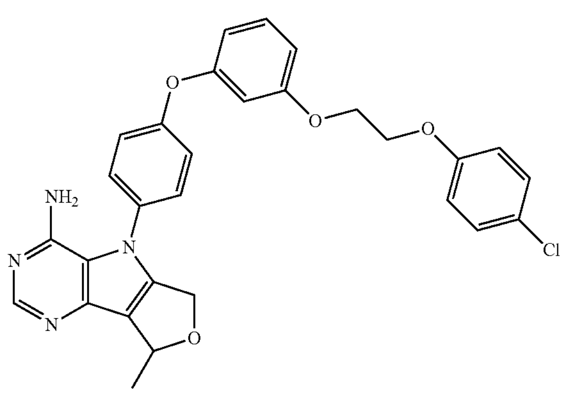 [SMILES: CC1OCc2c1c1ncnc(N)c1n2-c1ccc(Oc2cccc(OCCOc3ccc(Cl)cc3)c2)cc1] | [M + H]⁺ = 529.3 |

TABLE 1-continued
Example Compounds of Formula 1
| Compound | Structure | MS (m/z) |
|---|---|---|
| 51 | 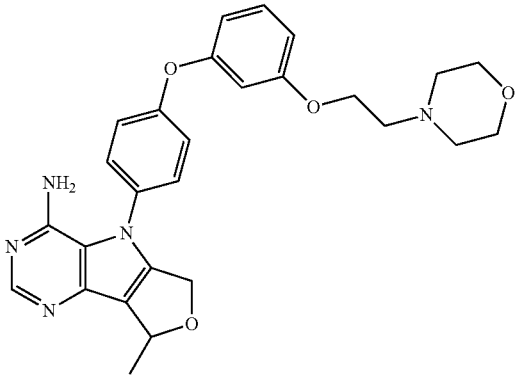 [SMILES: CC1OCc2c1c1ncnc(N)c1n2-c1ccc(Oc2cccc(OCCN3CCOCC3)c2)cc1] | [M + H]+ = 488.2 |
| 52 | 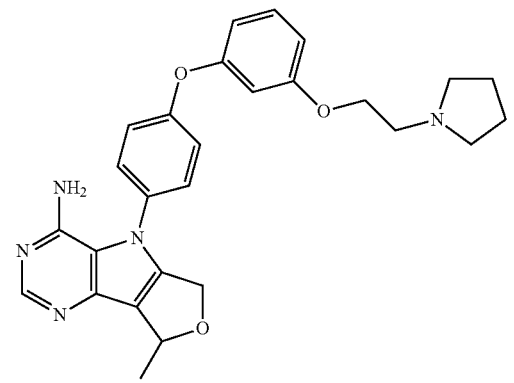 [SMILES: CC1OCc2c1c1ncnc(N)c1n2-c1ccc(Oc2cccc(OCCN3CCCC3)c2)cc1] | [M + H]+ = 472.3 |
| 53 | 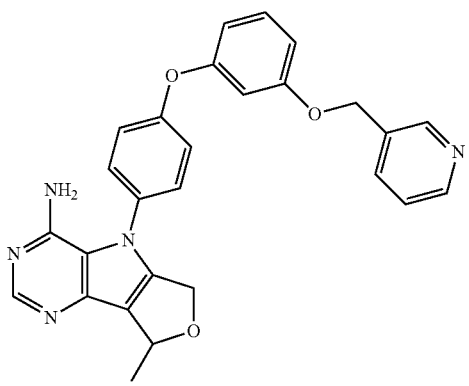 [SMILES: CC1OCc2c1c1ncnc(N)c1n2-c1ccc(Oc2cccc(OCc3cccnc3)c2)cc1] | [M + H]+ = 466.2 |
| 54 | 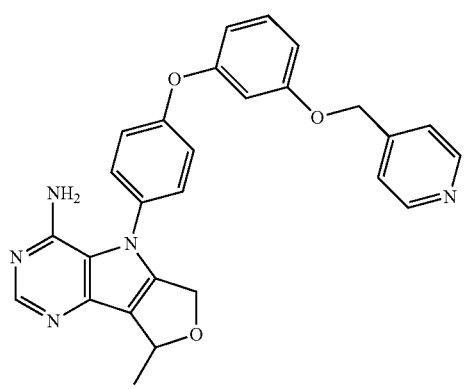 [SMILES: CC1OCc2c1c1ncnc(N)c1n2-c1ccc(Oc2cccc(OCc3ccncc3)c2)cc1] | [M + H]+ = 466.2 |

TABLE 1-continued

Example Compounds of Formula 1

| Compound | Structure | MS (m/z) |
|---|---|---|
| 55 | 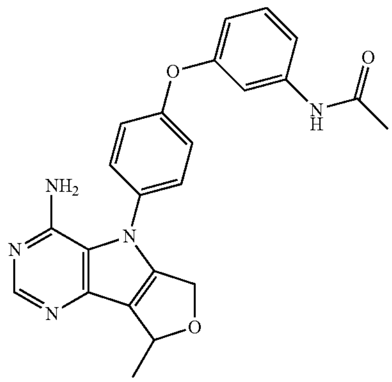 [SMILES: CC(=O)Nc1cccc(Oc2ccc(-n3c4c(c5ncnc(N)c53)C(C)OC4)cc2)c1] | [M + H]+ = 416.3 |
| 56 | 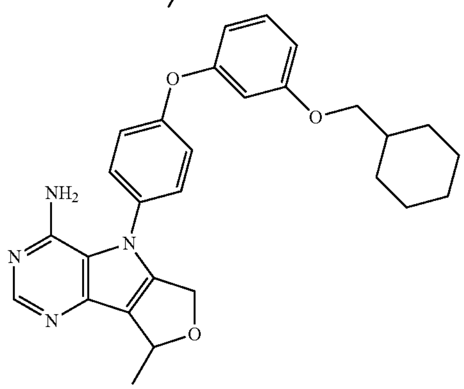 | [M + H]+ = 471.3 |
| 57 | 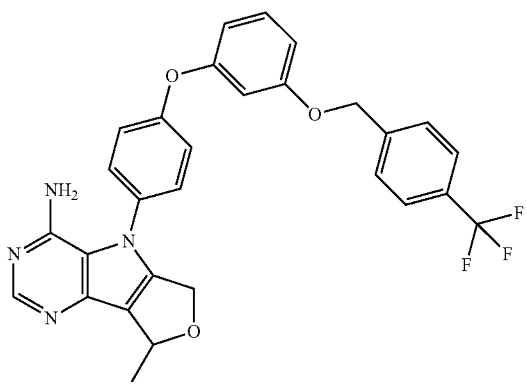 [SMILES: CC1OCc2c1c1ncnc(N)c1n2-c1ccc(Oc2cccc(OCc3ccc(C(F)(F)F)cc3)c2)cc1] | [M + H]+ = 533.1 |
| 58 | 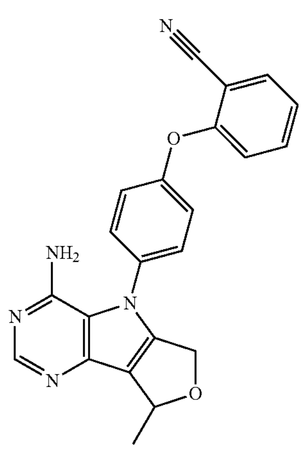 [SMILES: CC1OCc2c1c1ncnc(N)c1n2-c1ccc(Oc2ccccc2C#N)cc1] | [M + H]+ = 384.4 |

TABLE 1-continued
Example Compounds of Formula 1
| Compound | Structure | MS (m/z) |
|---|---|---|
| 59 | 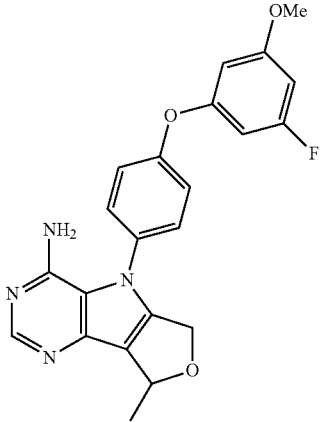 [SMILES: COc1cc(F)cc(Oc2ccc(-n3c4c(c5ncnc(N)c53)C(C)OC4)cc2)c1] | [M + H]⁺ = 407.4 |
| 60 | 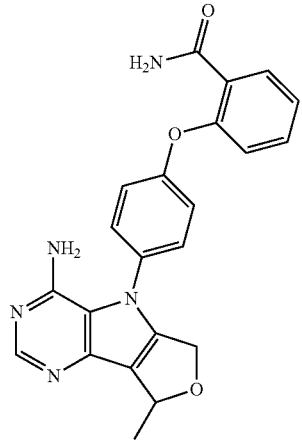 [SMILES: CC1OCc2c1c1ncnc(N)c1n2-c1ccc(Oc2ccccc2C(N)=O)cc1] | [M + H]⁺ = 402.2 |
| 61 | 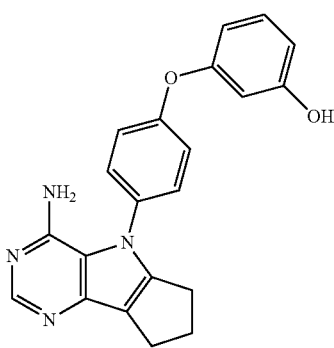 [SMILES: Nc1ncnc2c3c(n(-c4ccc(Oc5cccc(O)c5)cc4)c12)CCC3] | [M + H]⁺ = 359.2 |
| 62 | 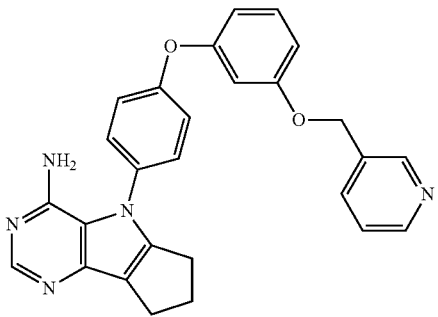 [SMILES: Nc1ncnc2c3c(n(-c4ccc(Oc5cccc(OCc6cccnc6)c5)cc4)c12)CCC3] | [M + H]⁺ = 450.2 |

TABLE 1-continued

Example Compounds of Formula 1

| Compound | Structure | MS (m/z) |
|---|---|---|
| 63 | 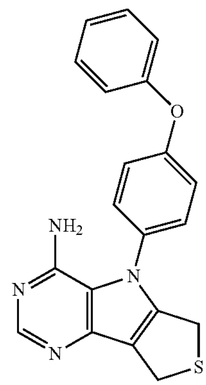 [SMILES: Nc1ncnc2c3c(n(-c4ccc(Oc5ccccc5)cc4)c12)CSC3] | [M + H]⁺ = 361.2 |
| 64 | 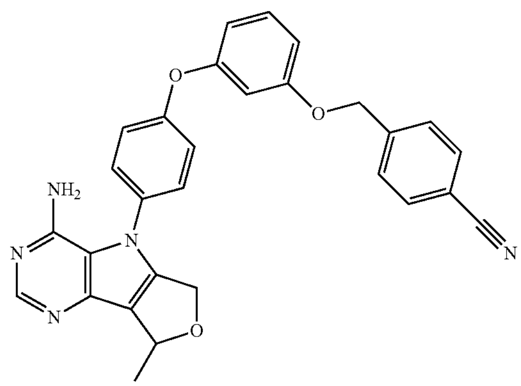 [SMILES: CC1OCc2c1c1ncnc(N)c1n2-c1ccc(Oc2cccc(OCc3ccc(C#N)cc3)c2)cc1] | [M + H]⁺ = 490.2 |
| 65 | 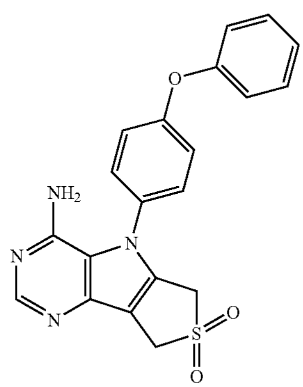 [SMILES: Nc1ncnc2c3c(n(-c4ccc(Oc5ccccc5)cc4)c12)CS(=O)(=O)C3] | [M + H]⁺ = 393.2 |
| 66 | 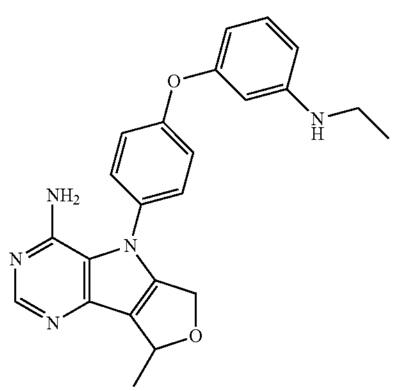 [SMILES: CCNc1cccc(Oc2ccc(-n3c4c(c5ncnc(N)c53)C(C)OC4)cc2)c1] | [M + H]⁺ = 402.2 |

TABLE 1-continued

Example Compounds of Formula 1

| Compound | Structure | MS (m/z) |
|---|---|---|
| 67 | 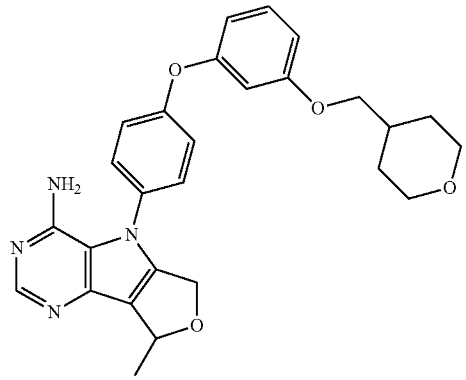 [SMILES: CC1OCc2c1c1ncnc(N)c1n2-c1ccc(Oc2cccc(OCC3CCOCC3)c2)cc1] | [M + H]⁺ = 473.3 |
| 68 | 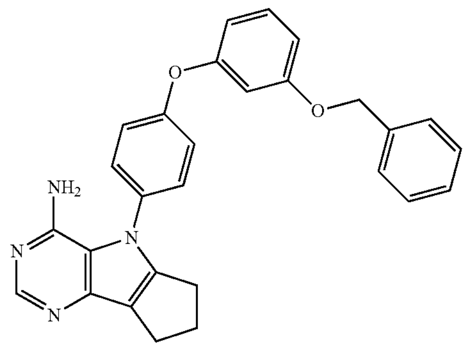 [SMILES: Nc1ncnc2c3c(n(-c4ccc(Oc5cccc(OCc6ccccc6)c5)cc4)c12)CCC3] | [M + H]⁺ = 449.2 |
| 69 | 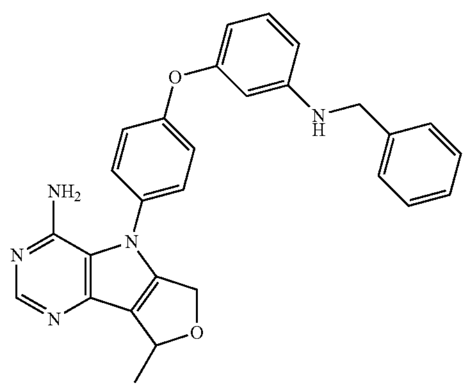 [SMILES: CC1OCc2c1c1ncnc(N)c1n2-c1ccc(Oc2cccc(NCc3ccccc3)c2)cc1] | [M + H]⁺ = 464.2 |
| 70 | 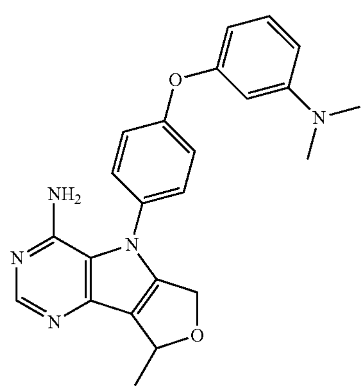 [SMILES: CC1OCc2c1c1ncnc(N)c1n2-c1ccc(Oc2cccc(N(C)C)c2)cc1] | [M + H]⁺ = 402.3 |

TABLE 1-continued

Example Compounds of Formula 1

| Compound | Structure | MS (m/z) |
|---|---|---|
| 71 | 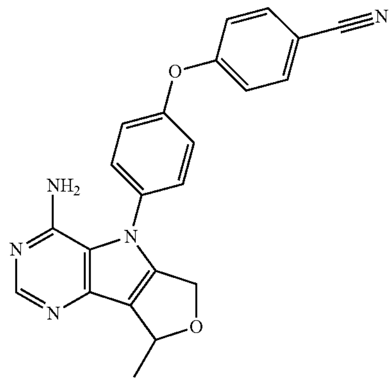 [SMILES: CC1OCc2c1c1ncnc(N)c1n2-c1ccc(Oc2ccc(C#N)cc2)cc1] | [M + H]+ = 384.2 |
| 72 | 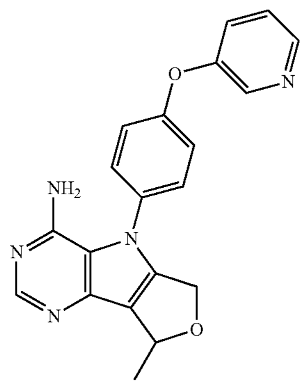 | [M + H]+ = 360.2 |
| 73 | 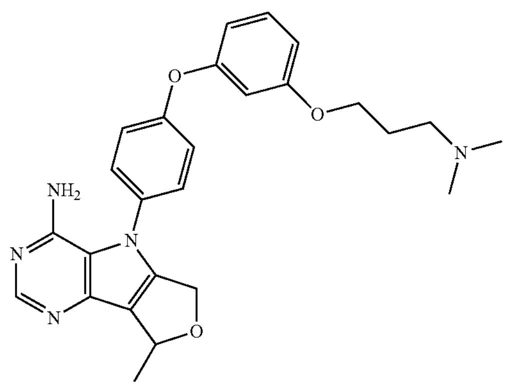 [SMILES: CC1OCc2c1c1ncnc(N)c1n2-c1ccc(Oc2cccc(OCCCN(C)C)c2)cc1] | [M + H]+ = 460.2 |
| 74 | 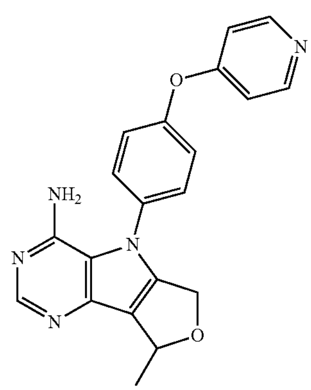 [SMILES: CC1OCc2c1c1ncnc(N)c1n2-c1ccc(Oc2ccncc2)cc1] | [M + H]+ = 360.3 |

TABLE 1-continued

Example Compounds of Formula 1

| Compound | Structure | MS (m/z) |
|---|---|---|
| 75 | 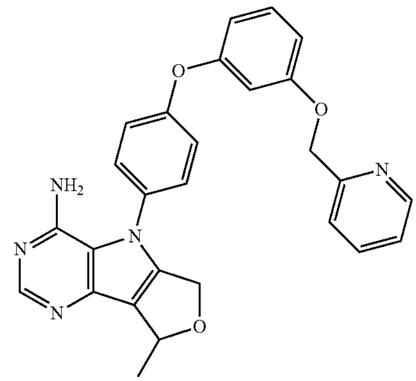 [SMILES: CC1OCc2c1c1ncnc(N)c1n2-c1ccc(Oc2cccc(OCc3ccccn3)c2)cc1] | [M + H]⁺ = 466.2 |
| 76 | 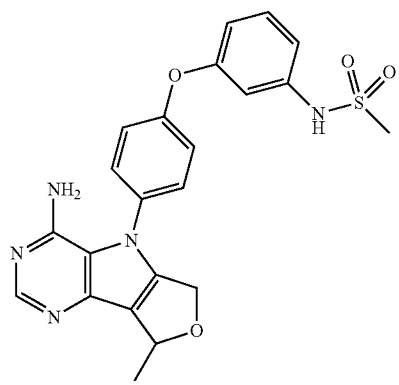 [SMILES: CC1OCc2c1c1ncnc(N)c1n2-c1ccc(Oc2cccc(NS(C)(=O)=O)c2)cc1] | [M + H]⁺ = 452.2 |
| 77 | 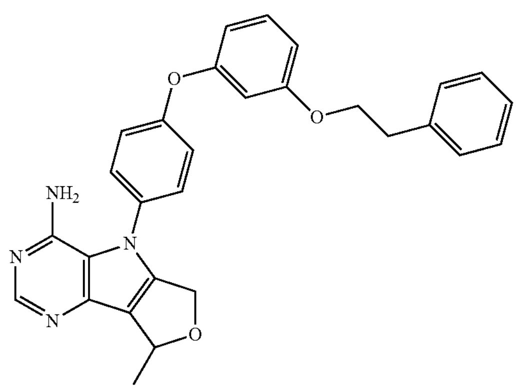 [SMILES: CC1OCc2c1c1ncnc(N)c1n2-c1ccc(Oc2cccc(OCCc3ccccc3)c2)cc1] | [M + H]⁺ = 479.2 |
| 78 | 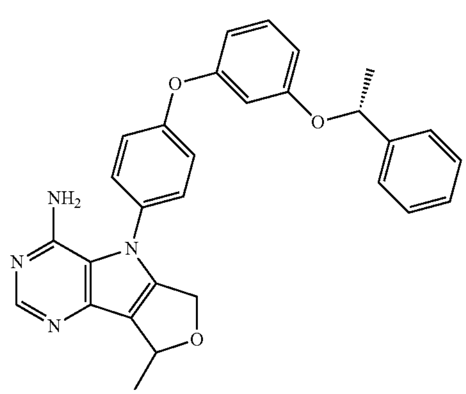 [SMILES: CC1OCc2c1c1ncnc(N)c1n2-c1ccc(Oc2cccc(O[C@H](C)c3ccccc3)c2)cc1] | [M + H]⁺ = 479.2 |

TABLE 1-continued

Example Compounds of Formula 1

| Compound | Structure | MS (m/z) |
|---|---|---|
| 79 | 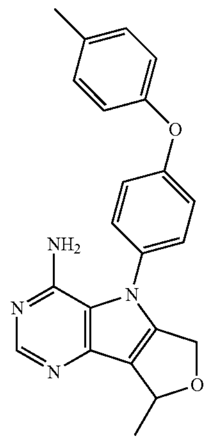 [SMILES: Cc1ccc(Oc2ccc(-n3c4c(c5ncnc(N)c53)C(C)OC4)cc2)cc1] | [M + H]⁺ = 373.3 |
| 80 | 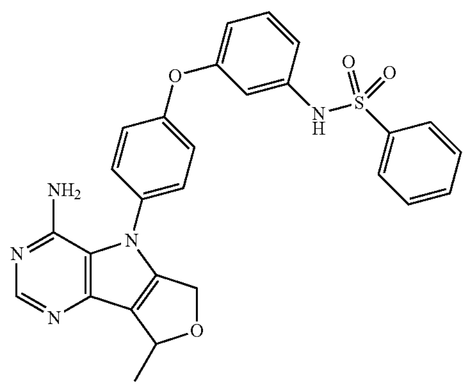 [SMILES: CC1OCc2c1c1ncnc(N)c1n2-c1ccc(Oc2cccc(NS(=O)(=O)c3ccccc3)c2)cc1] | [M + H]⁺ = 514.1 |
| 81 | 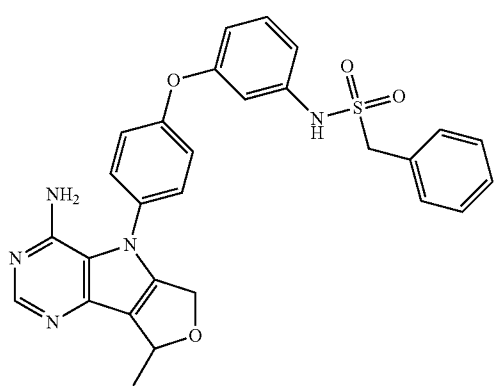 [SMILES: CC1OCc2c1c1ncnc(N)c1n2-c1ccc(Oc2cccc(NS(=O)(=O)Cc3ccccc3)c2)cc1] | [M + H]⁺ = 528.1 |

TABLE 1-continued

Example Compounds of Formula 1

| Compound | Structure | MS (m/z) |
|---|---|---|
| 82 | 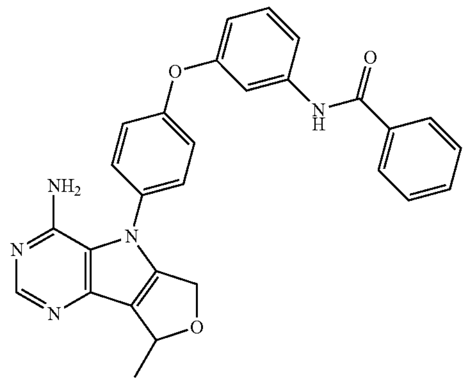 [SMILES: CC1OCc2c1c1ncnc(N)c1n2-c1ccc(Oc2cccc(NC(=O)c3ccccc3)c2)cc1] | [M + H]⁺ = 478.2 |
| 83 | 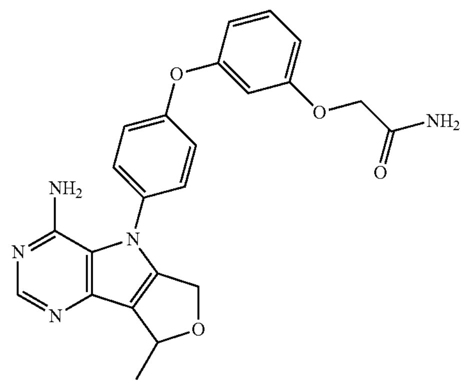 [SMILES: CC1OCc2c1c1ncnc(N)c1n2-c1ccc(Oc2cccc(OCC(N)=O)c2)cc1] | [M + H]⁺ = 432.2 |
| 84 | 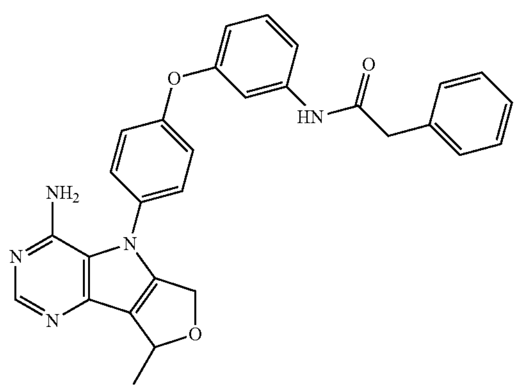 [SMILES: CC1OCc2c1c1ncnc(N)c1n2-c1ccc(Oc2cccc(NC(=O)Cc3ccccc3)c2)cc1] | [M + H]⁺ = 492.2 |
| 85 | 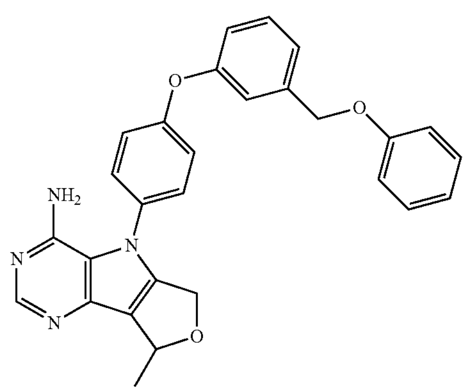 [SMILES: CC1OCc2c1c1ncnc(N)c1n2-c1ccc(Oc2cccc(COc3ccccc3)c2)cc1] | [M + H]⁺ = 465.2 |

US 9,624,239 B2
TABLE 1-continued
Example Compounds of Formula 1
| Compound | Structure | MS (m/z) |
|---|---|---|
| 86 | 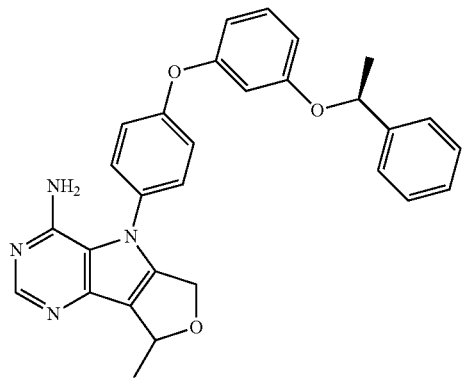 [SMILES: CC1OCc2c1c1ncnc(N)c1n2-c1ccc(Oc2cccc(O[C@@H](C)c3ccccc3)c2)cc1] | [M + H]⁺ = 479.2 |
| 87 | 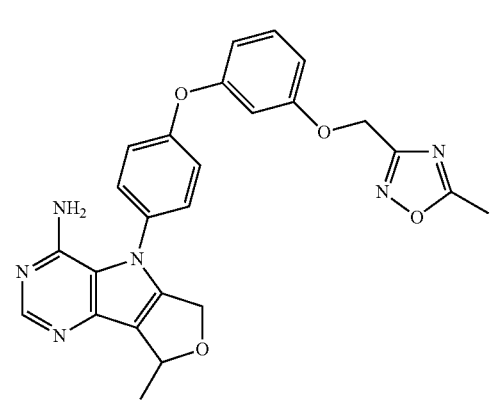 [SMILES: Cc1nc(COc2cccc(Oc3ccc(-n4c5c(c6ncnc(N)c64)C(C)OC5)cc3)c2)no1] | [M + H]⁺ = 471.2 |
| 88 | 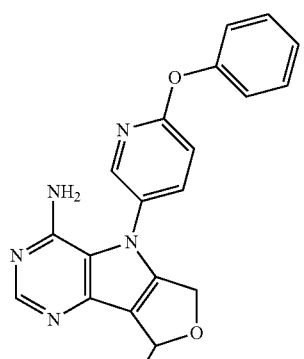 | [M + H]⁺ = 360.2 |
| 89 | 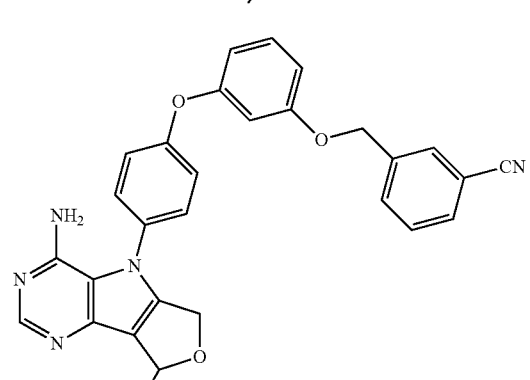 | [M + H]⁺ = 490.1 |

TABLE 1-continued
Example Compounds of Formula 1
| Compound | Structure | MS (m/z) |
|---|---|---|
| 90 | 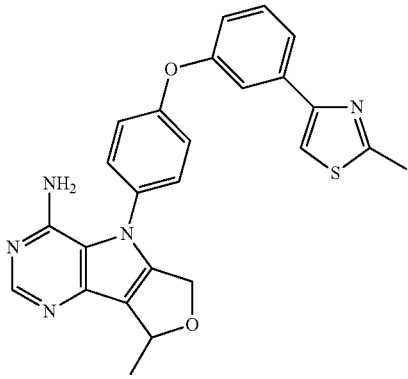 | [M + H]⁺ = 456.2 |
| 91 | 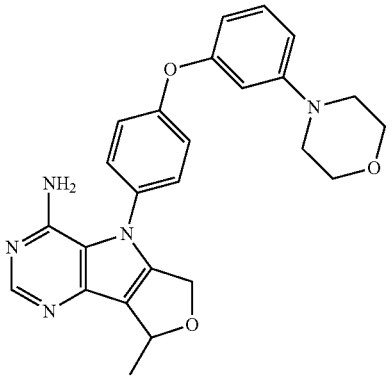 [SMILES: CC1OCc2c1c1ncnc(N)c1n2-c1ccc(Oc2cccc(N3CCOCC3)c2)cc1] | [M + H]⁺ = 444.2 |
| 92 | 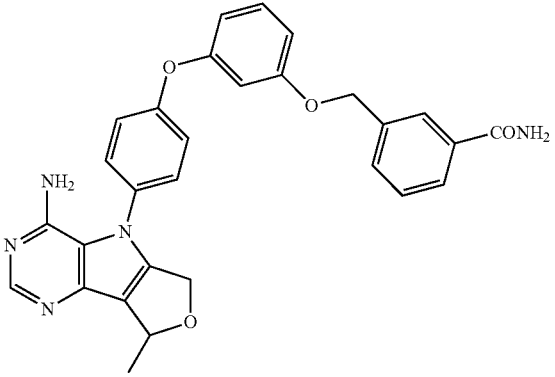 [SMILES: CC1OCc2c1c1ncnc(N)c1n2-c1ccc(Oc2cccc(OCc3cccc(C(N)=O)c3)c2)cc1] | [M + H]⁺ = 508.1 |
| 93 | 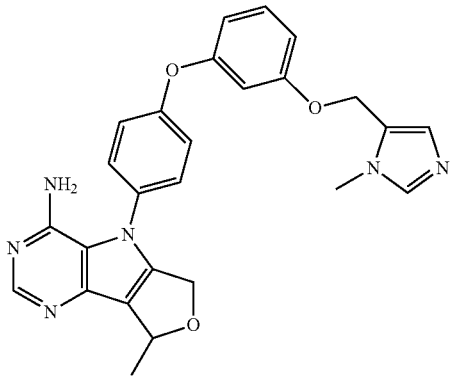 [SMILES: CC1OCc2c1c1ncnc(N)c1n2-c1ccc(Oc2cccc(OCc3cncn3C)c2)cc1] | [M + H]⁺ = 469.3 |

TABLE 1-continued

Example Compounds of Formula 1

| Compound | Structure | MS (m/z) |
|---|---|---|
| 94 | 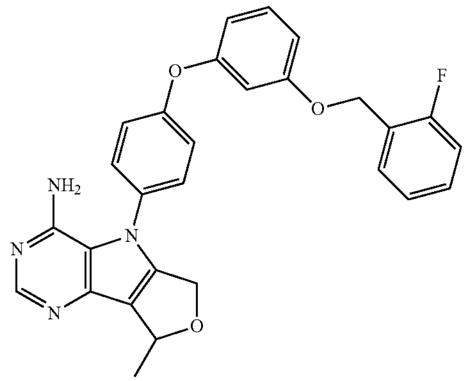 [SMILES: CC1OCc2c1c1ncnc(N)c1n2-c1ccc(Oc2cccc(OCc3ccccc3F)c2)cc1] | [M + H]⁺ = 483.1 |
| 95 | 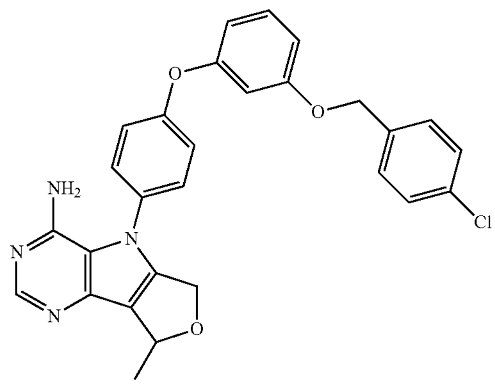 [SMILES: CC1OCc2c1c1ncnc(N)c1n2-c1ccc(Oc2cccc(OCc3ccc(Cl)cc3)c2)cc1] | [M + H]⁺ = 499.3 |
| 96 | 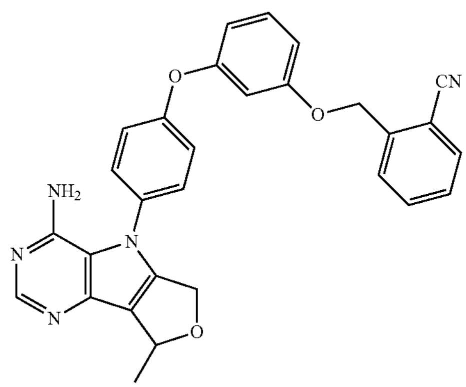 | [M + H]⁺ = 490.2 |
| 97 | 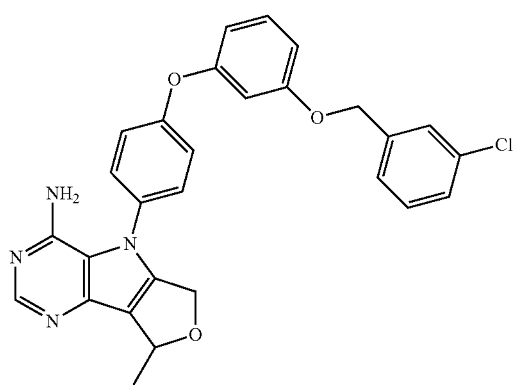 [SMILES: CC1OCc2c1c1ncnc(N)c1n2-c1ccc(Oc2cccc(OCc3cccc(Cl)c3)c2)cc1] | [M + H]⁺ = 499.3 |

TABLE 1-continued

Example Compounds of Formula 1

| Compound | Structure | MS (m/z) |
|---|---|---|
| 98 | 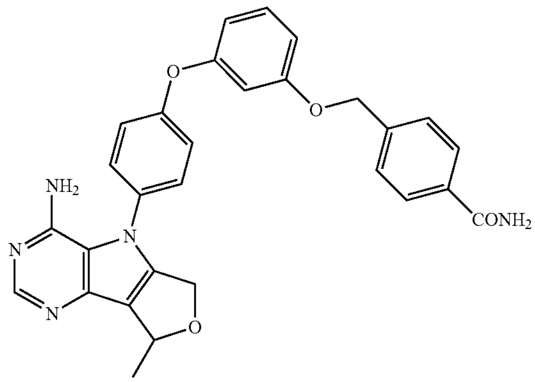 [SMILES: CC1OCc2c1c1ncnc(N)c1n2-c1ccc(Oc2cccc(OCc3ccc(C(N)=O)cc3)c2)cc1] | [M + H]+ = 508.2 |
| 99 | 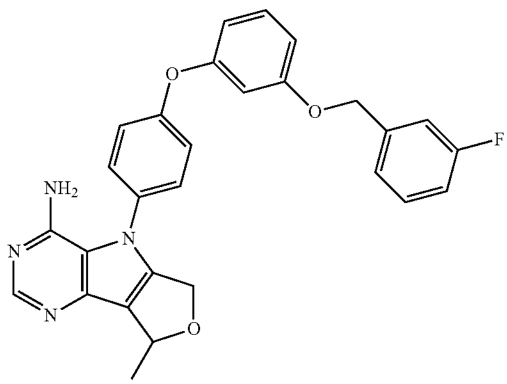 [SMILES: CC1OCc2c1c1ncnc(N)c1n2-c1ccc(Oc2cccc(OCc3cccc(F)c3)c2)cc1] | [M + H]+ = 483.1 |
| 100 | 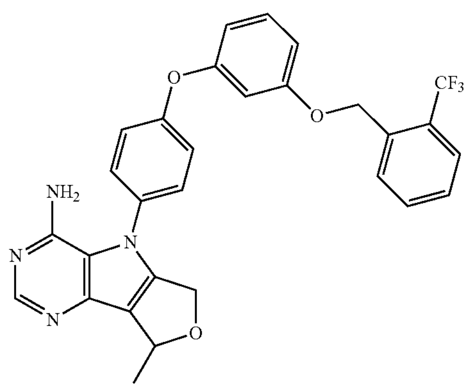 [SMILES: CC1OCc2c1c1ncnc(N)c1n2-c1ccc(Oc2cccc(OCc3ccccc3C(F)(F)F)c2)cc1] | [M + H]+ = 533.1 |
| 101 | 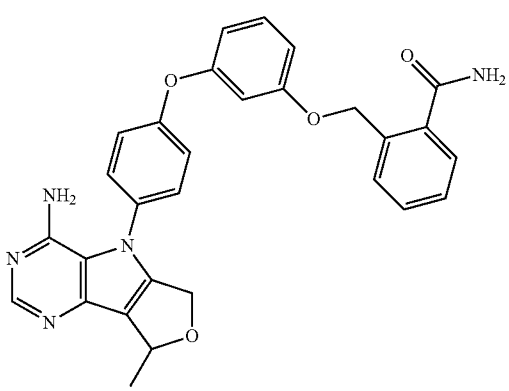 [SMILES: CC1OCc2c1c1ncnc(N)c1n2-c1ccc(Oc2cccc(OCc3ccccc3C(N)=O)c2)cc1] | [M + H]+ = 508.1 |

TABLE 1-continued
Example Compounds of Formula 1
| Compound | Structure | MS (m/z) |
|---|---|---|
| 102 | 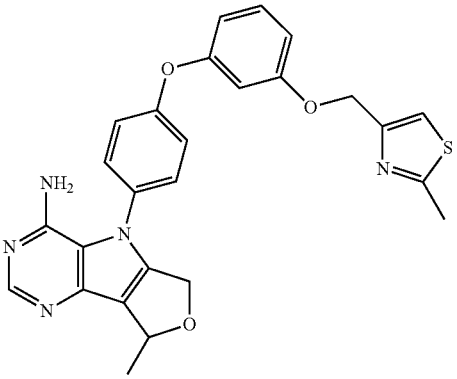 [SMILES: Cc1nc(COc2cccc(Oc3ccc(-n4c5c(c6ncnc(N)c64)C(C)OC5)cc3)c2)cs1] | [M + H]⁺ = 486.2 |
| 103 | 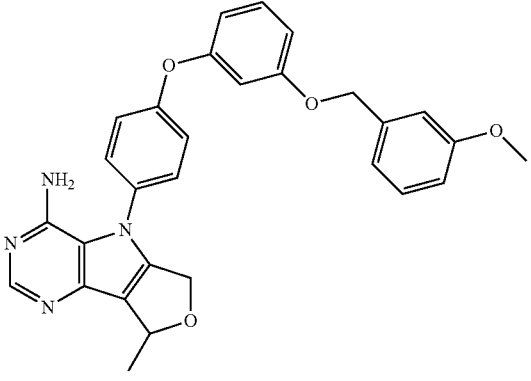 [SMILES: COc1cccc(COc2cccc(Oc3ccc(-n4c5c(c6ncnc(N)c64)C(C)OC5)cc3)c2)c1] | [M + H]⁺ = 495.1 |
| 104 | 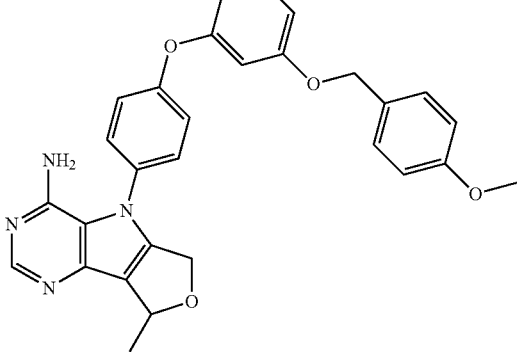 | [M + H]⁺ = 495.0 |
| 105 | 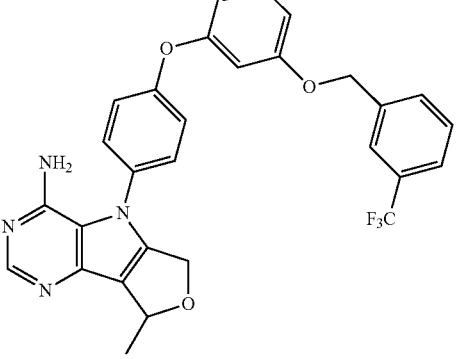 | [M + H]⁺ = 533.0 |

TABLE 1-continued

Example Compounds of Formula 1

| Compound | Structure | MS (m/z) |
|---|---|---|
| 106 | 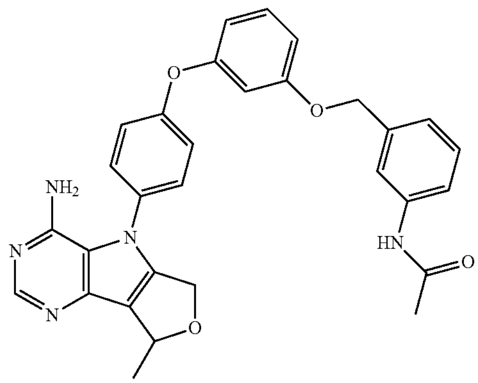 [SMILES: CC(=O)Nc1cccc(COc2cccc(Oc3ccc(-n4c5c(c6ncnc(N)c64)C(C)OC5)cc3)c2)c1] | [M + H]+ = 522.1 |
| 107 | 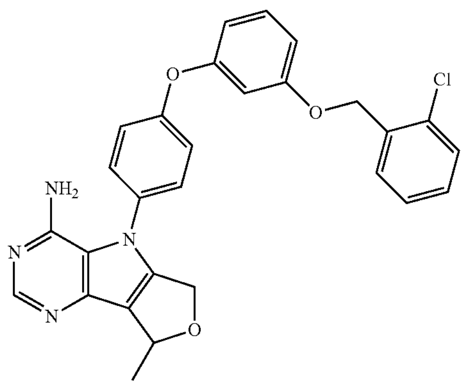 | [M + H]+ = 499.3 |
| 108 | 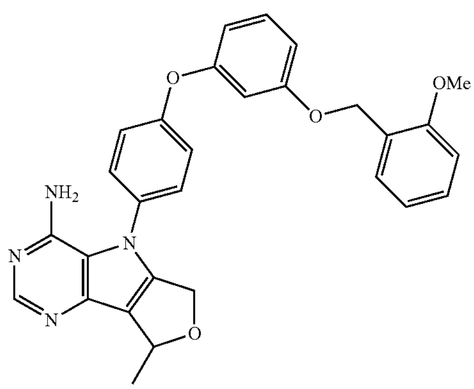 [SMILES: COc1ccccc1COc1cccc(Oc2ccc(-n3c4c(c5ncnc(N)c53)C(C)OC4)cc2)c1] | [M + H]+ = 495.1 |
| 109 | 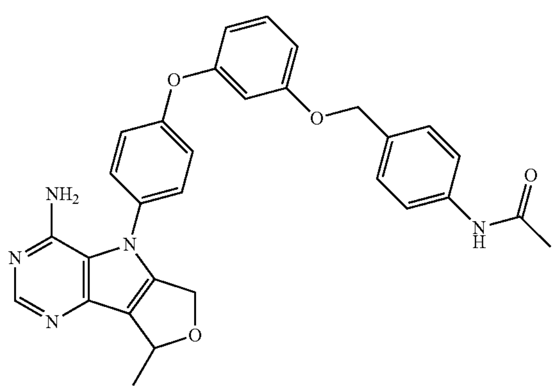 [SMILES: CC(=O)Nc1ccc(COc2cccc(Oc3ccc(-n4c5c(c6ncnc(N)c64)C(C)OC5)cc3)c2)cc1] | [M + H]+ = 522.1 |

TABLE 1-continued

Example Compounds of Formula 1

| Compound | Structure | MS (m/z) |
|---|---|---|
| 110 | 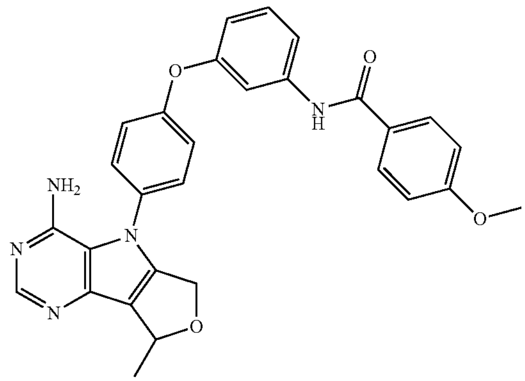 [SMILES: COc1ccc(C(=O)Nc2cccc(Oc3ccc(-n4c5c(c6ncnc(N)c64)C(C)OC5)cc3)c2)cc1] | [M + H]⁺ = 508.1 |
| 111 | 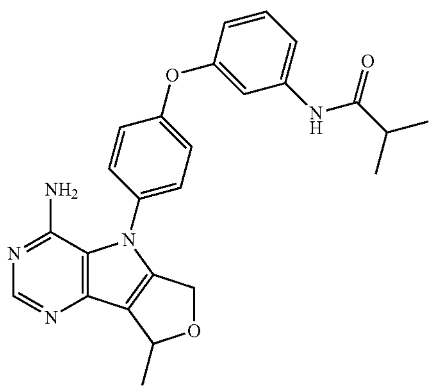 [SMILES: CC(C)C(=O)Nc1cccc(Oc2ccc(-n3c4c(c5ncnc(N)c53)C(C)OC4)cc2)c1] | [M + H]⁺ = 444.2 |
| 112 | 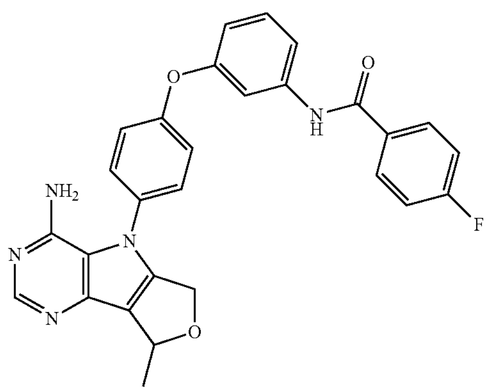 [SMILES: CC1OCc2c1c1ncnc(N)c1n2-c1ccc(Oc2cccc(NC(=O)c3ccc(F)cc3)c2)cc1] | [M + H]⁺ = 496.1 |
| 113 | 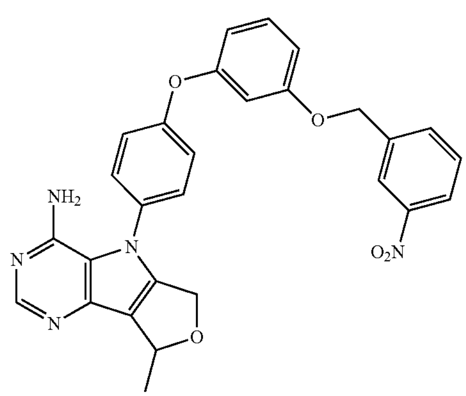 [SMILES: CC1OCc2c1c1ncnc(N)c1n2-c1ccc(Oc2cccc(OCc3cccc([N+](=O)[O-])c3)c2)cc1] | [M + H]⁺ = 510.1 |

TABLE 1-continued

Example Compounds of Formula 1

| Compound | Structure | MS (m/z) |
| --- | --- | --- |
| 114 | 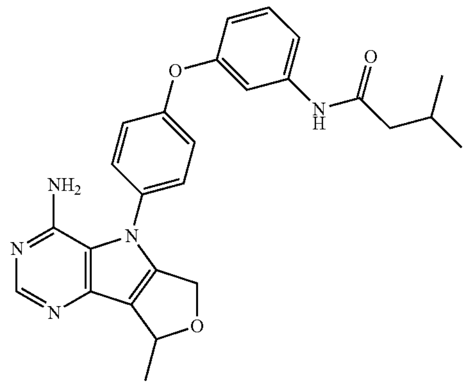 [SMILES: CC(C)CC(=O)Nc1cccc(Oc2ccc(-n3c4c(c5ncnc(N)c53)C(C)OC4)cc2)c1] | [M + H]⁺ = 458.1 |
| 115 | 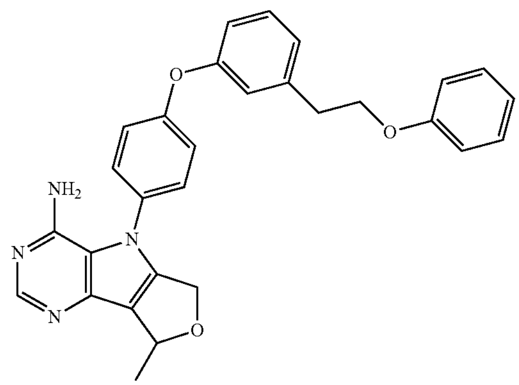 [SMILES: CC1OCc2c1c1ncnc(N)c1n2-c1ccc(Oc2cccc(CCOc3ccccc3)c2)cc1] | [M + H]⁺ = 479.1 |
| 116 | 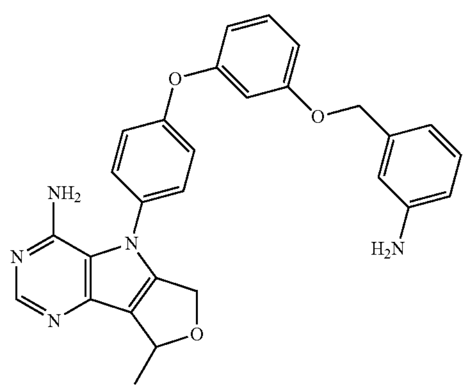 [SMILES: CC1OCc2c1c1ncnc(N)c1n2-c1ccc(Oc2cccc(OCc3cccc(N)c3)c2)cc1] | [M + H]⁺ = 480.3 |
| 117 | 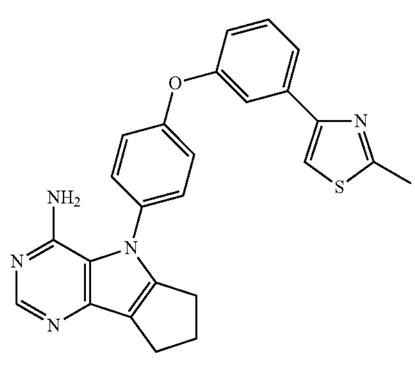 [SMILES: Cc1nc(-c2cccc(Oc3ccc(-n4c5c(c6ncnc(N)c64)CCC5)cc3)c2)cs1] | [M + H]⁺ = 440.1 |

TABLE 1-continued

Example Compounds of Formula 1

| Compound | Structure | MS (m/z) |
|---|---|---|
| 118 | 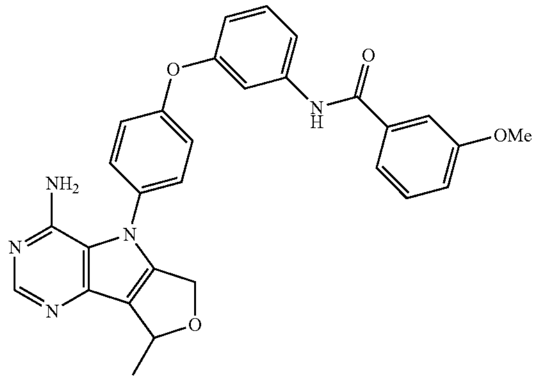 [SMILES: COc1cccc(C(=O)Nc2cccc(Oc3ccc(-n4c5c(c6ncnc(N)c64)C(C)OC5)cc3)c2)c1] | [M + H]⁺ = 508.1 |
| 119 | 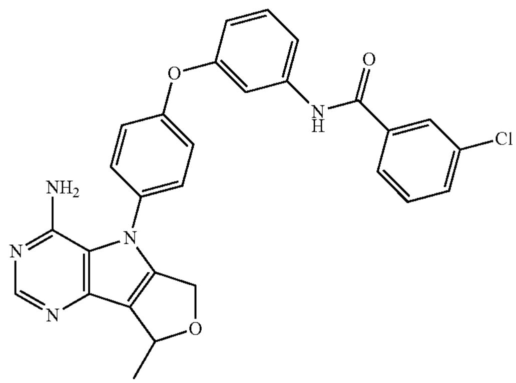 [SMILES: CC1OCc2c1c1ncnc(N)c1n2-c1ccc(Oc2cccc(NC(=O)c3cccc(Cl)c3)c2)cc1] | [M + H]⁺ = 512.3 |
| 120 | 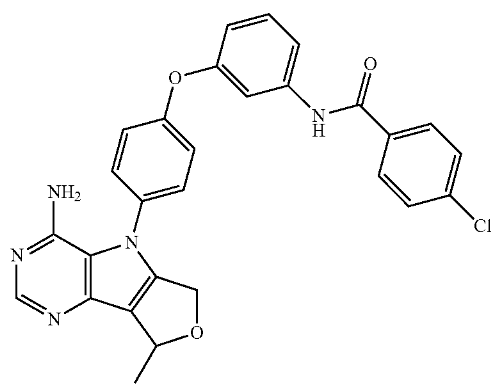 [SMILES: CC1OCc2c1c1ncnc(N)c1n2-c1ccc(Oc2cccc(NC(=O)c3ccc(Cl)cc3)c2)cc1] | [M + H]⁺ = 512.3 |
| 121 | 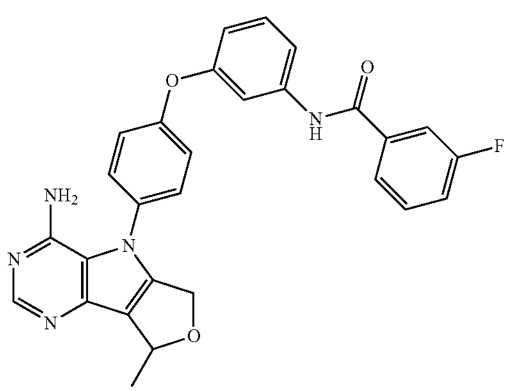 [SMILES: CC1OCc2c1c1ncnc(N)c1n2-c1ccc(Oc2cccc(NC(=O)c3cccc(F)c3)c2)cc1] | [M + H]⁺ = 496.1 |

TABLE 1-continued

Example Compounds of Formula 1

| Compound | Structure | MS (m/z) |
|---|---|---|
| 122 | 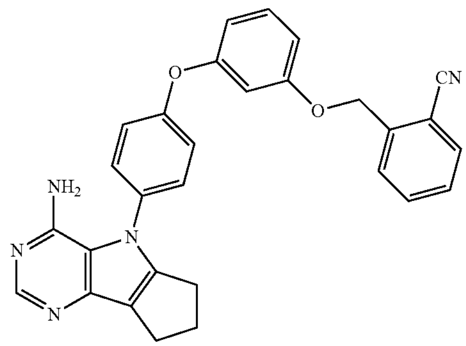 [SMILES: N#Cc1ccccc1COc1cccc(Oc2ccc(-n3c4c(c5ncnc(N)c53)CCC4)cc2)c1] | [M + H]⁺ = 474.2 |
| 123 | 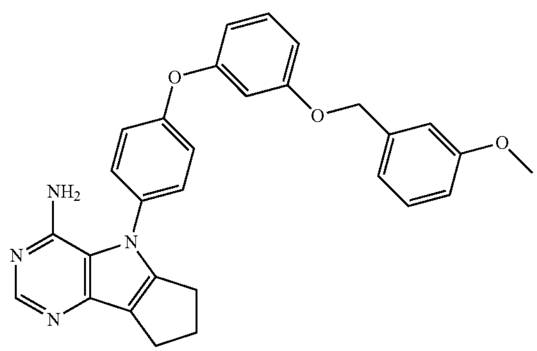 [SMILES: COc1cccc(COc2cccc(Oc3ccc(-n4c5c(c6ncnc(N)c64)CCC5)cc3)c2)c1] | [M + H]⁺ = 479.1 |
| 124 | 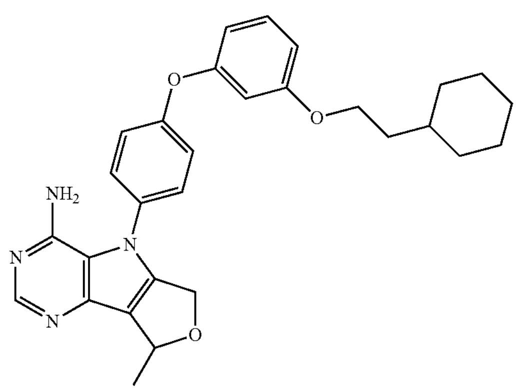 [SMILES: CC1OCc2c1c1ncnc(N)c1n2-c1ccc(Oc2cccc(OCCC3CCCCC3)c2)cc1] | [M + H]⁺ = 485.2 |
| 125 | 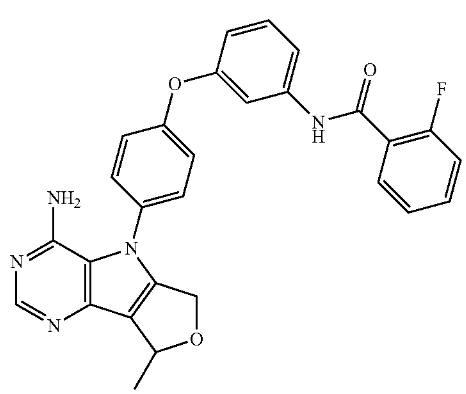 [SMILES: CC1OCc2c1c1ncnc(N)c1n2-c1ccc(Oc2cccc(NC(=O)c3ccccc3F)c2)cc1] | [M + H]⁺ = 496.1 |

TABLE 1-continued

Example Compounds of Formula 1

| Compound | Structure | MS (m/z) |
|---|---|---|
| 126 | 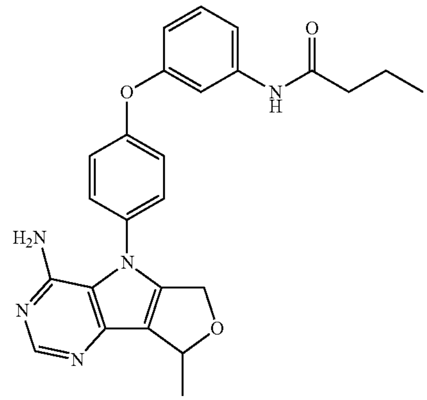 [SMILES: CCCC(=O)Nc1cccc(Oc2ccc(-n3c4c(c5ncnc(N)c53)C(C)OC4)cc2)c1] | [M + H]⁺ = 444.2 |
| 127 | 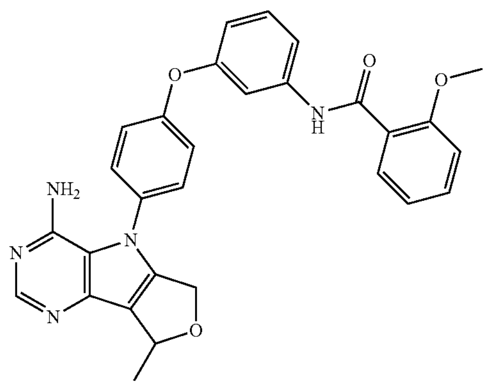 [SMILES: COc1ccccc1C(=O)Nc1cccc(Oc2ccc(-n3c4c(c5ncnc(N)c53)C(C)OC4)cc2)c1] | [M + H]⁺ = 508.1 |
| 128 | 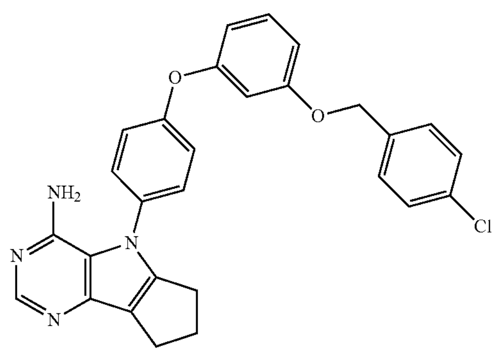 [SMILES: Nc1ncnc2c3c(n(-c4ccc(Oc5cccc(OCc6ccc(Cl)cc6)c5)cc4)c12)CCC3] | [M + H]⁺ = 483.3 |
| 129 | 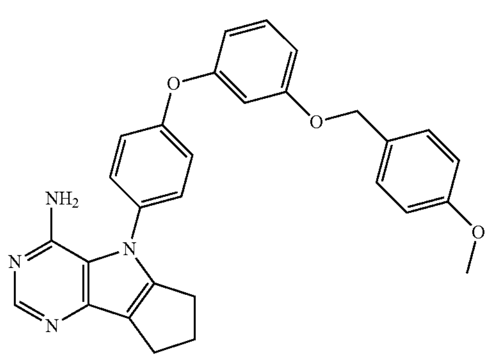 [SMILES: COc1ccc(COc2cccc(Oc3ccc(-n4c5c(c6ncnc(N)c64)CCC5)cc3)c2)cc1] | [M + H]⁺ = 479.1 |

TABLE 1-continued

Example Compounds of Formula 1

| Compound | Structure | MS (m/z) |
|---|---|---|
| 130 | 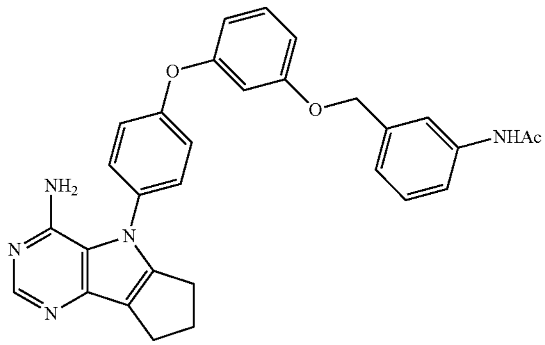 [SMILES: CC(=O)Nc1cccc(COc2cccc(Oc3ccc(-n4c5c(c6ncnc(N)c64)CCC5)cc3)c2)c1] | [M + H]⁺ = 506.3 |
| 131 | 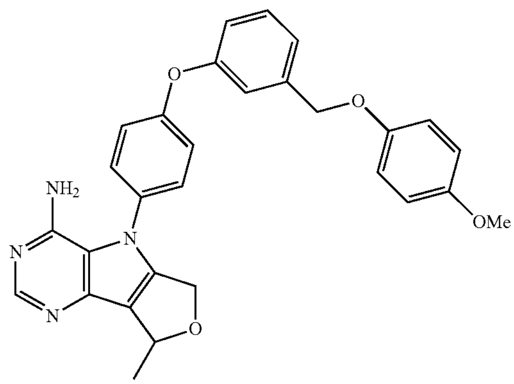 [SMILES: COc1ccc(OCc2cccc(Oc3ccc(-n4c5c(c6ncnc(N)c64)C(C)OC5)cc3)c2)cc1] | [M + H]⁺ = 495.1 |
| 132 | 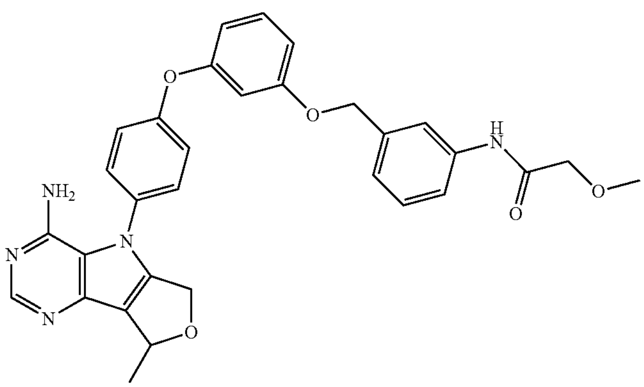 [SMILES: COCC(=O)Nc1cccc(COc2cccc(Oc3ccc(-n4c5c(c6ncnc(N)c64)C(C)OC5)cc3)c2)c1] | [M + H]⁺ = 552.1 |
| 133 | 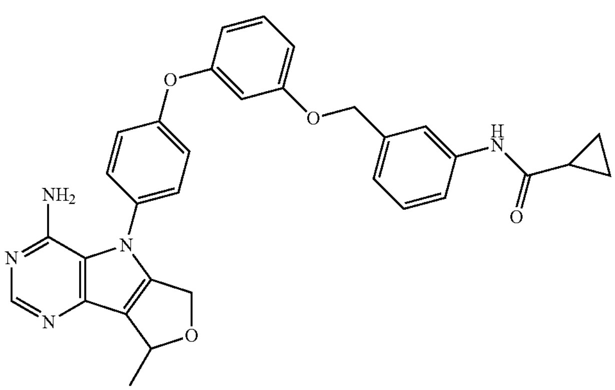 [SMILES: CC1OCc2c1c1ncnc(N)c1n2-c1ccc(Oc2cccc(OCc3cccc(NC(=O)C4CC4)c3)c2)cc1] | [M + H]⁺ = 548.1 |

TABLE 1-continued

Example Compounds of Formula 1

| Compound | Structure | MS (m/z) |
|---|---|---|
| 134 | 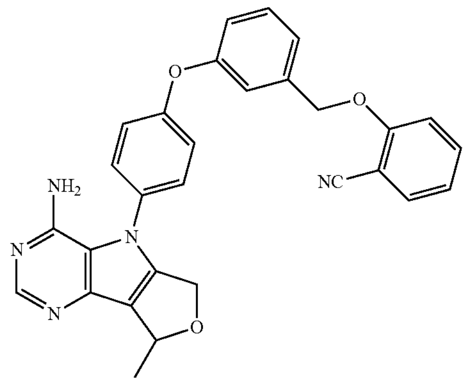 [SMILES: CC1OCc2c1c1ncnc(N)c1n2-c1ccc(Oc2cccc(COc3ccccc3C#N)c2)cc1] | [M + H]⁺ = 490.1 |
| 135 | 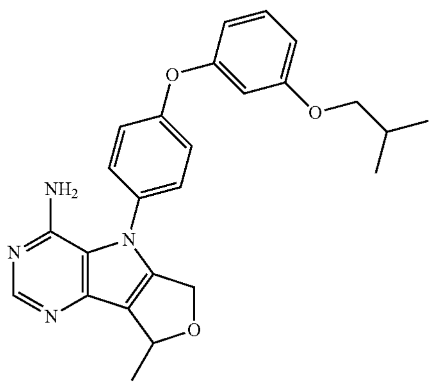 [SMILES: CC(C)COc1cccc(Oc2ccc(-n3c4c(c5ncnc(N)c53)C(C)OC4)cc2)c1] | [M + H]⁺ = 431.2 |
| 136 | 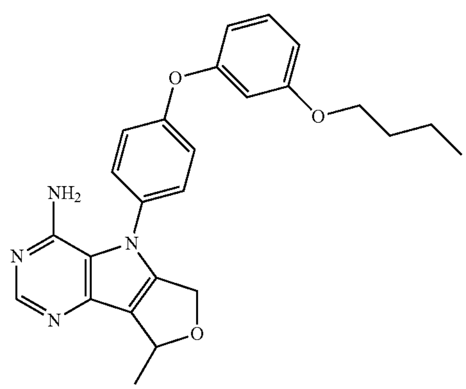 [SMILES: CCCCOc1cccc(Oc2ccc(-n3c4c(c5ncnc(N)c53)C(C)OC4)cc2)c1] | [M + H]⁺ = 431.2 |
| 137 | 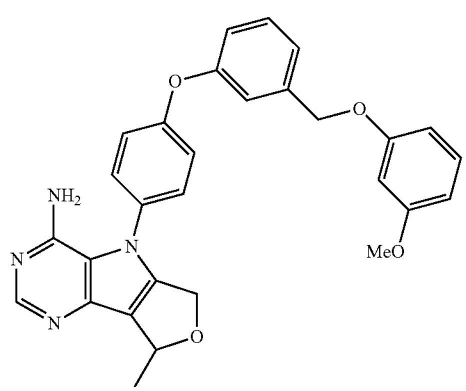 [SMILES: COc1cccc(OCc2cccc(Oc3ccc(-n4c5c(c6ncnc(N)c64)C(C)OC5)cc3)c2)c1] | [M + H]⁺ = 495.1 |

TABLE 1-continued
Example Compounds of Formula 1
| Compound | Structure | MS (m/z) |
|---|---|---|
| 138 | 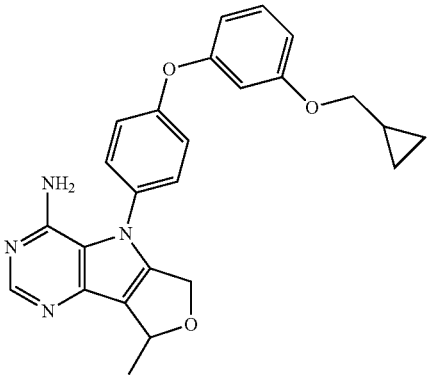 [SMILES: CC1OCc2c1c1ncnc(N)c1n2-c1ccc(Oc2cccc(OCC3CC3)c2)cc1] | [M + H]+ = 429.2 |
| 139 | 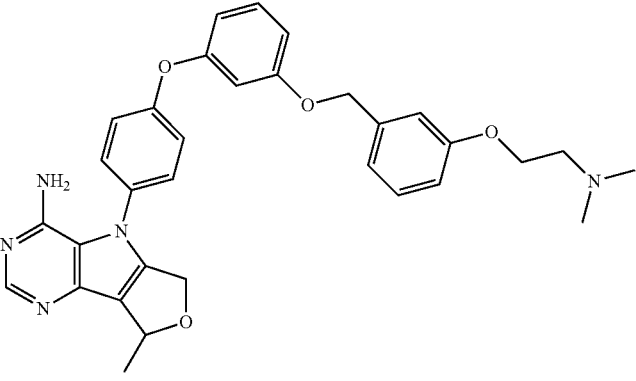 [SMILES: CC1OCc2c1c1ncnc(N)c1n2-c1ccc(Oc2cccc(OCc3cccc(OCCN(C)C)c3)c2)cc1] | [M + H]+ = 552.1 |
| 140 | 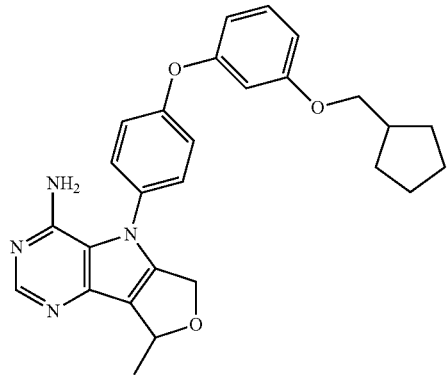 [SMILES: CC1OCc2c1c1ncnc(N)c1n2-c1ccc(Oc2cccc(OCC3CCCC3)c2)cc1] | [M + H]+ = 457.2 |
| 141 | 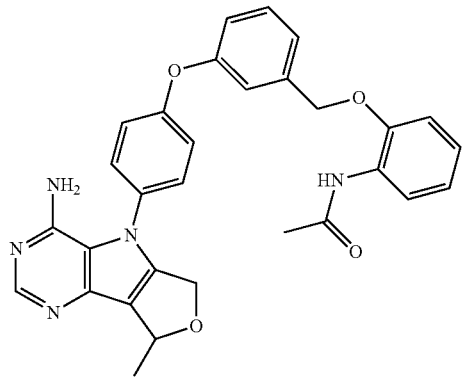 [SMILES: CC(=O)Nc1ccccc1OCc1cccc(Oc2ccc(-n3c4c(c5ncnc(N)c53)C(C)OC4)cc2)c1] | [M + H]+ = 522.1 |

TABLE 1-continued

Example Compounds of Formula 1

| Compound | Structure | MS (m/z) |
|---|---|---|
| 142 | 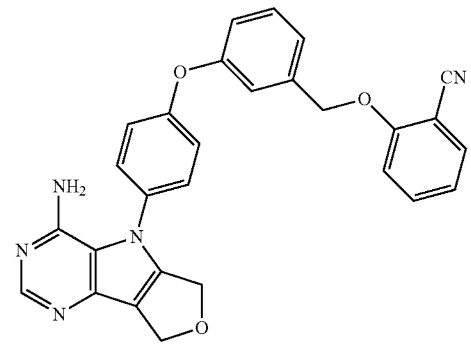 [SMILES: N#Cc1ccccc1OCc1cccc(Oc2ccc(-n3c4c(c5ncnc(N)c53)COC4)cc2)c1] | [M + H]⁺ = 476.1 |
| 143 | 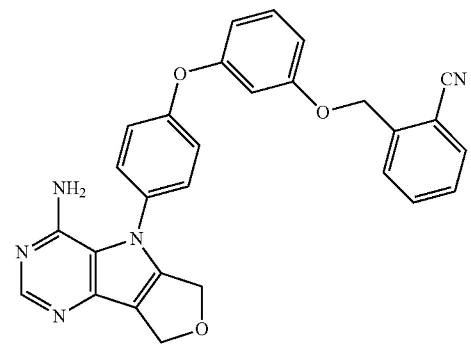 | [M + H]⁺ = 476.2 |
| 144 | 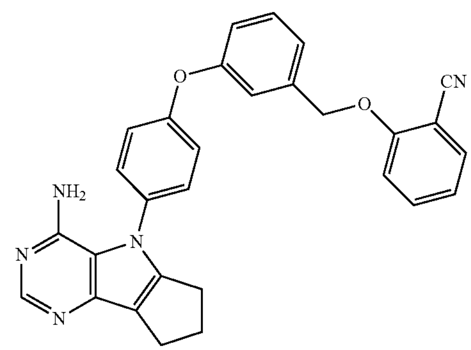 [SMILES: N#Cc1ccccc1OCc1cccc(Oc2ccc(-n3c4c(c5ncnc(N)c53)CCC4)cc2)c1] | [M + H]⁺ = 474.2 |

Kinase Binding

Btk and Lck Kinase Inhibition Assay

Fluorescence polarization-based kinase assays were performed in 384 well-plate format using histidine tagged recombinant human full-length Bruton Agammaglobulinemia Tyrosine Kinase (Btk) or histidine tagged recombinant Human Lymphocyte-Specific Protein Tyrosine Kinase (Lck) and a modified protocol of the KinEASE™ FP Fluorescein Green Assay supplied from Millipore. Kinase reaction were performed at room temperature for 60 minutes in presence of 250 µM substrate, 10 µM ATP and variable test article concentrations. The reaction was stopped with EDTA/kinease detection reagents and the polarization measured on a Tecan 500 instrument. From the dose-response curve obtained, the $IC_{50}$ was calculated using Graph Pad Prisms® using a non-linear fit curve. The Km for ATP on each enzyme was experimentally determined and the Ki values calculated using the Cheng-Prusoff equation (see: Cheng Y, Prusoff W H. (1973) Relationship between the inhibition constant (K1) and the concentration of inhibitor which causes 50 percent inhibition ($I_{50}$) of an enzymatic reaction". *Biochem Pharmacol* 22 (23): 3099-108).

$k_i$ values are reported in Tables 2 and 3:
a—Less than 100 nM; b—less than 1000 nM; c—more than 1000 nM

TABLE 2

Inhibition of Btk

| Compound | $ki_{50}$ (nM) |
|---|---|
| 1 | b |
| 2 | c |
| 3 | b |
| 4 | b |
| 5 | c |
| 6 | c |
| 7 | c |
| 8 | c |

TABLE 2-continued

Inhibition of Btk

| Compound | ki₅₀ (nM) |
|---|---|
| 9 | c |
| 10 | c |
| 11 | c |
| 12 | c |
| 13 | b |
| 14 | c |
| 15 | c |
| 16 | c |
| 17 | c |
| 18 | c |
| 19 | c |
| 20 | a |
| 21 | b |
| 22 | c |
| 23 | b |
| 24 | b |
| 25 | a |
| 26 | c |
| 27 | b |
| 28 | b |
| 29 | b |
| 30 | a |
| 31 | b |
| 32 | b |
| 33 | b |
| 34 | a |
| 35 | b |
| 36 | c |
| 37 | c |
| 38 | c |
| 39 | b |
| 40 | b |
| 41 | a |
| 42 | c |
| 43 | a |
| 44 | a |
| 45 | c |
| 46 | a |
| 47 | b |
| 48 | c |
| 49 | a |
| 50 | a |
| 51 | c |
| 52 | c |
| 53 | a |
| 54 | a |
| 55 | b |
| 56 | a |
| 57 | a |
| 58 | b |
| 59 | b |
| 60 | c |
| 61 | c |
| 62 | a |
| 63 | c |
| 64 | b |
| 65 | c |
| 66 | b |
| 67 | a |
| 68 | a |
| 69 | a |
| 70 | b |
| 71 | c |
| 72 | c |
| 73 | c |
| 74 | c |
| 75 | a |
| 76 | b |
| 77 | a |
| 78 | b |
| 79 | b |
| 80 | b |
| 81 | a |
| 82 | a |
| 83 | c |
| 84 | a |
| 85 | a |
| 86 | a |
| 87 | a |
| 88 | c |
| 89 | a |
| 90 | a |
| 91 | b |
| 92 | a |
| 93 | a |
| 94 | a |
| 95 | a |
| 96 | a |
| 97 | a |
| 98 | a |
| 99 | a |
| 100 | a |
| 101 | b |
| 102 | a |
| 103 | a |
| 104 | a |
| 105 | a |
| 106 | a |
| 107 | a |
| 108 | a |
| 109 | b |
| 110 | b |
| 111 | b |
| 112 | a |
| 113 | a |
| 114 | a |
| 115 | a |
| 116 | a |
| 117 | a |
| 118 | a |
| 119 | a |
| 120 | a |
| 121 | a |
| 122 | a |
| 123 | a |
| 124 | a |
| 125 | a |
| 126 | b |
| 127 | a |
| 128 | a |
| 129 | a |
| 130 | a |
| 131 | a |
| 132 | a |
| 133 | a |
| 134 | a |
| 135 | a |
| 136 | a |
| 137 | a |
| 138 | a |
| 139 | a |
| 140 | b |
| 141 | b |
| 142 | a |
| 143 | a |
| 144 | a |

TABLE 3

Inhibition of Lck

| Compound | $k_i$ Lck (nM) |
|---|---|
| 1 | a |
| 2 | c |
| 3 | b |
| 4 | b |
| 5 | — |
| 6 | — |

TABLE 3-continued

Inhibition of Lck

| Compound | $k_i$ Lck (nM) |
| --- | --- |
| 7 | b |
| 8 | b |
| 9 | b |
| 10 | — |
| 11 | — |
| 12 | — |
| 13 | b |
| 14 | b |
| 15 | a |
| 16 | — |
| 17 | — |
| 18 | b |
| 19 | — |
| 20 | a |
| 21 | a |
| 22 | a |
| 23 | a |
| 24 | a |
| 25 | a |
| 26 | b |
| 27 | a |
| 28 | b |
| 29 | b |
| 30 | b |
| 31 | a |
| 32 | b |
| 33 | a |
| 34 | a |
| 35 | b |
| 36 | b |
| 37 | c |
| 38 | c |
| 39 | a |
| 40 | a |
| 41 | a |
| 42 | b |
| 43 | a |
| 44 | a |
| 45 | b |
| 46 | a |
| 47 | — |
| 48 | — |
| 49 | a |
| 50 | a |
| 51 | — |
| 52 | — |
| 53 | a |
| 54 | a |
| 55 | — |
| 56 | a |
| 57 | a |
| 58 | a |
| 59 | a |
| 60 | b |
| 61 | a |

Splenic Cell Proliferation Assay

Splenocytes were obtained from 6 week old male CD1 mice (Charles River Laboratories Inc.). Mouse spleens were manually disrupted in PBS and filtered using a 70 μm cell strainer followed by ammonium chloride red blood cell lysis. Cells were washed, resuspended in Splenocyte Medium (HyClone RPMI supplemented with 10% heat-inactivated FBS, 0.5× non-essential amino acids, 10 mM HEPES, 50 uM beta mercaptoethanol) and incubated at 37° C., 5% $CO_2$ for 2 h to remove adherent cells. Suspension cells were seeded in 96 well plates at 50,000 cells per well and incubated at 37° C., 5% $CO_2$ for 1 h. Splenocytes were pre-treated in triplicate with 10,000 nM curves of Formula 1 compounds for 1 h, followed by stimulation of B cell proliferation with 2.5 ug/ml anti-IgM F(ab')$_2$ (Jackson ImmunoResearch) for 72 h. Cell proliferation was measured by Cell Titer-Glo Luminescent Assay (Promega). $EC_{50}$ values (50% proliferation in the presence of compound as compared to vehicle treated controls) were calculated from dose response compound curves using GraphPad Prism Software.

$EC_{50}$ values are reported in Table 4:
a—Less than 100 nM; b—less than 1000 nM; c—more than 1000 nM

TABLE 4

Inhibition of splenic cell proliferation

| Compound | $EC_{50}$ (nM) |
| --- | --- |
| 1 | c |
| 2 | c |
| 3 | c |
| 4 | c |
| 5 | — |
| 6 | — |
| 7 | c |
| 8 | — |
| 9 | — |
| 10 | — |
| 11 | — |
| 12 | — |
| 13 | c |
| 14 | c |
| 15 | — |
| 16 | — |
| 17 | — |
| 18 | — |
| 19 | — |
| 20 | b |
| 21 | c |
| 22 | — |
| 23 | c |
| 24 | b |
| 25 | b |
| 26 | c |
| 27 | c |
| 28 | c |
| 29 | b |
| 30 | c |
| 31 | b |
| 32 | b |
| 33 | b |
| 34 | c |
| 35 | c |
| 36 | c |
| 37 | c |
| 38 | c |
| 39 | c |
| 40 | b |
| 41 | b |
| 42 | c |
| 43 | b |
| 44 | c |
| 45 | c |
| 46 | b |
| 47 | — |
| 48 | — |
| 49 | b |
| 50 | c |
| 51 | — |
| 52 | — |
| 53 | b |
| 54 | c |
| 55 | — |
| 56 | c |
| 57 | c |
| 58 | b |
| 59 | b |
| 60 | c |
| 61 | c |
| 62 | b |
| 63 | c |
| 64 | c |
| 65 | c |

TABLE 4-continued

Inhibition of splenic cell proliferation

| Compound | $EC_{50}$ (nM) |
|---|---|
| 66 | b |
| 67 | c |
| 68 | b |
| 69 | c |
| 70 | b |
| 71 | c |
| 72 | c |
| 73 | C |
| 74 | C |
| 75 | C |
| 76 | c |
| 77 | b |
| 78 | c |
| 79 | c |
| 80 | c |
| 81 | c |
| 82 | c |
| 83 | c |
| 84 | c |
| 85 | b |
| 86 | c |
| 87 | c |
| 88 | — |
| 89 | b |
| 90 | b |
| 91 | — |
| 92 | b |
| 93 | — |
| 94 | b |
| 95 | b |
| 96 | a |
| 97 | b |
| 98 | — |
| 99 | b |
| 100 | a |
| 101 | — |
| 102 | b |
| 103 | b |
| 104 | b |
| 105 | b |
| 106 | b |
| 107 | a |
| 108 | b |
| 109 | — |
| 110 | c |
| 111 | c |
| 112 | b |
| 113 | b |
| 114 | b |
| 115 | b |
| 116 | b |
| 117 | b |
| 118 | b |
| 119 | b |
| 120 | b |
| 121 | b |
| 122 | b |
| 123 | b |
| 124 | b |
| 125 | b |
| 126 | b |
| 127 | b |
| 128 | b |
| 129 | b |
| 130 | b |
| 131 | b |
| 132 | b |
| 133 | a |
| 134 | a |
| 135 | b |
| 136 | b |
| 137 | b |
| 138 | b |
| 139 | b |
| 140 | b |
| 141 | b |
| 142 | b |
| 143 | b |
| 144 | b |

We claim:

1. A compound of Formula 1:

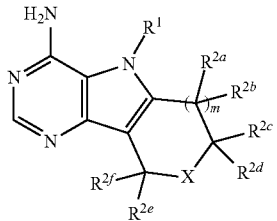

Formula 1 m is 0;

X is $CH_2$ or O;

n is an integer from 0 to 2;

$R^1$ is

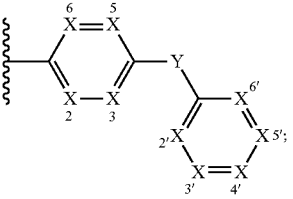

wherein Y is selected from O or $CH_2$;

wherein $X^2$, $X^3$, $X^5$, $X^6$, $X^{2'}$, $X^{3'}$, $X^{4'}$, $X^{5'}$, $X^{6'}$ are independently selected from CR and N;

each R is independently selected from hydrogen, halogen, $-NO_2$, $-CN$, alkyl, alkenyl, alkynyl, $-OR^3$, $-OC(O)R^3$, $-OC(O)NR^4R^5$, $-NR^4R^5$, $-S(O)_nR^3$, $-C(O)R^3$, $-C(O)OR^3$, $-C(O)NR^4R^5$, $-S(O)_2NR^4R^5$, $-NR^2C(O)R^3$, $-NR^2S(O)_nR^3$, $-NR^2C(O)NR^4R^5$, $-NR^2S(O)_2NR^4R^5$, aryl, heteroaryl, carbocyclyl, and heterocyclyl;

$R^2$ is selected from hydrogen, alkyl, alkenyl, alkynyl, heteroalkyl, carbocyclyl, heterocyclyl, aryl, and heteroaryl, $R^{2a}$, $R^{2b}$, $R^{2c}$, $R^{2d}$, $R^{2e}$, $R^{2f}$ are independently selected from hydrogen, alkyl, heteroalkyl, carbocyclyl, heterocyclyl, aryl, and heteroaryl;

$R^3$ is selected from hydrogen, alkyl, alkenyl, alkynyl, heteroalkyl, carbocyclyl, heterocyclyl, aryl, and heteroaryl; and $R^4$ and $R^5$ are independently selected from hydrogen, alkyl, heteroalkyl, carbocyclyl, heterocyclyl, aryl, and heteroaryl; or $R^4$ and $R^5$ can be fused to form a 3 to 8 membered heterocyclyl ring system.

2. The compound of claim 1 wherein Formula I is:
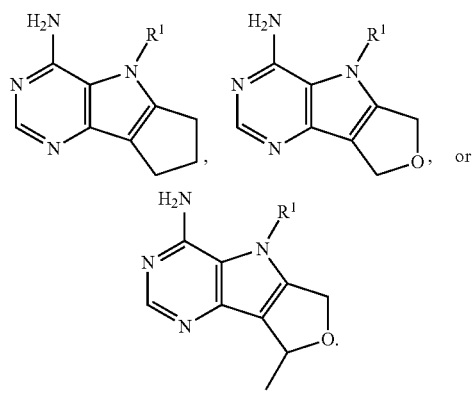
3. The compound according to claim 1, wherein $R^1$ is selected from the group consisting of:
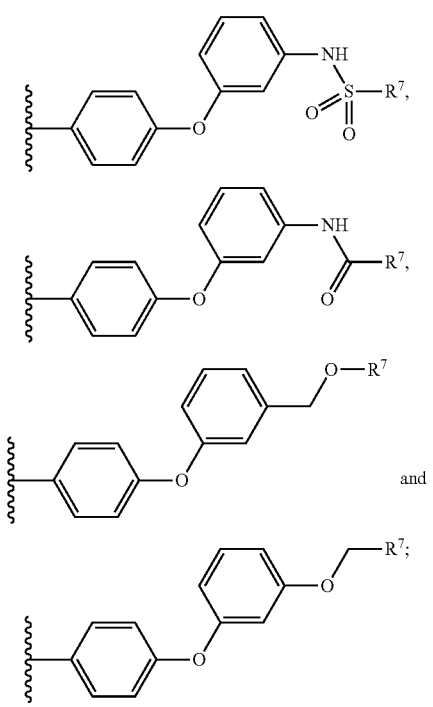
wherein $R^7$ is substituted or unsubstituted alkyl, aryl and heteroaryl.
4. The compound of according to claim 1, wherein $R^1$ is selected from the group consisting of:
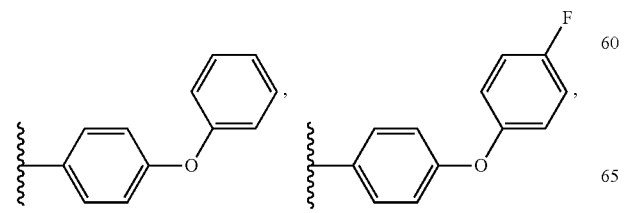
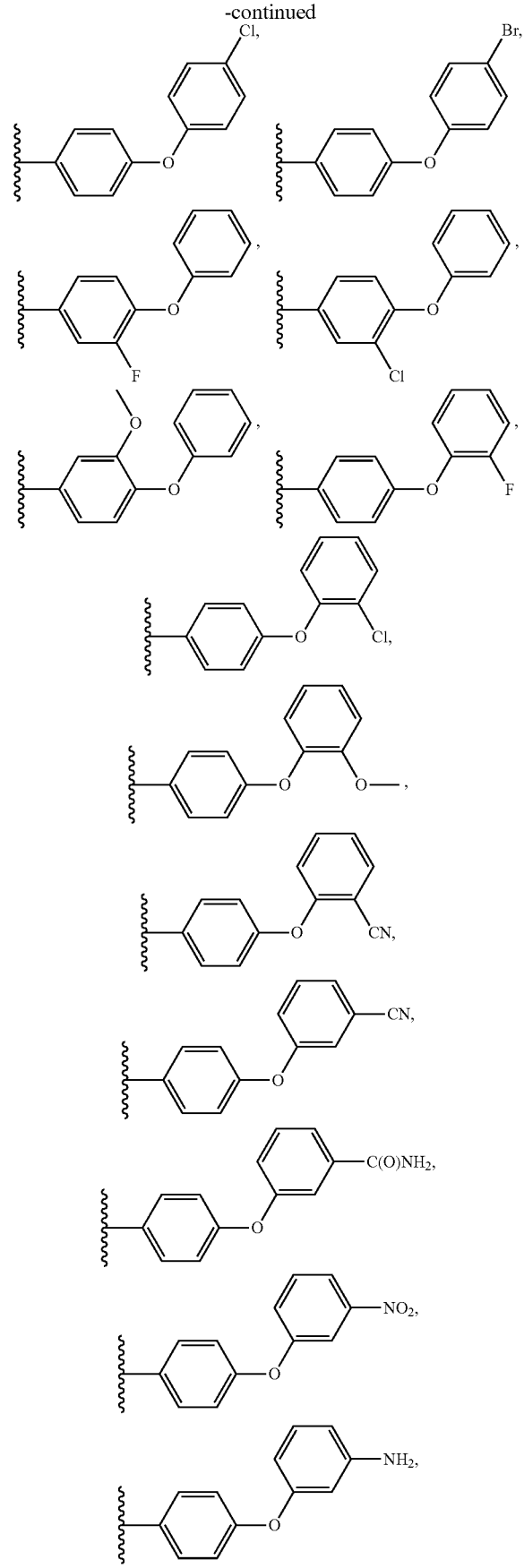

207
-continued
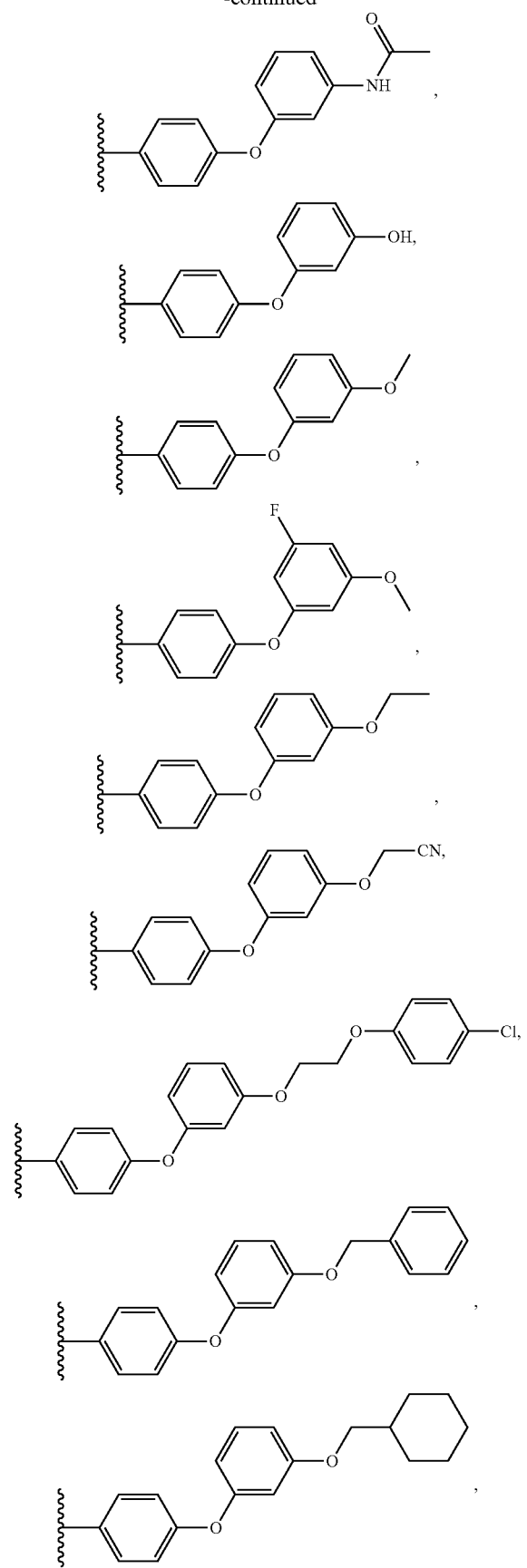
208
-continued
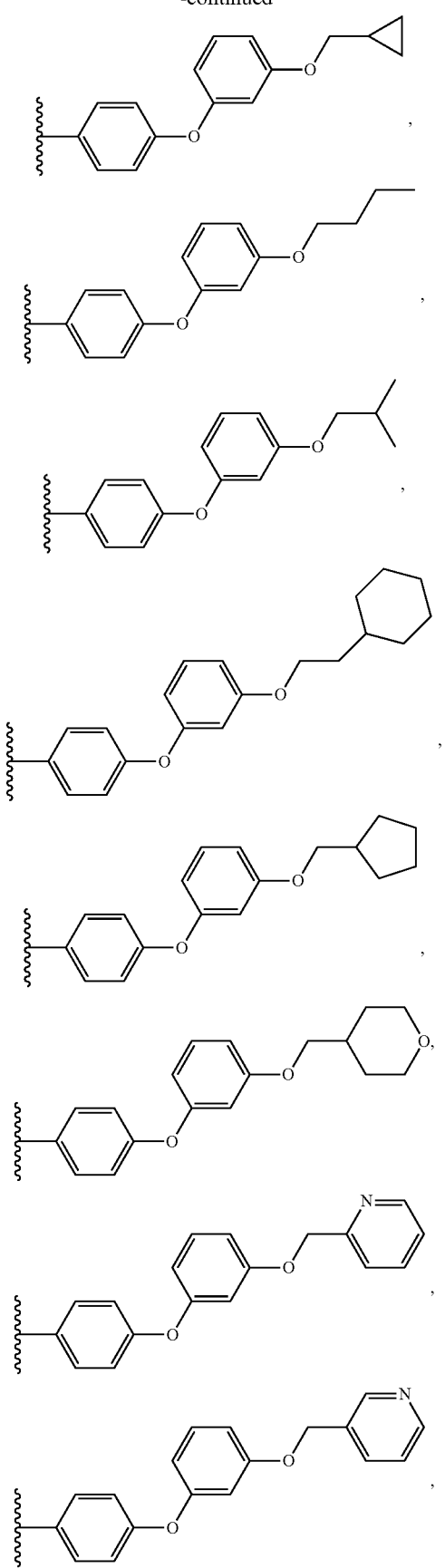

209
-continued
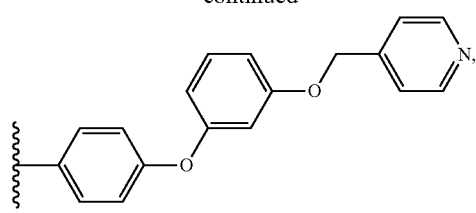,
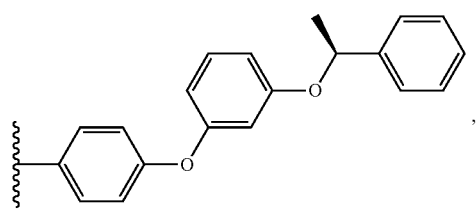,
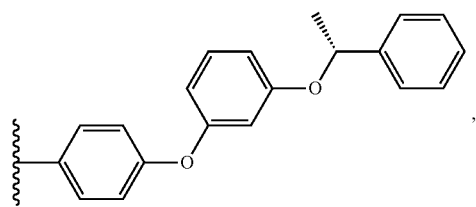,
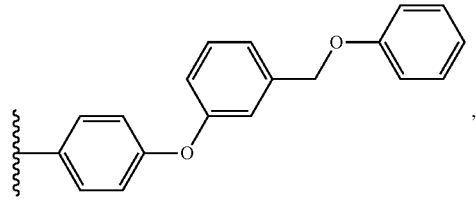,
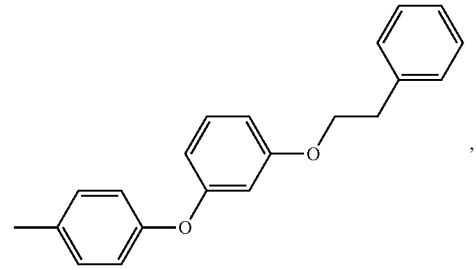,
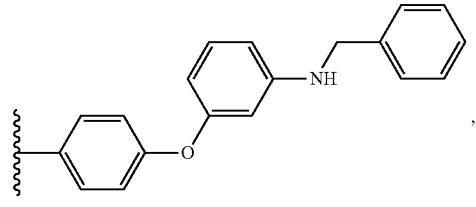,
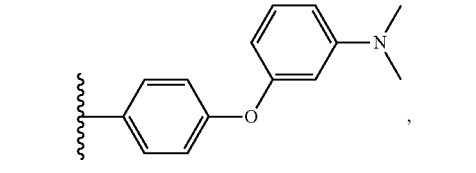,
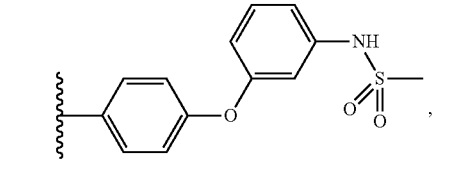,
210
-continued
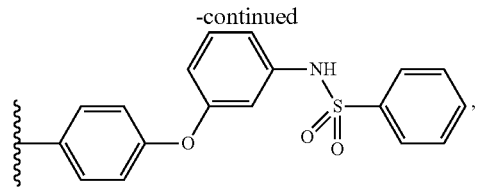,
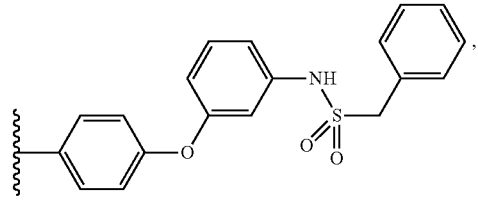,
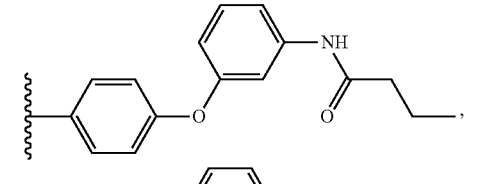,
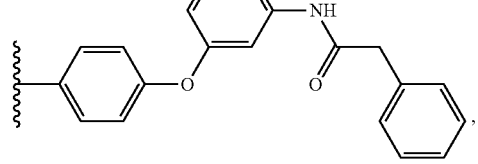,
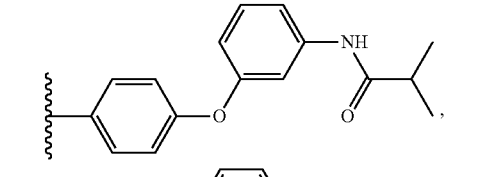,
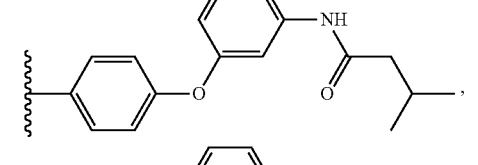,
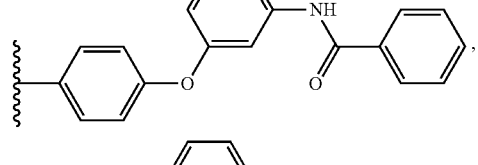,
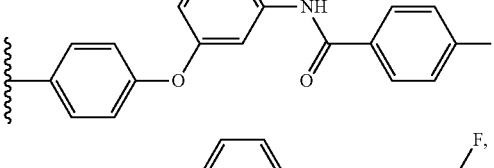,
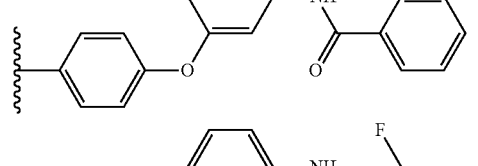,
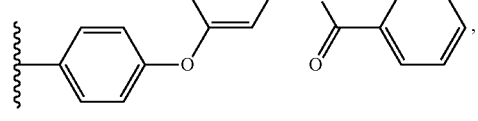, 211
-continued
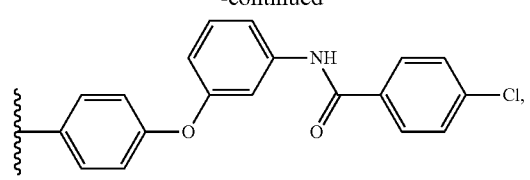
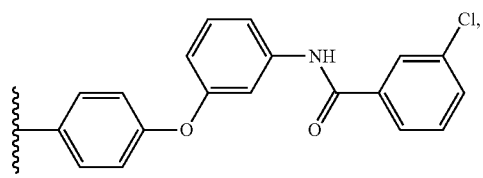
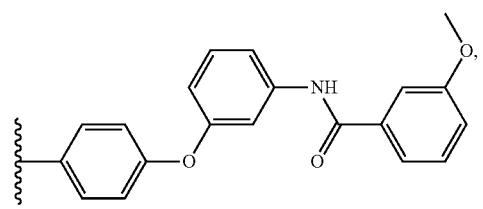
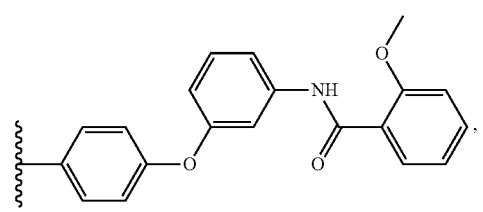
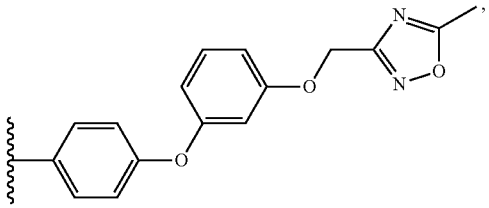
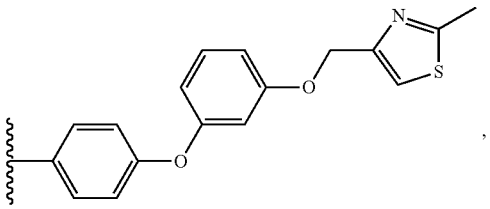
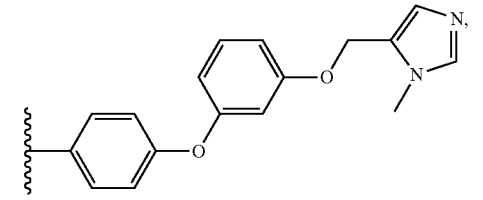
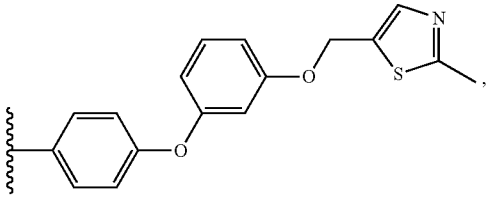
212
-continued
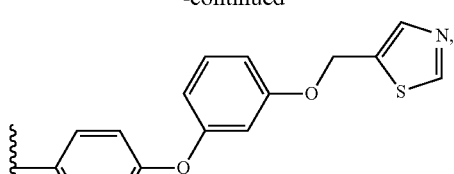
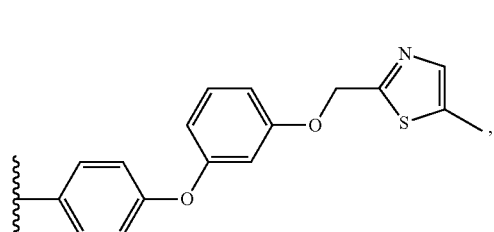
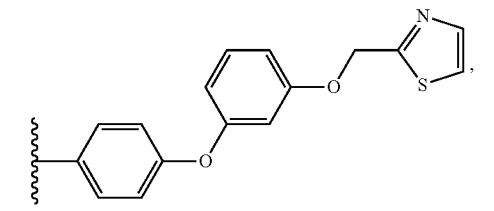
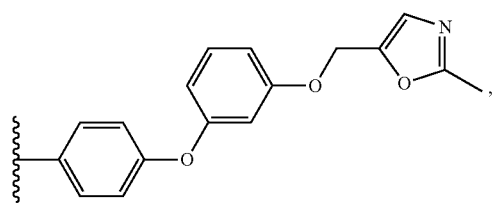
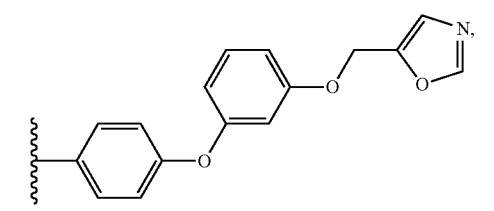
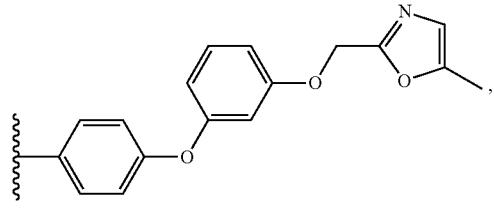
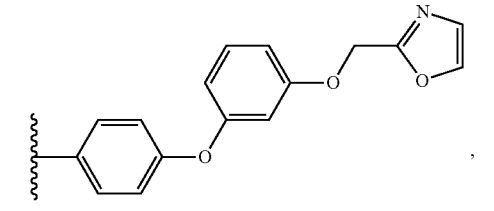
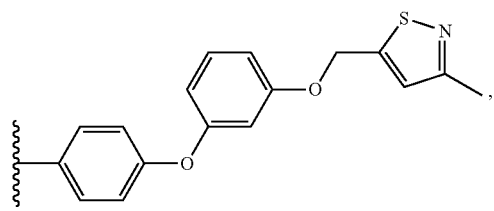

213
-continued
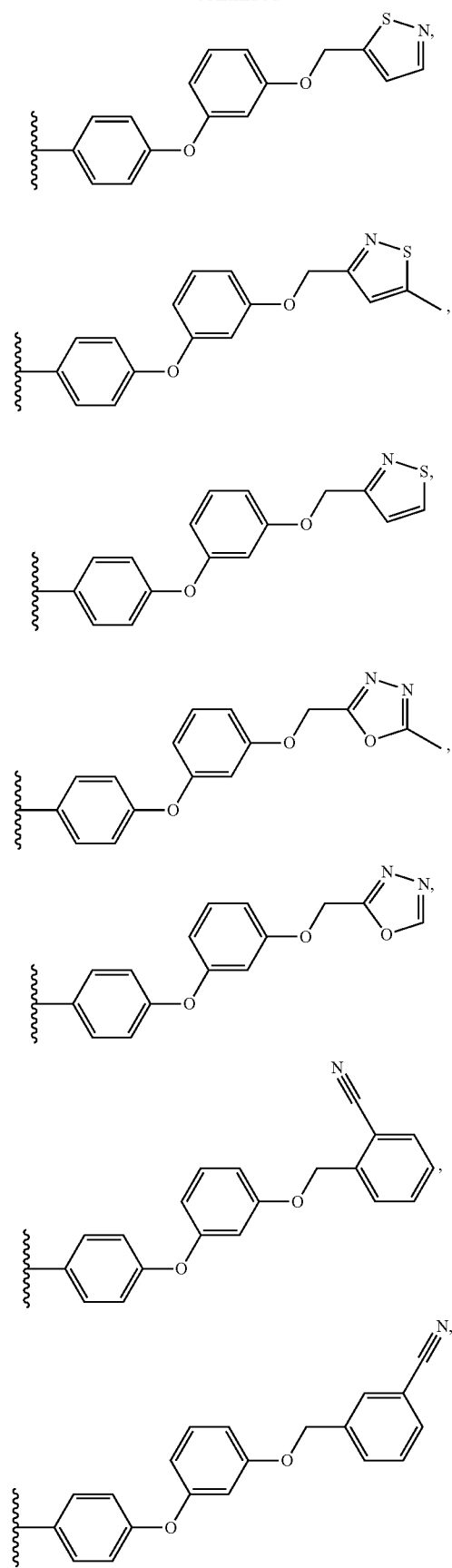
214
-continued
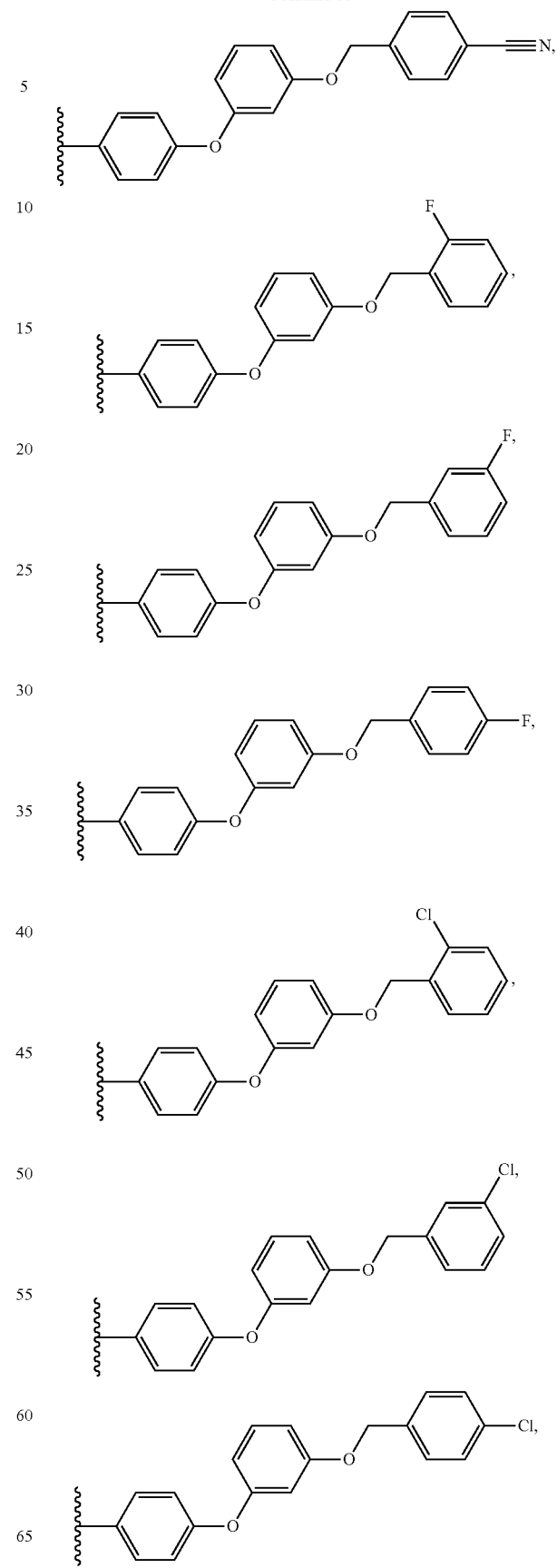

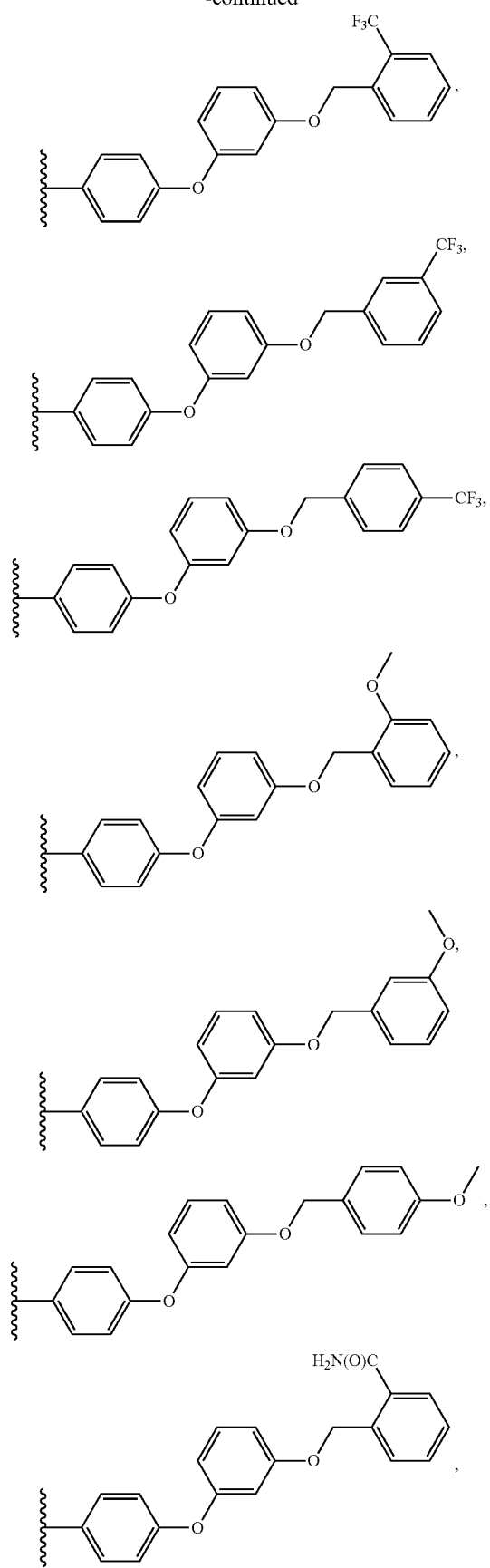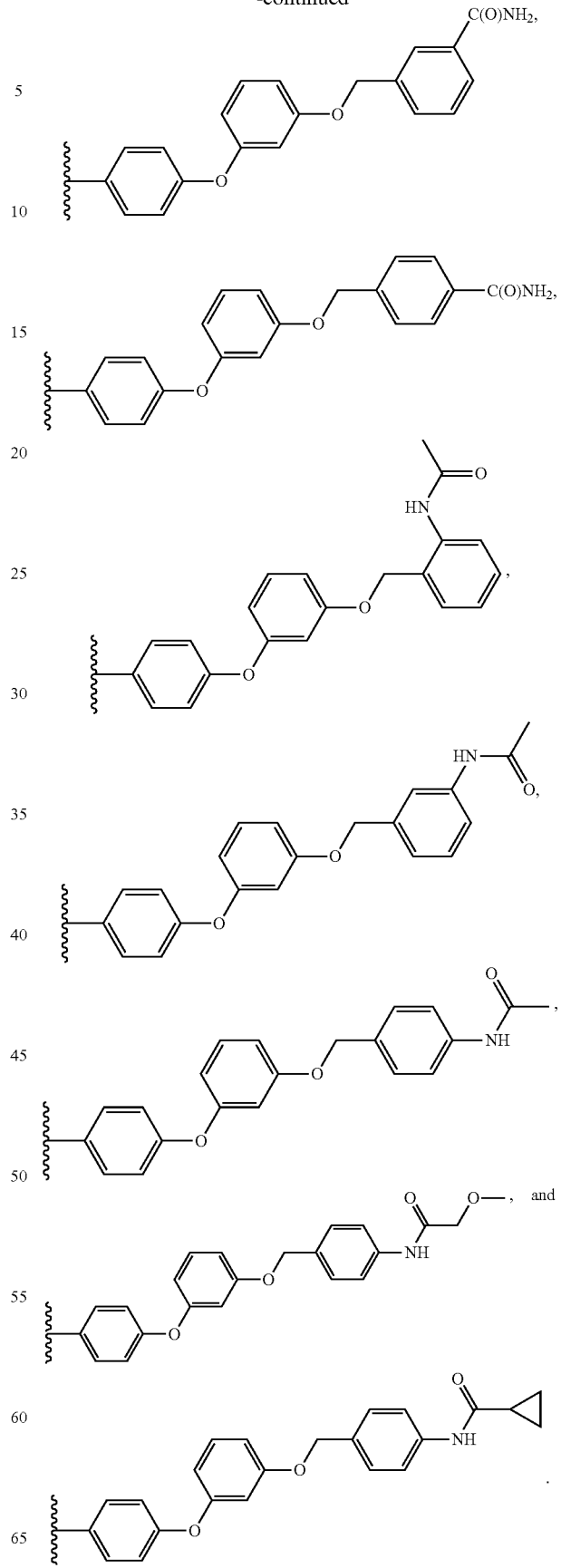

5. The compound according to claim 1 represented by formulas 1a, 1b or 1c:
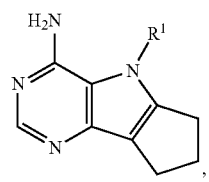
1a
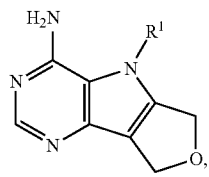
1b
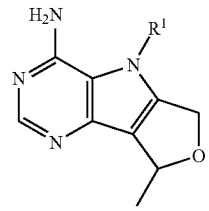
1c
wherein R¹ is selected from the group consisting of:
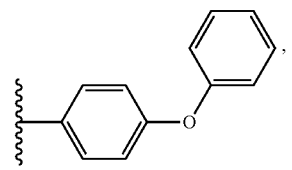 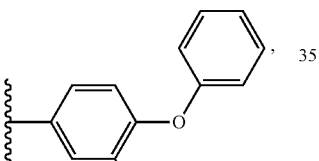
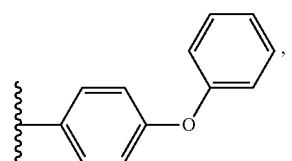 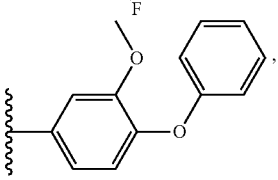
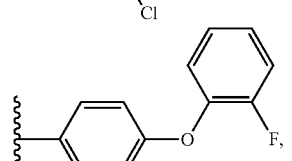 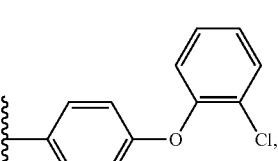
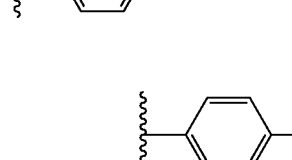 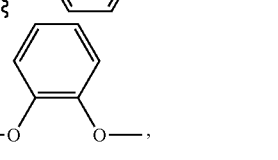
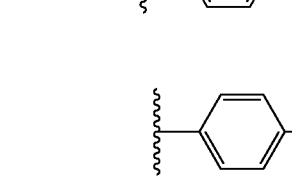 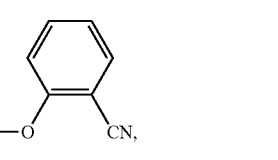
-continued
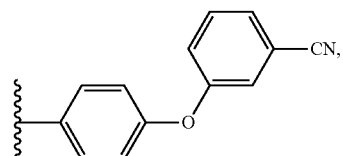
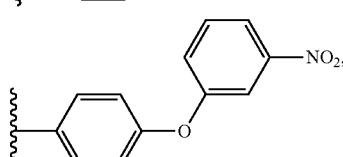
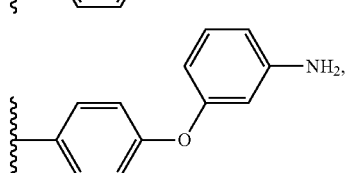
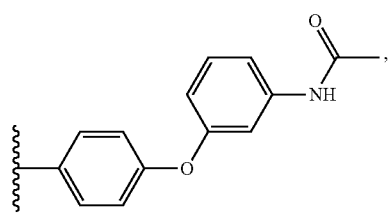
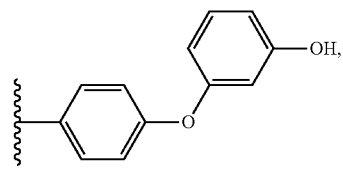
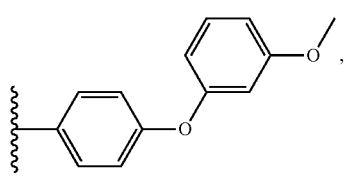 [SMILES: *c1ccc(Oc2cccc(N)c2)cc1]
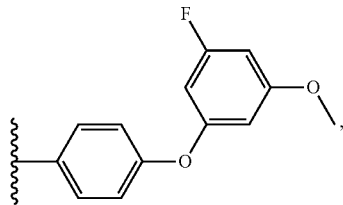
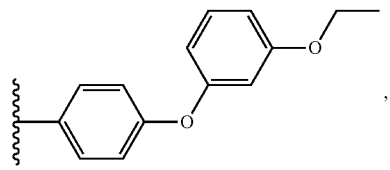
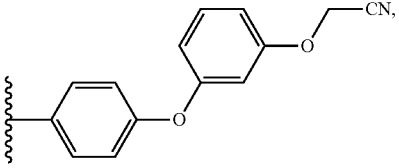

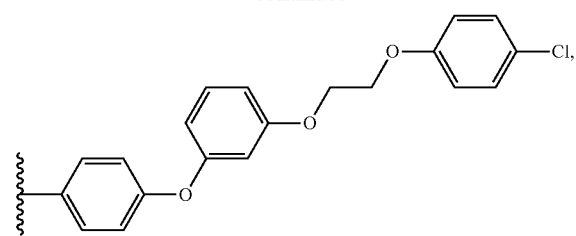
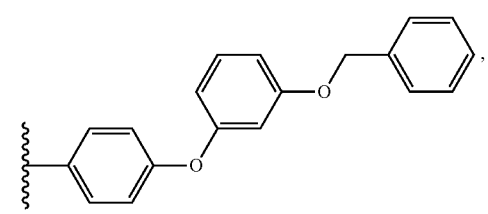
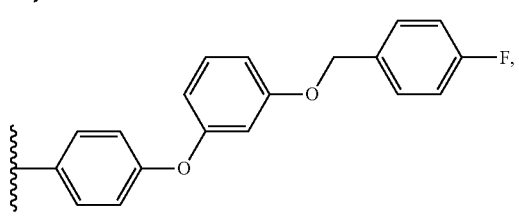
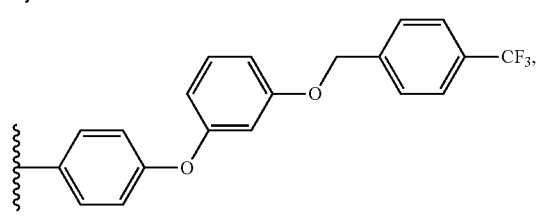
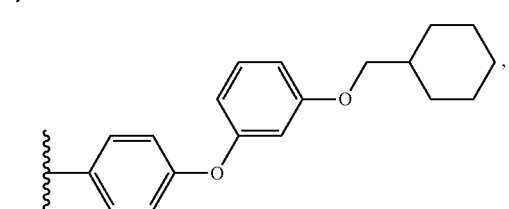
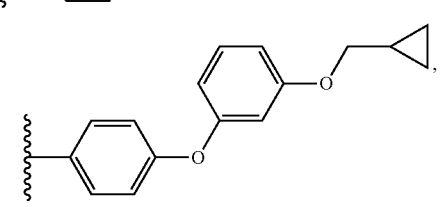
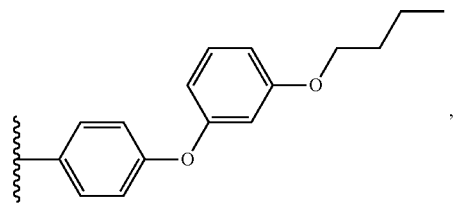
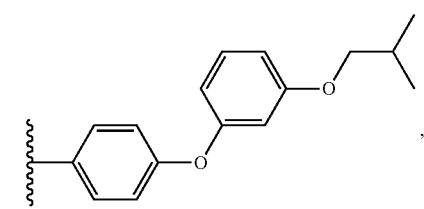
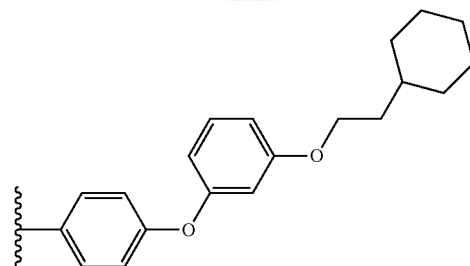
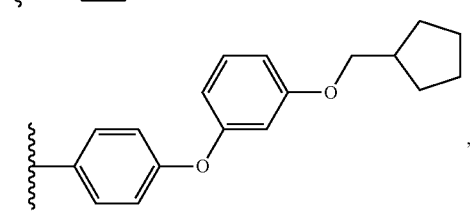
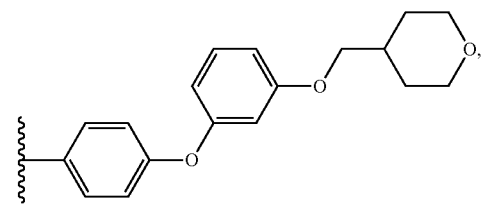
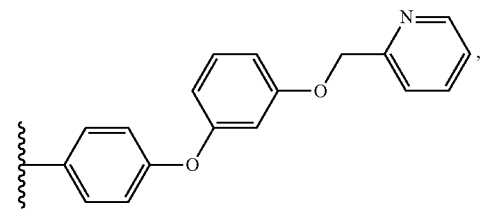
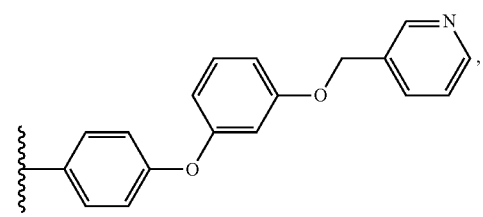
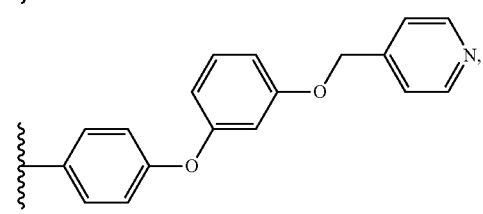
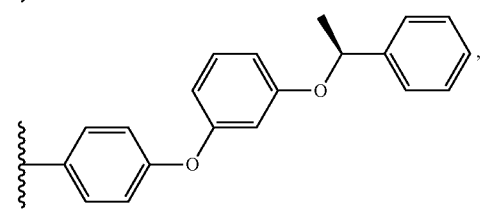
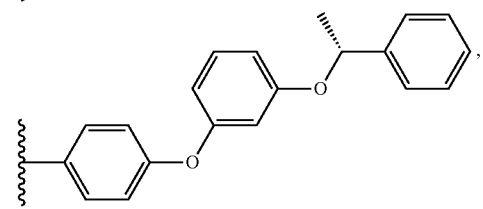

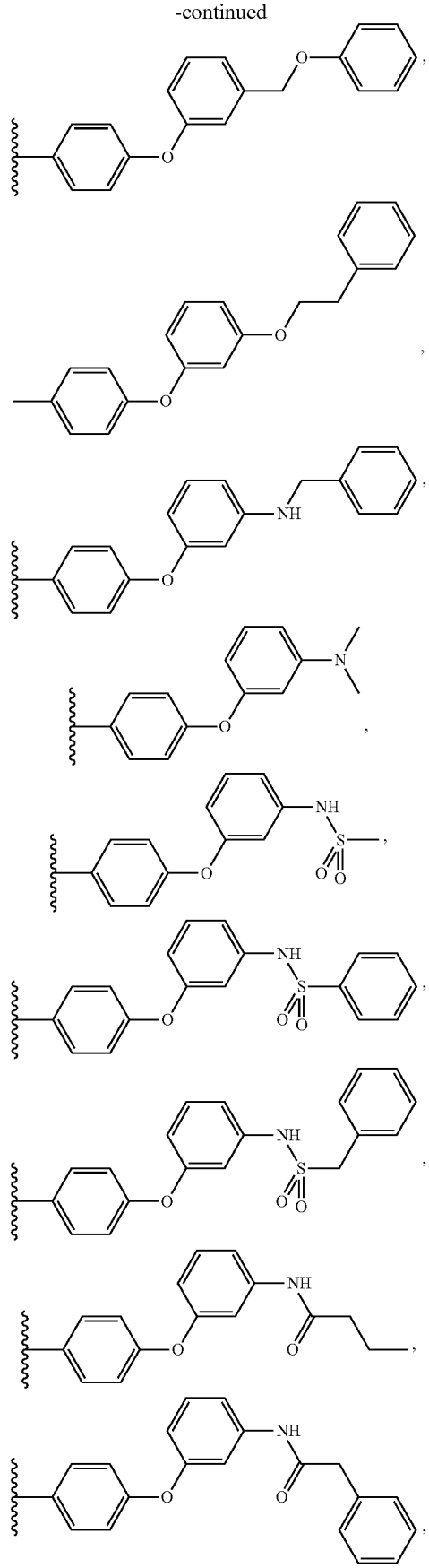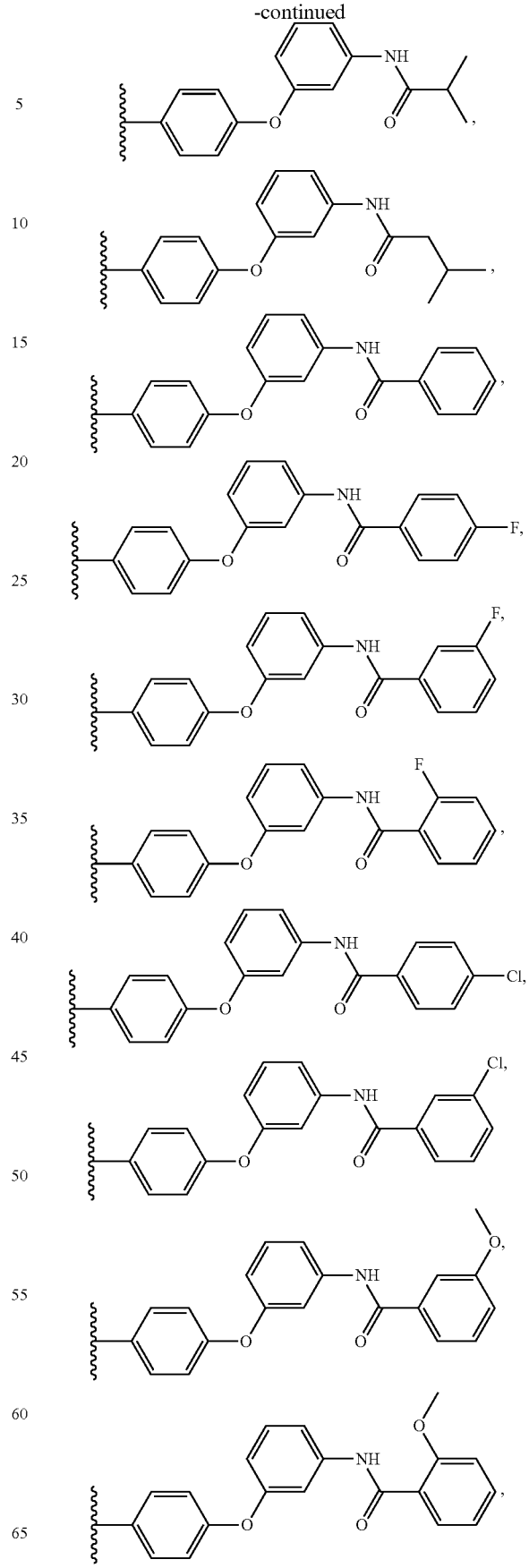

223
-continued
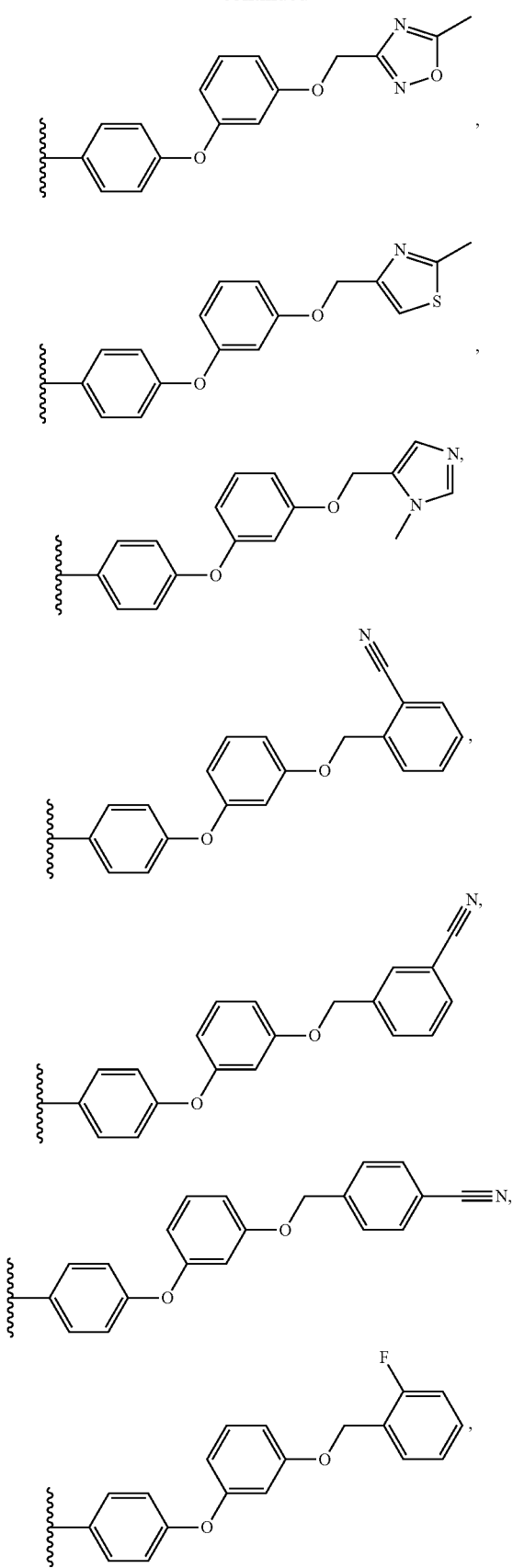
224
-continued
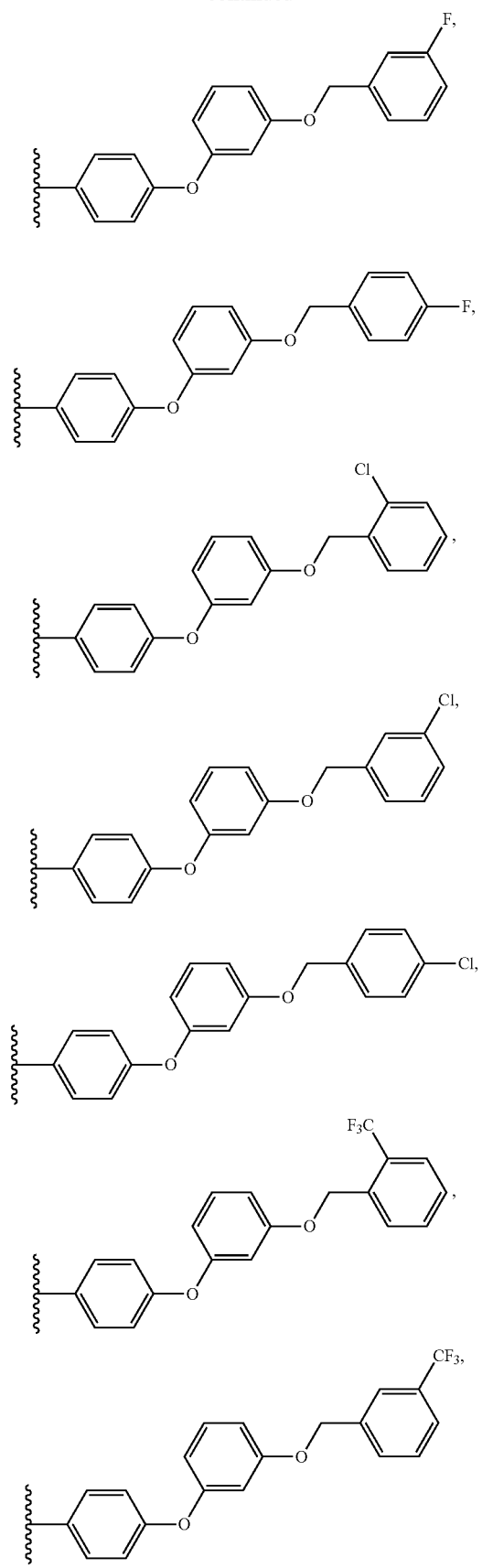

225
-continued
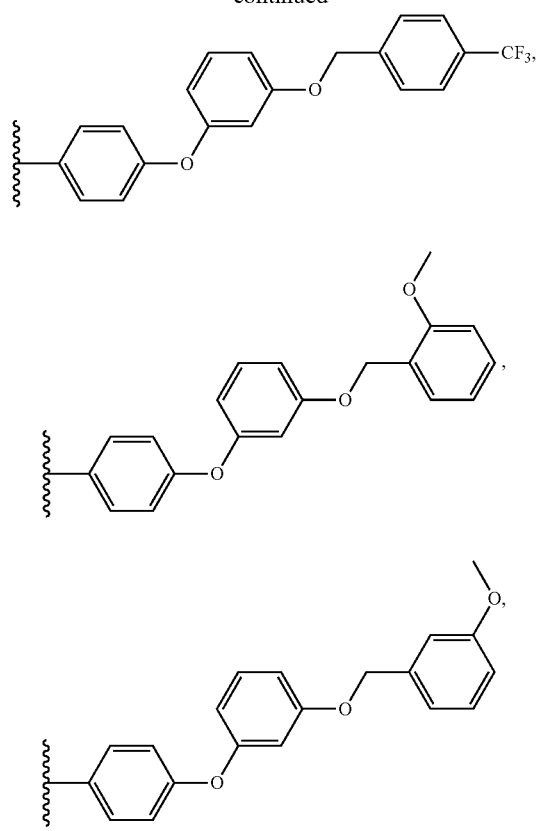
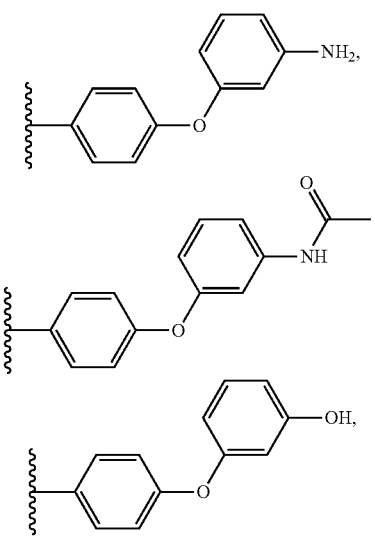
226
-continued
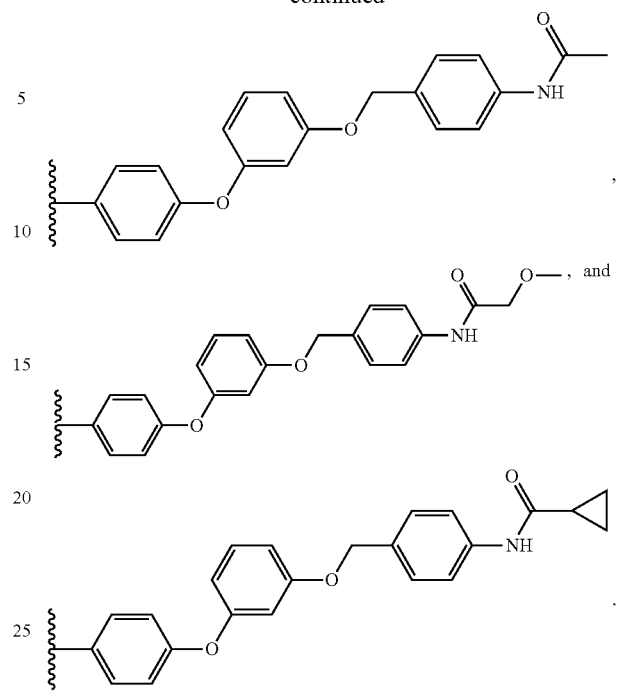
6. The compound according to claim 1 represented by formula 1c:
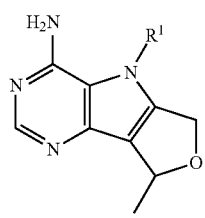
1c
wherein R¹ is selected from the group consisting of:

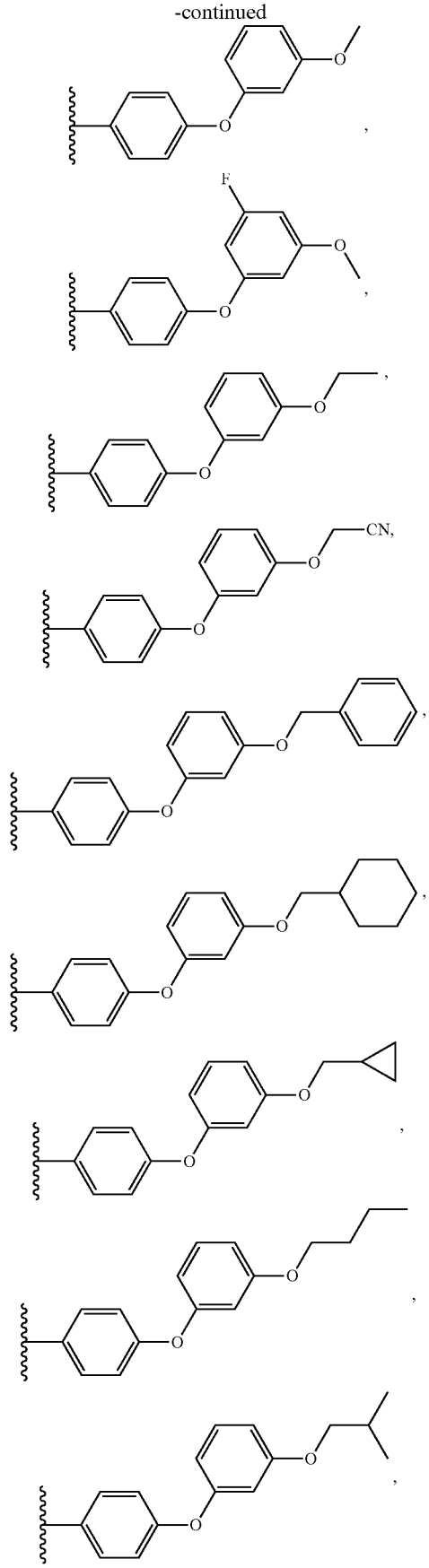
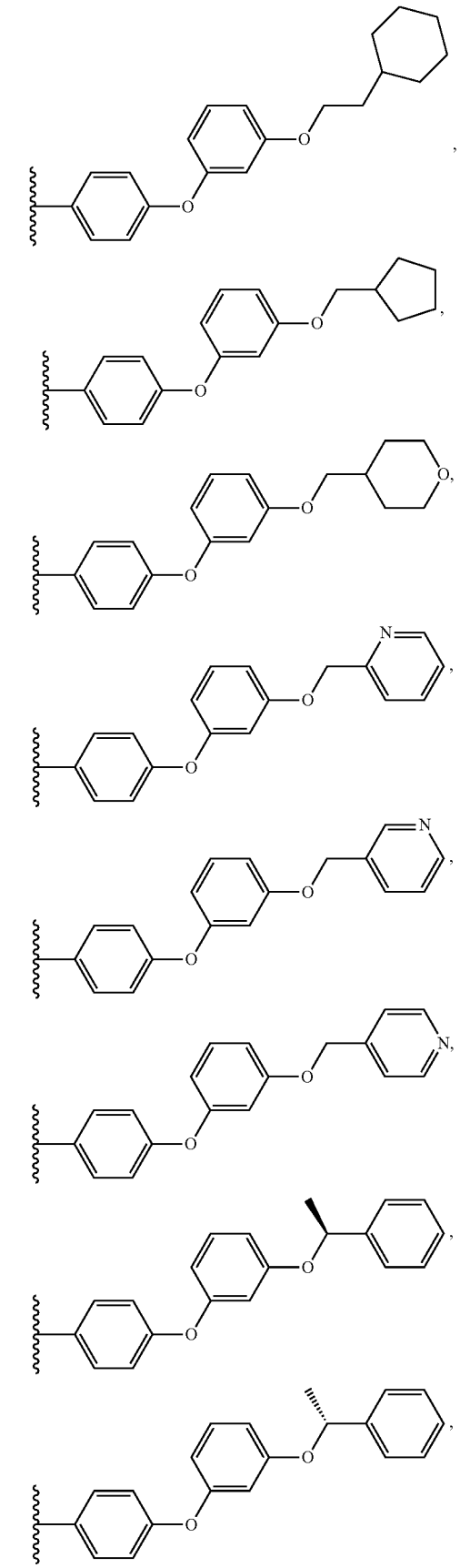

-continued
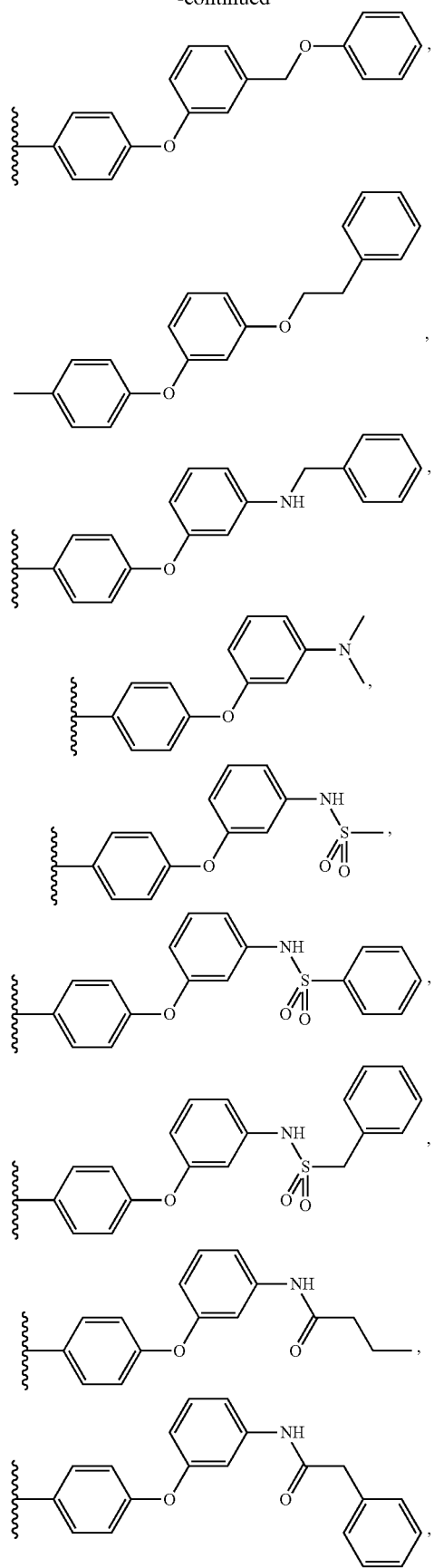
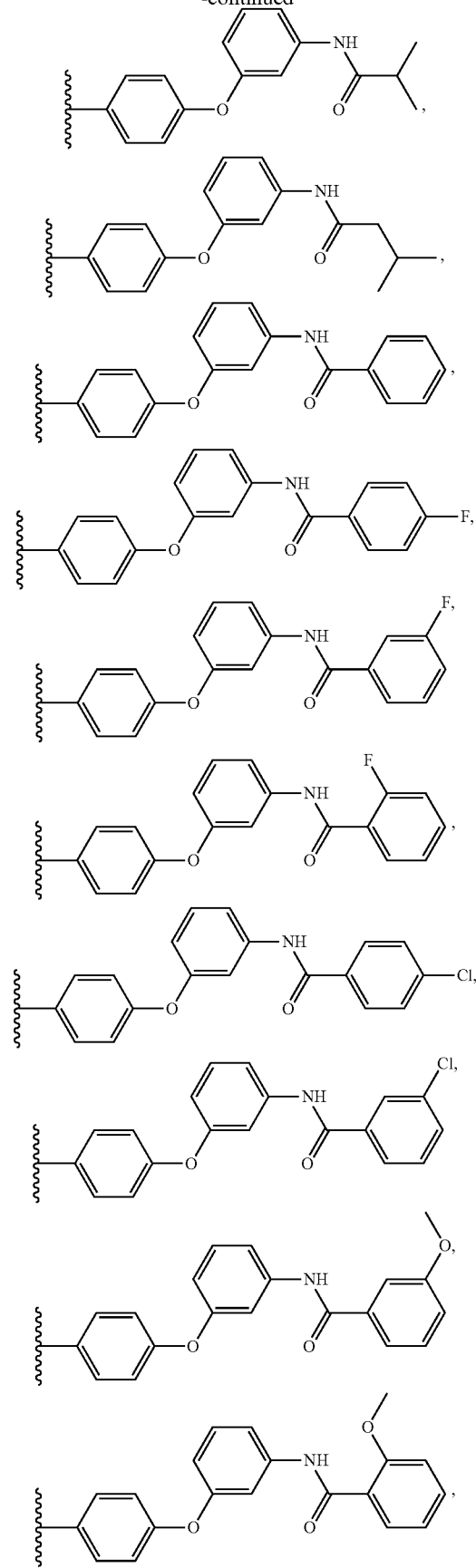

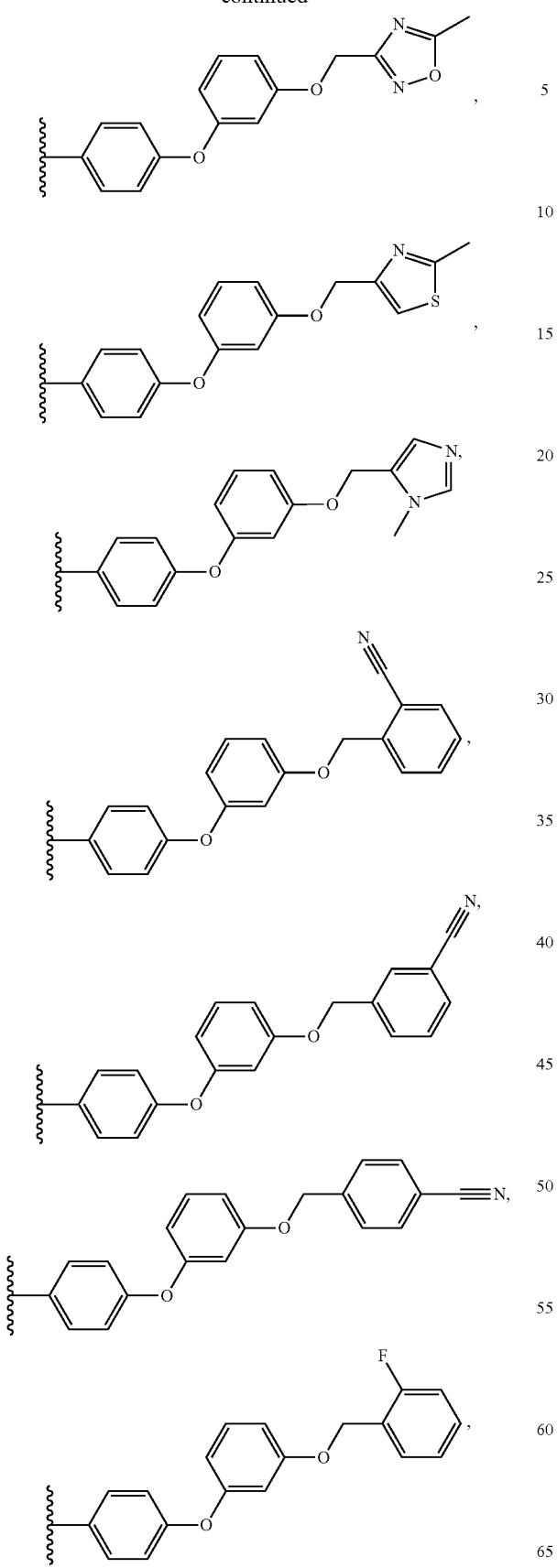
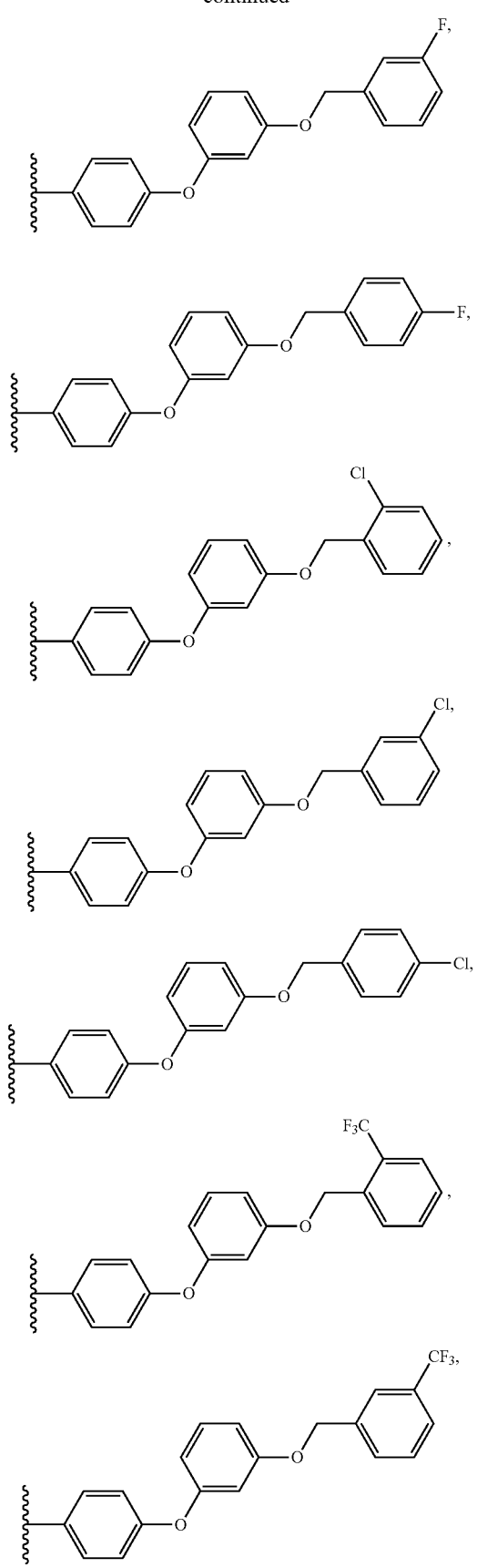

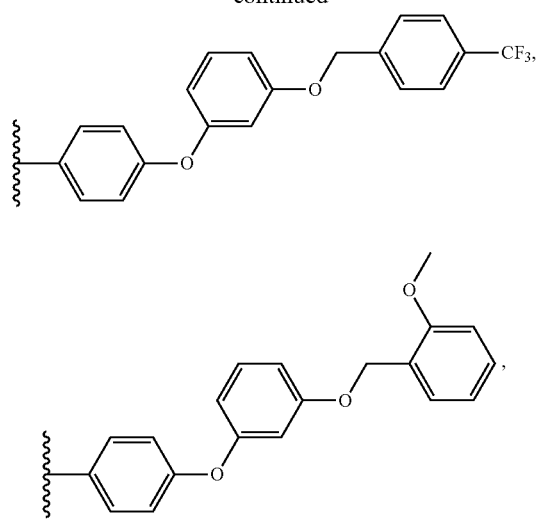
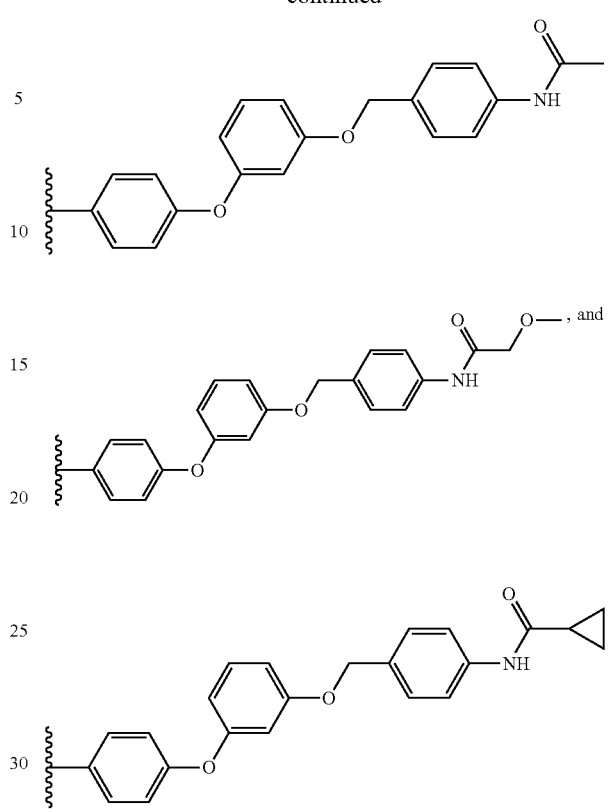
7. A compound selected from the group consisting of:
| Compound | Structure |
|---|---|
| 1 | 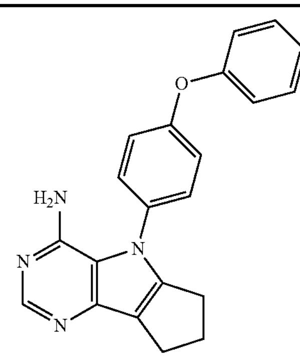 |
| 2 | 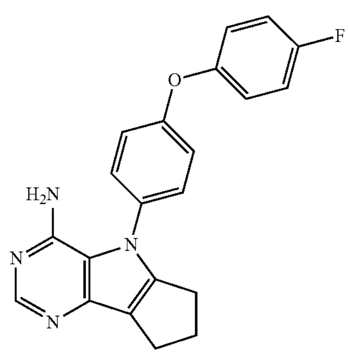 [SMILES: Nc1ncnc2c3c(n(-c4ccc(Oc5ccc(F)cc5)cc4)c12)CCC3] |

-continued
| Compound | Structure |
|---|---|
| 3 | 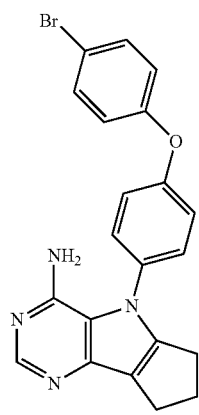 [SMILES: Nc1ncnc2c3c(n(-c4ccc(Oc5ccc(Br)cc5)cc4)c12)CCC3] |
| 4 | 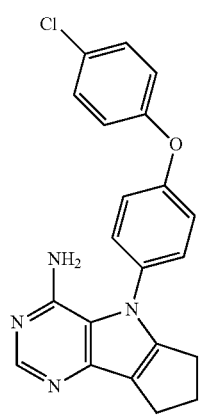 |
| 20 | 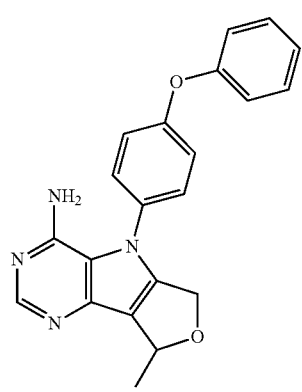 |
| 21 | 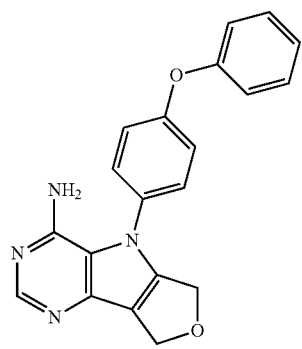 [SMILES: Nc1ncnc2c3c(n(-c4ccc(Oc5ccccc5)cc4)c12)COC3] |
-continued
| Compound | Structure |
|---|---|
| 22 | 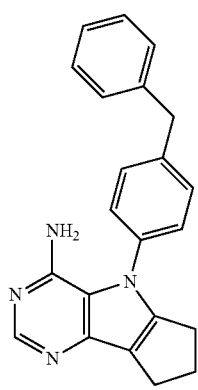 [SMILES: Nc1ncnc2c3c(n(-c4ccc(Cc5ccccc5)cc4)c12)CCC3] |
| 23 | 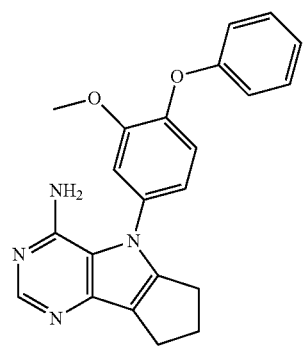 |
| 24 | 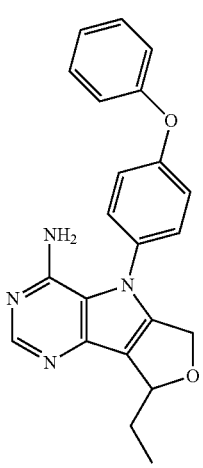 [SMILES: CCC1OCc2c1c1ncnc(N)c1n2-c1ccc(Oc2ccccc2)cc1] |

| Compound | Structure |
|---|---|
| 25 | 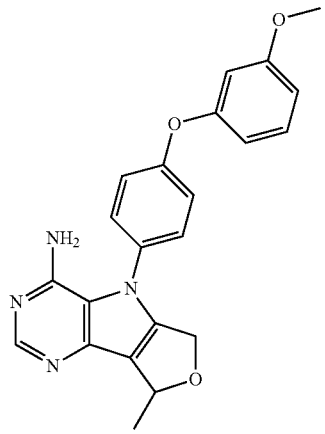 |
| 26 | 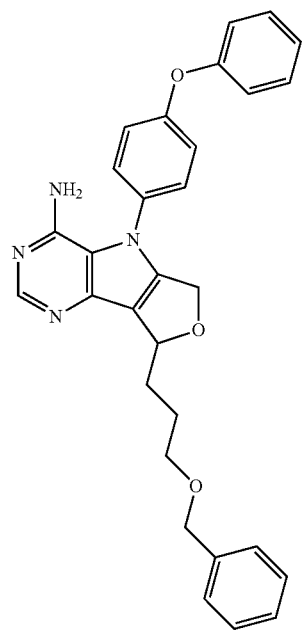 [SMILES: Nc1ncnc2c3c(n(-c4ccc(Oc5ccccc5)cc4)c12)COC3CCCOCc1ccccc1] |
| 27 | 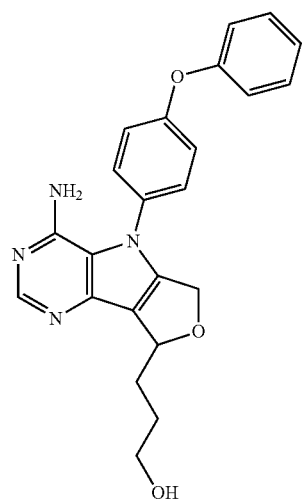 [SMILES: Nc1ncnc2c3c(n(-c4ccc(Oc5ccccc5)cc4)c12)COC3CCCO] |
| Compound | Structure |
|---|---|
| 28 | 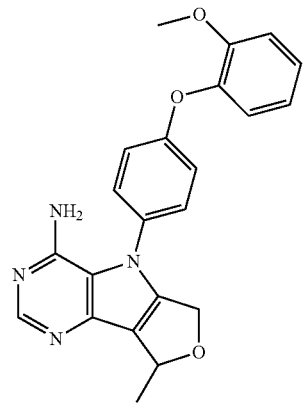 [SMILES: COc1ccccc1Oc1ccc(-n2c3c(c4ncnc(N)c42)C(C)OC3)cc1] |
| 29 | 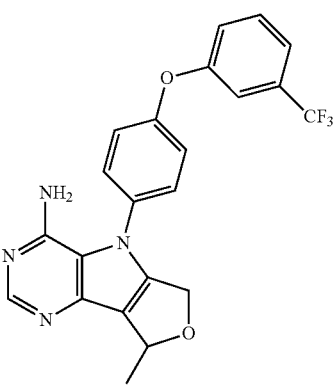 |
| 30 | 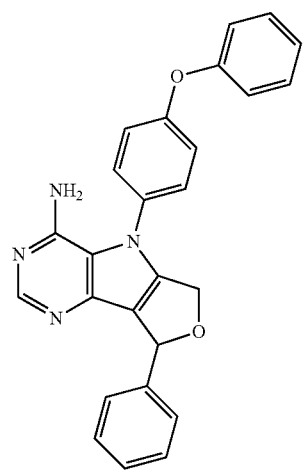 [SMILES: Nc1ncnc2c3c(n(-c4ccc(Oc5ccccc5)cc4)c12)COC3c1ccccc1] |

| Compound | Structure |
|---|---|
| 31 | 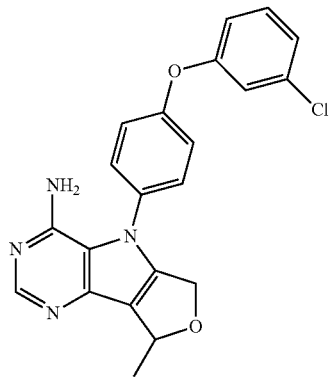 [SMILES: CC1OCc2c1c1ncnc(N)c1n2-c1ccc(Oc2cccc(Cl)c2)cc1] |
| 32 | 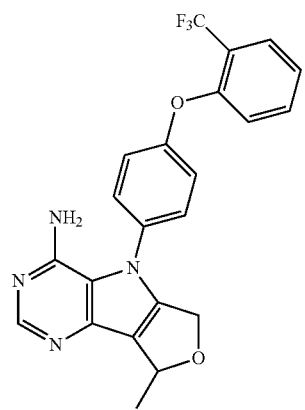 [SMILES: CC1OCc2c1c1ncnc(N)c1n2-c1ccc(Oc2ccccc2C(F)(F)F)cc1] |
| 33 | 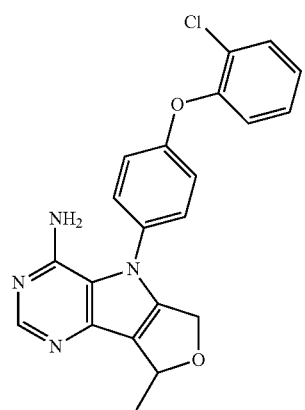 [SMILES: CC1OCc2c1c1ncnc(N)c1n2-c1ccc(Oc2ccccc2Cl)cc1] |
| 34 | 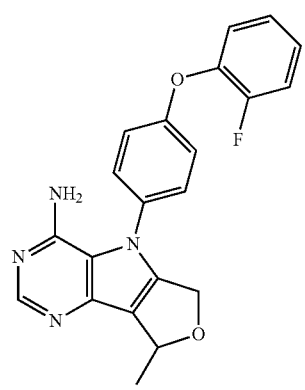 [SMILES: CC1OCc2c1c1ncnc(N)c1n2-c1ccc(Oc2ccccc2F)cc1] |
| 35 | 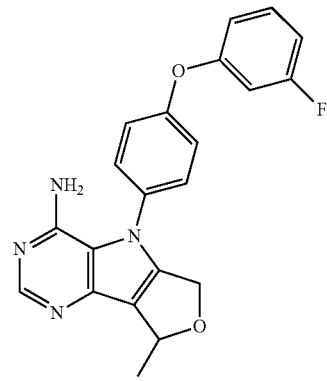 [SMILES: CC1OCc2c1c1ncnc(N)c1n2-c1ccc(Oc2cccc(F)c2)cc1] |
| 36 | 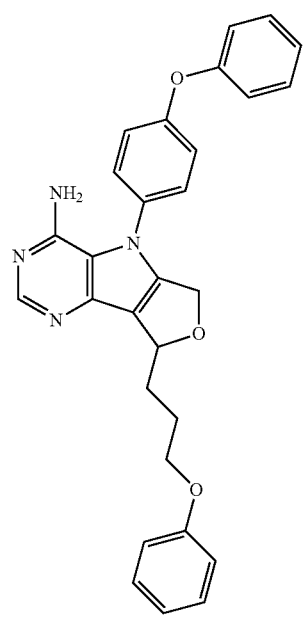 [SMILES: Nc1ncnc2c3c(n(-c4ccc(Oc5ccccc5)cc4)c12)COC3CCCOc1ccccc1] |
| 37 | 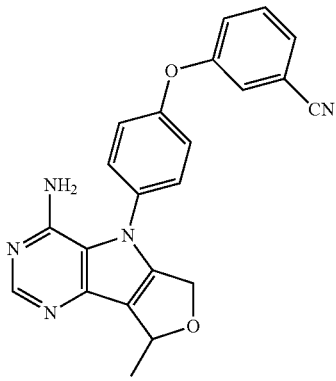 [SMILES: CC1OCc2c1c1ncnc(N)c1n2-c1ccc(Oc2cccc(C#N)c2)cc1] |

| Compound | Structure |
|---|---|
| 38 | 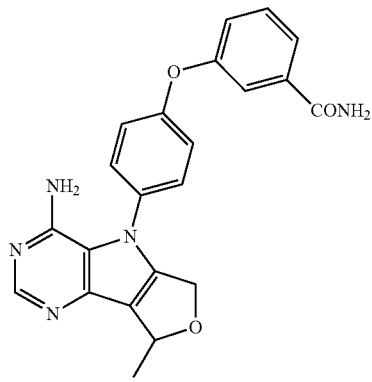 [SMILES: CC1OCc2c1c1ncnc(N)c1n2-c1ccc(Oc2cccc(C(N)=O)c2)cc1] |
| 39 | 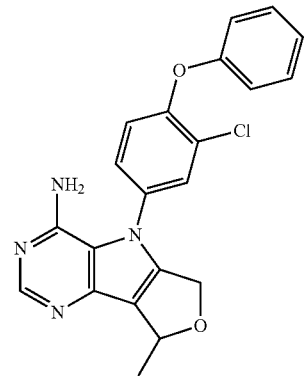 |
| 40 | 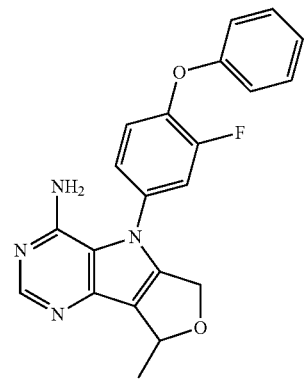 [SMILES: CC1OCc2c1c1ncnc(N)c1n2-c1ccc(Oc2ccccc2)c(F)c1] |
| 41 | 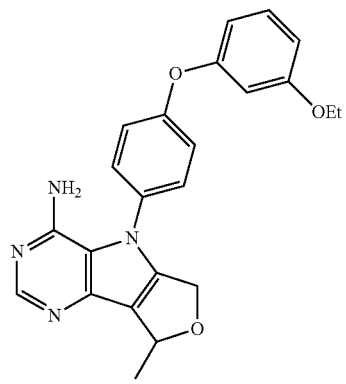 [SMILES: CCOc1cccc(Oc2ccc(-n3c4c(c5ncnc(N)c53)C(C)OC4)cc2)c1] |
| Compound | Structure |
|---|---|
| 42 | 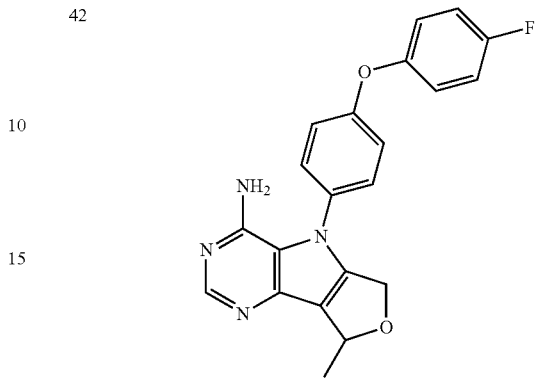 |
| 43 | 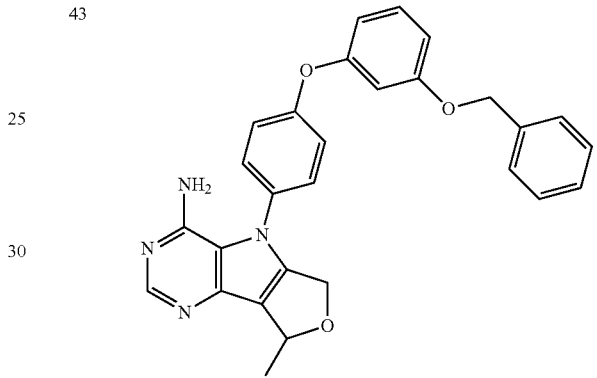 |
| 44 | 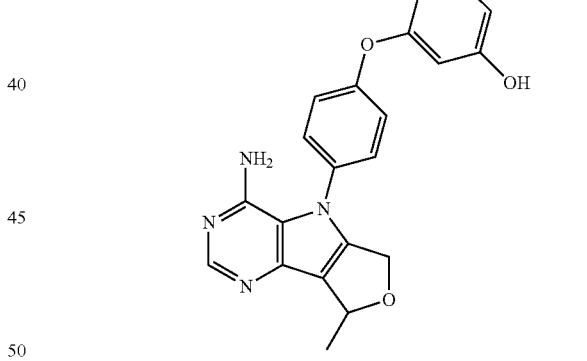 |
| 45 | 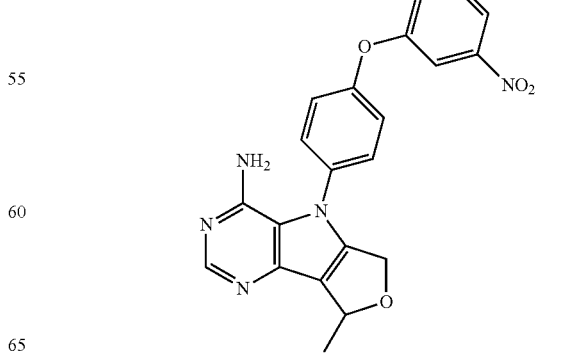 |

| Compound | Structure |
|---|---|
| 46 | 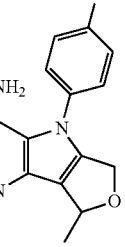 |
| 47 | |
| 48 | |
| 49 | |
| Compound | Structure |
|---|---|
| 50 | 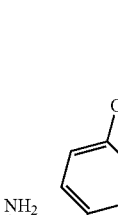 |
| 51 | |
| 52 | |
| 53 | |

| Compound | Structure |
|---|---|
| 54 | 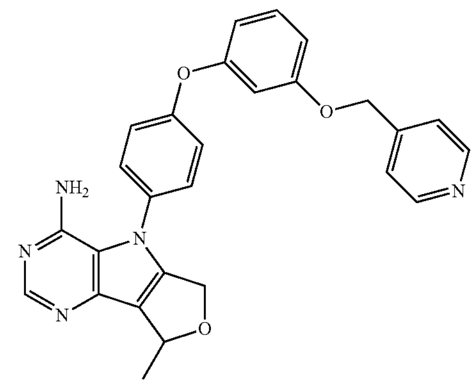 |
| 55 | 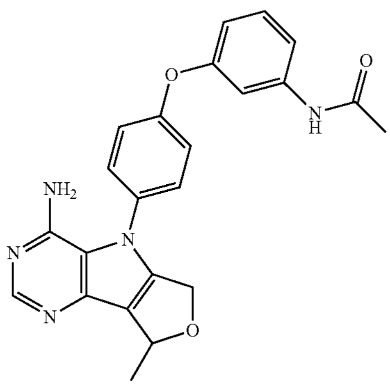 [SMILES: CC(=O)Nc1cccc(Oc2ccc(-n3c4c(c5ncnc(N)c53)C(C)OC4)cc2)c1] |
| 56 | 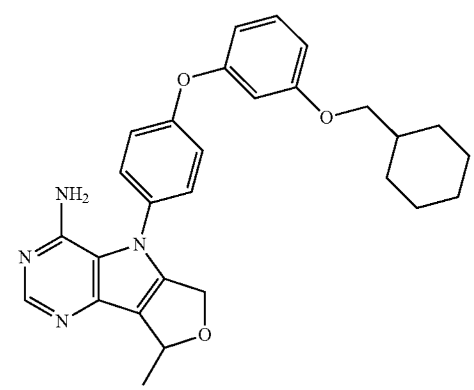 |
| 57 | 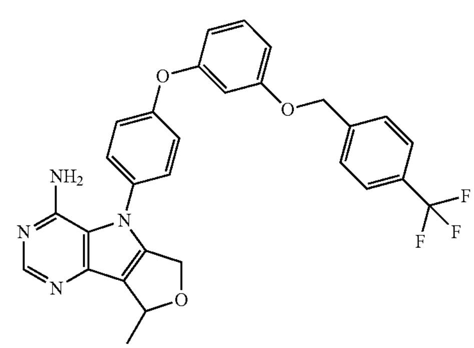 [SMILES: CC1OCc2c1c1ncnc(N)c1n2-c1ccc(Oc2cccc(OCc3ccc(C(F)(F)F)cc3)c2)cc1] |
| 58 | 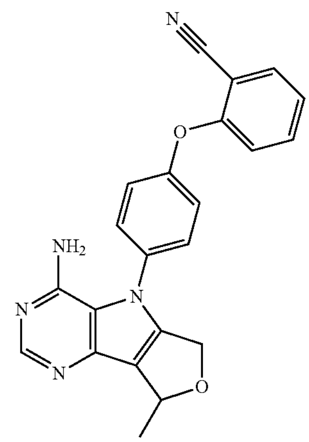 [SMILES: CC1OCc2c1c1ncnc(N)c1n2-c1ccc(Oc2ccccc2C#N)cc1] |
| 59 | 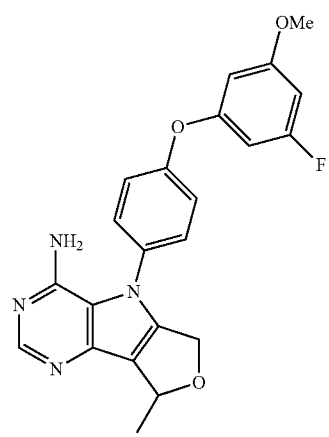 [SMILES: COc1cc(F)cc(Oc2ccc(-n3c4c(c5ncnc(N)c53)C(C)OC4)cc2)c1] |
| 60 | 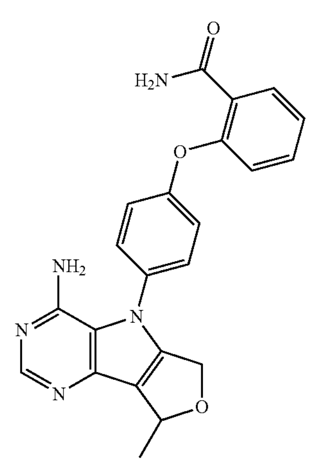 [SMILES: CC1OCc2c1c1ncnc(N)c1n2-c1ccc(Oc2ccccc2C(N)=O)cc1] |

TABLE-continued
| Compound | Structure |
|---|---|
| 61 | 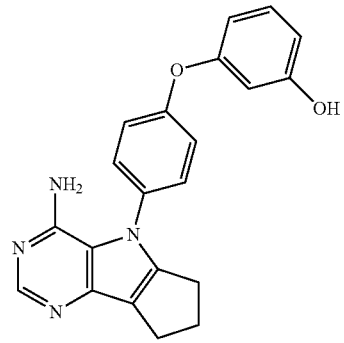 [SMILES: Nc1ncnc2c3c(n(-c4ccc(Oc5cccc(O)c5)cc4)c12)CCC3] |
| 62 | 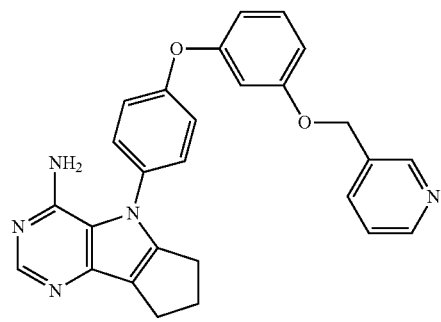 [SMILES: Nc1ncnc2c3c(n(-c4ccc(Oc5cccc(OCc6cccnc6)c5)cc4)c12)CCC3] |
| 64 | 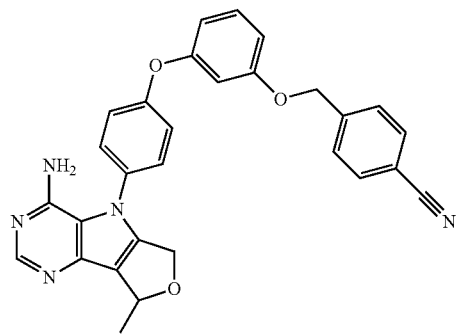 [SMILES: CC1OCc2c1c1ncnc(N)c1n2-c1ccc(Oc2cccc(OCc3ccc(C#N)cc3)c2)cc1] |
| 66 | 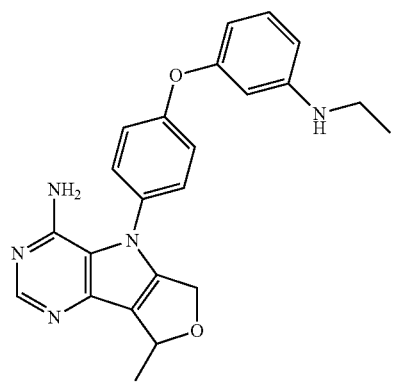 |
TABLE-continued
| Compound | Structure |
|---|---|
| 67 | 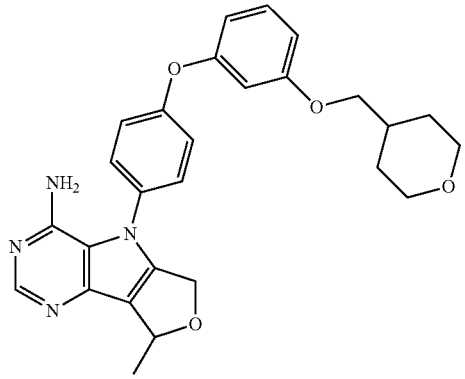 |
| 68 | 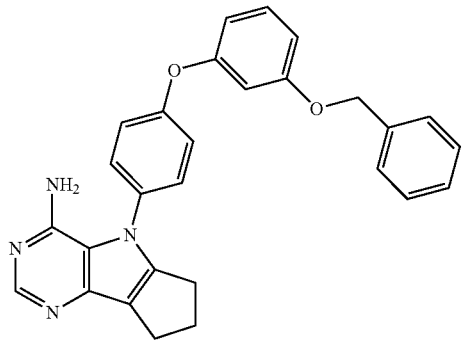 [SMILES: Nc1ncnc2c3c(n(-c4ccc(Oc5cccc(OCc6ccccc6)c5)cc4)c12)CCC3] |
| 69 | 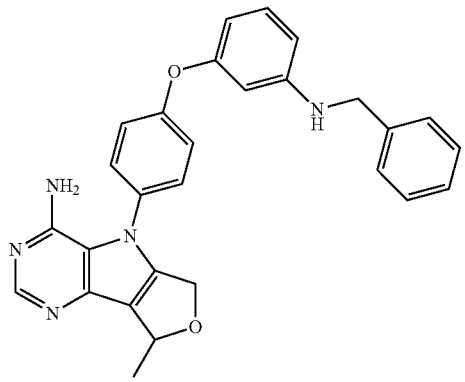 [SMILES: CC1OCc2c1c1ncnc(N)c1n2-c1ccc(Oc2cccc(NCc3ccccc3)c2)cc1] |
| 70 | 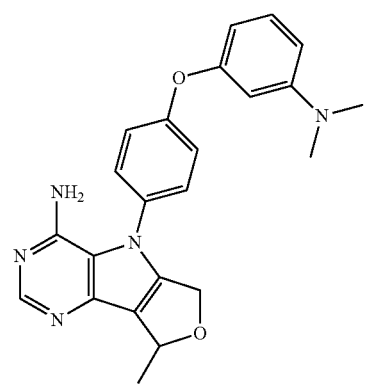 [SMILES: CC1OCc2c1c1ncnc(N)c1n2-c1ccc(Oc2cccc(N(C)C)c2)cc1] |

| Compound | Structure |
|---|---|
| 71 | 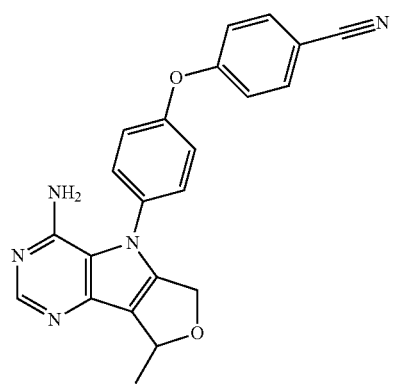 [SMILES: CC1OCc2c1c1ncnc(N)c1n2-c1ccc(Oc2ccc(C#N)cc2)cc1] |
| 72 | 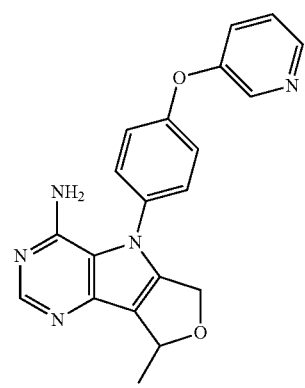 [SMILES: CC1OCc2c1c1ncnc(N)c1n2-c1ccc(Oc2cccnc2)cc1] |
| 73 | 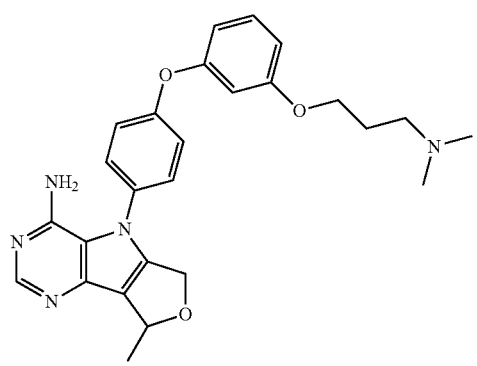 [SMILES: CC1OCc2c1c1ncnc(N)c1n2-c1ccc(Oc2cccc(OCCCN(C)C)c2)cc1] |
| 74 | 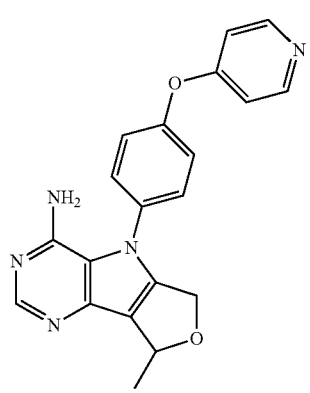 [SMILES: CC1OCc2c1c1ncnc(N)c1n2-c1ccc(Oc2ccncc2)cc1] |
| Compound | Structure |
|---|---|
| 75 | 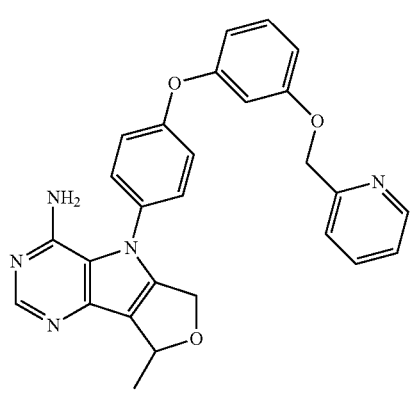 |
| 76 | 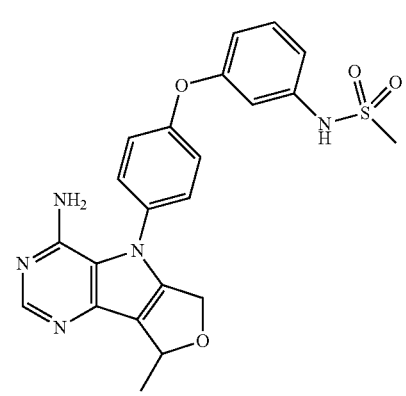 [SMILES: CC1OCc2c1c1ncnc(N)c1n2-c1ccc(Oc2cccc(NS(C)(=O)=O)c2)cc1] |
| 77 | 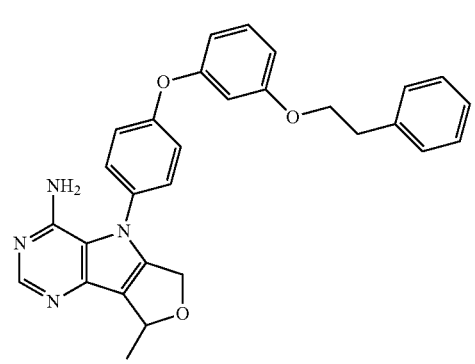 [SMILES: CC1OCc2c1c1ncnc(N)c1n2-c1ccc(Oc2cccc(OCCc3ccccc3)c2)cc1] |
| 78 | 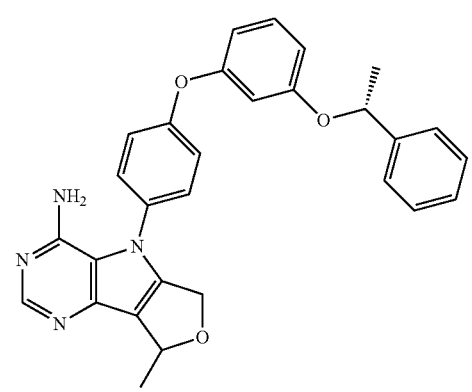 [SMILES: CC1OCc2c1c1ncnc(N)c1n2-c1ccc(Oc2cccc(O[C@H](C)c3ccccc3)c2)cc1] |

-continued
| Compound | Structure |
|---|---|
| 79 | 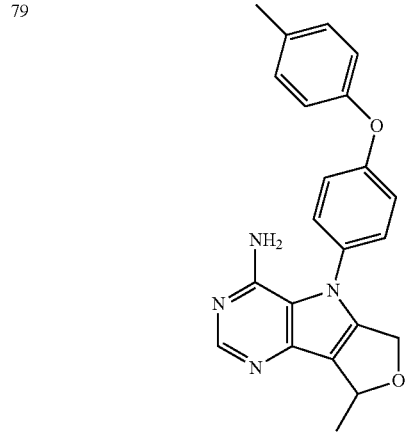 |
| 80 | 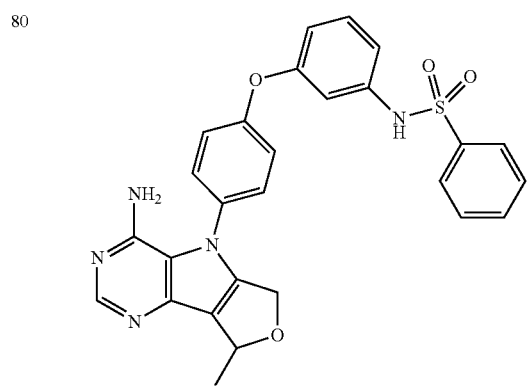 |
| 81 | 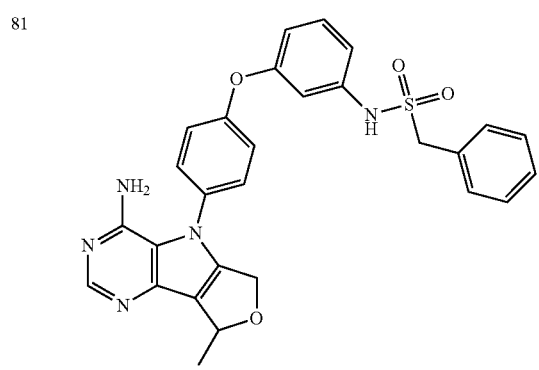 |
| 82 | 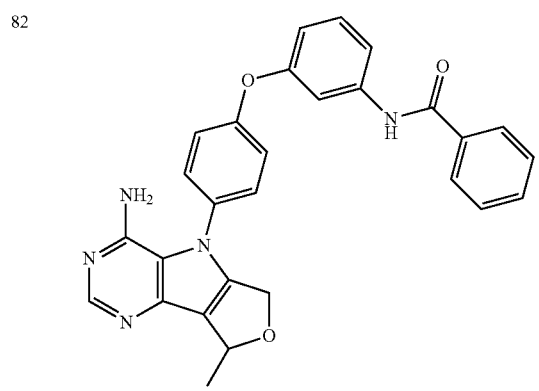 |
-continued
| Compound | Structure |
|---|---|
| 83 | 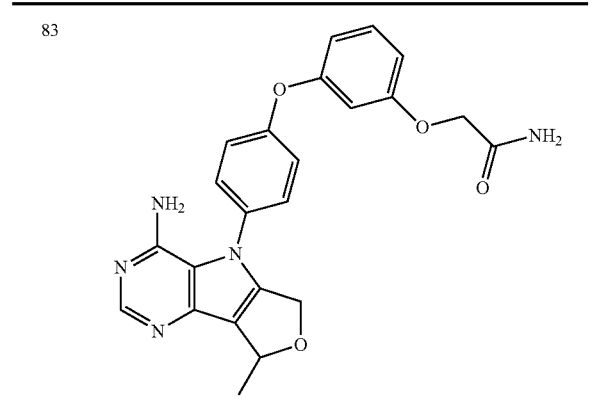 |
| 84 | 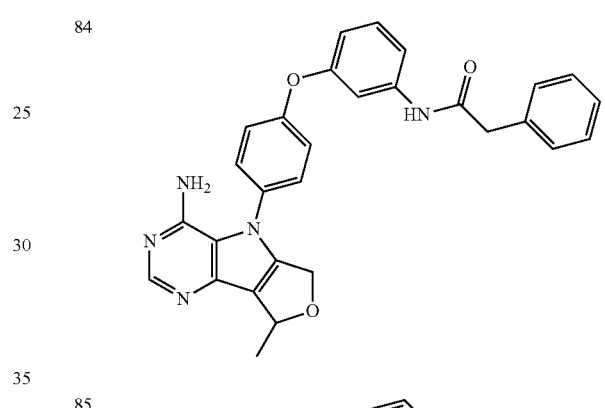 |
| 85 | 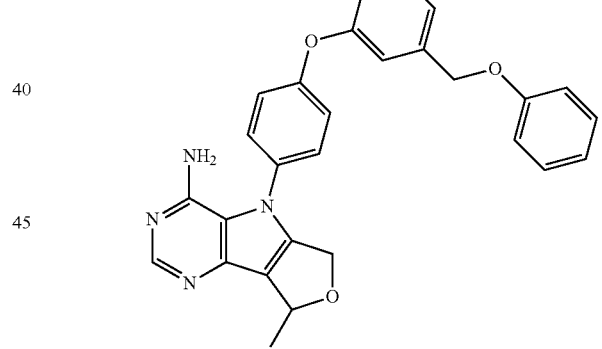 |
| 86 | 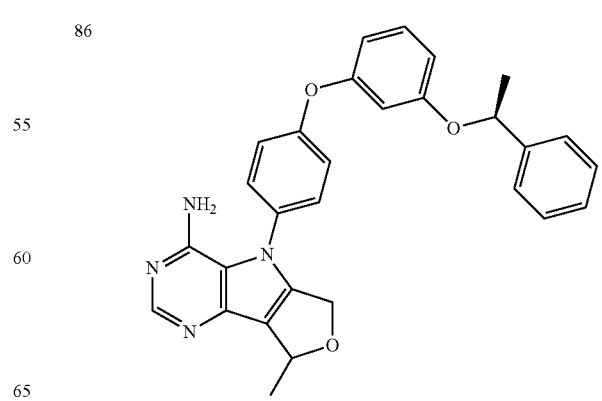 |

| Compound | Structure |
|---|---|
| 87 | 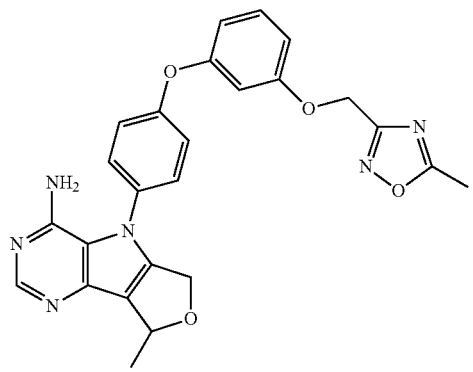 [SMILES: Cc1nc(COc2cccc(Oc3ccc(-n4c5c(c6ncnc(N)c64)C(C)OC5)cc3)c2)no1] |
| 88 | 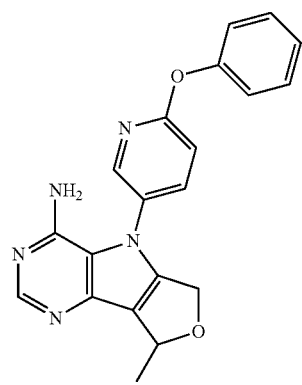 [SMILES: CC1OCc2c1c1ncnc(N)c1n2-c1ccc(Oc2ccccc2)nc1] |
| 89 | 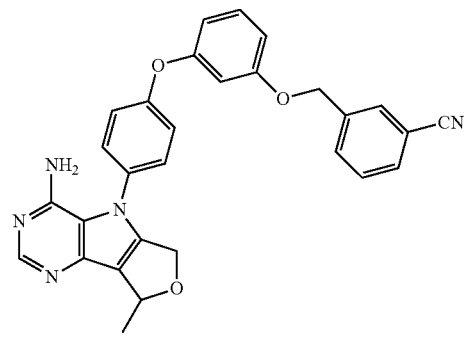 [SMILES: CC1OCc2c1c1ncnc(N)c1n2-c1ccc(Oc2cccc(OCc3cccc(C#N)c3)c2)cc1] |
| 90 | 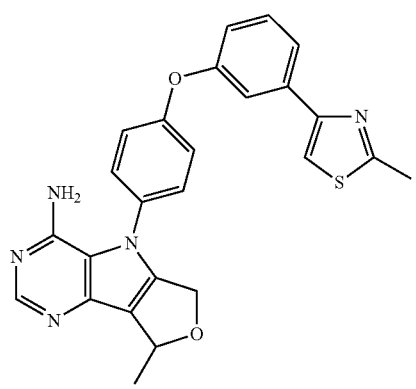 [SMILES: Cc1nc(-c2cccc(Oc3ccc(-n4c5c(c6ncnc(N)c64)C(C)OC5)cc3)c2)cs1] |
| Compound | Structure |
|---|---|
| 91 | 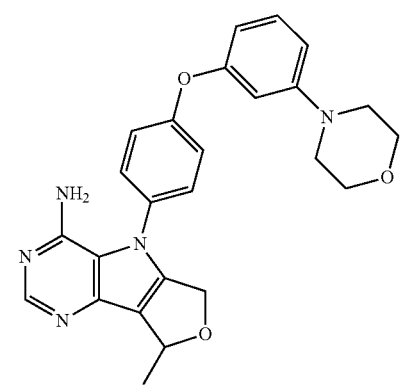 [SMILES: CC1OCc2c1c1ncnc(N)c1n2-c1ccc(Oc2cccc(N3CCOCC3)c2)cc1] |
| 92 | 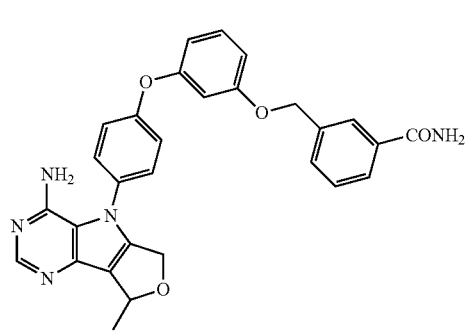 [SMILES: CC1OCc2c1c1ncnc(N)c1n2-c1ccc(Oc2cccc(OCc3cccc(C(N)=O)c3)c2)cc1] |
| 93 | 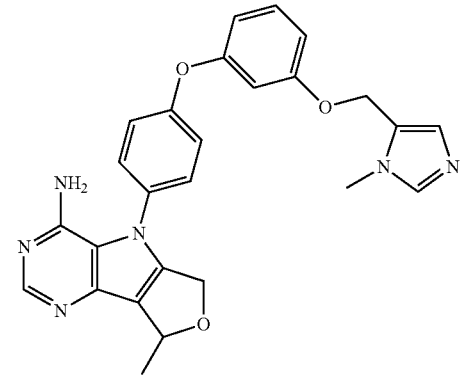 [SMILES: CC1OCc2c1c1ncnc(N)c1n2-c1ccc(Oc2cccc(OCc3cncn3C)c2)cc1] |
| 94 | 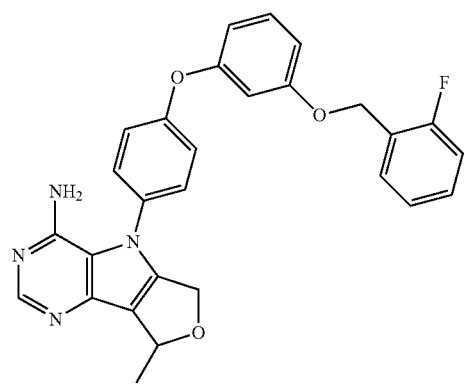 |

-continued
| Compound | Structure |
|---|---|
| 95 | 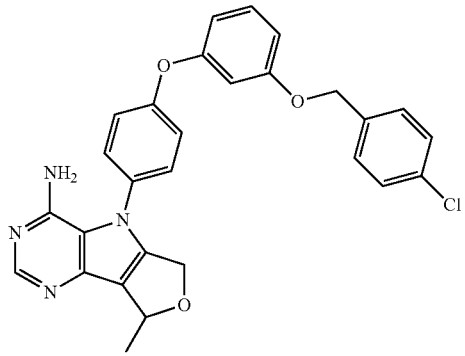 [SMILES: CC1OCc2c1c1ncnc(N)c1n2-c1ccc(Oc2cccc(OCc3ccc(Cl)cc3)c2)cc1] |
| 96 | 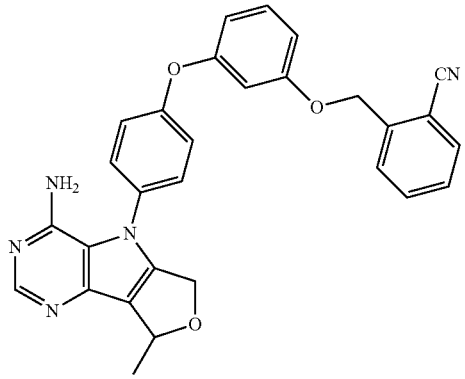 [SMILES: CC1OCc2c1c1ncnc(N)c1n2-c1ccc(Oc2cccc(OCc3ccccc3C#N)c2)cc1] |
| 97 | 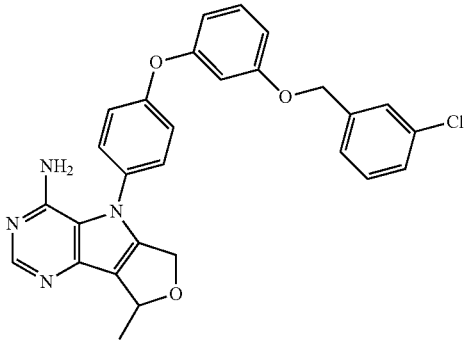 [SMILES: CC1OCc2c1c1ncnc(N)c1n2-c1ccc(Oc2cccc(OCc3cccc(Cl)c3)c2)cc1] |
| 98 | 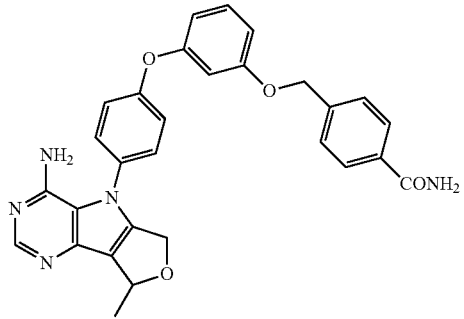 [SMILES: CC1OCc2c1c1ncnc(N)c1n2-c1ccc(Oc2cccc(OCc3ccc(C(N)=O)cc3)c2)cc1] |
-continued
| Compound | Structure |
|---|---|
| 99 | 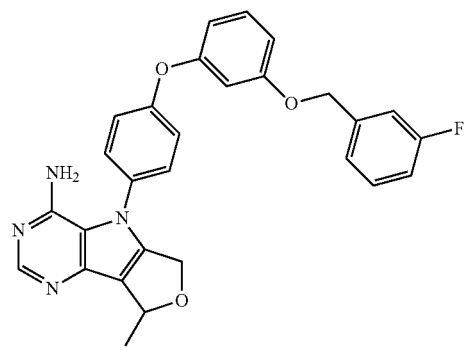 [SMILES: CC1OCc2c1c1ncnc(N)c1n2-c1ccc(Oc2cccc(OCc3cccc(F)c3)c2)cc1] |
| 100 | 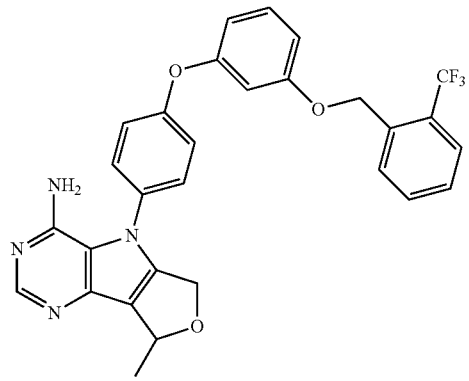 [SMILES: CC1OCc2c1c1ncnc(N)c1n2-c1ccc(Oc2cccc(OCc3ccccc3C(F)(F)F)c2)cc1] |
| 101 | 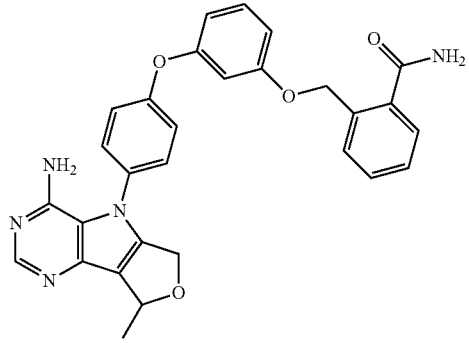 [SMILES: CC1OCc2c1c1ncnc(N)c1n2-c1ccc(Oc2cccc(OCc3ccccc3C(N)=O)c2)cc1] |
| 102 | 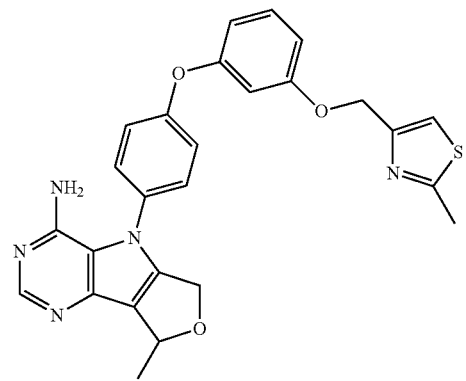 [SMILES: Cc1nc(COc2cccc(Oc3ccc(-n4c5c(c6ncnc(N)c64)C(C)OC5)cc3)c2)cs1] |

| Compound | Structure |
|---|---|
| 103 | 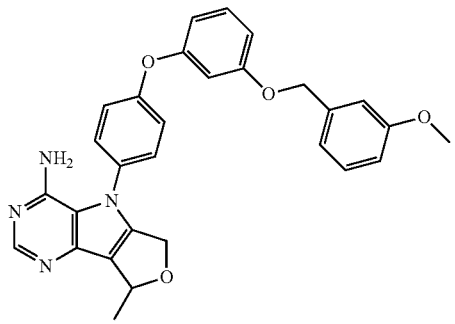 [SMILES: COc1cccc(COc2cccc(Oc3ccc(-n4c5c(c6ncnc(N)c64)C(C)OC5)cc3)c2)c1] |
| 104 | 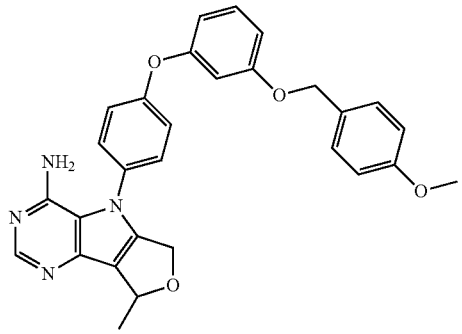 [SMILES: COc1ccc(COc2cccc(Oc3ccc(-n4c5c(c6ncnc(N)c64)C(C)OC5)cc3)c2)cc1] |
| 105 | 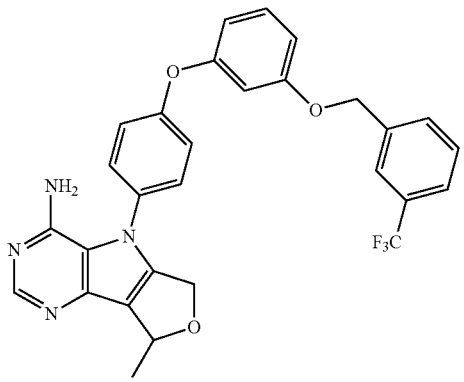 [SMILES: CC1OCc2c1c1ncnc(N)c1n2-c1ccc(Oc2cccc(OCc3cccc(C(F)(F)F)c3)c2)cc1] |
| 106 | 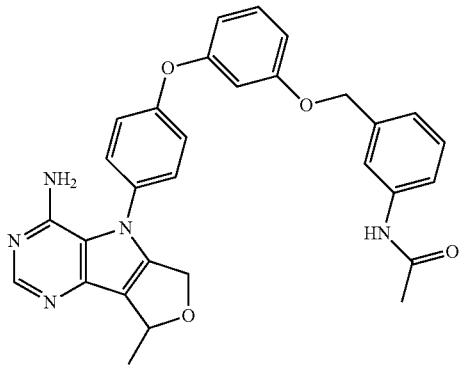 [SMILES: CC(=O)Nc1cccc(COc2cccc(Oc3ccc(-n4c5c(c6ncnc(N)c64)C(C)OC5)cc3)c2)c1] |
| Compound | Structure |
|---|---|
| 107 | 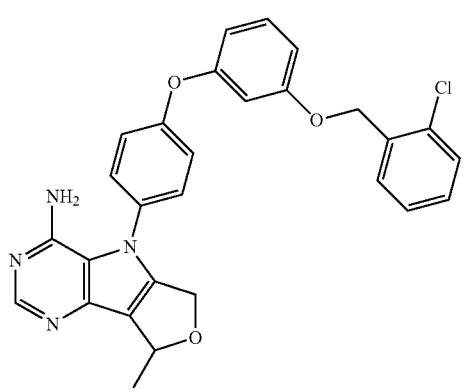 |
| 108 | 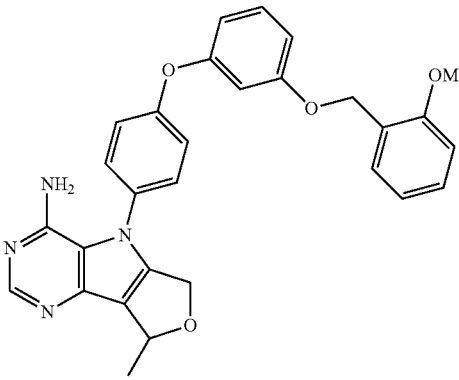 |
| 109 | 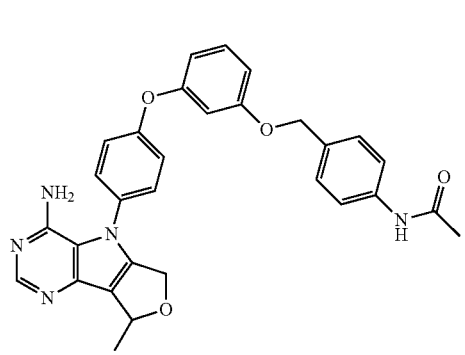 [SMILES: CC(=O)Nc1ccc(COc2cccc(Oc3ccc(-n4c5c(c6ncnc(N)c64)C(C)OC5)cc3)c2)cc1] |
| 110 | 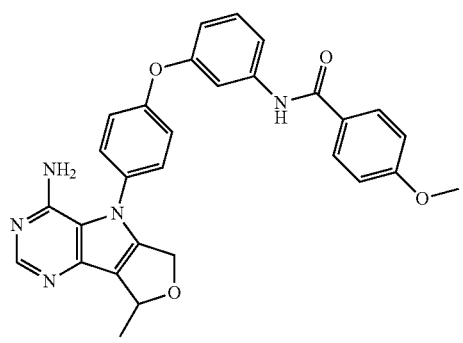 [SMILES: COc1ccc(C(=O)Nc2cccc(Oc3ccc(-n4c5c(c6ncnc(N)c64)C(C)OC5)cc3)c2)cc1] |

US 9,624,239 B2
259
-continued
| Compound | Structure |
|---|---|
| 111 | 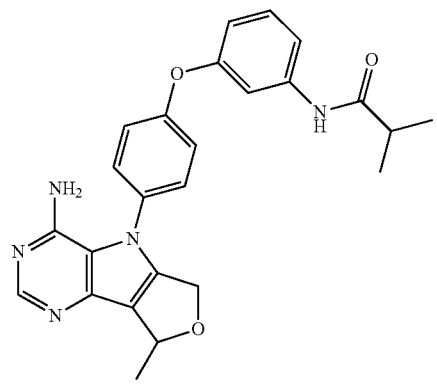 [SMILES: CC(C)C(=O)Nc1cccc(Oc2ccc(-n3c4c(c5ncnc(N)c53)C(C)OC4)cc2)c1] |
| 112 | 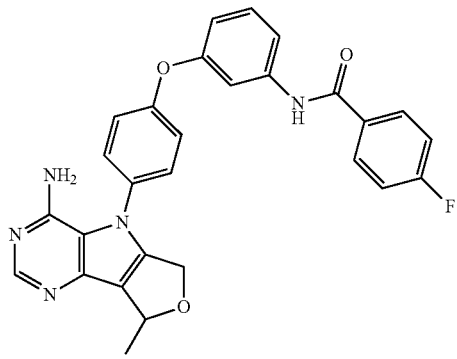 [SMILES: CC1OCc2c1c1ncnc(N)c1n2-c1ccc(Oc2cccc(NC(=O)c3ccc(F)cc3)c2)cc1] |
| 113 | 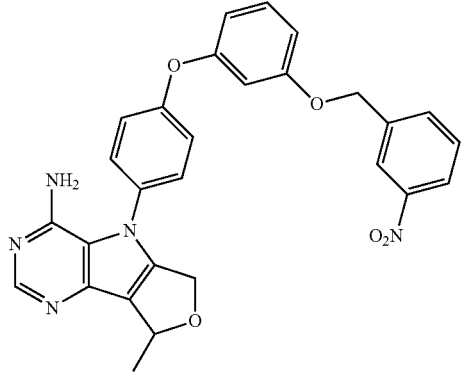 |
| 114 | 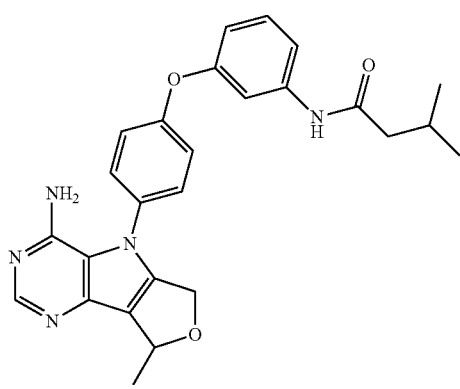 [SMILES: CC(C)CC(=O)Nc1cccc(Oc2ccc(-n3c4c(c5ncnc(N)c53)C(C)OC4)cc2)c1] |
260
-continued
| Compound | Structure |
|---|---|
| 115 | 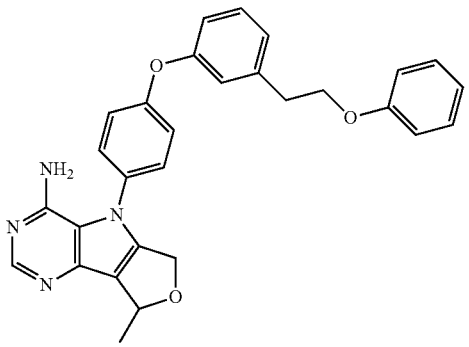 [SMILES: CC1OCc2c1c1ncnc(N)c1n2-c1ccc(Oc2cccc(CCOc3ccccc3)c2)cc1] |
| 116 | 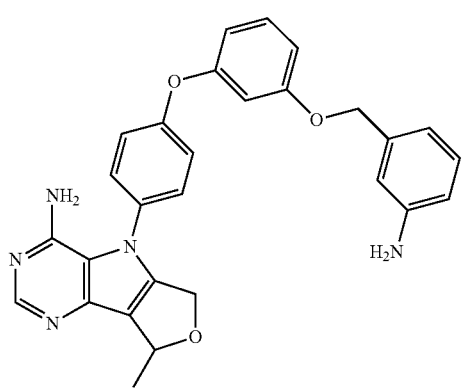 |
| 117 | 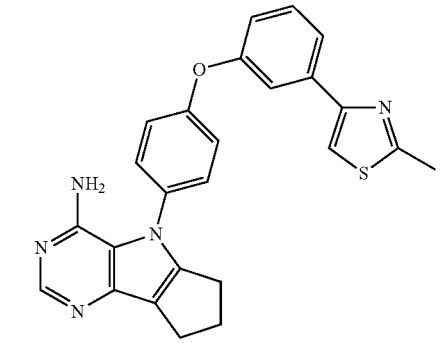 [SMILES: Cc1nc(-c2cccc(Oc3ccc(-n4c5c(c6ncnc(N)c64)CCC5)cc3)c2)cs1] |
| 118 | 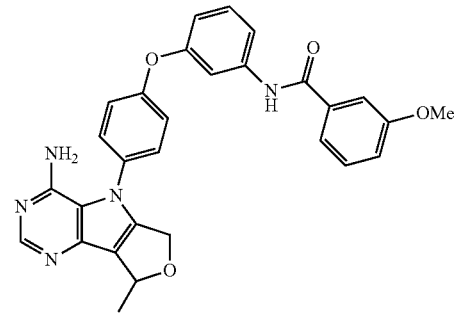 [SMILES: COc1cccc(C(=O)Nc2cccc(Oc3ccc(-n4c5c(c6ncnc(N)c64)C(C)OC5)cc3)c2)c1] |

| Compound | Structure |
|---|---|
| 119 | 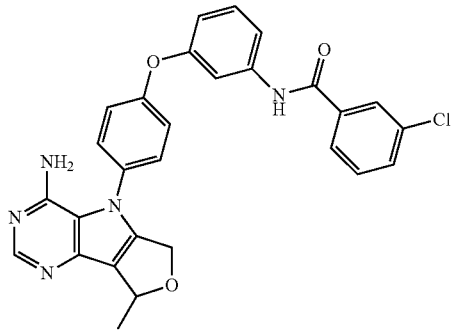 [SMILES: CC1OCc2c1c1ncnc(N)c1n2-c1ccc(Oc2cccc(NC(=O)c3cccc(Cl)c3)c2)cc1] |
| 120 | 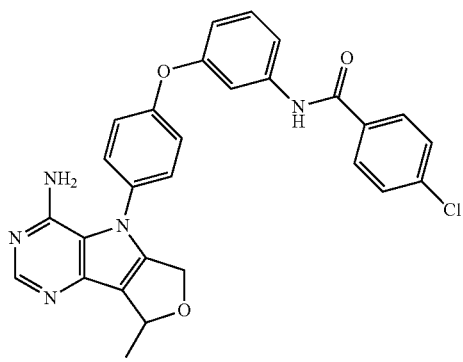 [SMILES: CC1OCc2c1c1ncnc(N)c1n2-c1ccc(Oc2cccc(NC(=O)c3ccc(Cl)cc3)c2)cc1] |
| 121 | 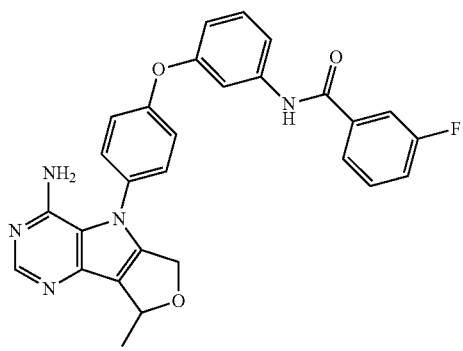 [SMILES: CC1OCc2c1c1ncnc(N)c1n2-c1ccc(Oc2cccc(NC(=O)c3cccc(F)c3)c2)cc1] |
| 122 | 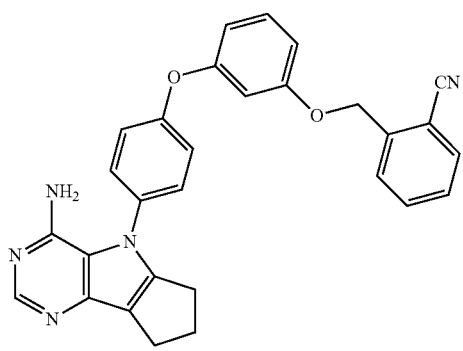 [SMILES: N#Cc1ccccc1COc1cccc(Oc2ccc(-n3c4c(c5ncnc(N)c53)CCC4)cc2)c1] |
| Compound | Structure |
|---|---|
| 123 | 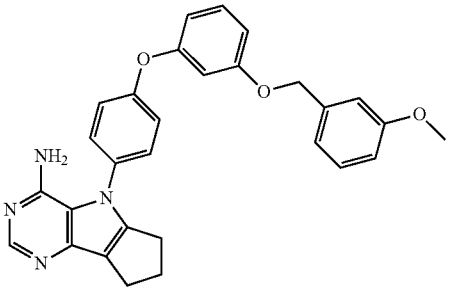 [SMILES: COc1cccc(COc2cccc(Oc3ccc(-n4c5c(c6ncnc(N)c64)CCC5)cc3)c2)c1] |
| 124 | 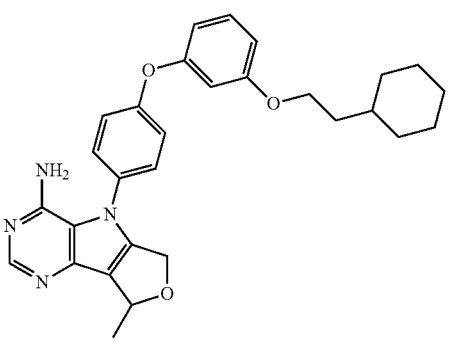 [SMILES: CC1OCc2c1c1ncnc(N)c1n2-c1ccc(Oc2cccc(OCCC3CCCCC3)c2)cc1] |
| 125 | 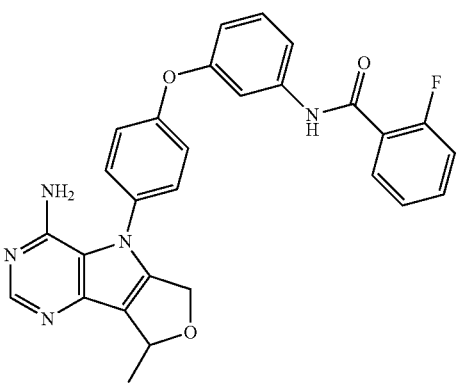 [SMILES: CC1OCc2c1c1ncnc(N)c1n2-c1ccc(Oc2cccc(NC(=O)c3ccccc3F)c2)cc1] |
| 126 | 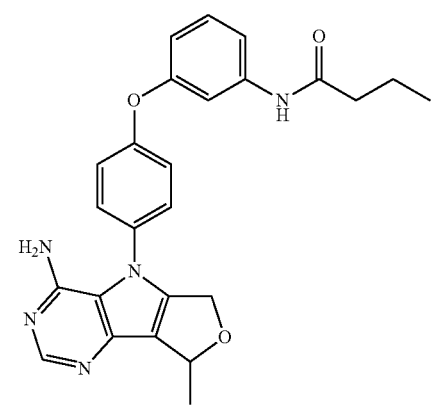 [SMILES: CCCC(=O)Nc1cccc(Oc2ccc(-n3c4c(c5ncnc(N)c53)C(C)OC4)cc2)c1] |

-continued
| Compound | Structure |
|---|---|
| 127 | 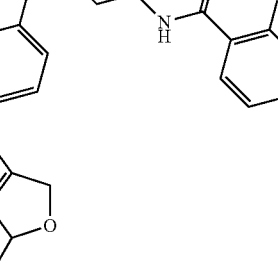 |
| 128 | 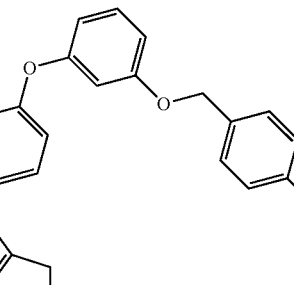 |
| 129 | 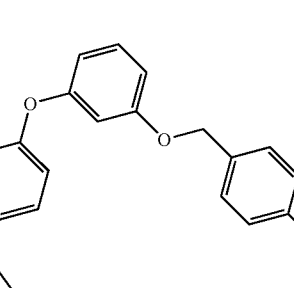 |
| 130 | 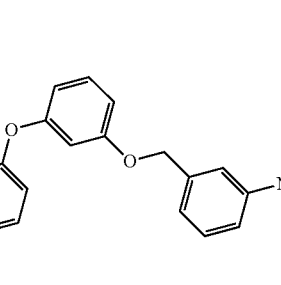 |
-continued
| Compound | Structure |
|---|---|
| 131 | 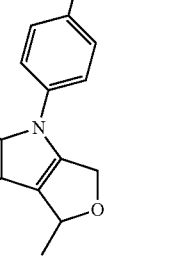 |
| 132 | 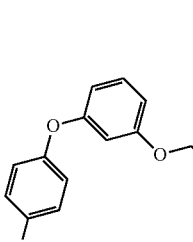 |
| 133 | 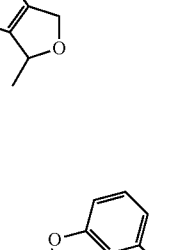 |
| 134 | 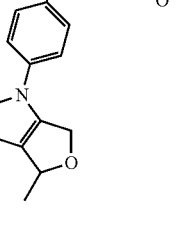 |

-continued
| Compound | Structure |
|---|---|
| 135 | 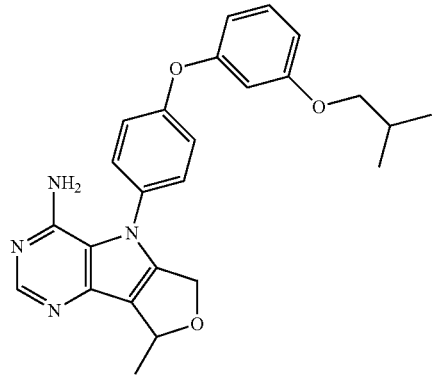 [SMILES: CC(C)COc1cccc(Oc2ccc(-n3c4c(c5ncnc(N)c53)C(C)OC4)cc2)c1] |
| 136 | 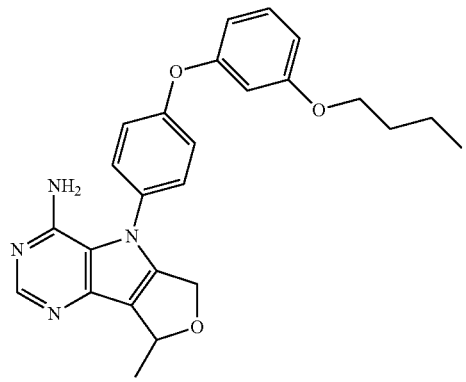 [SMILES: CCCCOc1cccc(Oc2ccc(-n3c4c(c5ncnc(N)c53)C(C)OC4)cc2)c1] |
| 137 | 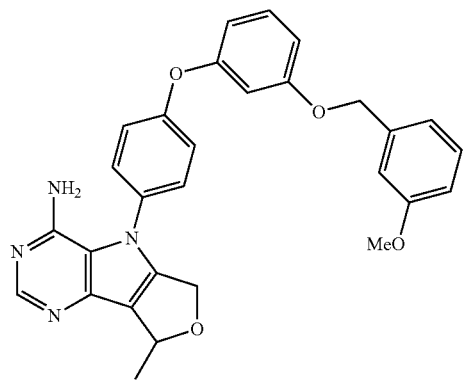 |
| 138 | 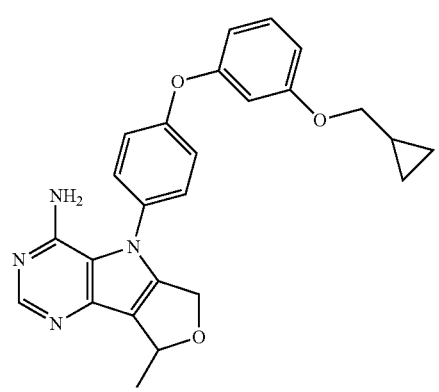 [SMILES: CC1OCc2c1c1ncnc(N)c1n2-c1ccc(Oc2cccc(OCC3CC3)c2)cc1] |
-continued
| Compound | Structure |
|---|---|
| 139 | 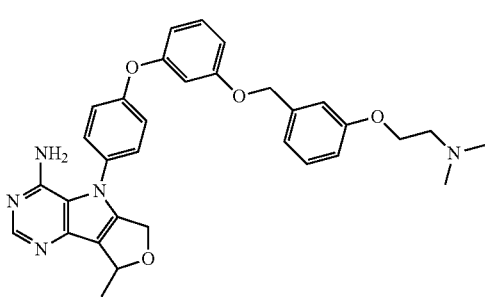 [SMILES: CC1OCc2c1c1ncnc(N)c1n2-c1ccc(Oc2cccc(OCc3cccc(OCCN(C)C)c3)c2)cc1] |
| 140 | 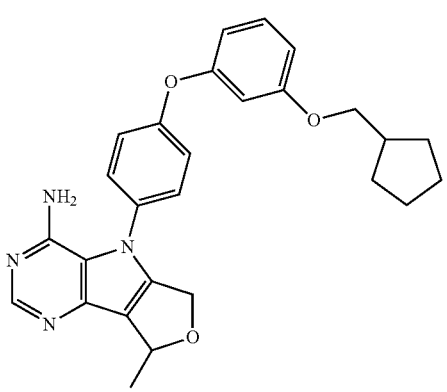 [SMILES: CC1OCc2c1c1ncnc(N)c1n2-c1ccc(Oc2cccc(OCC3CCCC3)c2)cc1] |
| 141 | 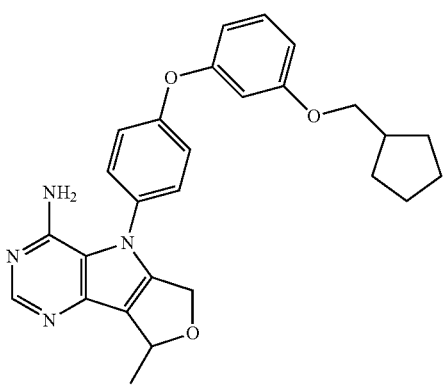 |
| 142 | 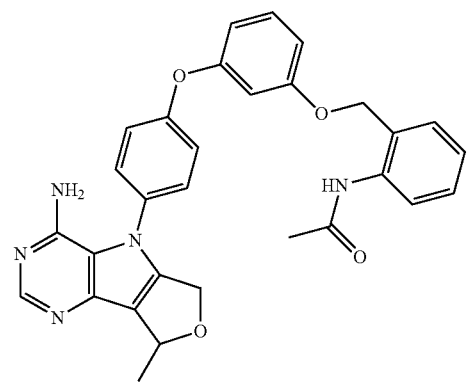 |

-continued

| Compound | Structure |
|---|---|
| 143 | 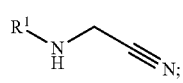 |
| 144 | 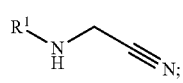 |

8. The compound according to claim 7, wherein the compound is selected from the group consisting of compounds 25, 41, 43, 44, 46, 49, 50, 53, 54, 56, 57, 58, 59, 61, 62, 64, 67, 68, 75, 77, 78, 85, 86, 87, 89, 93, 94, 95, 96, 97, 99, 100, 102, 103, 104, 105, 106, 107, 108, 109, 115, 112, 123, 124, 128, 129, 130, 131, 132, 133, 134, 135, 136, 137, 138, 140, 141, 142, 143, and 144.

9. The compound according to claim 7, wherein the compound is selected from the group consisting of compounds 47, 66, 69, 70, 76, 80, 81, 82, 84, 111, 112, 114, 118, 119, 120, 121, 125, 126, and 127.

10. A pharmaceutical composition comprising a compound of claim 1 and a pharmaceutically acceptable carrier or diluent.

11. A process for preparing a compound of claim 1 of Formula 1-v, comprising the steps of:

a) alkylation of R¹NH2 with bromoacetonitrile to provide intermediate 1-i

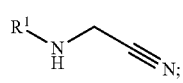

b) condensation of 1-i with 1-ii

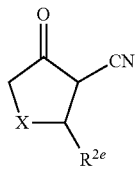

in the presence of an acid to provide intermediate 1-iii 1-iii

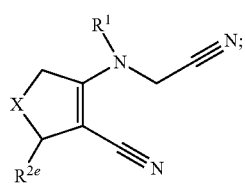

c) treatment of intermediate 1-iii with a base to provide intermediate 1-iv 1-iv

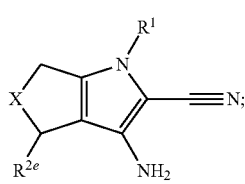

d) treatment of intermediate 1-iv with formamadine acetate in an alcohol to provide a compound of formula 1-v 1-v

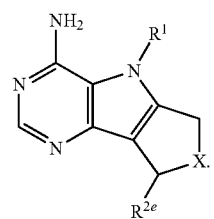

12. The process according to claim 11, comprising the following steps:

a)

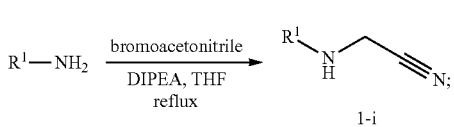

b)

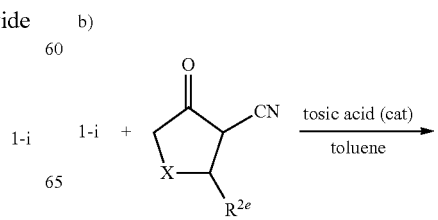

-continued
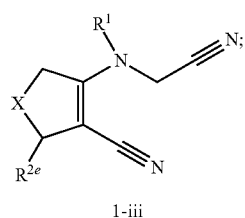
1-iii
c)
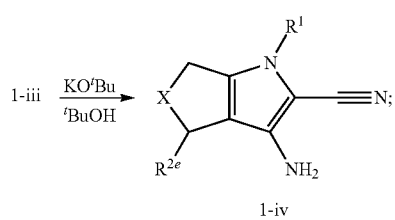
-continued
d)
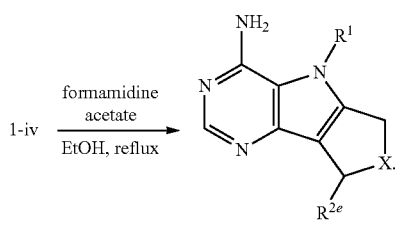
13. The compound according to claim 7, wherein the compound is selected from the group consisting of compounds 1, 20, 21, 23, 24, 28, 29, 31, 32, 33, 34, 35, 37, 39, 40, and 45.
* * * * *